United States Patent
Campbell et al.

(10) Patent No.: US 6,872,805 B2
(45) Date of Patent: Mar. 29, 2005

(54) HEPATITIS C VIRUS INHIBITORS

(75) Inventors: Jeffrey Allen Campbell, Cheshire, CT (US); Andrew Good, Wallingford, CT (US)

(73) Assignee: Bristol-Myers Squibb Company, Princeton, NJ (US)

(*) Notice: Subject to any disclaimer, the term of this patent is extended or adjusted under 35 U.S.C. 154(b) by 464 days.

(21) Appl. No.: 10/001,850

(22) Filed: Nov. 20, 2001

(65) Prior Publication Data

US 2002/0111313 A1 Aug. 15, 2002

Related U.S. Application Data

(60) Provisional application No. 60/249,968, filed on Nov. 20, 2000.

(51) Int. Cl.[7] .................................................. C07K 5/08
(52) U.S. Cl. ......................... 530/331; 514/18; 514/19; 546/134; 546/153; 548/535
(58) Field of Search ..................... 514/18, 19; 530/331; 546/134, 153; 548/535

(56) References Cited

FOREIGN PATENT DOCUMENTS

| WO | WO 00/09543 | 2/2000 |
|---|---|---|
| WO | WO 03/064416 A1 | 8/2003 |
| WO | WO 03/064455 A2 | 8/2003 |
| WO | WO 03/064456 A1 | 8/2003 |
| WO | WO 03/066103 A1 | 8/2003 |

OTHER PUBLICATIONS

Q.-L. Choo, et al., "Isolation of a cDNA Clone Derived from a Bloodborne Non–A, Non–B Viral Hepatitis Genome", *Science*, 244, p. 359–362 (1989).

G. Kuo, et al., "An Assay for Circulating Antibodies to a Major Etiologic Virus of Human Non–A, Non–B Hepatitis", *Science*, 244, p. 362–364 (1989).

*Primary Examiner*—Jon Weber
*Assistant Examiner*—David Lukton
(74) *Attorney, Agent, or Firm*—Jennifer T. Chin

(57) ABSTRACT

The present invention relates to tripeptide compounds, compositions and methods for the treatment of hepatitis C virus (HCV) infection. In particular, the present invention provides novel tripeptide analogs, pharmaceutical compositions containing such analogs and methods for using these analogs in the treatment of HCV infection.

33 Claims, No Drawings

HEPATITIS C VIRUS INHIBITORS

CROSS-REFERENCE TO RELATED APPLICATIONS

This is a nonprovisional application which claims the benefit of provisional application U.S. Ser. No. 60/249,968 filed Nov. 20, 2000.

BACKGROUND OF THE INVENTION

Hepatitis C virus (HCV) is the major etiological agent of 90% of all cases of non-A, non-B hepatitis (Choo et al., 1989, Kuo et al., 1989). The incidence of HCV infection is becoming an increasingly severe public health concern with 2–15% individuals infected worldwide. While primary infection with HCV is often asymptomatic, most HCV infections progress to a chronic state that can persist for decades. Of those with chronic HCV infections, it is believed that about 20–50% will eventually develop chronic liver disease (e.g. cirrhosis) and 20–30% of these cases will lead to liver failure or liver cancer. As the current HCV-infected population ages, the morbidity and mortality associated with HCV are expected to triple.

An approved treatment for HCV infection uses interferon (IFN) which indirectly effects HCV infection by stimulating the host antiviral response. IFN treatment is largely ineffective, however, as a sustained antiviral response is produced in less than 30% of treated patients. Further, IFN treatment induces an array of side effects of varying severity in upwards of 90% of patients (eg: acute pancreatitis, depression, retinopathy, thyroiditis). Therapy with a combination of IFN and ribavirin has provided a slightly higher sustained response rate, but has not alleviated the IFN-induced side effects.

A general strategy for the development of antiviral agents has been to inactivate virally encoded enzymes essential for viral replication. In the case of HCV, an inhibitor selectively targeting the HCV serine protease, NS3, would likely provide an advantageous therapy for treating HCV infections in patients by inhibiting HCV replication.

Amongst the compounds that have demonstrated efficacy in inhibiting HCV replication, as selective HCV NS3 serine protease inhibitors, are the tri-peptide compounds disclosed in International Application Number PCT/CA99/00736, Publication No. WO 00/09543, titled Hepatitis C Inhibitor Tri-Peptides. However, these compounds do not sufficiently inhibit HCV serine protease or do not have sufficient potency, and thus, may not provide optimal treatment of HCV-infected patients.

What is needed are compounds, useful for treating HCV-infected patients, by selectively inhibiting HCV NS3 serine protease, wherein these compounds have a suitable cell permeability to sufficiently inhibit HCV replication within the patient's body.

SUMMARY OF THE INVENTION

The present invention relates to compounds, or pharmaceutically acceptable salts, solvates or prodrugs thereof, having the structure of Formula I

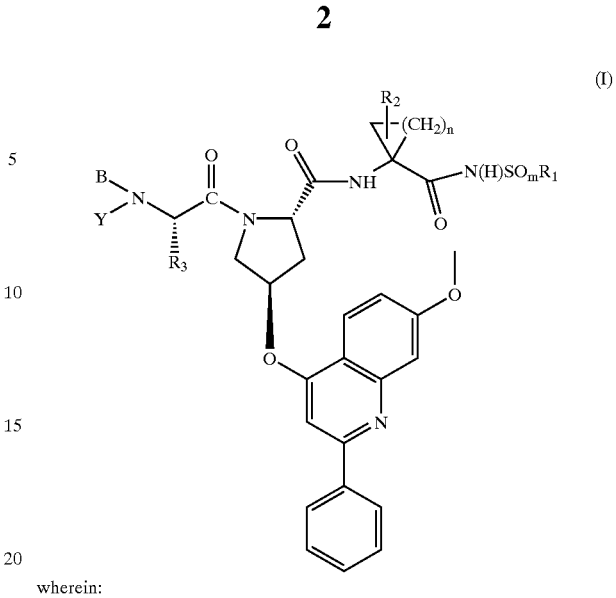

(I)

wherein:

wherein:

(a) $R_1$ is $C_{1-8}$ alkyl, $C_{3-7}$ cycloalkyl, or $C_{4-10}$ (alkylcycloalkyl), which are all optionally substituted from one to three times with halo, cyano, nitro, $C_{1-6}$ alkoxy, amido, amino or phenyl, or $R_1$ is $C_6$ or $C_{10}$ aryl which is optionally substituted from one to three times with halo, cyano, nitro, $C_{1-6}$ alkyl, $C_{1-6}$ alkoxy, amido, amino or phenyl;

(b) m is 1 or 2;

(c) n is 1 or 2;

(d) $R_2$ is $C_{1-6}$ alkyl, $C_{2-6}$ alkenyl or $C_{3-7}$ cycloalkyl, each optionally substituted from one to three times with halogen, or $R_2$ is H;

(e) $R_3$ is $C_{1-8}$ alkyl optionally substituted with phenyl, $C_{3-12}$ alkenyl, $C_{3-7}$ cycloalkyl, or $C_{4-10}$ (alkylcycloalkyl), wherein the cycloalkyl or alkylcycloalkyl are optionally substituted with hydroxy, $C_{1-6}$ alkyl, $C_{2-6}$ alkenyl; or $C_{1-6}$ alkoxy or $R_3$ together with the carbon atom to which it is attached forms a $C_{3-7}$ cycloalkyl group optionally substituted with $C_{2-6}$ alkenyl;

(f) Y is H, phenyl substituted with nitro, pyridyl substituted with nitro, or $C_{1-6}$ alkyl wherein said alkyl is optionally substituted with cyano, OH or $C_{3-7}$ cycloalkyl;

(g) B is H, $C_{1-6}$ alkyl, $R_4$—(C=O)—, $R_4O(C=O)$—, $R_4$—N($R_5$)—C(=O)—, $R_4$—N($R_5$)—C(=S)—, $R_4SO_2$—, or $R_4$—N($R_5$)—$SO_2$—;

(h) $R_4$ is (i) $C_{1-10}$ alkyl optionally substituted with phenyl, carboxyl, $C_{1-6}$ alkanoyl, 1–3 halogen, hydroxy, —OC(O) $C_{1-6}$ alkyl, $C_{1-6}$ alkoxy, amino optionally mono-or-di substituted with $C_{1-6}$ alkyl, amido, or (lower alkyl) amido; or —O-phenyl optionally substituted with halogen or $C_{1-6}$ alkoxy; (ii) $C_{3-7}$ cycloalkyl, $C_{3-7}$ cycloalkoxy, or $C_{4-10}$ alkylcyclo-alklyl, all optionally substituted with hydroxy, carboxyl, ($C_{1-6}$ alkoxy)carbonyl, amino optionally mono- or disubstituted with $C_{1-6}$ alkyl, amido, or (lower alkyl) amido; (iii) amino optionally mono-or-di-substituted with $C_{1-6}$ alkyl; amido; or (lower alkyl)amido; (iv) $C_6$ or $C_{10}$ aryl or $C_{7-16}$ aralkyl, all optionally substituted with $C_{1-6}$ alkyl, halogen, nitro, hydroxy, amido, (lower alkyl) amido, or amino optionally mono-or-di-substituted with $C_{1-6}$ alkyl; or (v) Het or (lower alkyl)-Het, both optionally substituted with $C_{1-6}$ alkyl, hydroxy, amido, (lower alkyl) amido, or amino optionally mono-or-di-substituted with $C_{1-6}$ alkyl; (vi) bicyclo(1.1.1)pentane; (vii) —C(O)O $C_{1-6}$ alkyl, $C_{2-6}$alkenyl, $C_{2-6}$alkynyl; and (i) $R_5$ is H or $C_{1-6}$ alkyl, said $C_{1-6}$alkyl optionally substituted with 1–3 halogens;

or a pharmaceutically acceptable salt, solvate or prodrug thereof.

The present invention also relates to a pharmaceutical composition, useful for inhibiting HCV NS3 protease, or for treating patients infected with the hepatitis C virus, comprising a therapeutically effective amount of a compound of the present invention, or a salt, solvate or prodrug thereof, and a pharmaceutically acceptable carrier.

The present invention further relates to a method of treating mammals infected with hepatitis C virus, comprising administering to said mammal an effective amount of a compound of the present invention or a salt, solvate or prodrug thereof.

Additionally, the present invention relates to a method of inhibiting HCV NS3 protease by administering to a patient an effective amount of a compound of the present invention or a pharmaceutically salt, solvate or prodrug thereof.

DETAILED DESCRIPTION OF THE INVENTION

As used herein, the following definitions apply unless otherwise noted. With reference to the instances where (R) or (S) is used to designate the configuration of a substituent in context to the whole compound and not in context to the substituent alone.

The term "halo" as used herein means a halogen substituent selected from bromo, chloro, fluoro or iodo.

The term "$C_{1-6}$ alkyl" as used herein means acyclic, straight or branched chain alkyl substituents containing from 1 to six carbon atoms and includes, for example, methyl, ethyl, propyl, butyl, tert-butyl, hexyl, 1-methylethyl, 1-methylpropyl, 2-methypropyl, 1,1-dimethylethyl.

The term "$C_{2-10}$ alkenyl", as used herein, either alone or in combination with another radical, means an alkyl radical as defined above containing from 2 to 10 carbon atoms, and further containing at least one double bond. For example alkenyl includes allyl and ethenyl.

Haloalkyl refers to an alkyl radical that is substituted with one or more halo radicals, such as trifluoromethyl.

The term "$C_{1-6}$ alkoxy" as used herein means the radical —O($C_{1-6}$ alkyl) wherein alkyl is as defined above containing up to six carbon atoms. Alkoxy includes, for example, methoxy, ethoxy, propoxy, 1-methylethoxy, butoxy and 1,1-dimethylethoxy. The latter radical is known commonly as tert-butoxy.

The term "$C_{1-6}$ haloalkoxy" as used herein means the radical —O($C_{1-6}$ haloalkyl) wherein haloalkyl is as defined above.

The term "$C_{1-6}$ alkanoyl" as used herein means straight or branched 1-oxoalkyl radicals containing one to six carbon atoms and includes, for example, formyl, acetyl, 1-oxopropyl (propionyl), 2-methyl-1-oxopropyl, 1-oxohexyl and the like.

The term "$C_{3-7}$ cycloalkyl" as used herein means a cycloalkyl substituent containing from three to seven carbon atoms and includes, for example, cyclopropyl, cyclobutyl, cyclopentyl, cyclohexyl and cycloheptyl. This term also includes "spiro"-cyclic group such as spiro-cyclopropyl or spiro-cyclobutyl:

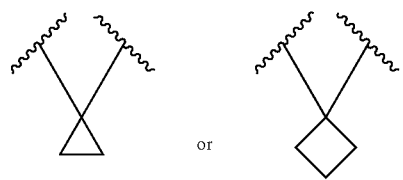

The term "unsaturated cycloalkyl" includes, for example, cyclohexenyl.

The term "$C_{4-10}$ alkylcycloalkyl", as used herein means a cycloalkyl radical containing from three to seven carbon atoms linked to an alkyl radical, the linked radicals containing up to ten carbon atoms, for example, cyclopropylmethyl, cyclopentylethyl, cyclohexylmethyl, cyclohexylethyl or cycloheptylethyl.

The term "$C_{3-7}$ cycloalkoxy" as used herein means a $C_{3-7}$ cycloalkyl group linked to an oxygen atom, such as, for example, butyloxy or cyclopropyloxy.

The term "$C_6$ or $C_{10}$ aryl" as used herein means either an aromatic monocyclic group containing 6 carbon atoms or an aromatic bicyclic group containing 10 carbon atoms, for example, aryl includes phenyl, 1-naphthyl or 2-naphthyl.

The term "$C_{7-16}$ aralkyl" as used herein means a $C_6$ or $C_{10}$ aryl as defined above linked to an alkyl group and include, for example, benzyl, butylphenyl and 1-naphthylmethyl.

The term "amino aralkyl" as used herein means an amino group substituted with a $C_{7-16}$ aralkyl group, such as the following amino aralkyl

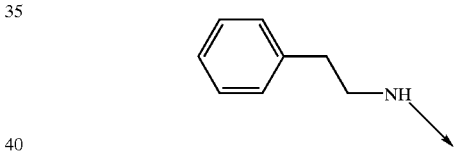

The term "($C_{1-6}$ alkyl)amide" as used herein means an amide mono-substituted with a $C_{1-6}$ alkyl, such as

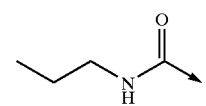

The term "carboxy($C_{1-6}$ alkyl)" as used herein means a carboxyl group (COOH) linked through a $C_{1-6}$ alkyl group as defined above and includes, for example, butyric acid.

The term "heterocycle", as used herein means a monovalent radical derived by removal of a hydrogen from a five-, six-, or seven-membered saturated or unsaturated (including aromatic) heterocycle containing from one to four heteroatoms selected from nitrogen, oxygen and sulfur. Furthermore, the term heterocycle includes heterocycles, as defined above, that are fused to one or more other ring structure. Examples of suitable heterocycles include, but are not limited to, pyrrolidine, tetrahydrofuran, thiazolidine, pyrrole, thiophene, diazepine, 1H-imidazole, isoxazole, thiazole, tetrazole, piperidine, 1,4-dioxane, 4-morpholine, pyridine, pyrimidine, thiazolo[4,5-b]-pyridine, quinoline, or indole, or the following heterocycles:

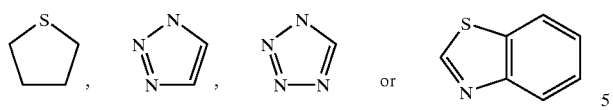

The term "C$_{1-6}$ alkyl-heterocycle" as used herein, means a heterocyclic radical as defined above linked through a chain or branched alkyl group, wherein alkyl as defined above containing from 1 to 6 carbon atoms. Examples of C$_{1-6}$ alkyl-Het include:

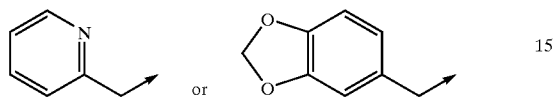

Where used in naming compounds of the present invention, the designations "P1', P1, P2, P3 and P4", as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend towards the C-terminus. For example, P1' refers to the first position away from the right hand end of the C-terminus of the cleavage site (ie. N-terminus first position); whereas P1 starts the numbering from the left hand side of the C-terminus cleavage site, P2: second position from the C-terminus, etc.) (see Berger A. & Schechter I., Transactions of the Royal Society London series (1970), B257, 249–264].

Thus in the compounds of formula I, the "P1' to P4" portions of the molecule are indicated below:

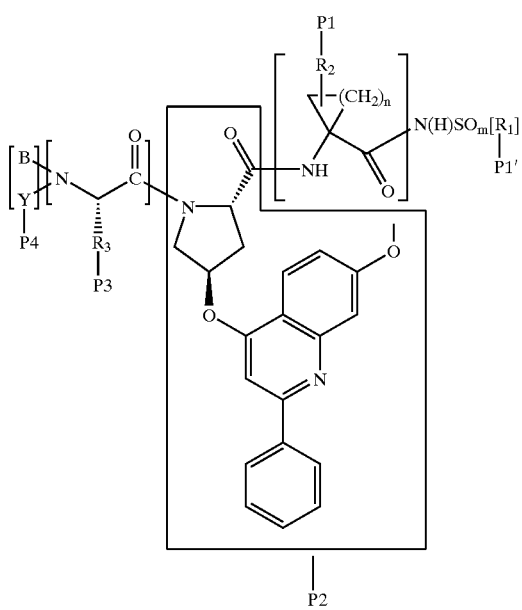

As used herein the term "1-aminocyclopropylcarboxylic acid" (Acca) refers to a compound of formula:

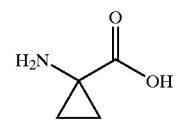

As used herein the term "tert-butylglycine" refers to a compound of the formula:

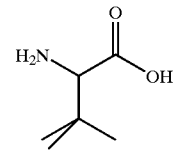

The term "residue" with reference to an amino acid or amino acid derivative means a radical derived from the corresponding α-amino acid by eliminating the hydroxyl of the carboxy group and one hydrogen of the α-amino acid group. For instance, the terms Gln, Ala, Gly, Ile, Arg, Asp, Phe, Ser, Leu, Cys, Asn, Sar and Tyr represent the "residues" of L-glutamine, L-alanine, glycine, L-isoleucine, L-arginine, L-aspartic acid, L-phenylalanine, L-serine, L-leucine, L-cysteine, L-asparagine, sarcosine and L-tyrosine, respectively.

The term "side chain" with reference to an amino acid or amino acid residue means a group attached to the α-carbon atom of the α-amino acid. For example, the R-group side chain for glycine is hydrogen, for alanine it is methyl, for valine it is isopropyl. For the specific R-groups or side chains of the α-amino acids reference is made to A. L. Lehninger's text on Biochemistry (see chapter 4).

For compounds of the present invention, it is preferred that m is 2. It is also preferred that n is 1. It is additionally preferred that R$_2$ is ethyl or ethenyl. It is further preferred that R$_1$ is cyclopropyl, cyclobutyl or an optionally substituted phenyl.

Additionally, it is preferred that R$_1$ is cyclopentyl.

In a preferred embodiment, compounds of the present invention have the structure of Formula II Formula II

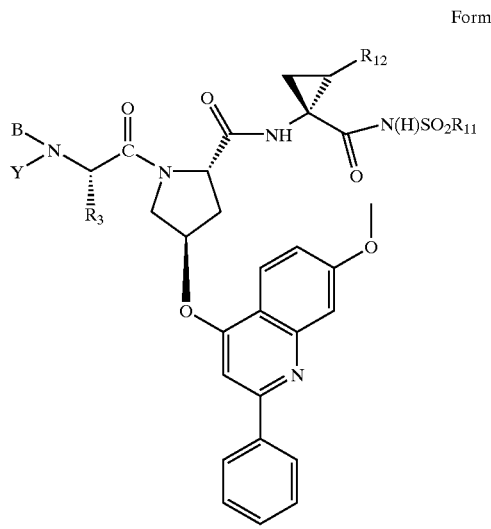

wherein $R_3$, B and Y are as defined in Formula I while $R_{11}$ is $C_{1-8}$ alkyl, $C_{3-7}$ cycloalkyl, or $C_{4-10}$(alkylcycloalkyl), naphthyl, or phenyl wherein said phenyl is optionally substituted from one to three times with halo, cyano, nitro, $C_{1-6}$ alkyl, $C_{1-6}$ alkoxy, amido, or phenyl. Further, $R_{12}$ is $C_{1-6}$ alkyl, $C_{2-6}$ alkenyl or H. The present invention further comprises salts, solvates, prodrugs of compounds of Formula II, as well as pharmaceutical compositions comprising compounds of Formula II, or salts, solvates or prodrugs thereof.

In another preferred embodiment, compounds of the present invention have the structure of Formula III Formula III

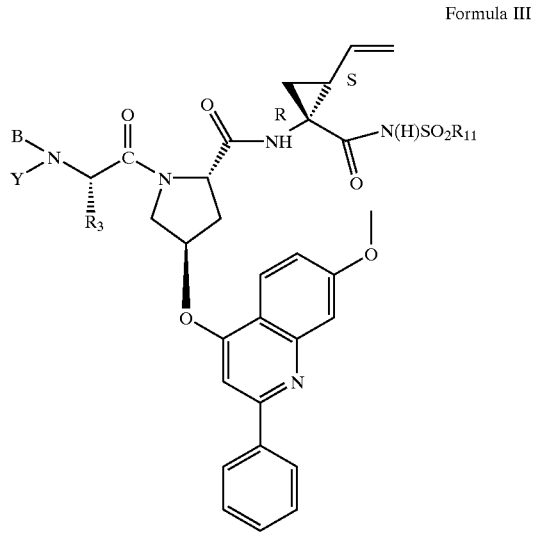

wherein $R_3$, B and Y are as defined in Formula I and $R_{11}$ is as defined in Formula II. Preferably, in compounds of Formula III, $R_{11}$ is selected from cyclopropyl, cyclobutyl or optionally substituted phenyl. The present invention further comprises salts, solvates, prodrugs of compounds of Formula III, as well as pharmaceutical compositions comprising compounds of Formula III, or salts, solvates or prodrugs thereof.

In another preferred embodiment, compounds of the present invention have the structure of Formula IV Formula IV

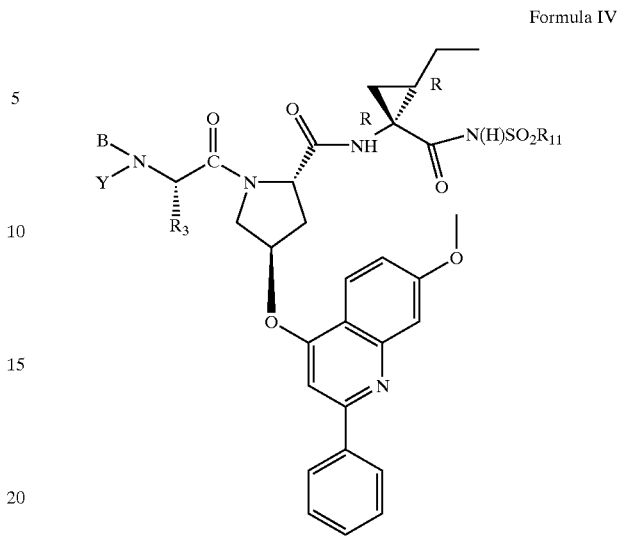

wherein $R_3$, B and Y are as defined in Formula I and $R_{11}$ is as defined in Formula II. Preferably, in compounds of Formula IV, $R_{11}$ is selected from cyclopropyl, cyclobutyl or optionally substituted phenyl. The present invention further comprises salts, solvates, prodrugs of compounds of Formula IV, as well as pharmaceutical compositions comprising compounds of Formula IV, or salts, solvates or prodrugs thereof.

Another preferred embodiment are the compounds of Formula V

Formula V

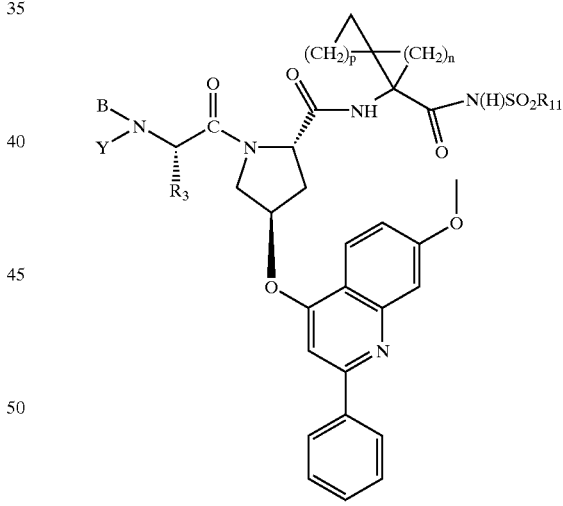

wherein $R_3$, n, B and Y are as defined in Formula I, $R_{11}$ is as defined in Formula II, and p is 1–5.

Preferably, in compounds of Formula V, $R_{11}$ is selected from cyclopropyl, cyclobutyl or optionally substituted phenyl. The compounds of the present invention include diastereomers of the spiral functionality of the compounds of Formula V wherein the diastereomers are either in a mixture or are a single diastereomer has been individually prepared or has been isolated from a diastereomeric mixture.

The present invention further comprises salts, solvates, prodrugs of compounds of Formula V, as well as pharmaceutical compositions comprising compounds of Formula V, or salts, solvates or prodrugs thereof.

In yet another alternate preferred embodiment, compounds of the present invention have the following structural formula Formula VI

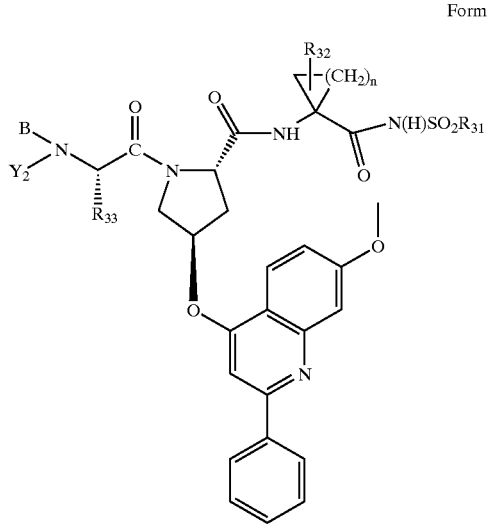

wherein:

(a) $R_{31}$ is $C_{1-8}$ alkyl, $C_{3-7}$ cycloalkyl, or $C_{4-10}$ (alkylcycloalkyl), all optionally substituted with hydroxy, halo, $C_{1-6}$ alkoxy, $C_{1-6}$ thioalkyl, amido, amino, ($C_{1-6}$ alkyl) amido, C6 or $C_{10}$ aryl, $C_{7-16}$ aralkyl, Het, or ($C_{1-6}$ alkyl)-Het, said aryl, arylalkyl or Het being optionally substituted with halo, alkyl or lower alkyl Het;

(b) n is 1 or 2;

(c) $R_{32}$ is H, $C_{1-6}$ alkyl, $C_{1-3}$ alkoxy, $C_{3-7}$ cycloalkyl, $C_{2-6}$ alkenyl, or $C_{2-6}$ alkynyl, all optionally substituted with halogen;

(d) $R_{33}$ is $C_{1-8}$ alkyl, $C_{3-12}$ alkenyl, $C_3$–$C_7$ cycloalkyl, $C_{4-13}$ cycloalkenyl, or $C_4$–$C_{10}$(alkylcycloalkyl), all optionally substituted with hydroxy, $C_1$–$C_6$ alkoxy, $C_1$–$C_6$ thioalkyl, amino, amido, (loweralkyl) amido, $C_6$ or $C_{10}$ aryl, or $C_7$–$C_{16}$ aralkyl;

(e) $Y_2$ is H or $C_1$–$C_6$ alkyl;

(f) $B_2$ is H, $R_{14}$—(C=O)—; $R_{14}$O(C=O)—, $R_{14}$—N($R_{15}$)—C(=O)—; $R_{14}$—N($R_{15}$)—C(=S)—; $R_{14}SO_2$—, or $R_{14}$—N($R_{15}$)—$SO_2$—;

(g) $R_{14}$ is (i) $C_{1-10}$ alkyl optionally substituted with carboxyl, $C_{1-6}$ alkanoyl, hydroxy, $C_{1-6}$ alkoxy, amino optionally mono-or-di substituted with $C_{1-6}$ alkyl, amido, or (lower alkyl) amido; (ii) $C_{3-7}$ cycloalkyl, $C_{3-7}$ cycloalkoxy, or $C_{4-10}$ alkylcycloalklyl, all optionally substituted with hydroxy, carboxyl, ($C_{1-6}$ alkoxy)carbonyl, amino optionally monosubstituted or disubstituted with $C_{1-6}$ alkyl, amido, or (lower alkyl) amido; (iii) amino optionally monosubstituted or disubstituted with $C_{1-6}$ alkyl; amido; or (lower alkyl)amido; (iv) $C_6$ or $C_{10}$ aryl or $C_{7-16}$ aralkyl, all optionally substituted with $C_{1-6}$ alkyl, hydroxy, amido, (lower alkyl) amido, or amino optionally monosubstituted or disubstituted with $C_{1-6}$ alkyl; or (v) Het or (lower alkyl)-Het, both optionally substituted with $C_{1-6}$ alkyl, hydroxy, amido, (lower alkyl) amido, or amino optionally monosubstituted or disubstituted with $C_{1-6}$ alkyl; and (h) $R_{15}$ is H or $C_{1-6}$ alkyl.

The present invention further comprises salts, solvates, prodrugs of compounds of Formula VI, as well as pharmaceutical compositions comprising compounds of Formula VI, or salts, solvates or prodrugs thereof.

Compounds of the present invention, by virtue of their basic moiety, can form salts by the addition of a pharmaceutically acceptable acid. The acid addition salts are formed from a compound of Formula I and a pharmaceutically acceptable inorganic acid, including but not limited to hydrochloric, hydrobromic, hydroiodic, sulfuric, phosphoric, or organic acid such as p-toluenesulfonic, methanesulfonic, acetic, benzoic, citric, malonic, fumaric, maleic, oxalic, succinic, sulfamic, or tartaric. Thus, examples of such pharmaceutically acceptable salts include chloride, bromide, iodide, sulfate, phosphate, methanesulfonate, citrate, acetate, malonate, fumarate, sulfamate, and tartrate.

Salts of an amine group may also comprise quaternary ammonium salts in which the amino nitrogen carries a suitable organic group such as an alkyl, alkenyl, alkynyl or aralkyl moiety.

Compounds of the present invention, which are substituted with a basic group, may exist as salts formed through base addition. Such base addition salts include those derived from inorganic bases which include, for example, alkali metal salts (e.g. sodium and potassium), alkaline earth metal salts (e.g. calcium and magnesium), aluminum salts and ammonium salts. In addition, suitable base addition salts include salts of physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-β-phenethylamine, dehydroabietylamine, N,N'-bishydroabietylamine, glucamine, N-methylglucamine, collidine, quinine, quinoline, ethylenediamine, ornithine, choline, N,N'-benzylphenethylamine, chloroprocaine, diethanolamine, diethylamine, piperazine, tris(hydroxymethyl) aminomethane and tetramethylammonium hydroxide and basic amino acids such as lysine, arginine and N-methylglutamine. These salts may be prepared by methods known to those skilled in the art.

Certain compounds of the present invention, and their salts, may also exist in the form of solvates with water, for example hydrates, or with organic solvents such as methanol, ethanol or acetonitrile to form, respectively, a methanolate, ethanolate or acetonitrilate. The present invention includes each solvate and mixtures thereof.

This invention also encompasses pharmaceutically acceptable prodrugs of the compounds of the present invention. Prodrugs are derivatives of the compounds of the invention which have chemically or metabolically cleavable groups and become, by solvolysis or under physiological conditions, the compounds of the invention which are pharmaceutically active in vivo. A prodrug of a compound of Formulas I–VI may be formed in a conventional manner with a functional group of the compounds such as with an amino, hydroxy or carboxy group. The prodrug derivative form often offers advantages of solubility, tissue compatibility, or delayed release in a mammalian organism (see, Bundgard, H., Design of Prodrugs, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from, when present, acidic groups pendent on the compounds of this invention are preferred prodrugs. In some cases it is desirable to prepare double ester type prodrugs such as (acyloxy) alkyl esters or (alkoxycarbonyl)oxy)alkyl esters.

In addition, compounds of the present invention, or a salt, solvate or prodrug thereof, may exhibit polymorphism. The present invention also encompasses any such polymorphic form.

Compounds of the present invention (Formulas I–IV and VI) also contain two or more chiral centers. For example, compounds of Formulas I–IV and VI may include P1 cyclopropyl element of formula

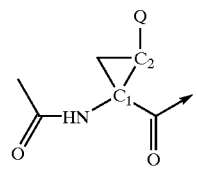

wherein $C_1$ and $C_2$ each represent an asymmetric carbon atom at positions 1 and 2 of the cyclopropyl ring. Not withstanding other possible asymmetric centers at other segments of the compounds of Formulas I–IV and VI, the presence of these two asymmetric centers means that the compounds of Formulas I–IV and VI can exist as racemic mixtures of diastereomers, such as the diastereomers of compounds of Formulas I–IV and VI wherein Q is configured either syn to the amide or syn to the carbonyl as shown below.

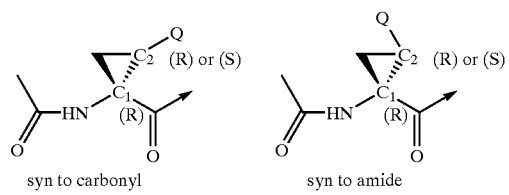

syn to carbonyl     syn to amide

The present invention includes both enantiomers and mixtures of enantiomers such as racemic mixtures.

As illustrated in the examples hereinafter, the racemic mixtures can be prepared and thereafter separated into individual optical isomers, or these optical isomers can be prepared by chiral synthesis.

The enantiomers may be resolved by methods known to those skilled in the art, for example, by formation of diastereoisomeric salts which may be separated by crystallization, gas-liquid or liquid chromatography, selective reaction of one enantiomer with an enantiomer-specific reagent. It will be appreciated that where the desired enantiomer is converted into another chemical entity by a separation technique, then an additional step is required to form the desired enantiomeric form. Alternatively, specific enantiomers may be synthesized by asymmetric synthesis using optically active reagents, substrates, catalysts or solvents, or by converting one enantiomer into the other by asymmetric transformation.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

Certain compounds of the present invention may exist in zwitterionic form and the present invention includes each zwitterionic form of these compounds and mixtures thereof.

The compounds of the present invention are useful in the inhibition of HCV NS3 protease, as well as, the prevention or treatment of infection by the hepatitis C virus and the treatment of consequent pathological conditions. The treatment involves administering to a patient, in need of such treatment, a compound of the present invention, or a pharmaceutically acceptable salt, solvate or prodrug thereof, or a pharmaceutical composition comprising a pharmaceutical carrier and a therapeutically effective amount of a compound of the present invention, or a pharmaceutically acceptable salt, solvate or prodrug therefor.

It will be appreciated by those skilled in the art that reference herein to treatment extends to prophylaxis as well as the treatment of established infections or symptoms. This includes initiating treatment pre- and post-exposure to the virus. In addition, the present invention can be administered in conjunction with immunomodulators, such as α-, β-, or γ-interferons; other antiviral agents such as ribavirin, amantadine; other inhibitors of HCV NS3 protease; inhibitors of other targets in the HCV life cycle, which include but not limited to, helicase, polymerase, metalloprotease, or internal ribosome entry site (IRES); or combinations thereof. The additional agents may be combined with the compounds of this invention to create a single dosage form. Alternatively these additional agents may be separately administered to a mammal as part of a multiple dosage form.

These methods are useful in decreasing HCV NS3 protease activity in a mammal. These methods are useful for inhibiting viral replication in a mammal. If the pharmaceutical composition comprises only a compound of this invention as the active component, such methods may additionally comprise the step of administering to said mammal an agent selected from an immunomodulatory agent, an antiviral agent, a HCV protease inhibitor, or an inhibitor of other targets in the HCV life cycle such as helicase, polymerase, or metalloprotease or IRES. Such additional agent may be administered to the mammal prior to, concurrently with, or following the administration of the compositions of this invention.

The compounds of the present invention are also useful in the preparation and execution of screening or replication assays for antiviral compounds. Further, the compounds of the present invention are useful in establishing or determining the binding site of other antiviral compounds to HCV NS3 protease, for example, by competitive inhibition.

The compounds of the present invention may be administered orally, parenterally (including subcutaneous injections, intravenous, intramuscular, intrasternal injection or infusion techniques), by inhalation spray or rectally, in dosage unit formulations containing conventional non-toxic pharmaceutically acceptable carriers, adjuvants and vehicles.

This invention also provides a pharmaceutical composition for use in the above-described therapeutic method. A pharmaceutical composition of the present invention comprises an effective amount of a compound of Formulas I–VI in association with a pharmaceutically acceptable carrier, excipient or diluent.

The active ingredient in such formulations comprises from 0.1 percent to 99.9 percent by weight of the formulation. By "pharmaceutically acceptable" it is meant that the carrier, diluent or excipient must be compatible with the other ingredients of the formulation and not deleterious to the recipient thereof.

The present pharmaceutical compositions are prepared by known procedures using well-known and readily available ingredients. The compositions of this invention may be formulated so as to provide quick, sustained or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, beadlets, lozenges, sachets, elixirs, suspensions, emulsions, solutions, syrups, aerosols, (as a solid or in a liquid medium), soft and hard gelatin capsules, suppositories, sterile injectable solutions, sterile packaged powders and the like.

The compounds can be administered by a variety of routes including oral, intranasally, rectal, transdermal, subcutaneous, intravenous, intramuscular and intranasal.

When administered orally, these compositions are prepared according to techniques well-known in the art of pharmaceutical formulation. For oral administration, the compound is typically formulated with excipients such as binders, fillers, lubricants, extenders, diluents, disintegration agents and the like as are known in the art.

For parenteral administration, the compound is formulated in pharmaceutically acceptable non-toxic, parenterally-acceptable diluents or solvents, such as mannitol, 1,3-butanediol, water, 5 percent dextrose, Ringer's solution or isotonic sodium chloride solution, or suitable dispersing or wetting and suspending agents, such as sterile, bland, fixed oils, including synthetic mono- or diglycerides, and fatty acids, including oleic acid.

A compound of the present invention, or a salt or solvate thereof, can be formulated in unit dosage formulations comprising a dose between about 0.1 mg and about 1000 mg, or more, according to the particular treatment involved. An example of a unit dosage formulation comprises 5 mg of a compound of the present invention in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds of the present invention can also be administered to humans in a dosage range of 1 to 100 mg/kg body weight in divided doses. One preferred dosage range is 1 to 20 mg/kg body weight orally in divided doses. It will be understood, however, that the specific dose level and frequency of dosage for any particular patient may be varied and will depend upon a variety of factors including the activity of the specific compound employed, the metabolic stability and length of action of that compound, the route of administration, the age, body weight, general health, sex, diet, mode and time of administration, rate of excretion, drug combination, the severity of the particular condition, and the host undergoing therapy.

A general method useful for the syntheses of compounds embodied in this invention is shown below. The preparations shown below are disclosed for the purpose of illustration and are not meant to be interpreted as limiting the processes to make the compounds by any other methods.

It will be appreciated by those skilled in the art that a number of methods are available for the preparation of the compounds of the present invention. These compounds may be prepared by processes which include processes known in the chemical art for the production of structurally analogous compounds or by a novel process described herein. A process for the preparation of these compounds (or a pharmaceutically acceptable salt thereof) and novel intermediates for the manufacture of these compounds provide further features of the invention and are illustrated by the following procedures in which the meanings of the generic radicals are as defined above, unless otherwise specified. It will be recognized that it may be preferred or necessary to prepare such a compound in which a functional group is protected using a conventional protecting group then to remove the protecting group to provide a compound of the present invention.

The compounds of the present invention may be synthesized according to a general process as illustrated in Scheme I (wherein CPG is a carboxyl protecting group and APG is an amino protecting group):

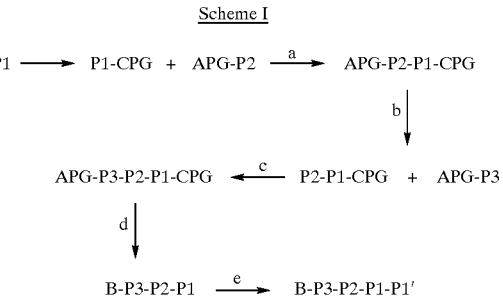

Briefly, the P1, P2, and P3 can be linked by well known peptide coupling techniques. The P1, P2, and P3 groups may be linked together in any order as long as the final compound corresponds to peptides of Formulas I–VI. For example, P3 can be linked to P2–P1; or P1 linked to P3–P2.

Generally, peptides are elongated by deprotecting the α-amino group of the N-terminal residue and coupling the unprotected carboxyl group of the next suitably N-protected amino acid through a peptide linkage using the methods described. This deprotection and coupling procedure is repeated until the desired sequence is obtained. This coupling can be performed with the constituent amino acids in stepwise fashion, as depicted in Scheme I. Coupling between two amino acids, an amino acid and a peptide, or two peptide fragments can be carried out using standard coupling procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxysuccinic imido ester) method, Woodward reagent K-method, carbonyldiimidazole method, phosphorus reagents or oxidation-reduction methods. Some of these methods (especially the carbodiimide method) can be enhanced by adding 1-hydroxybenzotriazole or 4-DMAP. These coupling reactions can be performed in either solution (liquid phase) or solid phase.

More explicitly, the coupling step involves the dehydrative coupling of a free carboxyl of one reactant with the free amino group of the other reactant in the present of a coupling agent to form a linking amide bond. Descriptions of such coupling agents are found in general textbooks on peptide chemistry, for example, M. Bodanszky, "Peptide Chemistry", $2^{nd}$ rev ed., Springer-Verlag, Berlin, Germany, (1993). Examples of suitable coupling agents are N,N'-dicyclohexylcarbodiimide, 1-hydroxybenzotriazole in the presence of N,N'-dicyclohexylcarbodiimide or N-ethyl-N'-[(3-dimethylamino)propyl]carbodiimide. A practical and useful coupling agent is the commercially available (benzotriazol-1-yloxy)tris-(dimethylamino)phosphonium hexafluorophosphate, either by itself or in the present of 1-hydroxybenzotriazole or 4-DMAP. Another practical and useful coupling agent is commercially available 2-(1H-benzotriazol-1-yl)-N,N,N',N'-tetramethyluronium tetrafluoroborate. Still another practical and useful coupling agent is commercially available O-(7-azabenzotrizol-1-yl)-N,N,N',N'-tetramethyluronium hexafluorophosphate.

The coupling reaction is conducted in an inert solvent, e.g. dichloromethane, acetonitrile or dimethylformamide. An excess of a tertiary amine, e.g. diisopropylethylamine, N-methylmorpholine, N-methylpyrrolidine or 4-DMAP is added to maintain the reaction mixture at a pH of about 8. The reaction temperature usually ranges between 0° C. and 50° C. and the reaction time usually ranges between 15 min and 24 h.

The functional groups of the constituent amino acids generally must be protected during the coupling reactions to avoid formation of undesired bonds. The protecting groups that can be used are listed in Greene, "Protective Groups in Organic Chemistry", John Wiley & Sons, New York (1981) and "The Peptides: Analysis, Synthesis, Biology", Vol. 3, Academic Press, New York (1981), the disclosures of which are hereby incorporated by reference.

The α-amino group of each amino acid to be coupled to the growing peptide chain must be protected (APG). Any protecting group known in the art can be used. Examples of such groups include: 1) acyl groups such as formyl, trifluoroacetyl, phthalyl, and p-toluenesulfonyl; 2) aromatic carbamate groups such as benzyloxycarbonyl (Cbz or Z) and substituted bensyloxycarbonyls, and 9-fluorenylmethyloxycarbonyl (Fmoc); 3) aliphatic carbamate groups such as tert-butyloxycarbonyl (Boc), ethoxycarbonyl, diisopropylmethoxycarbonyl, and allyloxycarbonyl; 4) cyclic alkyl carbamate groups such as cyclopentyloxycarbonyl and adamantyloxycarbonyl; 5) alkyl groups such as triphenylmethyl and benzyl; 6)trialkylsilyl such as trimethylsilyl; and 7) thiol containing groups such as phenylthiocarbonyl and dithiasuccinoyl.

The preferred α-amino protecting group is either Boc or Fmoc. Many amino acid derivatives suitably protected for peptide synthesis are commercially available.

The α-amino protecting group of the newly added amino acid residue is cleaved prior to the coupling of the next amino acid. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethylformamide. When the Fmoc group is used, the reagents of choice are piperidine or substituted piperidine in dimethylformamide, but any secondary amine can be used. The deprotection is carried out at a temperature between 0° C. and room temperature (rt or RT) usually 20–22° C.

Any of the amino acids having side chain functionalities must be protected during the preparation of the peptide using any of the above-described groups. Those skilled in the art will appreciate that the selection and use of appropriate protecting groups for these side chain functionalities depend upon the amino acid and presence of other protecting groups in the peptide. The selection of such protecting groups is important in that the group must not be removed during the deprotection and coupling of the α-amino group.

For example, when Boc is used as the α-amino protecting group, the following side chain protecting group are suitable: p-toluenesulfonyl (tosyl) moieties can be used to protect the amino side chain of amino acids such as Lys and Arg; acetamidomethyl, benzyl (Bn), or tert-butylsulfonyl moieties can be used to protect the sulfide containing side chain of cysteine; bencyl (Bn) ethers can be used to protect the hydroxy containing side chains of serine, threonine or hydroxyproline; and benzyl esters can be used to protect the carboxy containing side chains of aspartic acid and glutamic acid.

When Fmoc is chosen for the α-amine protection, usually tert-butyl based protecting groups are acceptable. For instance, Boc can be used for lysine and arginine, tert-butyl ether for serine, threonine and hydroxyproline, and tert-butyl ester for aspartic acid and glutamic acid. Triphenylmethyl (Trityl) moiety can be used to protect the sulfide containing side chain of cysteine.

Once the elongation of the peptide is completed all of the protecting groups are removed. When a liquid phase synthesis is used, the protecting groups are removed in whatever manner is dictated by the choice of protecting groups. These procedures are well known to those skilled in the art.

Further, the following guidance may be followed in the preparation of compounds of the present invention. For example, to form a compound where $R_4$—C(O)—, $R_4$—S(O)$_2$, a protected P3 or the whole peptide or a peptide segment is coupled to an appropriate acyl chloride or sulfonyl chloride respectively, that is either commercially available or for which the synthesis is well known in the art.

In preparing a compound where $R_4$O—C(O)—, a protected P3 or the whole peptide or a peptide segment is coupled to an appropriate chloroformate that is either commercially available or for which the synthesis is well known in the art. For Boc-derivatives (Boc)$_2$O is used.

For example:

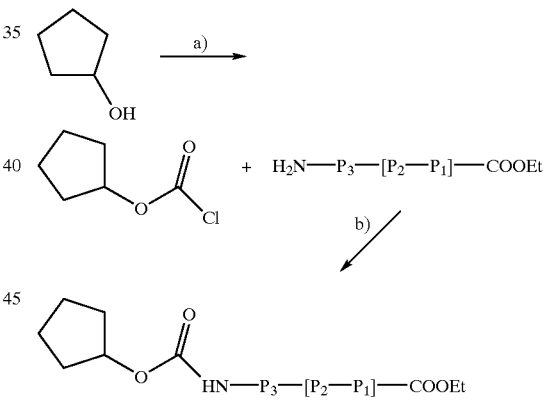

a) Cyclopentanol is treated with phosgene to furnish the corresponding chloroformate.

b) The chloroformate is treated with the desired NH$_2$-tripeptide in the presence of a base such as triethylamine to afford the cyclopentylcarbamate. In preparing a compound where $R_4$—N($R_5$)—C(O)—, or $R_4$—NH—C(S)—, a protected P3 or the whole peptide or a peptide segment is treated with phosgene followed by amine as described in SynLett. February 1995; (2); 142–144 or is reacted with the commercially available isocyanate and a suitable base such as triethylamine.

In preparing a compound where $R_4$—N($R_5$)—S (O$_2$), a protected P3 or the whole peptide or a peptide segment is treated with either a freshly prepared or commercially available sulfamyl chloride followed by amine as described in patent Ger. Offen. (1998), 84 pp. DE 19802350 or WO 98/32748.

The α-carboxyl group of the C-terminal residue is usually protected as an ester (CPG) that can be cleaved to give the carboxylic acid. Protecting groups that can be used include: 1) alkyl esters such as methyl, trimethylsilylethyl and t-butyl, 2) aralkyl esters such as benzyl and substituted benzyl, or 3) esters that can be cleaved by mild base treatment or mild reductive means such as trichloroethyl and phenacyl esters.

The resulting α-carboxylic acid (resulting from cleavage by mild acid, mild base treatment or mild reductive means) is coupled with a $R_0SO_2NH_2$ [prepared quantitatively by treatment of $R_0SO_2Cl$ in ammonia saturated tetrahydrofuran solution] in the presence of peptide coupling agent such as CDI or EDAC in the presence of a base such as 4-dimethylaminopyridine (4-DMAP) and/or 1,8-diazabicyclo[5.4.0]undec-7-ene (DBU) to incorporate the P1' moiety, effectively assembling the tripeptide P1'-P1-P2-P3-APG.

Furthermore, if the P3 protecting group APG is removed and replaced with a B moiety by the methods described above, and the resulting α-carboxylic acid resulting from cleavage (resulting from cleavage by mild acid, mild base treatment or mild reductive means) is coupled with a $R_0SO_2NH_2$ [prepared by treatment of $R_0SO_2Cl$ in ammonia saturated tetrahydrofuran solution] in the presence of peptide coupling agent such as CDI or EDAC in the presence of a base such as 4-dimethylaminopyridine (4-DMAP) and/or 1,8-diazabicyclo[5.4.0]undec-7-ene (DBU) to incorporate the P1' moiety, the tripeptide P1'-P1-P2-P3-B is prepared.

Compounds of the present invention can be prepared by many methods including those described in the examples, below, and as described in U.S. Provisional Application No. 60/249,968, titled "Hepatitis C Tripeptide Inhibitors", by Campbell and Good, filed on Nov. 20, 2000. The teachings of U.S. Provisional Application No. 60/249,968 are incorporated herein, in their entirety, by reference.

Exemplification

The specific examples that follow illustrate the syntheses of the compounds of the instant invention, and are not to be construed as limiting the invention in sphere or scope. The methods may be adapted to variations in order to produce compounds embraced by this invention but not specifically disclosed. Further, variations of the methods to produce the same compounds in somewhat different manner will also be evident to one skilled in the art.

Solution percentages express a weight to volume relationship, and solution ratios express a volume to volume relationship, unless stated otherwise. Nuclear magnetic resonance (NMR) spectra were recorded either on a Bruker 300, 400 or 500 MHz spectrometer; the chemical shifts (δ) are reported in parts per million. Flash chromatography was carried out on silica gel ($SiO_2$) according to Still's flash chromatography technique (W. C. Still et al., J. Org. Chem., (1978), 43, 2923).

All Liquid Chromatography (LC) data were recorded on a Shimadzu LC-10AS liquid chromatograph using a SPD-10AV UV-Vis detector and Mass Spectrometry (MS) data were determined with a Micromass Platform for LC in electrospray mode (ES+).

Unless otherwise noted, each compound was analyzed, by LC/MS, using one of seven methodologies, having the following conditions.

Columns: (Method A)—YMC ODS S7 C18 3.0×50 mm
(Method B)—YMC ODS-A S7 C18 3.0×50 mm
(Method C)—YMC S7 C18 3.0×50 mm
(Method D)—YMC Xterra ODS S7 3.0×50 mm
(Method E)—YMC Xterra ODS S7 3.0×50 mm
(Method F)—YMC ODS-A S7 C18 3.0×50 mm
(Method G)—YMC C18 S5 4.6×50 mm]
Gradient: 100% Solvent A/0% Solvent B to 0% Solvent A/100% Solvent B
Gradient time: 2 min. (A, B, D, F, G); 8 min. (C, E)
Hold time: 1 min. (A, B, D, F, G); 2 min. (C, E)
Flow rate: 5 mL/min
Detector Wavelength: 220 nm
Solvent A: 10% MeOH/90% $H_2O$/0.1% TFA
Solvent B: 10% $H_2O$/90% MeOH/0.1% TFA.

The compounds and chemical intermediates of the present invention, described in the following examples, were prepared according to the following methods.

EXAMPLE 1

Boc-(4R)-(2-phenyl-7-methoxyquinoline-4-oxo)-S-proline, shown below, was prepared as described in Steps 1a–c.

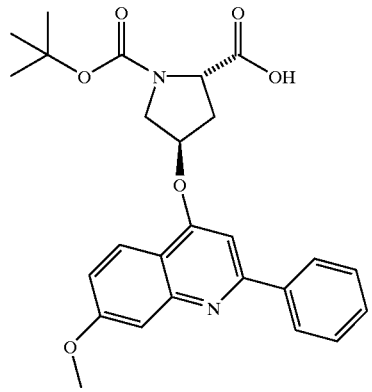

Step 1a: Preparation of 4-hydroxy-2-phenyl-7-methoxyquinoline, shown below.

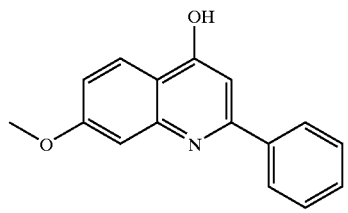

To a solution of m-anisidine (300 g, 2.44 mole) and ethyl benzoylacetate (234.2 g, 1.22 mole) in toluene (2.0 L) was added HCl (4.0 N in dioxane, 12.2 mL, 48.8 mmole). The resulting solution was refluxed for 6.5 hr using a Dean-Stark apparatus (about 56 ml of aqueous solution was collected). The mixture was cooled to rt, partitioned multiple times with aqueous HCl (10%, 3×500 mL), aqueous NaOH (1.0 N, 2×200 mL), water (3×200 mL), and the organic layer dried ($MgSO_4$) and concentrated in vacuo to supply an oily residue (329.5 g). The crude product was heated in an oil bath (280° C.) for 80 min using a Dean-Stark apparatus (about 85 mL liquid was collected). The reaction mixture was cooled down to rt, the solid residue triturated with $CH_2Cl_2$ (400 mL), the resulting suspension filtered, and the filter cake washed with more $CH_2Cl_2$ (2×150 mL). The resulting solid was dried in vacuo (50° C.; 1 torr; 1 day) affording analytically pure 4-hydroxy-7-methoxy-2- phenylquinoline as a light brown solid (60.7 g, 20% overall). $^1$H NMR δ (DMSO): 3.86 (s, 3H), 6.26 (s, 1H), 6.94 (dd, J=9.0, 2.4 Hz, 1H), 7.21 (d, J=2.4 Hz, 1H), 7.55–7.62 (m, 3H), 7.80–7.84 (m, 2H), 8.00 (d, J=9.0 Hz, 1H), 11.54 (s, 1H); $^{13}$C NMR (DMSO-$d_6$) δ: 55.38, 99.69, 107.07, 113.18, 119.22, 126.52, 127.17, 128.97, 130.34, 134.17, 142.27, 149.53, 161.92, 176.48. LC-MS (retention time: 1.26, method D), MS m/z 252 (M$^+$+1).

Step 1b: Preparation of 4-chloro-7-methoxy-2-phenylquinoline, shown below.

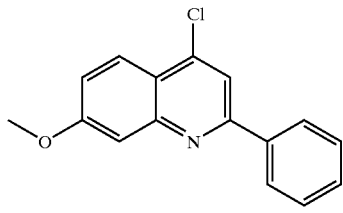

The product of Step 1a (21.7 g, 86.4 mmole) was suspended in POCl$_3$ (240 mL). The suspension was refluxed for 2 hours. After removal of the POCl$_3$ in vacuo, the residue was partitioned between EtOAc (1 L), and cold aqueous NaOH (generated from 1.0N 200 mL NaOH and 20 mL 10.0 N NaOH) and stirred for 15 min. The organic layer was washed with water (2×200 mL), brine (200 mL), dried (MgSO$_4$), and concentrated in vacuo to supply 4-chloro-2-phenyl-7-methoxyquinoline (21.0 g, 90%) as a light brown solid. $^1$H NMR (DMSO-$d_6$) δ: 3.97 (s, 3H), 7.36 (dd, J=9.2, 2.6 Hz, 1H), 7.49–7.59 (m, 4H), 8.08 (d, J=9.2 Hz, 1H), 8.19 (s, 1H), 8.26–8.30 (m, 2H); $^{13}$C NMR (DMSO-$d_6$) δ: 55.72, 108.00, 116.51, 119.52, 120.48, 124.74, 127.26, 128.81, 130.00, 137.58, 141.98, 150.20, 156.65, 161.30. LC-MS (retention time: 1.547, Method D), MS m/z 270 (M$^+$+1).

Step 1c: Preparation of Boc-(4R)-(2-phenyl-7-methoxy-quinoline-4-oxo)-S-proline, shown below.

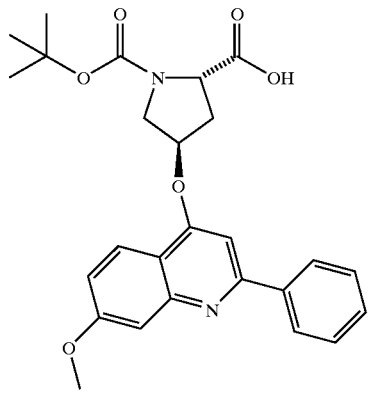

To a suspension of Boc-4R-hydroxyproline (16.44 g, 71.1 mmol) in DMSO (250 mL) was added t-BuOK (19.93 g, 177.6 mmol) at 0° C. The generated mixture was stirred for 1.5 hour and then the product of Step 1b (21.02 g, 77.9 mmol) was added in three portions over 1 h. The reaction was stirred for one day, the reaction mixture was poured into cold water (1.5 L) and washed with Et$_2$O (4×200 mL). The aqueous solution was acidified to pH 4.6, filtered to obtain a white solid, and dried in vacuo to supply the product, Boc (4R)-(2-phenyl-7-methoxyquinoline-4-oxo)proline (32.5 g, 98%). $^1$H NMR (DMSO) δ 1.32, 1.35 (two s (rotamers) 9H), 2.30–2.42 (m, 1H), 2.62–2.73 (m, 1H), 3.76 (m, 2H), 3.91 (s, 3H), 4.33–4.40 (m, 1H), 5.55 (m, 1H), 7.15 (dd, J=9.2, 2.6 Hz, 1H), 7.37 (d, J=2.6 Hz, 1H), 7.42–7.56 (m, 4H), 7.94–7.99 (m, 1H), 8.25, 8.28 (2s, 2H), 12.53 (brs, 1H); LC-MS (retention time: 1.40, Method D), MS m/z 465 (M$^+$+1).

EXAMPLE 2

Preparation of 1-{[1-(2-tert-Butoxycarbonylamino-3-methylbutyryl)-4-(7-methoxy-2-phenylquinolin-4-yloxy)-pyrrolidine-2-carbonyl]amino}-2-ethylcyclopropanecarboxylic acid, shown below, was prepared as described below in Steps 2a–2h.

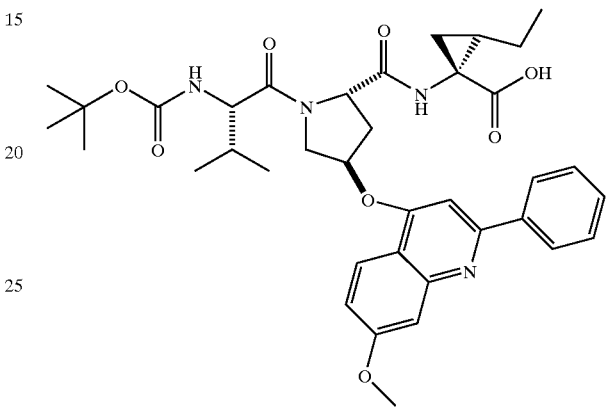

Step 2a: Preparation of 2-Ethylcyclopropane-1,1-dicarboxylic acid di-tert-butyl ester, shown below.

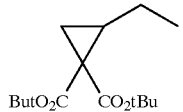

To a suspension of benzyltriethylammonium chloride (21.0 g, 92.2 mmol) in a 50% aqueous NaOH solution (92.4 g in 185 mL H$_2$O) was added 1,2-dibromobutane (30.0 g, 138.9 mmol) and di-tert-butylmalonate (20.0 g, 92.5 mmol). The reaction mixture was vigorously stirred 18 h at rt, a mixture of ice and water was then added. The crude product was extracted with CH$_2$Cl$_2$ (3×) and sequentially washed with water (3×), brine and the organic extracts combined. The organic layer was dried (MgSO$_4$), filtered and concentrated in vacuo. The resulting residue was flash chromatographed (100 g SiO$_2$, 3% Et$_2$O in hexane) to afford the titled product (18.3 g, 67.8 mmol, 73% yield) which was used directly in the next reaction.

Step 2b: Preparation of racemic 2-Ethylcyclopropane-1,1-dicarboxylic acid tert-butyl ester, shown below.

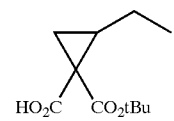

The product of Step 2a (18.3 g, 67.8 mmol) was added to a suspension of potassium tert-butoxide (33.55 g, 299.0 mmol) in dry ether (500 mL) at 0° C., followed by H$_2$O (1.35 mL, 75.0 mmol) and was vigorously stirred overnight at rt. The reaction mixture was poured in a mixture of ice and water and washed with ether (3×). The aqueous layer was acidified with a 10% aq. citric acid solution at 0° C. and extracted with EtOAc (3×). The combined organic layers were washed with water (2×), brine, dried (MgSO₄) and concentrated in vacuo to afford the titled product as a pale yellow oil (10 g, 46.8 mmol, 69% yield).

Step 2c: Preparation of (1R,2R)/(1S,2S) 2-Ethyl-1-(2-trimethylsilanylethoxycarbonylamino)cyclopropanecarboxylic acid tert-butyl ester, shown below.

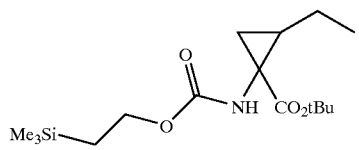

To a suspension, of the product of Step 2b (10 g, 46.8 mmol) and 3 g of freshly activated 4A molecular sieves in dry benzene (160 mL), was added Et₃N (7.50 mL, 53.8 mmol) and DPPA (11 mL, 10.21 mmol). The reaction mixture was refluxed for 3.5 h, 2-trimethylsilylethanol (13.5 mL, 94.2 mmol) was then added, and the reaction mixture was refluxed overnite. The reaction mixture was filtered, diluted with Et₂O, washed with a 10% aqueous citric acid solution, water, saturated aqueous NaHCO₃, water (2×), brine (2×), dried (MgSO₄) and concentrated in vacuo. The residue was suspended with 10 g of Aldrich polyisocyanate scavenger resin in 120 mL of CH₂Cl₂, stirred at rt overnite and filtered to afford the titled product (8 g, 24.3 mmol; 52%) as a pale yellow oil: ¹H NMR (CDCl₃) δ 0.03 (s, 9H), 0.97 (m, 5H), 1.20 (bm, 1H), 1.45 (s, 9H), 1.40–1.70 (m, 4H), 4.16 (m, 2H), 5.30 (bs, 1H).

Step 2d: Preparation of (1R,2R)/(1S,2S) 1-Amino-2-ethylcyclopropanecarboxylic acid tert-butyl ester, shown below.

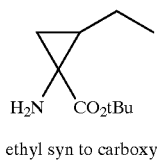

ethyl syn to carboxy

To the product of Step 2c (3 g, 9 mmol) was added a 1.0 M TBAF solution in THF (9.3 mL, 9.3 mmol) and the mixture heated to reflux for 1.5 h, cooled to rt and then diluted with 500 ml of EtOAc. The solution was successively washed with water (2×100 mL), brine (2×100 mL), dried (MgSO₄), concentrated in vacuo.

Step 2e: Preparation of (1R,2R) and (1S,2S) P1 isomers of 2-ethyl-1-{[4-(7-methoxy-2-phenylquinolin-4-yloxy)pyrrolidine-2-carbonyl]amino}cyclopropanecarboxylic acid methyl ester, shown below.

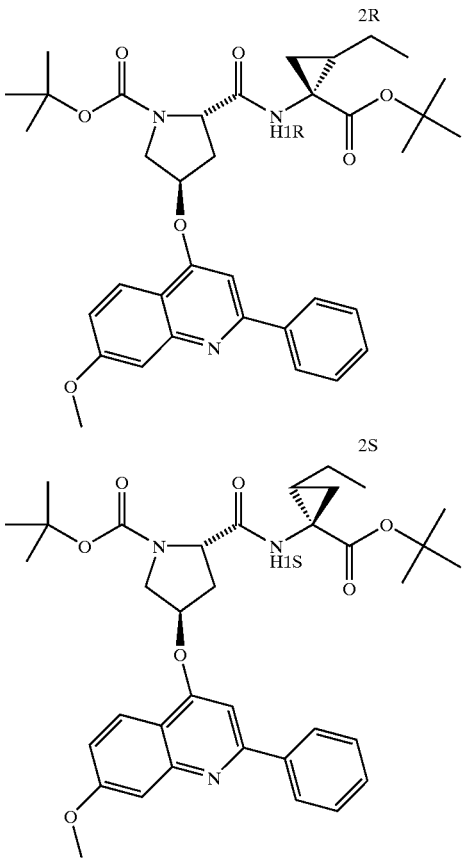

A solution of the crude product of Step 2d (assumed to be 9 mmol), in 10 mL of CH₂Cl₂, was added dropwise to a mixture of 3.5 g (7.53 mmol, 0.84 equivalents) of Boc (4R)-(2-phenyl-7-methoxyquinoline-4-oxo)-S-proline from Step 1c, 4.1 g (10.8 mmol, 1.2 equivalents) of HATU and 3 mL of NMM in 32 mL of CH₂Cl₂. The solution was stirred at rt for one day, diluted with 100 mL of CH₂Cl₂ and then was washed with pH 4.0 buffer (4×50 mL). The organic layer was washed with saturated aqueous NaHCO₃ (100 mL), the aqueous washing extracted with ethyl acetate (150 mL), and the organic layer backwashed with pH 4.0 buffer (50 mL), and saturated aqueous NaHCO₃ (50 mL). The combined organic solution was dried (MgSO₄), concentrated and purified twice using an Isco 110 g column (eluted with 20% to 50% EtOAc/Hexanes) to provide 1.38 g (32%) of the (1R,2R) P1 isomer and 1.60 g (37%) of the (1S,2S) P1 isomer.

Data for (1R,2R) P1 isomer: ¹H NMR (methanol-d₄) δ 0.95–1.05 (m, 3H), 1.11 (dd, J=9, 5 Hz, 1H), 1.38, 1.42, 1.44 (3s, 18H), 1.35–1.69 (m, 4H), 2.35–2.52 (m, 1H), 2.64–2.80 (m, 1H), 3.87–3.97 (m, 2H), 3.95 (s, 3H), 4.37–4.45 (m, 1H), 5.47 (m, 1H), 7.15 (dd, J=9, 2.4 Hz, 1H), 7.24 (s, 1H), 7.40 (d, J=2.4 Hz, 1H), 7.48–7.55 (m, 3H), 8.01–8.04 (m, 3H).

Data for the (1S,2S) P1 isomer: ¹H NMR (Methanol-d₄) δ 0.98 (t, J=7.2 Hz, 3H), 1.12–1.26 (m, 1H), 1.39, 1.41 (two s (rotamers) 9H), 1.44 (s, 9H), 1.39–1.69 (m, 4H), 2.35–2.52 (m, 1H), 2.67–2.80 (m, 1H), 3.93 (m, 2H), 3.96 (s, 3H), 4.36–4.46 (m, 1H), 5.48 (m, 1H), 7.14–7.17 (m, 1H), 7.26 (s, 1H), 7.41 (m, 1H), 7.47–7.57 (m, 3H), 8.02–8.05 (m, 3H).

Step 2f: Preparation of the (1R,2R) P1 isomer of 2-ethyl-1-{[4-(7-methoxy-2-phenyl-quinolin-4-yloxy)-pyrrolidine-2-carbonyl]-amino}-cyclopropanecarboxylic acid methyl ester, shown below.

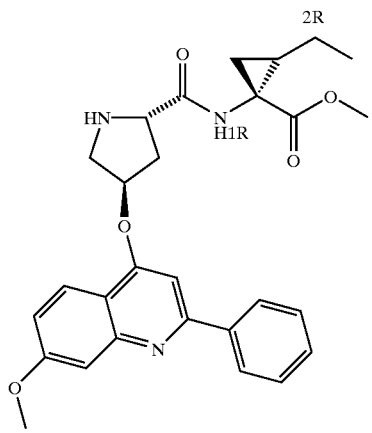

A solution of the (1R,2R) P1 isomer of 2-(1-tert-butoxycarbonyl-2-ethylcyclopropyl-1-carbamoyl)-4-(7-methoxy-2-phenyl-quinolin-4-yloxy) pyrrolidine-1-carboxylic acid tert-butyl ester (830 mg, 1.3 mmol), from Step 2e, was treated with 100 mL of 4N HCl/dioxanes for 1 day and concentrated in vacuo. The resulting solid was triturated with 100 mL of ether to afford 670 mg (95%) of 2-ethyl-1-{[4-(7-methoxy-2-phenyl-quinolin-4-yloxy)-pyrrolidine-2-carbonyl]-amino}cyclopropane-carboxylic acid which was immediately dissolved in 100 mL of 60% MeOH/CH$_2$Cl$_2$. The reaction mixture was cooled to 0° C., 3.1 mL of 2M TMSCHN$_2$ added, and was warmed to rt over 10 min. the reaction was only 50% complete and was quenched by the dropwise addition of 4N HCl/dioxane and was then resubjected to the reaction conditions which completed the reaction and was then quenched with excess 4N HCl/dioxane. The solution was concentrated to afford 700 mg of 2-ethyl-1-{[4-(7-methoxy-2-phenylquinolin-4-yloxy)-pyrrolidine-2-carbonyl]amino}-cyclopropanecarboxylic methyl ester dihydrochloride. $^1$H NMR (Methanol-d$_4$) δ 0.99 (t, J=7.2 Hz, 3H), 1.24–1.29 (m, 1H), 1.50–1.68 (m, 4H), 2.55–2.65 (m, 1H), 2.96 (dd, J=14.7, 7.5 Hz, 1H), 3.71 (s, 3H), 3.96 (bs, 2H), 4.07 (s, 3H), 4.66 (dd, J=10.3, 7.5 Hz, 1H), 5.97 (s, 1H), 7.48 (d, J=9.1 Hz, 1H), 7.56 (d, J=2.2 Hz, 1H), 7.62 (s, 1H), 7.70–7.75 (m, 3H), 8.07–8.09 (m, 2H), 8.42 (d, J=9.1 Hz, 1H).

Optionally, this dihydrochloride salt was converted to the N-BOC analogue by reacting with Et$_3$N/(BOC)$_2$O in MeOH to form the 1R,2R P1 isomer of 2-(1-tert-butoxycarbonyl-2-ethylcyclopropyl-1-carbamoyl)-4-(7-methoxy-2-phenylquinolin-4-yloxy)pyrrolidine-1-carboxylic acid methyl ester. $^1$H NMR (CDCl$_3$) δ 0.99 (t, J=7 Hz, 3H), 1.15–1.29 (m, 1H) 1.40, 1.44 (two s (rotamers) 9H), 1.40–1.62 (m, 4H), 2.39–2.46 (m, 1H), 2.65–2.76 (m, 1H), 3.68 (s, 3H), 3.89–3.98 (m, 2H), 3.96 (s, 3H), 4.40–4.45 (m, 1H), 5.48 (m, 1H), 7.16 (dd, J=9, 2 Hz, 1H), 7.26 (s, 1H), 7.41 (d, J=2 Hz, 1H), 7.48–7.56 (m, 3H), 8.02–8.05 (m, 3H).

Step 2g: Preparation of the (1R,2R) P1 isomer of 1-{[1-(2-tert-butoxycarbonyl-amino-3-methyl-butyryl)-4-(7-methoxy-2-phenyl-quinolin-4-yloxy)-pyrrolidine-2-carbonyl]amino}-2-ethylcyclopropanecarboxylic acid methyl ester, shown below.

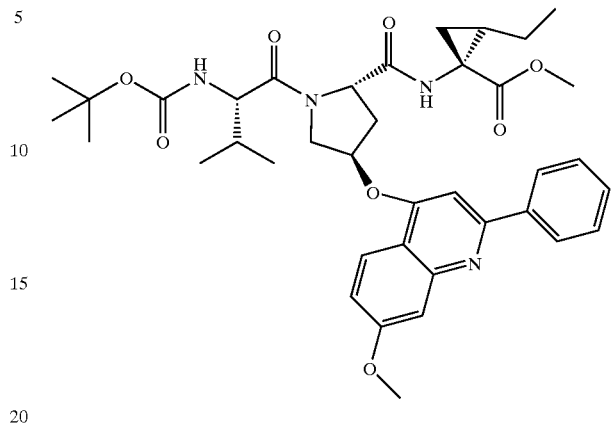

To suspension of the product of Step 2f (120 mg, 0.21 mmol), N-BOC-L-Valine (51 mg, 0.23 mmol), NMM (0.10 ml, 0.84 mmol) in DMF (2.5 mL) was added HATU (89 mg, 0.23 mmol) at 0° C. After being stirred for 2 days, the reaction mixture was diluted with EtOAc (80 mL), washed with pH 4.0 buffer (2×30 mL), saturated aqueous NaHCO$_3$ (30 mL), brine (30 mL), dried (MgSO$_4$), purified by a Isco 10 g column (eluted with 15% to 60% EtOAc in Hexanes) to supply the titled product as an opaque glass (132 mg, 0.19 mmol, 91%). $^1$H NMR δ 0.97–1.01 (m, 6H), 1.13 (m, 1H), 1.23 (dd, J=9, 5 Hz, 1H), 1.27 (s, 9H), 1.44 (dd, J=8, 5 Hz, 1H), 1.52–1.66 (m, 3H), 1.98–2.05 (m, 1H), 2.41–2.47 (m, 1H), 2.71–2.76 (m, 1H), 3.69 (s, 3H), 3.98 (s, 3H), 4.05–4.12 (m, 2H), 4.59–4.69 (m, 2H), 5.58 (m, 1H), 7.12 (dd, J=9.2, 2 Hz, 1H), 7.28 (s, 1H), 7.42 (d, J=2 Hz, 1H), 8.07, 8.08 (2s, 2H), 8.12 (d, J=9.2 Hz, 1H). LC-MS (retention time: 1.54, Method D), MS m/z 689 (M$^+$+1).

Step 2h: Preparation of the (1R,2R) P1 isomer of 1-{[1-(2-tert-Butoxycarbonylamino-3-methylbutyryl)-4-(7-methoxy-2-phenyl-quinolin-4-yloxy)pyrrolidine-2-carbonyl]amino}-2-ethylcyclopropanecarboxylic acid, shown below.

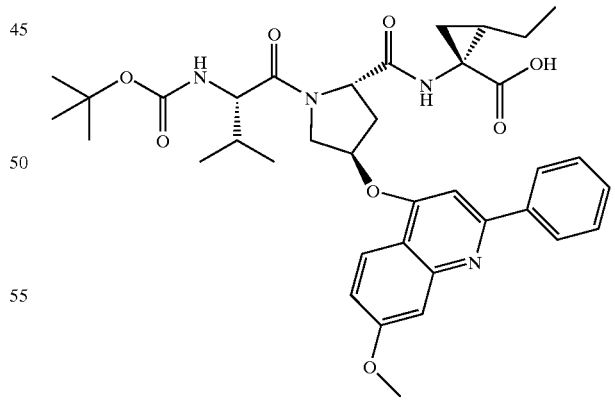

To a suspension of the product of Step 2g (124 mg, 0.18 mmol) in THF (7.9 mL), CH$_3$OH (0.8 mL), and H$_2$O (4.2 mL) was added LiOH (62 mg, 1.1 mmol). The reaction mixture was stirred for two days, acidified to neutral pH, and concentrated in vacuo until only the aqueous layer remained. The resulting aqueous residue was acidified to pH 3.0 by addition of 1.0 N aqueous HCl, and extracted with EtOAc (4×80 mL). Combined organic solvent was washed by brine (20 mL), dried (Na$_2$SO$_4$), filtered, and concentrated in vacuo to supply the titled product as an opaque glass (100 mg, 0.148 mmol, 82%). $^1$H NMR δ 0.88–1.03 (m, 9H), 1.11 (m, 1H), 1.23 (s, 9H), 1.19–1.70 (m, 5H), 1.96–2.01 (m, H), 2.43–2.52 (m, 1H), 2.70–2.77 (m, 1H), 3.98 (s, 3H), 4.00–4.10 (m, 2H), 4.57–4.65 (m, 2H), 5.59 (s, 1H), 7.11–7.15 (m, 1H), 7.30 (s, 1H), 7.41 (m, 1H), 7.53–7.60 (m, 3H), 8.04–8.07 (m, 2H), 8.12 (d, J=9 Hz, 1H); LC-MS (retention time: 1.50, Method D), MS m/z 675 (M$^+$+1).

EXAMPLE 3

Compound 1, the (1R,2R) P1 isomer of {1-[2-(2-ethyl-1-methanesulfonylaminocarbonylcyclopropylcarbamoyl)-4-(7-methoxy-2-phenylquinolin-4-yloxy)pyrrolidine-1-carbonyl]-2-methylpropyl}carbamic acid isopropyl ester, shown below, was prepared as follows.

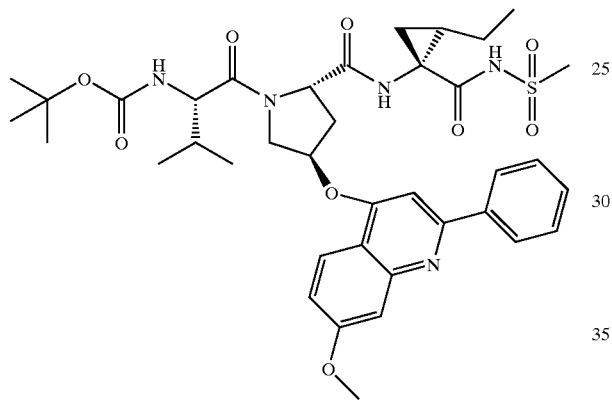

To a solution of EDAC (21 mg, 0.11 mmol) in CH$_2$Cl$_2$ (1 mL) was added a solution of the product of Step 2h (40 mg, 0.06 mmol) in CH$_2$Cl$_2$ (2×0.5 mL portions, followed by 4-DMAP (14.5 mg, 0.11 mmol and commercially available (Aldrich) methanesulfonamide (11.3 mg, 0.11 mmol). The resulting solution was stirred for 8 days, then DBU was added (16.7 mg, 0.11 mmol. The reaction was stirred for two additional days, diluted with EtOAc (80 mL) and washed with pH 4.0 buffer (3×30 mL), aqueous NaHCO$_3$ (2×30 mL), brine (30 mL), dried (MgSO$_4$) and purified by a Isco 10 g column (eluted with 15% to 100% EtOAc in Hexanes) to provide Compound 1 as an opaque glass (23.4 mg, 50%). $^1$H NMR (methanol-d$_4$) δ 0.93–0.97 (m, 9H), 1.13–1.17 (m, 1H), 1.22 (s, 9H), 1.43–1.65 (m, 4H), 2.06–2.15 (m, 1H), 2.31–2.40 (m, 1H), 2.62 (dd, J=14, 7 Hz, 1H), 3.20 (s, 3H), 3.94 (s, 3H), 4.02–4.11 (m, 2H), 4.52–4.64 (m, 2H), 5.56 (m, 1H), 7.09 (d, J=9, 2 Hz, 1H), 7.23 (s, 1H), 7.38 (d, J=2 Hz, 1H), 7.47–7.57 (m 3H), 8.03–8.09 (m, 3H); LC-MS (retention time: 1.45, Method D), MS m/z 752 (M$^+$+1).

The coupling procedure, described herein in Example 3, may be used to prepare N-acylsulfonamide derivatives of tripeptide acids containing either a vinyl Acca, such as contained in the product of Step 1e, or an ethyl Acca such as contained in the product of Step 2h.

EXAMPLE 4

Compound 2: (1R,2R) P1 isomer of {1-[2-(1-cyclopropanesulfonylamino-carbonyl-2-ethylcyclopropyl-carbamoyl)-4-(7-methoxy-2-phenyl-quinolin-4-yloxy)-pyrrolidine-1-carbonyl]-2,2-dimethylpropyl}carbamic acid tert-butyl ester, shown below, was prepared as described in Steps 4a–d.

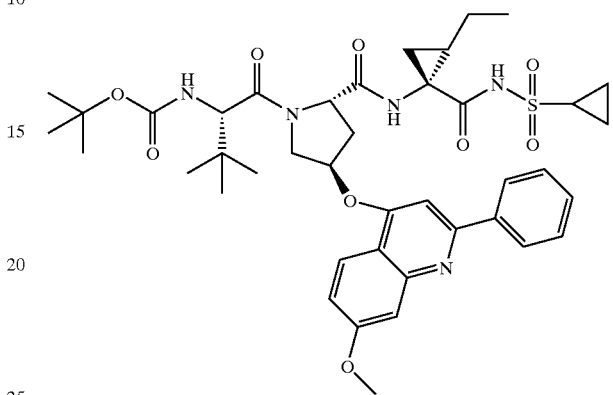

Step 4a: Preparation of the (1R,2R) P1 isomer of (2-(1-carboxy-2-ethyl-cyclopropylcarbamoyl)-4-(7-methoxy-2-phenylquinolin-4-yloxy)pyrrolidine-1-carboxylic acid tert-butylester), shown below.

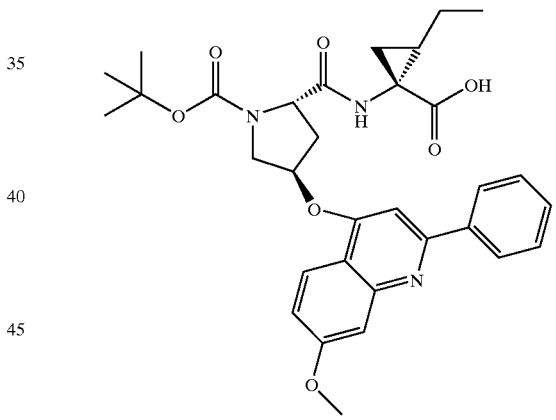

To a suspension of 1.55 g (2.83 mmol) of the dihydrochloride salt of the product of Step 2f, in 60 mL of CH$_3$CN, was added 1.60 mL (12 mmol) of TMSCN and the mixture heated to reflux for 30 min under Ar. To the resulting solution was added 0.93 g (4.26 mmol) of (BOC)$_2$O, the mixture heated to reflux for 5 h, and was then cooled to rt. Approximately 10 mL of MeOH was added, the reaction stirred for 10 min, and was then concentrated in vacuo. The residue was chromatographed over a Biotage 25M column (eluted with 0% to 5% MeOH/CH$_2$Cl$_2$ to afford 1.550 g (95%) of the titled product as a foam. $^1$H NMR (CD$_3$OD) δ 1.03 (m, 3H), 1.11–1.56 (m, 3H), 1.44 (s, 9H), 0.66 (m, 2H), 2.47 (m, 1H), 2.65–2.78 (m, 1H), 3.95 (s, 5H), 4.41–4.46 (m, 1H), 5.50 (m, 1H), 7.21 (dd, J=9.0, 2.0 Hz, 1H), 7.31 (s, 1H), 7.39 (d, J=2.0 Hz, 1H), 7.56–7.58 (m, 3H), 7.98–8.08 (m, 3H); $^{13}$C NMR (CD$_3$OD, rotomers, 2 C=O at δ 175 weak intensity) δ 13.85, 21.69, 23.08, 28.66, 33.90, 37.88, 49.64, 49.93, 53.35, 56.39, 60.53, 78.28, 82.24, 100.82, 105.23, 116.26, 120.29, 124.63, 129.30, 130.20, 131.79, 138.45, 149.26, 156.19, 160.16, 164.16, 164.36; LC-MS (retention time: 1.54, Method D), MS m/z 575 (M$^+$+1). HRMS m/z (M+H)$^+$ calcd for $C_{32}H_{38}N_3O_7$: 576.2710, found 576.2716.

Step 4b: Preparation of the (1R,1S) isomer of 2-(1-cyclopropanesulfonylamino-carbonyl-2-ethylcyclopropyl-carbamoyl)-4-(7-methoxy-2-phenyl-quinolin-4-yloxy)pyrrolidine-1-carboxylic acid tert-butyl ester, shown below.

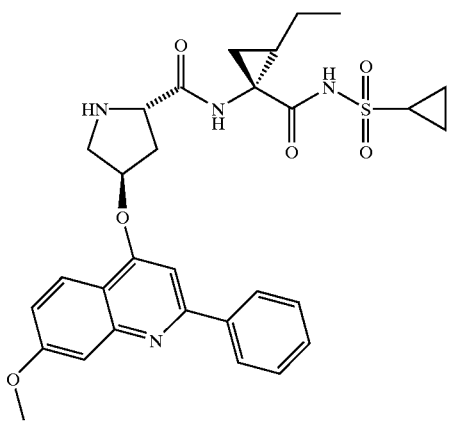

A solution of the product of Step 4a (1.55 g, 2.70 mmol) and CDI (0.568 g, 3.50 mmol) in THF (22 mL), DMF (3 mL) and CH$_2$Cl$_2$ (25 mL) was refluxed for 60 min, 2 drops of Et$_3$N added, the mixture refluxed 30 min more, and was then allowed to cool down to rt. Cyclopropylsulfonamide (0.424 g, 3.50 mmol) was added in one portion before the addition of a solution of DBU (523 □l, 0.291 mmol). The reaction was stirred for 14 h, 150 uL (1 mmol) of DBU and 100 mg (0.83 mmol) of cyclopropylsulfonamide added, and the mixture stirred 11 more hours. The mixture was diluted with EtOAc (100 mL) and washed with pH 4.0 buffer (3×30 mL), water (20 mL), brine (20 mL), dried (MgSO$_4$) and purified by a Biotage 65 M column (eluted with 0% to 5% MeOH in CH$_2$Cl$_2$) to supply the titled product as a foam (1.52, 83%). $^1$H NMR (Methanol-d$_4$) δ 0.94–1.65 (m, 12H), 1.44 (s, 9H), 2.27–2.36 (m, 1H), 2.53–2.59 (m, 1H), 2.93–3.01 (m, 1H), 3.93 (s, 3H), 3.87–3.97 (m, 2H), 4.22–4.36 (m, 1H), 5.47 (m, 1H), 7.14 (dd, J=9.0, 2.0 Hz, 1H), 7.20 (s, 1H), 7.38 (d, J=2.0 Hz, 1H), 7.48–7.56(m, 3H), 7.97–8.04 (m, 3H); $^{13}$C NMR (CD$_3$OD, rotomers) δ 6.00, 6.30, 6.73, 13.95, 20.83, 23.90, 28.75, 31.72, 32.07, 33.09, 35.41, 36.47, 37.00, 40.56, 56.11, 60.42, 78.07, 82.68, 100.16, 107.54, 116.46, 119.52, 124.01, 129.01, 129.91, 130.76, 141.08, 156.38, 161.20, 162.13, 163.33, 164.91, 171.84, 175.85; LC-MS (retention time: 1.67, method B), MS m/z 679 (M$^+$+1). HRMS m/z (M+H)$^+$ calcd for $C_{35}H_{43}N_4SO_8$: 679.2802, found 679.2805.

Step 4c: Preparation of the (1R,2R) P1 isomer of (4-(7-methoxy-2-phenylquinolin-4-yloxy)pyrrolidine-2-carboxylic acid (1-cyclopropanesulfonylaminocarbonyl-2-ethylcyclopropyl)amide dihydrochloride, shown below.

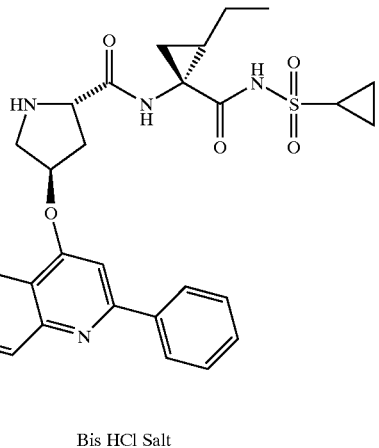

Bis HCl Salt

A solution of 1.50 g (2.20 mmol) of the product of Step 4b in 125 mL of 4N HCl in dioxanes was stirred for 2.5 h. The mixture was concentrated in vacuo to ~2 mL and 30 mL of Et$_2$O added. The resulting precipitate was filtered and the white solid dried under high vacuum (40° C., 1 torr) overnite to afford 1.424 g (99%) of the titled product. $^1$H NMR (Methanol-d$_4$) δ 0.97–1.75 (m, 13H), 2.27–2.36 (m, 1H), 2.53–2.61 (m, 1H), 2.92–3.01 (m, 1H), 4.07 (s, 3H), 3.87–4.30 (m, 2H), 6.01 (m, 1H), 7.48 (dm, J=8.0 Hz, 1H), 7.62–7.79 (m, 5H), 8.13 (d, J=3.1 Hz, 1H), 8.57 (d, J=9.1 Hz, 1H); $^{13}$C NMR (CD$_3$OD, rotomers) δ 6.02, 6.48, 6.56, 13.89, 21.22, 22.69, 32.00, 33.11, 33.86, 37.10, 41.63, 52.86, 57.14, 60.46, 81.18, 100.68, 102.44, 116.11, 122.13, 126.93, 130.22, 130.85, 133.27, 134.01, 143.82, 158.35, 162.72, 167.31, 170.26, 171.15; LC-MS (retention time: 1.23, method B), MS m/z 579 (M$^+$+1). HRMS m/z (M+H)$^+$ calcd for $C_{30}H_{35}SN_4O_6$: 579.2277, found 579.2250.

Step 4d: Preparation of Compound 2. To a solution of (100 mg, 0.154 mmol) of the product of Step 4c, in 2 mL of CH$_2$Cl$_2$, was added 53.2 mg (0.23 mmol) of BOC-L-tert-leucine, 31.3 mg (0.23 mmol) of HOAT, 87.5 mg (0.23 mmol) of HATU, and 161 µL (0.92 mmol) of DIPEA. The mixture was stirred 1 day and was partitioned between 100 mL of EtOAc and 50 mL of pH 4.0 buffer. The EtOAc layer was washed with brine (50 mL), dried (MgSO$_4$) and concentrated in vacuo. The residue was chromatographed over two 1000µ PTLC plates (each 20×40 cm, eluted with 2% MeOH in CH$_2$Cl$_2$) from Analtech to afford 115 mg (94%) of Compound 2 as a foam. $^1$H NMR (Methanol-d$_4$) δ 0.90–1.08 (m, 2H), 0.96 (t, J=7 Hz, 3H), 1.03 (s, 9H), 1.12–1.33 (m, 2H), 1.26 (s, 9H), 1.43–1.66 (m, 5H), 2.29–2.40 (m, 1H), 2.64 (dd, J=14, 7 Hz, 1H), 2.85–3.02 (m, 1H), 3.93 (s, 3H), 4.07–4.12 (m, 1H), 4.24–4.27 (m, 1H), 4.50–4.56 (m, 2H), 5.53 (m, 1H), 6.67 (d, J=9.5 Hz, 1H), 7.06 (dd, J=9.2, 2.2 Hz, 1H), 7.22 (s, 1H), 7.37 (d, J=2.2 Hz, 1H), 7.46–7.56 (m, 3H), 8.03–8.07 (m, 3H); LC-MS (retention time: 1.52 method A), MS m/z 792 (M$^+$+1). HRMS m/z (M+H)$^+$ calcd for $C_{41}H_{54}N_5O_9S$ 792.3642, found: 792.3654.

EXAMPLE 5

Compound 3, the (1R,2R) P1 isomer of {1-[2-(1-cyclopropanesulfonylaminocarbonyl-2-ethylcyclopropyl-carbamoyl)-4-(7-methoxy-2-phenylquinolin-4-yloxy)pyrrolidine-1-carbonyl]-2-methylpropyl}carbamic acid tert-butyl ester, shown below, was prepared as follows.

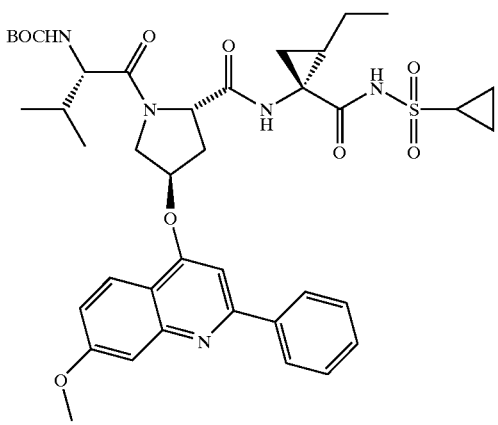

To a solution of (700 mg, 1.074 mmol) of the product of Step 4c in 14 mL of $CH_2Cl_2$, was added 350 mg (1.61 mmol) of N-BOC-L-Valine, 219.3 mg (1.61 mmol) of HOAT, 613 mg (1.61 mmol) of HATU, and 1.12 mL (6.45 mmol) of DIPEA. The mixture was stirred 1 day and was partitioned between 700 mL of EtOAc and 350 mL of pH 4.0 buffer. The EtOAc layer was washed with brine (350 mL), dried ($MgSO_4$) and concentrated in vacuo. The residue was chromatographed over a Biotage 40+ M column (eluted with 0% to 10% MeOH in $CH_2Cl_2$) to afford 800 mg of a slightly impure crude residue. This material was chromatographed over five 1000μ PTLC plates (each 20×40 cm, eluted with 2% MeOH in $CH_2Cl_2$) from Analtech to afford 650 mg (78%) of Compound 3 as a white solid. LC/MS rt-min ($MH^+$): 1.45 (778) (method A). HRMS m/z: (M+H) calcd for $C_{40}H_{52}N_5SO_9$: 778.3486, found: 778.3509.

$^1$H NMR: (Methanol-$d_4$, 300 MHz) δ 0.66–1.37 (m, 5H), 0.82 (d, J=7 Hz, 3H), 0.88 (t, J=7, 3H), 1.05 (m, 12H), 1.61–1.81 (m, 3H), 2.07–2.43 (m, 3H), 2.55–2.67 (m, 1H), 2.79–3.10 (m, 1H), 3.82–3.87 (m, 1H), 3.91 (s, 3H), 4.03 (d, J=12 Hz, 1H), 4.12–4.17 (m, 1H), 4.49–4.55 (m, 1H), 5.28 (m, 1H), 6.82–6.94 (m, 2H), 7.38–7.50 (m, 4H), 7.68–7.81 (m, 1H), 7.92–7.96 (m, 2H).

EXAMPLE 6

Compound 4, the (1R,2R) P1 isomer of (1-(2-amino-3-methylbutyryl)-4-(7-methoxy-2-phenylquinolin-4-yloxy)-pyrrolidine-2-carboxylic acid (1-cyclopropanesulfonyl-aminocarbonyl-2-ethylcyclopropyl) amide dihydrochloride, shown below, was prepared as follows.

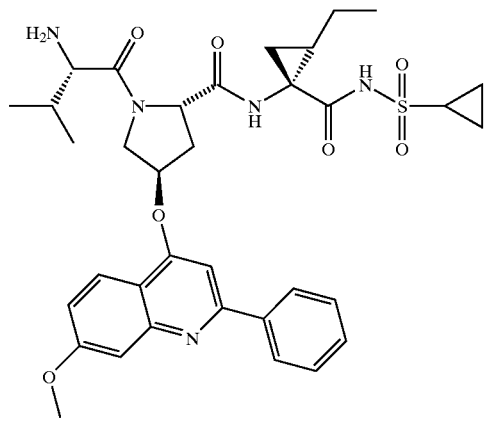

A total of 600 mg of Compound 3 was dissolved in 60 mL of 4N HCl/dioxanes and stirred 2.5 h. The slurry was concentrated until about 1 mL of solvent remained, 60 mL of $Et_2O$ added and the mixture filtered and the resulting solid dried in vacuo overnite (50° C., 25 torr) to afford 500 mg (86%) of Compound 4 as a white solid. $^1$H NMR (Methanol-$d_4$) δ 0.99 (t, J=7 Hz, 3H), 1.03–1.20 (m, 9H), 1.22–1.29 (m, 2H), 1.46–1.70 (m, 4H), 2.27–2.37 (m, 1H), 2.42–2.51 (m, 1H), 2.78–2.83 (m, 1H), 2.93–3.03 (m, 1H), 4.06 (s, 3H), 4.15–4.26 (m, 2H), 4.48 (d, J=13 Hz, 1H), 4.71–4.76 (m, 1H), 5.92 (m, 1H), 7.45–7.48 (m, 1H), 7.59 (d, J=2 Hz, 1H) 7.63 (s, 1H), 7.70–7.77 (m, 3H), 8.10, 8.10 (2s, 2H), 8.41 (d, J=9 Hz, 1H); LC-MS (retention time: 1.10 method A), MS m/z 677 ($M^++1$).

EXAMPLE 7

Compound 5, the (1R,2R) P1 isomer of 1-[2-(2-cyclopropylacetylamino)-3-methylbutyryl]-4-(7-methoxy-2-phenylquinolin-4-yloxy)pyrrolidine-2-carboxylic acid (1-cyclopropanesulfonylaminocarbonyl-2-ethylcyclopropyl)amide, shown below, was prepared as follows.

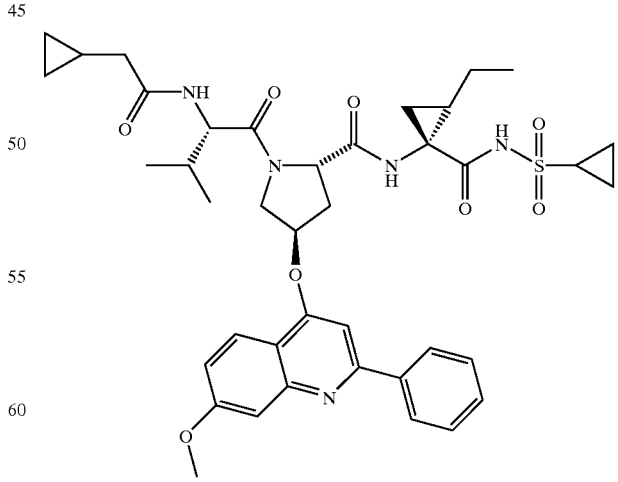

To a solution of 85 mg (0.113 mmol) of Compound 4, 119 μL (0.68 mmol) of DIPEA, 23.1 mg (0.17 mmol) of HOAT and 17 mg (0.17 mmol) of cyclopropyl acetic acid in 2 mL of CH$_2$Cl$_2$, was added 64.6 mg (0.17 mol) of HATU. The mixture was stirred 18 h and was partitioned between 100 mL of EtOAc and 35 mL of pH 4.0 buffer. The EtOAc layer was washed with brine (35 mL), dried (MgSO$_4$) and concentrated in vacuo. The residue was chromatographed over one 20×40 cm 1000μ PTLC plate (eluted with 2% MeOH in CH$_2$Cl$_2$) from Analtech to afford 63 mg (73%) of Compound 5 as a foam. $^1$H NMR (methanol-d$_4$) δ 0.07–0.10 (m, 2H), 0.37–0.44 (m, 2H), 0.80–0.86 (m, 1H), 0.94–0.97 (m, 6H), 1.00 (d, J=7 Hz, 3H), 1.05–1.10 (m, 2H), 1.16–1.21 (m, 2H), 1.25–1.30 (m, 1H), 1.50–1.57 (m, 2H), 1.60–1.65 (m, 2H), 1.93–2.01 (m, 2H), 2.15–2.22 (m, 1H), 2.33–2.38 (m, 1H), 2.61 (dd, J=14, 6.6 Hz, 1H), 2.93–2.98 (m, 1H), 3.94 (s, 3H), 4.13 (dd, J=12, 3.5 Hz, 1H), 4.44 (t, J=9 Hz, 1H), 4.49–4.56 (m, 2H), 5.60 (m, 1H), 7.12 (dd, J=9.1, 2.4 Hz, 1H), 7.27 (s, 1H), 7.38 (d, J=2.4 Hz, 1H), 7.50–7.55 (m, 3H), 7.91 (d, J=9 Hz, 1H), 8.04–8.05 (m, 3H); LC-MS (retention time: 1.51 method A), MS m/z 786 (M$^+$+1). HRMS m/z (M+H)$^+$ calcd for C$_{40}$H$_{50}$N$_5$O$_8$S 760.3380, found: 760.3398.

EXAMPLE 8

Compound 6, the (1R,2R) P1 isomer of 1-[2-(1-cyclopropanesulfonylaminocarbonyl-2-ethylcyclopropyl-carbamoyl)-4-(7-methoxy-2-phenylquinolin-4-yloxy)pyrrolidine-1-carbonyl]-2-methylpropyl}-carbamic acid cyclopentyl ester, shown below, was prepared as follows.

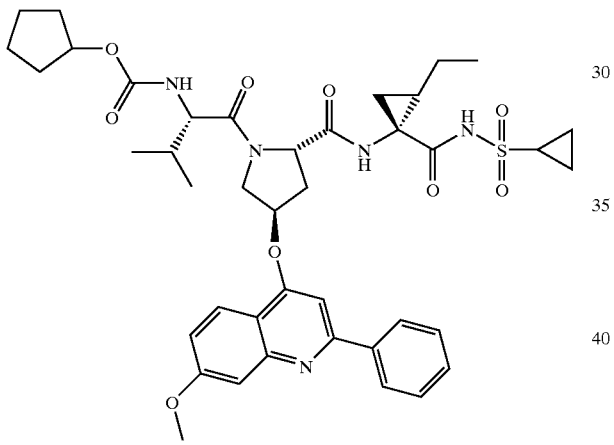

To a solution of 85 mg (0.113 mmol) of Compound 4 and 119 μL (0.68 mmol) of DIPEA in 2 mL of CH$_2$Cl$_2$, was added 400 μL (0.27 mol) of neat cyclopentyl chloroformate in THF (prepared in analogous fashion to the chloroformate used in Example 21, step 21a). The mixture was stirred 18 h and was partitioned between 100 mL of EtOAc and 35 mL of pH 4.0 buffer. The EtOAc layer was washed with brine (35 mL), dried (MgSO$_4$) and concentrated in vacuo. The residue was chromatographed over one 20×40 cm 1000μ PTLC plate (eluted with 2% MeOH in CH$_2$Cl$_2$) from Analtech to afford 71 mg (79%) of P4(cyclopentyl-O(C=O))N-P3(L-Val)-P2[(4R)-(2-phenyl-7-methoxy-quinoline-4-oxo)proline]-P1(1R,2R Ethyl Acca)-CONHSO$_2$Cyclopropane, {1-[2-(1-Cyclopropanesulfonyl-aminocarbonyl-2-ethyl-cyclopropylcarbamoyl)-4-(7-methoxy-2-phenyl-quinolin-4-yloxy)-pyrrolidine-1-carbonyl]-2-methylpropyl}carbamic acid cyclopentyl ester as a foam. $^1$H NMR (Methanol-d$_4$, rotamers~1/1) δ (Methanol d-4, rotamers~1/1) δ 0.80–1.80 (m, 26H), 2.04–2.22 (m, 1H), 2.24–2.39 (m, 1H), 2.61–2.69 (m, 1H), 2.95 (m, 1H), 3.94 (s, 3H), 4.04–4.12 (m, 2H), 4.53–4.65 (m, 3H), 5.51–5.57 (m, 1H), 7.11 (d, J=8 Hz, 1H), 7.21–7.25 (m, 1H), 7.39–7.40 (m, 1H), 7.49–7.56 (m, 3H), 8.03–8.09 (m, 3H); LC-MS (retention time: 1.69, method D), MS m/z 816 (M$^+$+1). HRMS m/z (M+H)$^+$ calcd for C$_{41}$H$_{52}$N$_5$O$_9$S 790.3486, found: 790.3479.

EXAMPLE 9

Compound 7, the (1R,2R) P1 isomer of 1-[2-(1-cyclopropanesulfonylaminocarbonyl-2-ethylcyclopropyl-carbamoyl)-4-(7-methoxy-2-phenylquinolin-4-yloxy)pyrrolidine-1-carbonyl]-2-methyl-propyl}carbamic acid ethyl ester, shown below, was prepared as follows.

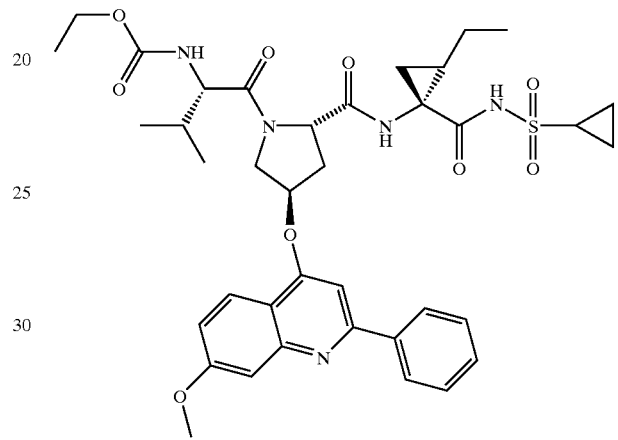

To a solution of 85 mg (0.113 mmol) of Compound 4 and 119 μL (0.68 mmol) of DIPEA in 2 mL of CH$_2$Cl$_2$, was added 27 μL (0.27 mol) of neat ethyl chloroformate (Aldrich). The mixture was stirred 18 h and was partitioned between 100 mL of EtOAc and 35 mL of pH 4.0 buffer. The EtOAc layer was washed with brine (35 mL), dried (MgSO$_4$) and concentrated in vacuo. The residue was chromatographed over one 20×40 cm 1000μ PTLC plate (eluted with 2% MeOH in CH$_2$Cl$_2$) from Analtech to afford 66 mg (78%) of Compound 7 as a white solid. $^1$H NMR (Methanol-d$_4$) δ 0.70 (t, J=7 Hz, 3H), 0.88–1.34 (m, 15H), 1.46–1.80 (m, 4H), 2.07–2.38 (m, 2H), 2.46 (m, 1H), 2.58–2.62 (m, 1H), 3.66–3.81 (m, 2H), 3.88 (s, 3H), 4.05–4.13 (m, 1H), 4.21 (s, 1H), 4.54 (dd, J=11, 6 Hz, 1H), 4.60 (dd, J=11.6 Hz, 1H), 5.49, 5.52 (m, 1H), 6.57 (d, J=8 Hz, NH), 7.20 (s, 1H), 7.35 (s, 1H), 7.47–7.55 (m, 4H), 7.74 (d, J=9 Hz, 1H), 8.02–8.05 (m, 3H); LC-MS (retention time: 1.39; method A), MS m/z 750 (M$^+$+1). HRMS m/z (M+H)$^+$ calcd for C$_{38}$H$_{48}$N$_5$O$_9$S 750.3173, found: 750.3172.

EXAMPLE 10

Compound 8, the (1R,2R) P1 isomer of 4-(7-methoxy-2-phenylquinolin-4-yloxy)-1-[3-methyl-2-(3-propylureido)

butyryl]pyrrolidine-2-carboxylic acid (1-cyclopropane-sulfonylaminocarbonyl-2-ethylcyclopropyl)amide, shown below, was prepared as follows.

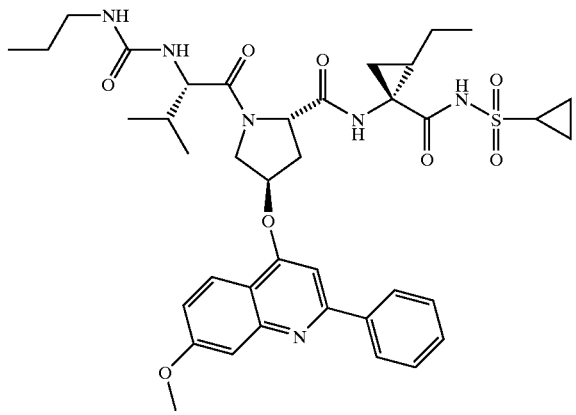

To a solution of 85 mg (0.113 mmol) of Compound 4 and 119 μL (0.68 mmol) of DIPEA in 2 mL of $CH_2Cl_2$, was added 27 μL (0.27 mol) of neat n-propyl isocyanate (Aldrich). The mixture was stirred 18 h and was partitioned between 100 mL of EtOAc and 35 mL of pH 4.0 buffer. The EtOAc layer was washed with brine (35 mL), dried ($MgSO_4$) and concentrated in vacuo. The residue was chromatographed over one 20×40 cm 1000μ PTLC plate (eluted with 2% MeOH in $CH_2Cl_2$) from Analtech to afford 74 mg (85%) of Compound 8 as a foam. $^1$H NMR (MeOD) δ 0.81 (t, J=7 Hz, 3H), 0.88–1.68 (m, 20H), 2.05–2.14 (m, 1H), 2.32–2.38 (m, 1H), 2.58–2.62 (m, 1H), 2.87–2.99 (m, 3H), 3.93 (s, 3H), 4.09–4.12 (m, 1H), 4.24–4.27 (m, 1H), 4.50–4.54 (m, 2H), 5.55 (m, 1H), 6.01 (d, J=9 Hz, NH), 7.09 (dd, J=9.1, 2.1 Hz, 1H), 7.37 (d, J=2.1 Hz, 1H), 7.47–7.52 (m, 3H), 8.02–8.04 (m, 2H), 8.06 (d, J=9.1 Hz, 1H); LC-MS (retention time: 1.38, method A), MS m/z 763 (M$^+$+1). HRMS m/z (M+H)$^+$ calcd for $C_{39}H_{51}N_6O_8S$ 763.3489, found: 763.3477.

EXAMPLE 11

Compound 9, the (1R,2R) P1 isomer of 1-[2-(1-Cyclopropanesulfonylaminocarbonyl-2-ethylcyclopropylcarbamoyl)-4-(7-methoxy-2-phenylquinolin-4-yloxy)pyrrolidine-1-carbonyl]-2-methylpropyl}carbamic acid 2-fluoroethyl ester, shown below, was prepared as follows.

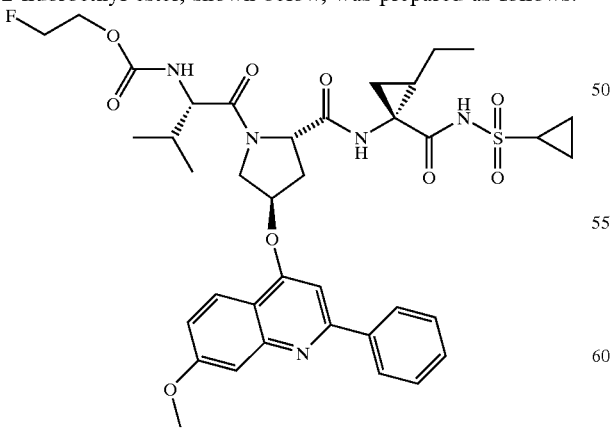

To a solution of 85 mg (0.113 mmol) of Compound 4 and 119 μL (0.68 mmol) of DIPEA in 2 mL of $CH_2Cl_2$, was added 32 μL (0.27 mol) of neat 2-fluoroethyl chloroformate (Aldrich). The mixture was stirred 18 h and was partitioned between 100 mL of EtOAc and 35 mL of pH 4.0 buffer. The EtOAc layer was washed with brine (35 mL), dried ($MgSO_4$) and concentrated in vacuo. The residue was chromatographed over one 20×40 cm 1000μ PTLC plate (eluted with 2% MeOH in $CH_2Cl_2$) from Analtech to afford 63 mg (72%) of Compound 9 as a white solid. $^1$H NMR (Methanol-$d_4$) δ 0.75–1.23 (m, 14H), 1.26–1.33 (m, 1H), 1.55–1.83 (m, 4H), 2.10–2.36 (m, 3H), 2.48 (m, 1H), 2.54–2.64 (m, 1H), 3.83 (s, 3H), 3.78–4.64 (m, 8H), 5.49 (m, 1H), 6.64 (m, NH), 7.18 (s, 1H), 7.29 (s, 1H), 7.46–7.54 (m, 4H), 7.74 (d, J=9 Hz, 1H), 8.04–8.05 (m, 3H); LC-MS (retention time: 1.33, method A), MS m/z 768 (M$^+$+1). HRMS m/z (M+H)$^+$ calcd for $C_{38}H_{47}FN_5O_9S$ 768.3079, found: 768.3091.

EXAMPLE 12

(1R,2S) P1 isomer of 1-{[1-2-tert-Butoxycarbonylamino-3,3-dimethylbutyryl)-4-(7-methoxy-2-phenylquinolin-4-yloxy)pyrrolidine-2-carbonyl]amino}-2-vinylcyclopropanecarboxylic acid, shown below, was prepared as described in Steps 12a–e.

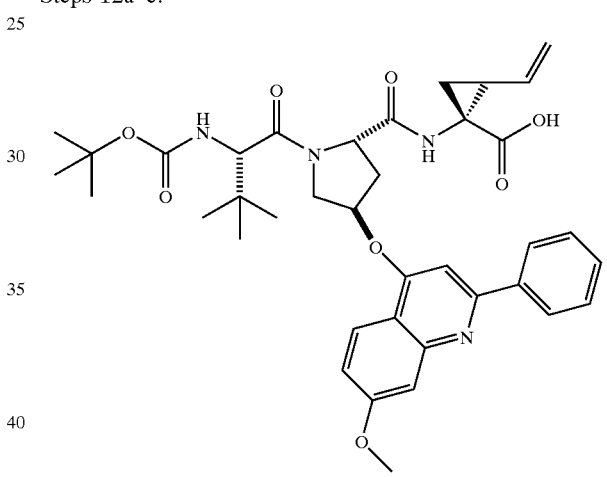

Step 12a: Preparation of (1R,2S)/(1S,2R)-1-amino-2-vinylcyclopropane carboxylic acid ethyl ester hydrochloride, shown below.

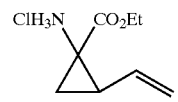

The named compound was made by each of the following methods A and B.

Method A

A.1) Preparation of N-benzyl imine of glycine ethyl ester, shown below.

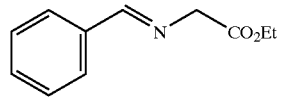

Glycine ethyl ester hydrochloride (303.8 g, 2.16 mole) was suspended in tert-butylmethyl ether (1.6 L). Benzaldehyde (231 g, 2.16 mole) and anhydrous sodium sulfate (154.6 g, 1.09 mole) were added and the mixture cooled to 0° C. using an ice-water bath. Triethylamine (455 mL, 3.26 mole) was added dropwise over 30 min and the mixture stirred for 48 h at rt. The reaction was then quenched by addition of ice-cold water (1 L) and the organic layer was separated. The aqueous phase was extracted with tert-butylmethyl ether (0.5 L) and the combined organic phases washed with a mixture of saturated aqueous $NaHCO_3$ (1 L) and brine (1 L). The solution was dried over $MgSO_4$, concentrated in vacuo to afford 392.4 g of the N-benzyl imine product as a thick yellow oil that was used directly in the next step. $^1$H NMR ($CDCl_3$, 300 MHz) δ 1.32 (t, J=7.1 Hz, 3H), 4.24 (q, J=7.1 Hz, 2H), 4.41 (d, J=1.1 Hz, 2H), 7.39–7.47 (m, 3H), 7.78–7.81 (m, 2H), 8.31 (s, 1H).

A.2) Preparation of racemic N-Boc-(1R,2S)/(1S,2R)-1-amino-2-vinylcyclopropane carboxylic acid ethyl ester

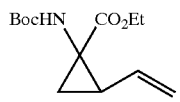

To a suspension of lithium tert-butoxide (84.06 g, 1.05 mol) in dry toluene (1.2 L), was added dropwise a mixture of the N-benzyl imine of glycine ethyl ester (100.4 g, 0.526 mol) and trans-1,4-dibromo-2-butene (107.0 g, 0.500 mol) in dry toluene (0.6 L) over 60 min. After completion of the addition, the deep red mixture was quenched by addition of water (1 L) and tert-butylmethyl ether (TBME, 1 L). The aqueous phase was separated and extracted a second time with TBME (1 L). The organic phases were combined, 1 N HCl (1 L) was added and the mixture stirred at room temperature for 2 h. The organic phase was separated and extracted with water (0.8 L). The aqueous phases were then combined, saturated with salt (700 g), TBME (1 L) was added and the mixture cooled to 0° C. The stirred mixture was then basified to pH 14 by the dropwise addition of 10 N NaOH, the organic layer separated, and the aqueous phase extracted with TBME (2×500 mL). The combined organic extracts were dried ($MgSO_4$) and concentrated to a volume of 1 L. To this solution of free amine, was added di-tert-butyldicarbonate (131.0 g, 0.6 mol) and the mixture stirred 4 days at rt. Additional di-tert-butyldicarbonate (50 g, 0.23 mol) was added to the reaction, the mixture refluxed for 3 h, and was then allowed cool to room temperature overnite. The reaction mixture was dried over $MgSO_4$ and concentrated in vacuo to afford 80 g of crude material. This residue was purified by flash chromatography (2.5 Kg of $SiO_2$, eluted with 1% to 2% $MeOH/CH_2Cl_2$) to afford 57 g (53%) of racemic N-Boc-(1R,2S)/(1S,2R)-1-amino-2-vinylcyclopropane carboxylic acid ethyl ester as a yellow oil which solidified while sitting in the refrigerator. $^1$H NMR ($CDCl_3$, 300 MHz) δ 1.26 (t, J=7.1 Hz, 3H), 1.46 (s, 9H), 1.43–1.49 (m, 1H), 1.76–1.82 (br m, 1H), 2.14 (q, J=8.6 Hz, 1H), 4.18 (q, J=7.2 Hz, 2H), 5.12 (dd, J=10.3, 1.7 Hz, 1H), 5.25 (br s, 1H), 5.29 (dd, J=17.6, 1.7 Hz, 1H), 5.77 (ddd, J=17.6, 10.3, 8.9 Hz, 1H); MS m/z 254.16 ($M^+$-1).

A.3 Preparation of Racemic (1R,2S)/(1S,2R) 1-amino-2-vinylcyclopropane carboxylic acid ethyl ester hydrochloride

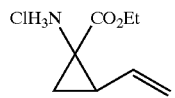

N-Boc-(1R,2S/1S,2R)-1-amino-2-vinylcyclopropane carboxylic acid ethyl ester (9.39 g, 36.8 mmol) was dissolved in 4N HCl/dioxane (90 ml, 360 mmol) and was stirred for 2 h at rt. The reaction mixture was concentrated to supply (1R,2S/1S,2R)-1-amino-2-vinylcyclopropane carboxylic acid ethyl ester hydrochloride in quanitative yield (7 g, 100%). $^1$H NMR (Methanol-$d_4$) δ: 1.32 (t, J=7.1, 3H), 1.72 (dd, J=10.2, 6.6 Hz, 1H), 1.81 (dd, J=8.3, 6.6 Hz, 1H), 2.38 (q, J=8.3 Hz, 1H), 4.26–4.34 (m, 2H), 5.24 (dd, 10.3, 1.3 Hz, 1H) 5.40 (d, J=17.2, 1H), 5.69–5.81 (m, 1H).

Method B

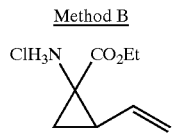

To a solution of potassium tert-butoxide (11.55 g, 102.9 mmol) in THF (450 mL) at −78° C. was added the commercially available N,N-dibenzyl imine of glycine ethyl ester (25.0 g, 93.53 mmol) in THF (112 mL). The reaction mixture was warmed to 0° C., stirred for 40 min, and was then cooled back to −78° C. To this solution was added trans-1,4-dibromo-2-butene (20.0 g, 93.50 mmol), the mixture stirred for 1 h at 0° C. and was cooled back to −78° C. Potassium tert-butoxide (11.55 g, 102.9 mmol) was added, the mixture immediately warmed to 0° C., and was stirred one more hour before concentrating in vacuo. The crude product was taken up in $Et_2O$ (530 mL), 1N aq. HCl solution (106 mL, 106 mmol) added and the resulting biphasic mixture stirred for 3.5 h at rt. The layers were separated and the aqueous layer was washed with $Et_2O$ (2×) and basified with a saturated aq. $NaHCO_3$ solution. The desired amine was extracted with $Et_2O$ (3×) and the combined organic extract was washed with brine, dried ($MgSO_4$), and concentrated in vacuo to obtain the free amine. This material was treated with a 4N HCl solution in dioxane (100 mL, 400 mmol) and concentrated to afford (1R,2S)/(1S,2R)-1-amino-2-vinylcyclopropane carboxylic acid ethyl ester hydrochloride as a brown semisolid (5.3 g, 34% yield) identical to the material obtained from procedure A, except for the presence of a small unidentified aromatic impurity (8%).

Step 12b: Preparation of the (1R,2S) P1 isomer of 2-(1-Ethoxycarbonyl-2-vinylcyclopropylcarbamyl-4-(7-methoxyl-2-phenylquinolin-4-yloxy)pyrrollindine-1-carboxylic acid tert-butyl ester, shown below.

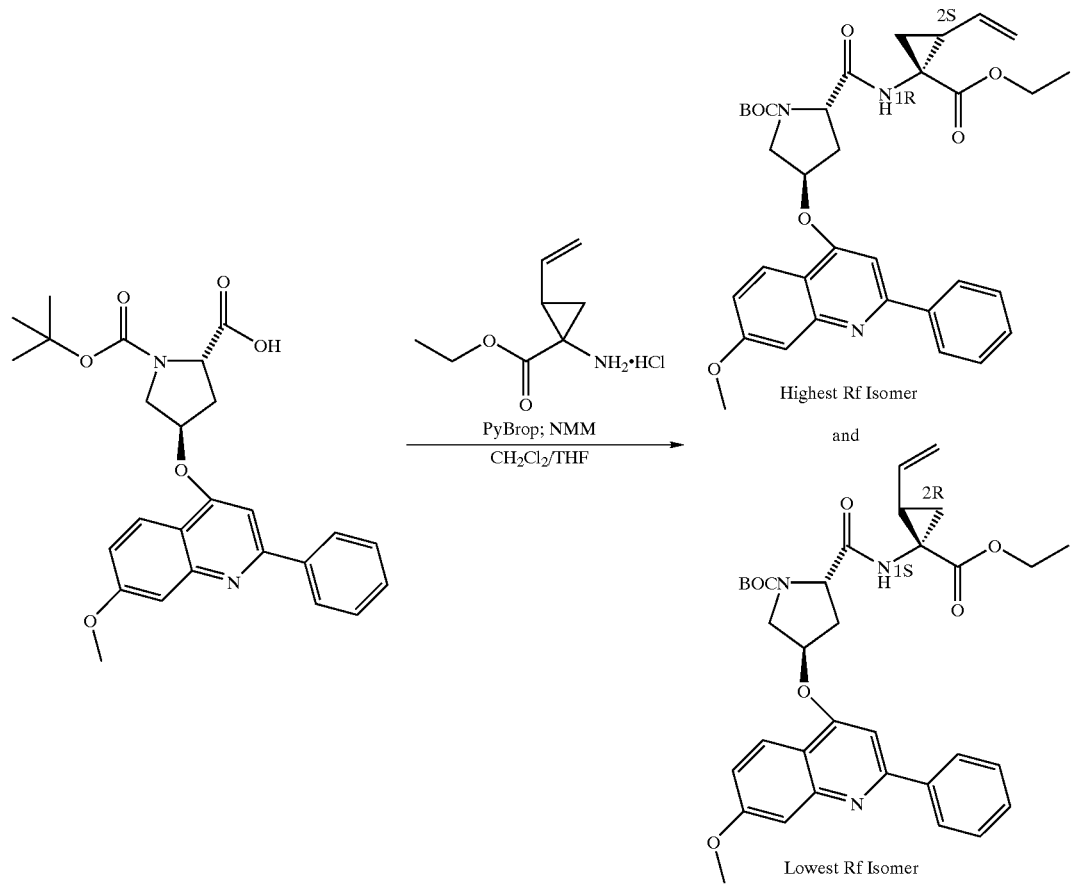

To a solution of Boc-4(R)-(2-phenyl-7-methoxyquinoline-4-oxo)proline from Step 1c (11.0 g, 23.7 mmole), HCl salt of a racemic mixture of (1R,2S) and (1S,2R) P1 derived diastereomers, from Step 11b, where carboxy group is syn to vinyl moiety (5.40 g, 28.2 mmole), NMM (20.8 mL; 18.9 mmole) in 500 mL of 50% CH$_2$Cl$_2$/THF was added the coupling reagent PyBrop or Bromotrispyrrolidino-phosphonium hexafluorophosphate (16.0 g, 34.3 mmole) in three portions in 10 min at 0° C. The solution was stirred at rt for one day and then was washed with pH 4.0 buffer (4×50 mL). The organic layer was washed with saturated aqueous NaHCO$_3$ (100 mL), the aqueous washing extracted with ethyl acetate (150 mL), and the organic layer backwashed with pH 4.0 buffer (50 mL), and saturated aqueous NaHCO$_3$ (50 mL). The organic solution was dried (MgSO$_4$), concentrated and purified using a Biotage 65M column (eluted with 50% EtOAc/Hexanes) to provide over 7.5 g of a 1:1 mixture of (1R,2S) and (1S,2R) P1 isomers of 2-(1-Ethoxycarbonyl-2-vinylcyclopropylcarbamyl-4-(7-methoxyl-2-phenylquinolin-4-yloxy)pyrrollindine-1-carboxylic acid tert-butyl ester (50% overall) or alternatively elution over a Biotage 65M column using a slow to 15% to 60% EtOAc in hexanes gradient to supply 3.54 g (25%) of the high Rf eluted (1R,2S) P1 isomer, and 3.54 g (25%) of the low Rf eluted (1S,2R) P1 isomer.

Data for (1R,2S) P1 isomer: $^1$H NMR (CDCl$_3$) δ 1.21 (t, J=7 Hz, 3H), 1.43 (s, 9H), 1.47–1.57 (m, 1H), 1.88 (m, 1H), 2.05–2.19 (m, 1H), 2.39 (m, 1H), 2.88 (m, 1H), 3.71–3.98 (m, 2H), 3.93 (s, 3H), 4.04–4.24 (m, 2H), 4.55 (m, 1H), 5.13 (d, J=10 Hz, 1H), 5.22–5.40 (m, 1H), 5.29 (d, J=17 Hz, 1H), 5.69–5.81 (m, 1H), 7.02 (brs, 1H), 7.09 (dd, J=9, 2 Hz, 1H), 7.41–7.52 (m, 4H), 7.95 (d, J=9 Hz, 1H), 8.03, 8.05 (2s, 2H); $^{13}$C NMR (CDCl$_3$) δ: 14.22; 22.83, 28.25, 33.14, 33.58, 39.92, 51.84, 55.47, 58.32, 61.30, 75.86, 81.27, 98.14, 107.42, 115.00, 117.84, 118.27, 122.63, 123.03, 127.50, 128.72, 129.26, 133.39, 140.06, 151.23, 159.16, 160.34, 161.35, 169.78, 171.68. LC-MS (retention time: 1.62, method D), MS m/z 602 (M$^+$+1).

Data for the (1S,2R) P1 isomer: $^1$H NMR δ 1.25 (t, J=7 Hz, 3H), 1.44 (s, 9H), 1.46–1.52 (m, 1H), 1.84 (m, 1H), 2.12–2.21 (m, 1H), 2.39 (m, 1H), 2.94 (m, 1H), 3.82 (m, 2H), 3.97 (s, 3H), 4.05–4.17 (m, 2H), 4.58 (m, 1H), 5.15 (d, J=10.8 Hz, 1H), 5.33 (d, J=17 Hz, 1H), 5.30–5.43 (m, 1H), 5.72–5.85 (m, 1H), 7.05 (s, 1H), 7.13 (dd, J=9, 2 Hz, 1H), 7.46–7.60 (m, 4H), 7.98 (d, J=9 Hz, 1H), 8.06–8.10 (m, 2H). LC-MS (retention time: 1.66, method D), MS m/z 602 (M$^+$+1).

Step 12c: Preparation of the (1R,2S) P1 diastereomer of 1-{[4-(7-Methoxy-2-phenylquinolin-4-yloxy)pyrrolidine-2-carbonyl]-1-amino}-2-vinylcyclopropanecarboxylic acid ethyl ester, dihydrochloride, shown below.

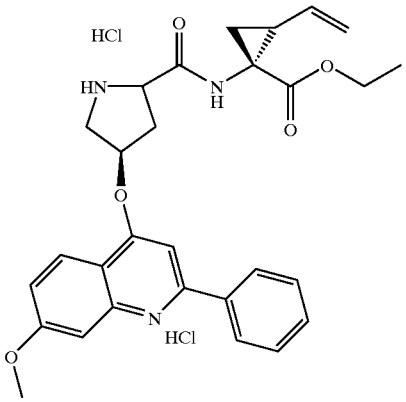

The product of Step 12b (5.88 g, 9.77 mmol) was dissolved in HCl/dioxane (4.0M; 200 ml) and was stirred for 2.5 h at rt. The reaction mixture was concentrated to supply the titled product. $^1$H NMR (Methanol-$d_4$) δ 1.24 (t, J=7 Hz, 3H), 1.50 (dd, J=10, 5 Hz, 1H), 1.78 (dd, J=8.4, 5.5 Hz, 1H), 2.24–2.33 (m, 1H), 2.56–2.66 (m, 1H), 3.05 (dd, J=14.6, 7.3 Hz, 1H), 3.98 (s, 2H), 4.06 (s, 3H), 4.15 (q, J=7 Hz, 2H), 4.76 (dd, J=10.6, 7.3 Hz, 1H), 5.13 (dd, J=10.2, 1.8 Hz), 5.32 (dd, J=17, 2 Hz), 5.70–5.83 (m, 1H), 6.05 (m, 1H), 7.48 (dd, J=9, 2 Hz, 1H), 7.65–7.79 (m, 5H), 8.12–8.15 (m, 2H), 8.54 (d, J=9.5 Hz, 1H); $^{13}$C NMR (methanol-$d_4$) δ: 14.77, 23.23, 34.86, 37.25, 41.19, 43.90, 52.66, 60.35, 62.32, 62.83, 68.27, 72.58, 73.70, 81.21, 100.70, 102.44, 116.13, 118.67, 122.25, 126.93, 130.27, 130.94, 133.19, 134.14, 134.89, 143.79, 158.39, 166.84, 167.44, 169.57, 171.33. LC-MS (retention time: 1.55, Method D), MS m/z 502 (M$^+$+1).

Step 12d: Preparation of the (1R,2S) P1 isomer of 1-{[1–2-tert-Butoxy-carbonylamino-3,3-dimethylbutyryl)-4-(7-methoxy-2-phenylquinolin-4-yloxy)p-pyrrolidine-2-carbonyl]-amino}-2-vinylcyclopropanecarboxylic acid ethyl ester, shown below.

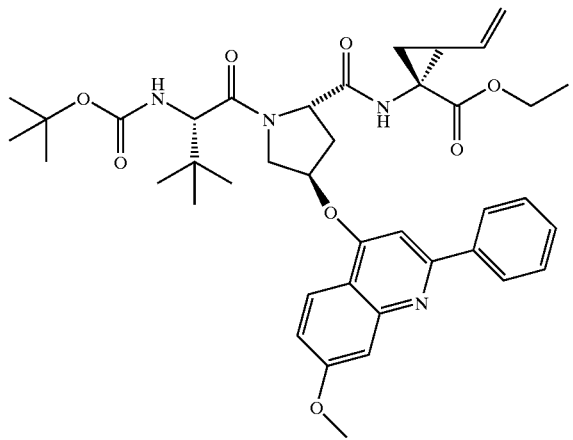

To a suspension of the product of Step 12c (1.95 g; 3.4 mmol), N-BOC-L-tert-leucine (0.94 g, 4.08 mmol), NMM (1.87 ml, 17 mmol) in DMF (15 mL) was added HATU (1.55 g, 4.08 mmol) at 0° C. After being stirred for 2 days, the reaction mixture was diluted with EtOAc (200 mL), washed with pH 4.0 buffer (2×30 mL), saturated aqueous NaHCO$_3$ (30 mL), brine (30 mL), dried (MgSO$_4$), purified by a Biotage 40 M column (eluted with 15% to 60% EtOAc in Hexanes) to supply the titled product as a white solid (2.21 g, 90%). $^1$H NMR (CDCl$_3$) δ 1.05 (s, 9H), 1.20 (t, J=7 Hz, 3H), 1.38–1.43 (m, 1H), 1.41 (s, 9H), 1.80–1.85 (m, 1H), 2.08–2.16 (m, 1H), 2.39–2.47 (m, 1H), 2.90–2.99 (m, 1H), 3.90–4.01 (m, 1H), 3.93 (s, 3H), 4.12 (q, J=7 Hz, 2H), 4.36 (d, J=10 Hz, 1H), 4.45 (d, J=12 Hz, 1H), 4.75–4.85 (m, 1H), 5.09–5.13 (m, 1H), 5.21–5.34 (m, 2H), 5.69–5.81 (m, 1H), 7.00–7.09 (m, 2H), 7.42–7.54 (m, 5H), 8.01–8.05 (m, 3H); $^{13}$C NMR (CDCl$_3$) δ 14.30, 22.85, 26.40, 28.25, 32.20, 34.09, 35.39, 39.97, 53.86, 55.47, 58.28, 58.96, 61.29, 75.94, 79.86, 97.98, 107.43, 115.06, 117.98, 118.38, 123.03, 127.52, 128.76, 129.24, 133.40, 140.26, 151.44, 155.74, 159.16, 160.09, 161.32, 169.55, 170.64, 172.63. LC-MS (retention time: 1.85, Method D), MS m/z 715 (M$^+$+1).

Step 12e: Preparation of the titled product, (1R,2S) P1 isomer of 1-{[1–2-tert-Butoxycarbonylamino-3,3-dimethylbutyryl)-4-(7-methoxy-2-phenylquinolin-4-yloxy)pyrrolidine-2-carbonyl]amino}-2-vinylcyclopropanecarboxylic acid. To a suspension of the product of Step 12d (2.63 g, 3.68 mmol) in THF (150 mL), CH$_3$OH (80 mL), and H$_2$O (20 mL) was added LiOH (1.32 g, 55.2 mmol). The reaction mixture was stirred for two days, acidified to neutral pH, and concentrated in vacuo until only the aqueous layer remained. The resulting aqueous residue was acidified to pH 3.0 by addition of 1.0 N aqueous HCl, and extracted with EtOAc (4×200 mL). Combined organic solvent was washed by brine (20 mL), dried (Na$_2$SO$_4$), filtered, and concentrated in vacuo to supply the titled product as white solid (2.41 g, 96%). $^1$H NMR (CDCl$_3$/Methanol-$d_4$) δ 0.98, 1.01 (two s (rotamers) 9H), 1.40, 1.42 (two s (rotamers) 9H), 1.35–1.47 (m, 1H), 1.89–1.93 (m, 1H), 2.03–2.14 (m, 1H), 2.45–2.52 (m, 1H), 2.64–2.78 (m, 1H), 3.94 (s, 3H), 3.96–4.12 (m, 1H), 4.34 (d, J=10 Hz, 1H), 4.52 (d, J=11 Hz, 1H), 4.58–4.64 (m, 1H), 5.10 (d, J=12 Hz, 1H), 5.24 (d, J=16 Hz, 1H), 5.34 (m, 1H), 5.68–5.86 (m, 2H), 7.02–7.05 (m, 1H), 7.32 (m, 1H), 7.40–7.54 (m, 4H), 7.97–8.03 (m, 3H); LC-MS (retention time: 1.64, method D), MS m/z 687 (M$^+$+1).

The hydrolysis procedure disclosed in Step 12e, herein, may be used for all N-BOC tripeptides containing vinyl Acca such as the product of Step 12d.

EXAMPLE 13

Compound 10, BOCNH-P3(L-t-BuGly)-P2[(4R)-(2-phenyl-7-methoxyquinoline-4-oxo)-S-proline]-P1(1R,2S Vinyl Acca)-CONHSO$_2$-Cyclopropane or alternate designation (1R,2S) P1 diastereomer of {1-[2-(1-Cyclopropane-sulfonylaminocarbonyl-2-vinylcyclopropylcarbamoyl)-4-(7-methoxy-2-phenylquinolin-4-yloxy)-pyrrolidine-1-carbonyl]-2,2-dimethylpropyl}carbamic acid tert-butyl ester, shown below, was prepared as described in Steps 13a–b.

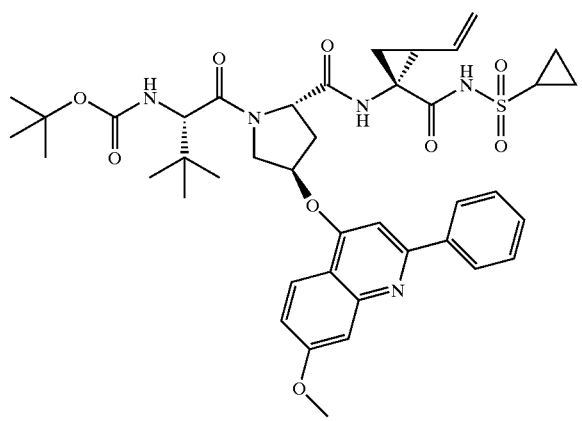

Step 13a: Preparation of Cyclopropyl Sulfonamide

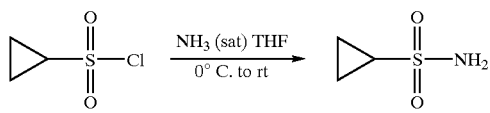

To a solution of 100 mL of THF cooled to 0° C. was bubbled in gaseous ammonia until saturation was reached. To this solution was added a solution of 5 g (28.45 mmol) of cyclopropylsulfonyl chloride (purchased from Array Biopharma) in 50 mL of THF, the solution warmed to rt overnite and stirred one additional day. The mixture was concentrated until 1–2 mL of solvent remained, applied onto 30 g plug of $SiO_2$ (eluted with 30% to 60% EtOAc/Hexanes) to afford 3.45 g (100%) of cyclopropyl sulfonamide as a white solid. $^1H$ NMR (Methanol-$d_4$) δ 0.94–1.07 (m, 4H), 2.52–2.60 (m, 1H); $^{13}C$ NMR (methanol-$d_4$) δ 5.92, 33.01.

Step 13b: Preparation of Compound 10. To a solution of CDI (0.238 g, 1.47 mmol) in THF (3 mL) was added a solution of the product of Step 12e (0.837 g, 1.22 mmol) in THF (20 mL) dropwise in 10 min under argon. The resulting solution was stirred for 30 min, refluxed for 30 min and allowed to cool down to rt. Cyclopropylsulfonamide (0.591 g, 4.88 mmol) was added in one portion before the addition of a solution of DBU (0.36 mL, 2.44 mmol) in THF (2 mL). The reaction was stirred for 18 h, diluted with EtOAc (200 mL) and washed pH 4.0 buffer (3×30 mL), water (2×30 mL), brine (30 mL), dried ($MgSO_4$) and purified by a Biotage 40 M column (eluted with 0% to 5% MeOH in $CH_2Cl_2$) to supply Compound 10 as an opaque glass (0.48 g, 50%) $^1H$ NMR (methanol-$d_4$) δ 0.80–1.10 (m, 2H), 1.03 (s, 9H), 1.17 (s, 2H), 1.27 (s, 9H), 1.38–1.41 (m, 1H), 1.83–1.85 (m, 1H), 2.15–2.20 (m, 1H), 2.35–2.40 (m, 1H), 2.60–2.70 (m, 1H), 2.84 (bs, 1H), 3.93 (s, 3H), 4.08–4.10 (m, 1H), 4.25 (s, 1H), 4.50–4.55 (m, 2H), 5.07 (d, J=10.1 Hz, 1H), 5.25 (d, J=17.1 Hz, 1H), 5.53 (m, 1H), 5.77–5.84 (m, 1H), 7.05–7.07 (m, 1H), 7.23 (s, 1H), 7.37 (d, J=2 Hz, 1H), 7.47–7.55 (m, 3H), 8.04–8.07 (m, 3H); LC-MS (retention time: 1.55, Method A), MS m/z 790 (M$^+$+1). HRMS m/z (M+H)$^+$ calcd for $C_{41}H_{52}N_5SO_9$: 790.3486, found 790.3505.

This coupling procedure may be used to prepare N-acylsulfonamides of tripeptide acids containing either a vinyl Acca or ethyl Acca P1 moiety.

EXAMPLE 14

Compound 11, BOCNH-P3(L-t-BuGly)-P2 [(4R)-(2-phenyl-7-methoxyquinoline-4-oxo)-S-proline)]-P1(1R,2S Vinyl Acca)-CONHSO$_2$Cyclobutane or alternate designation (1R,2S) P1 diastereomer of {1-[2-(1-Cyclobutanesulfonylaminocarbonyl-2-vinylcyclopropylcarbamoyl)-4-(7-methoxy-2-phenylquinolin-4-yloxy)-pyrrolidine-1-carbonyl]-2,2-dimethylpropyl}-carbamic acid tert-butyl ester, shown below, was prepared as described in Steps 14a–b.

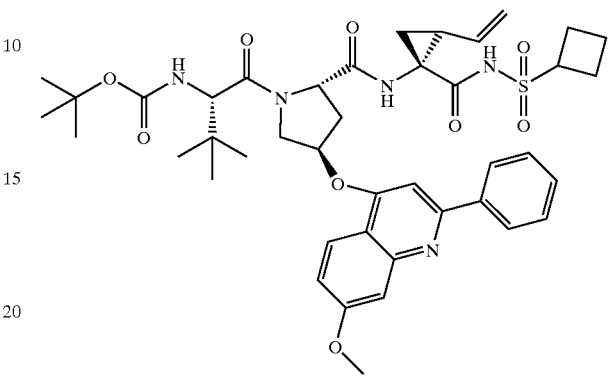

Step 14a: Preparation of Cyclobutyl Sulfonamide

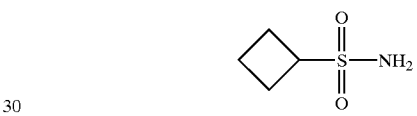

To a solution of 5.0 g (37.0 mmol) of cyclobutyl bromide in 30 mL of anhydrous diethyl ether ($Et_2O$) cooled to −78° C. was added 44 mL (74.8 mmol) of 1.7M tert-butyl lithium in pentanes and the solution slowly warmed to −35° C. over 1.5 h. This mixture was cannulated slowly into a solution of 5.0 g (37.0 mmol) freshly distilled sulfuryl chloride in 100 mL of hexanes cooled to −40° C., warmed to 0° C. over 1 h and carefully concentrated in vacuo. This mixture was redissolved in $Et_2O$, washed once with some ice-cold water, dried ($MgSO_4$) and concentrated carefully. This mixture was redissolved in 20 mL of THF, added dropwise to 500 mL of saturated $NH_3$ in THF and was allowed to stir overnite. The mixture was concentrated in vacuo to a crude yellow solid and was recrystallized from the minimum amount of $CH_2Cl_2$ in hexanes with 1–2 drops of MeOH to afford 1.90 g (38%) of cyclobutylsulfonamide as a white solid. $^1H$ NMR (CDCl$_3$) δ 1.95–2.06 (m, 2H), 2.30–2.54 (m, 4H), 3.86 (p, J=8 Hz, 1H), 4.75 (brs, 2H); $^{13}C$ NMR (CDCl$_3$) δ 16.43, 23.93, 56.29. HRMS m/z (M−H)$^-$ calcd for $C_4H_8NSO_2$: 134.0276, found 134.0282.

Step 14b: Preparation of Compound 11. Following the procedure of Step 13b, 100 mg (0.146 mmol) of the product of Step 12e was reacted with 33.1 mg (0.20 mmol) of CDI, 27.6 mg (0.20 mmol) of cyclobutylsulfonamide and 31 μL (0.20 mmol) of DBU to afford 84.1 mg (72%) of Compound 11 as a foam. LC/MS rt-min (MH$^+$): 1.62 (804) (method D). $^1H$ NMR: (methanol-$d_4$, 300 MHz) δ 1.03, 1.04 (2s, 9H), 1.27, 1.30 (2s, 9H), 1.33–1.43 (m, 1H), 1.80–2.50 (m, 11H), 2.66–2.80 (m, 1H), 3.71–3.88 (m, 1H), 3.92, 3.94 (2s, 3H), 4.00–4.13 (m, 2H), 4.51–4.59 (m, 2H), 4.97–5.04 (m, 1H), 5.54 (m, 1H), 5.74–5.92 (m, 1H), 7.24 (s, 1H), 7.36–7.38 (m, 1H), 7.45–7.55 (m, 3H), 8.04–8.11 (m, 3H).

EXAMPLE 15

Compound 12, BOCNH-P3(L-t-BuGly)-P2[(4R)-(2-phenyl-7-methoxyquinoline-4-oxo)-S-proline)]-P1(1R,2S Vinyl Acca)-CONHSo₂Cyclopentane or alternate designation (1R,2S) P1 diastereomer of {1-[2-(1-Cyclopentanesulfonylaminocarbonyl-2-vinylcyclopropyl-carbamoyl)-4-(7-methoxy-2-phenylquinolin-4-yloxy)-pyrrolidine-1-carbonyl]-2,2-dimethylpropyl}carbamic acid tert-butyl ester, shown below, was prepared as described in Steps 15a–b.

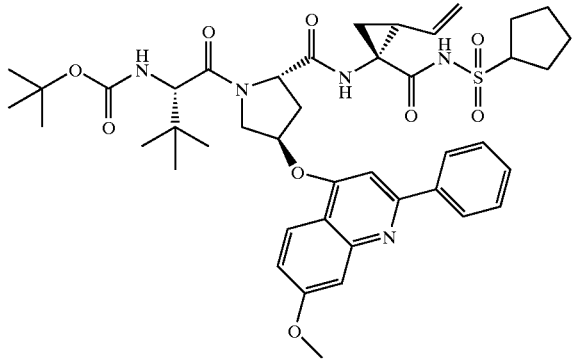

Step 15a: Preparation of Cyclopentyl Sulfonamide

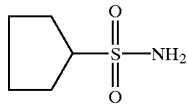

A solution of 18.5 mL (37.0 mmol) of 2M cyclopentylmagnesium chloride in ether was added dropwise to a solution of 3.0 mL (37.0 mmol) freshly distilled sulfuryl chloride (obtained from Aldrich) in 100 mL of hexanes cooled to −78° C. The mixture was warmed to 0° C. over 1 h and was then carefully concentrated in vacuo. This mixture was redissolved in Et₂O (200 mL), washed once with some ice-cold water (200 mL), dried (MgSO₄) and concentrated carefully. This mixture was redissolved in 35 mL of THF, added dropwise to 500 mL of saturated NH₃ in THF and was allowed to stir overnite. The mixture was concentrated in vacuo to a crude yellow solid, the residue filtered through 50 g of silica gel using 70% EtOAc-hexanes as the eluent and the solution was then concentrated. The residue was recrystallized from the minimum amount of CH₂Cl₂ in hexanes with 1–2 drops of MeOH to afford 2.49 g (41%) of cyclopentylsulfonamide as a white solid. $^1$H NMR (CDCl₃) δ 1.58–1.72 (m, 2H), 1.74–1.88 (m, 2H), 1.94–2.14 (m, 4H), 3.48–3.59 (m, 1H), 4.80 (bs, 2H); $^{13}$C NMR (CDCl₃) δ 25.90, 28.33, 63.54; MS m/e 148 (M−H)⁻.

Step 15b: Preparation of Compound 12. Following the procedure of Step 13b, 60 mg (0.087 mmol) of the product of Step 12e was reacted with 19.8 mg (0.122 mmol) of CDI, 18 mg (0.122 mmol) of cyclopentylsulfonamide and 18 μL (0.122 mmol) of DBU to afford 45.1 mg (63%) of Compound 12 as a foam. $^1$H NMR (Methanol-d₄) δ 1.03 (s, 9H), 1.29 (s, 9H), 1.37–1.43 (m, 1H), 1.55–2.09 (m, 9H), 2.15–2.22 (m, 1H), 2.29–2.39 (m, 1H), 2.63–2.70 (m, 1H), 3.43–3.53 (m, 1H), 3.94 (s, 3H), 4.04–4.15 (m, 1H), 4.23–4.30 (m, 1H), 4.47–4.57 (m, 2H), 5.08 (d, J=10.2 Hz, 1H), 5.25 (d, J=16.5 Hz. 1H), 5.52 (m, 1H), 5.70–5.80 (m, 1H), 6.54 (d, J=9 Hz, 1H), 7.05 (dd, J=9.2, 2.2 Hz. 1H), 7.37 (d, J=2.2 Hz, 1H), 7.45–7.55 (m, 3H), 8.00–8.06 (m, 3H). LC-MS (retention time: 1.66, Method A). MS m/z 818 (M+1)⁺; 816 (M−1)⁻.

EXAMPLE 16

Compound 13, BOCNH-P3 (L-t-BuGly)-P2 [(4R)-(2-phenyl-7-methoxyquinoline-4-oxo)-S-proline)]-P1(1R,2S Vinyl Acca)-CONHSo₂Cyclohexane or alternate designation (1R,2S) P1 diastereomer of {1-[2-(1-Cyclohexanesulfonylaminocarbonyl-2-vinylcyclopropyl-carbamoyl)-4-(7-methoxy-2-phenylquinolin-4-yloxy)-pyrrolidine-1-carbonyl]-2,2-dimethylpropyl}carbamic acid tert-butyl ester, shown below, was prepared as described in Steps 16a–b.

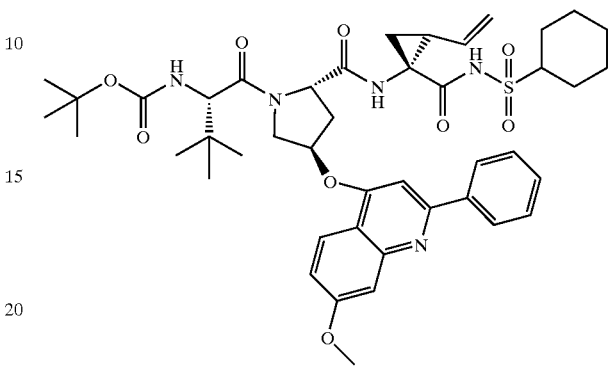

Step 16a: Preparation of Cyclohexyl Sulfonamide

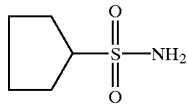

A solution of 18.5 mL (37.0 mmol) of 2M cyclohexyl-magnesium chloride (TCI Americas) in ether was added dropwise to a solution of 3.0 mL (37.0 mmol) freshly distilled sulfuryl chloride in 100 mL of hexanes cooled to −78° C. The mixture was warmed to 0° C. over 1 h and was then carefully concentrated in vacuo. This mixture was redissolved in Et₂O (200 mL), washed once with some ice-cold water (200 mL), dried (MgSO₄) and concentrated carefully. This mixture was redissolved in 35 mL of THF, added dropwise to 500 mL of saturated NH₃ in THF and was allowed to stir overnite. The mixture was concentrated in vacuo to a crude yellow solid, the residue filtered through 50 g of silica gel using 70% EtOAc-hexanes as the eluent and was concentrated. The residue was recrystallized from the minimum amount of CH₂Cl₂ in hexanes with 1–2 drops of MeOH to afford 1.66 g (30%) of cyclohexylsulfonamide as a white solid: $^1$H NMR (CDCl₃) δ 1.11–1.37 (m, 3H), 1.43–1.56 (m, 2H), 1.67–1.76 (m, 1H), 1.86–1.96 (m, 2H), 2.18–2.28 (m, 2H), 2.91 (tt, J=12, 3.5 Hz, 1H), 4.70 (bs, 2H); $^{13C}$H NMR (CDCl₃) δ 25.04, 25.04, 26.56, 62.74; MS m/e 162 (M−1)⁻.

Step 16b: Preparation of Compound 13. Following the procedure of Step 13b, 60 mg (0.087 mmol) of the product of Step 12e was reacted with 19.8 mg (0.122 mmol) of CDI, 20 mg (0.122 mmol) of cyclohexylsulfonamide and 18 μL (0.122 mmol) of DBU to afford 33.2 mg (46%) of Compound 13 as a foam. $^1$H NMR (Methanol-d₄) δ 1.03 (s, 9H), 1.14–1.55 (m, 6H), 1.29 (s, 9H), 1.59–1.73 (m, 1H), 1.73–1.92 (m, 3H), 2.04–2.23 (m, 3H), 2.30–2.49 (m, 1H), 2.63–2.69 (m, 1H), 3.41 (m, 1H), 3.94 (s, 3H), 4.04–4.13 (m, 1H), 4.24–4.28 (m, 1H), 4.47–4.56 (m, 2H), 5.05–5.09 (m, 1H), 5.21–5.28 (m, 1H), 5.51 (m, 1H), 5.69–5.84 (m, 1H), 7.05 (dd, J=9, 2 Hz, 1H), 7.18 (s, 1H), 7.37 (d, J=2.2 Hz, 1H), 7.47–7.55 (m, 3H), 7.99–8.07 (m, 3H) LC-MS (retention time: 1.72, method A), 832 (M⁺+H). MS m/z 832 (M+1)⁺; 830 (M−1)⁻.

EXAMPLE 17

Compound 14, BOCNH-P3(L-t-BuGly)-P2[(4R)-(2-phenyl-7-methoxyquinoline-4-oxo)-S-proline)]-P1(1R,2S Vinyl Acca)-CONHSO$_2$(neopentane) or alternate designation (1R,2S) P1 diastereomer of {1-[2-[1-(2,2-Dimethylpropane-1-sulfonylaminocarbonyl)-2-vinylcyclopropylcarbamoyl]-4-(7-methoxy-2-phenylquinolin-4-yloxy)pyrrolidine-1-carbonyl]-2,2-dimethylpropyl}-carbamic acid tert-butyl ester, shown below, was prepared as described in Steps 17a–b.

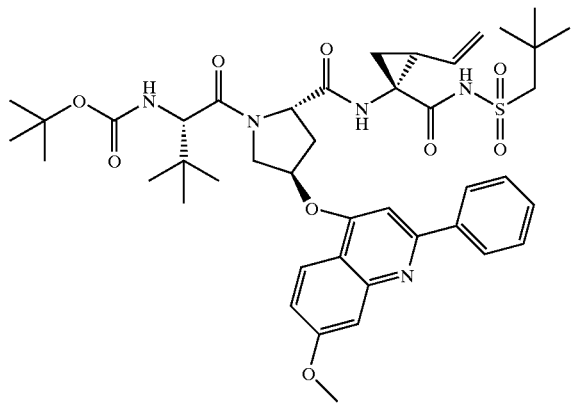

Step 17a: Preparation of Neopentylsulfonamide

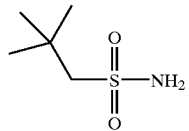

Following the procedure of Step 16a, 49 mL (37 mmol) of 0.75M neopentylmagnesium chloride (Alfa) in ether was converted to 1.52 g (27%) of neopentylsulfonamide as a white solid. $^1$H NMR (CDCl$_3$) δ 1.17 (s, 9H), 3.12 (s, 2H), 4.74 (brs, 2H); $^{13}$C NMR (CDCl$_3$) δ 29.46, 31.51, 67.38; MS m/e 150 (M−1)$^-$.

Step 17b: Preparation of Compound 14. Following the procedure of Step 13b, 60 mg (0.087 mmol) of the product of Step 12e was reacted with 19.8 mg (0.122 mmol) of CDI, 13.2 mg (0.096 mmol) of neopentylsulfonamide and 18 μL (0.122 mmol) of DBU to afford 39.1 mg (55%) of Compound 14 as a foam. $^1$H NMR (Methanol-d$_4$, ~1/2 rotamers) δ 1.04 (, 9H), 1.13, 1.15 (two s (rotomers), 9H), 1.29 (s, 9H), 1.37–1.44 (m, 1H), 1.79, 1.88 (two dd (rotomers), J=8, 5 Hz, 1H), 2.15–2.25 (m, 1H), 2.28–2.41 (m, 1H), 2.61–2.72 (m, 1H), 3.14 (d, J=13.9 Hz, 1H), 3.52 (d, J=13.9 Hz, 1H), 3.94 (s, 3H), 4.06–4.15 (m, 1H), 4.24–4.29 (m, 1H), 4.47–4.53 (m, 2H), 5.10 (d, J=10.6 Hz, 1H), 5.25, 5.29 (two d (rotomers), J=17 Hz, 1H), 5.53 (m, 1H), 5.70–5.86 (m, 1H), 6.54, 6.64 (two d (rotomers), J=9 Hz, 1H), 7.06 (d, J=9 Hz, 1H), 7.19 (s, 1H), 7.37 (d, J=2.2 Hz, 1H), 7.45–7.55 (m, 3H), 8.00–8.06 (m, 3H). LC-MS (retention time: 1.73, method A), 820 (M$^+$+H). MS m/z 820 (M+1)$^+$; 818 (M−1).

EXAMPLE 18

Compound 15, BOCNH-P3(L-t-BuGly)-P2[(4R)-(2-phenyl-7-methoxyquinoline-4-oxo)-S-proline)]-P1(1R,2S Vinyl Acca)-CONHSO$_2$ (CH$_2$cyclobutane) or alternate designation (1R,2S) P1 diastereomer of {1-[2-(1-Cyclobutylmethanesulfonylaminocarbonyl-2-vinylcyclopropylcarbamoyl)-4-(7-methoxy-2-phenylquinolin-4-yloxy)pyrrolidine-1-carbonyl]-2,2-dimethylpropyl}-carbamic acid tert-butyl ester, shown below, was prepared as described in Steps 18a–b.

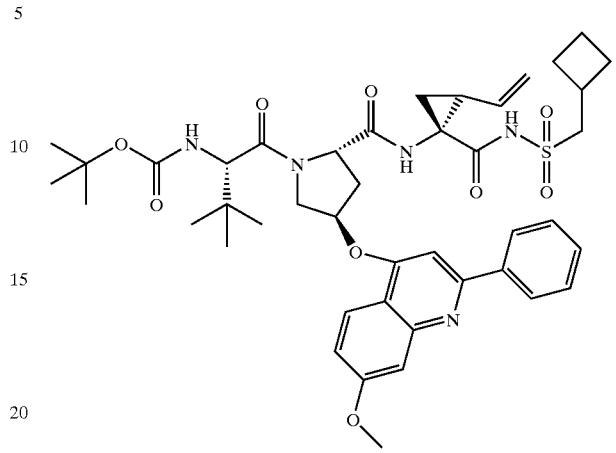

Step 18a: Preparation of cyclobutylcarbinylsulfonamide

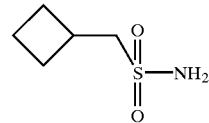

A solution of 12.3 g (83 mmol) of cyclobutylcarbinyl bromide (Aldrich) and 13.7 g (91 mmol) of sodium iodide in 150 mL of acetone was refluxed overnite and then cooled to rt. The inorganic solids were filtered off and the acetone and cyclopropylcarbinyl iodide (8.41 g, 46%) distilled off at ambient and 150 torr at 80° C., respectively.

A solution of 4.0 g (21.98 mmol) of cyclobutyl carbinyl iodide in 30 mL of anhydrous diethyl ether (Et$_2$O) cooled to −78° C. was cannulated into a solution of 17 mL (21.98 mmol) of 1.3M sec-butyl lithium in cyclohexanes and the solution was stirred for 5 min. To this mixture was cannulated a solution of 3.0 g (21.98 mmol) of freshly distilled sulfuryl chloride in 110 mL of hexanes cooled to −78° C., the mixture warmed to rt over 1 h and was then carefully concentrated in vacuo. This mixture was redissolved in Et$_2$O, washed once with some ice-cold water, dried (MgSO$_4$) and concentrated carefully. This mixture was redissolved in 30 mL of THF, added dropwise to 500 mL of saturated NH$_3$ in THF and was allowed to stir overnite. The mixture was concentrated in vacuo to a crude yellow solid and was recrystallized from the minimum amount of CH$_2$Cl$_2$ in hexanes with 1–2 drops of MeOH to afford 1.39 g (42%) of cyclobutyl carbinylsulfonamide as a white solid. $^1$H NMR (CDCl$_3$) δ 1.81–2.03 (m, 4H), 2.14–2.28 (m, 2H), 2.81–2.92 (m, 1H), 3.22 (d, J=7 Hz, 2H), 4.74 (brs, 2H); $^{13}$C NMR (CDCl$_3$) δ 19.10, 28.21, 30.64, 60.93; MS m/e 148 (M−1)$^-$.

Step 18b: Preparation of Compound 15. Following the procedure of Step 13b, 100 mg (0.146 mmol) of the product of Step 12e was reacted with 33.1 mg (0.204 mmol) of CDI, 30 mg (0.204 mmol) of cyclobutylcarbinyl sulfonamide and 31 μL (0.204 mmol) of DBU to afford 33 mg (28%) of Compound 15 as a foam. $^1$H NMR (Methanol-d$_4$, rotamers~2/3) δ 1.04, 1.05 (two s (rotamers) 9H), 1.27, 1.30 (two s (rotamers) 9H), 1.37–1.40 (m, 1H), 1.73–1.97 (m, 5H), 2.06–2.24 (m, 3H), 2.35–2.49 (m, 1H), 2.65–2.89 (m, 2H), 3.17–3.45 (m, 2H), 3.92, 3.93 (two s (rotamers) 3H), 4.04, 4.10 (two d (rotamers) J=12 Hz, 1H), 4.23–4.28 (m, 1H), 4.49–4.57 (m, 2H), 5.03–5.08 (m, 1H), 5.20–5.27 (m, 1H), 5.53 (m, 1H) 5.77–5.88 (m, 1H), 6.54, 6.62 (two d (rotomers), J=8 Hz, 1H), 7.06 (d, J=9 Hz, 1H), 7.23 (s, 1H), 7.37 (s, 1H), 7.45–7.54 (m, 3H), 8.03–8.09 (m, 3H). LC-MS (retention time: 1.73, method B), 818 (M$^+$+H).

EXAMPLE 19

Compound 16, BOCNH-P3(L-t-BuGly)-P2[(4R)-(2-phenyl-7-methoxyquinoline-4-oxo)-S-proline)]-P1(1R,2S Vinyl Acca)-CONHSO$_2$(CH$_2$cyclopropane) or alternate designation (1R,2S) P1 diastereomer of {1-[2-(1-Cyclopropylmethanesulfonylaminocarbonyl-2-vinylcyclopropylcarbamoyl)-4-(7-methoxy-2-phenylquinolin-4-yloxy)pyrrolidine-1-carbonyl]-2,2-dimethylpropyl}-carbamic acid tert-butyl ester, shown below, was prepared as described in Steps 19a–b.

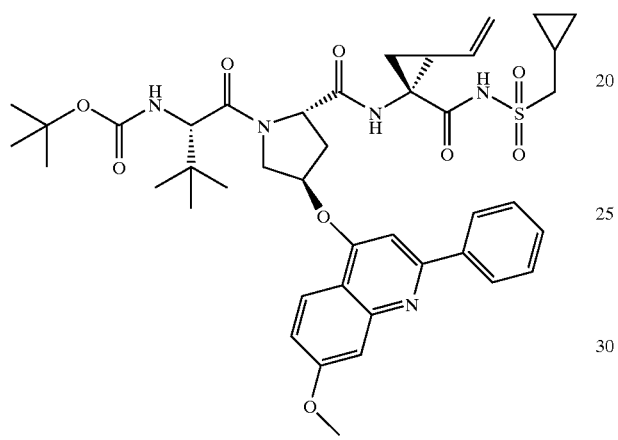

Step 19a: Preparation of Cyclopropylcarbinylsulfonamide

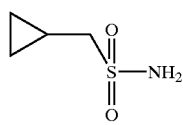

Using the procedure of Step 18a cyclopropylcarbinyl sulfonamide was prepared from cyclopropylcarbinyl bromide (Aldrich) (see also JACS 1981, p.442–445). $^1$H NMR (CDCl$_3$) δ 0.39–0.44 (m, 2H), 0.67–0.76 (m, 2H), 1.13–1.27 (m, 1H), 3.03 (d, J=7.3 Hz, 2H), 4.74 (brs, 2H); $^{13}$C NMR (CDCl$_3$) δ 4.33, 5.61, 59.93; MS m/e 134 (M−1)$^−$.

Step 19b: Preparation of Compound 16. Following the procedure of Step 13b, 108 mg (0.159 mmol) of the product of Step 12e was reacted with 36 mg (0.222 mmol) of CDI, 30 mg (0.222 mmol) of cyclopropylcarbinylsulfonamide and 33 μL (0.222 mmol) of DBU to afford 42 mg (33%) of Compound 16 as a foam. $^1$H NMR (Methanol-d$_4$, rotamers~2/3) δ 0.32–0.39 (m, 2H), 0.54–0.68 (m, 2H), 1.03 (s, 9H), 1.27, 1.29 (two s (rotomers), 9H), 1.08–1.41 (m, 1H), 1.55–1.86 (m, 2H), 2.10–2.25 (m, 1H), 2.35–2.51 (m, 1H), 2.62–2.80 (m, 1H), 3.07–3.15 (m, 1H), 3.37–3.44 (m, 1H), 3.94, 3.94 (two s (rotomers), 3H), 4.03–4.15 (m, 1H), 4.22–4.28 (m, 1H), 4.51–4.60 (m, 2H), 4.99–5.08 (m, 1H), 5.18–5.28 (m, 1H), 5.55 (m, 1H), 5.77–5.94 (m, 1H), 7.06 (d, J=8.4 Hz, 1H), 7.25 (s, 1H), 7.38 (s, 1H), 7.46–7.56 (m, 3H), 8.03–8.12 (m, 3H). LC-MS (retention time: 1.68, method D), 804 (M$^+$+H). MS m/e 804 (M+1)$^+$; 802 (m−1)$^−$.

EXAMPLE 20

Compound 17, BOCNH-P3(L-t-BuGly)-P2[(4R)-(2-phenyl-7-methoxyquinoline-4-oxo)-S-proline)]-P1(1R,2S Vinyl Acca)-CONHSO$_2$(4-bromobenzenesulfonamide) or alternate designation (1R,2S) P1 diastereomer of {1-[2-[1-(4-bromobenzenesulfonylaminocarbonyl-2-vinylcyclopropylcarbamoyl)-4-(7-methoxy-2-phenylquinolin-4-yloxy)pyrrolidine-1-carbonyl]-2,2-dimethylpropyl}-carbamic acid tert-butyl ester, shown below, was prepared as follows.

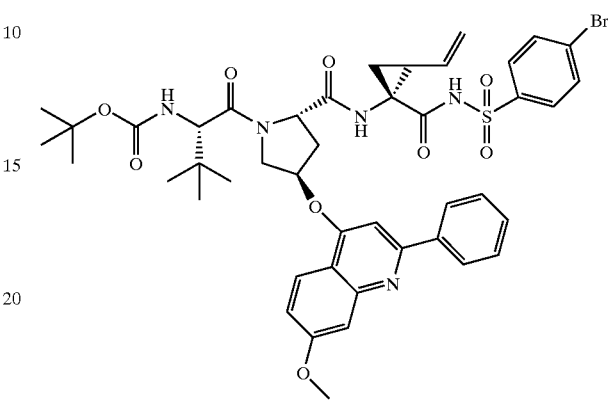

To a solution of the product of Step 12e (0.035 g, 0.05 mmol) in THF (2 mL) was added CDI (0.0165 g, 0.13 mmol) and the resulting solution was refluxed for 30 min and allowed to cool down to rt. To this solution was added 4-bromophenylsulfonamide (0.0482 g, 0.20 mmol), prepared by treatment of commercially available 4-bromosulfonyl chloride with saturated ammonia in THF, was added in one portion before the addition of a solution of DBU (0.0194 mL, 0.13 mmol). The reaction was stirred for 18 h, diluted with EtOAc (100 mL) and washed pH 4.0 buffer (10 mL), water (10 mL), brine (10 mL), dried (MgSO$_4$) and purified by a Isco 10 g column column (eluted with 0% to 15% MeOH in CH$_2$Cl$_2$) to provide the product in need of further purification. The residue was purified using one 20×40 cM 1000μ PTLC plate from Analtech to supply Compound 17 as a foam (0.0357 g, 79%): $^1$H NMR (Methanol-d$_4$) δ 1.03 (s, 9H) 1.26, 1.30 (two s (rotomers), 9H), 1.43 (m, 1H), 1.74 (dd, J=8, 5 Hz, 1H), 2.02–2.21 (m, 1H), 2.32–2.47 (m, 1H), 2.58–2.66 (m, 1H), 3.92, 3.93 (two s (rotomers), 3H), 4.03–4.10 (m, 1H), 4.24 (m, 1H), 4.46–4.58 (m, 2H), 4.87–4.91 (m, 1H), 5.13 (d, J=17 Hz, 1H), 5.39–5.46 (m, 1H), 5.56–5.88 (m, 1H), 7.04 (dd, J=9.2, 2.2 Hz, 1H), 7.20–7.18 (m, 1H), 7.35–7.37 (m, 1H), 7.44–7.58 (m, 5H), 7.68–7.79 (m, 2H), 8.00–8.10 (m, 3H). LC-MS (retention time: 1.77, method A). HRMS m/z (M$^+$+H) calcd for C$_{44}$H$_{51}$SBrN$_5$O$_9$: 904.2591, found 904.2580.

This method may also be used as a general procedure to prepare aryl N-acylsulfonamides.

EXAMPLE 21

Compound 18, (1R,2S) P1 diastereomer of {1-[2-(1-Cyclopropanesulfonylaminocarbonyl-2-vinylcyclopropyl-carbamoyl)-4-(7-methoxy-2-phenyl-quinolin-4-yloxy)- pyrrolidine-1-carbonyl]-2,2-dimethyl-propyl}carbamic acid tetrahydrofuran-3(S)-yl ester, shown below, was prepared as described in Steps 21a–b.

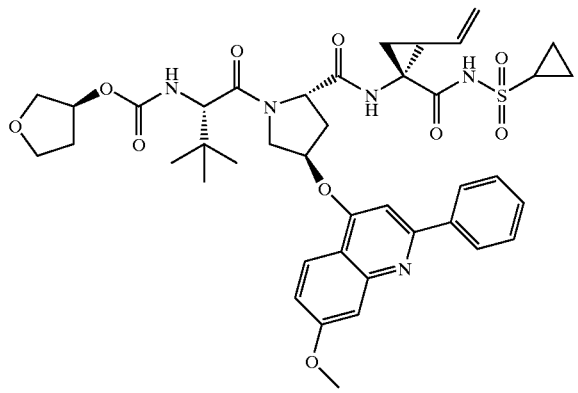

Step 21a: Preparation of Chloroformates

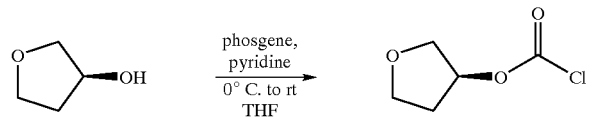

This procedure was used for the preparation of non-commercially available chloroformates. To a solution of 5.96 g (67.6 mmol) of commercially available reagents (S)-3-hydroxytetrahydrofuran and pyridine (5.8 mL; 72 mmol) in THF (150 mL) cooled to 0° C. was added a 1.93 M solution of phosgene in toluene (48 mL, 92.6 mmol over 10 min under argon. The resulting solution was allowed to warm to rt over 2 h, the resulting solid filtered, and the mother liquor carefully concentrated in vacuo at room temperature until theoretical mass was obtained. The resulting residue was dissolved in 100 mL of THF to prepare a 0.68M stock solution of 3(S)-oxo-tetrahydrofuran chloroformate that could be stored in the freezer until use. In analogous fashion, other commercially available alcohols could be converted to 0.68M stock solutions of the corresponding chloroformates.

Step 21b: Preparation of Compound 18. A solution of 3.5 grams (4.90 mmol)of the product of Step 12e (1R,2S) P1 diastereomer of (1-{[1–2-tert-Butoxycarbonylamino-3,3-dimethylbutyryl)-4-(7-methoxy-2-phenylquinolin-4-yloxy) pyrrolidine-2-carbonyl]amino}-2-vinylcyclopropanecarboxylic acid ethyl ester) was treated with 170 mL (680 mmol) of 4N HCl in dioxane for 2 h and then concentrated in vacuo to afford ~3.37 g (~100%). $^1$H NMR (methanol-$d_4$) δ 1.18 (s, 9H), 1.25 (t, J=7.0 Hz, 1H), 1.44 (dd, J=9.1, 5.1 Hz, 1H), 1.72 (dd, J=8.1, 5.5 Hz, 1H), 2.18–2.26 (m, 1H), 2.46–2.53 (m, 1H), 2.84 (dd, J=14, 7 Hz, 1H), 4.06 (s, 3H), 4.09–4.27 (m, 4H), 4.53 (d, J=12 Hz, 1H), 4.76–4.81 (m, 1H), 5.10 (dd, J=10, 1.5 Hz, 1H), 5.27 (dd, J=17.2, 1.5 Hz, 1H), 5.72–5.84 (m, 1H), 5.89 (m, 1H), 7.46 (dd, J=9.2, 2 Hz, 1H), 7.64 (m, 2H), 7.68–7.79 (m, 3H), 8.08–8.16 (m, 2H), 8.42 (d, J=9 Hz, 1H); $^{13}$C NMR (methanol-$d_4$) δ 14.62, 23.22, 26.70, 35.15, 35.89, 36.16, 40.90, 55.30, 57.06, 60.44, 60.86, 62.46, 81.47, 100.56, 102.42, 116.03, 118.04, 121.92, 126.60, 130.14, 130.77, 133.24, 133.89, 135.18, 143.58, 158.19, 166.57, 167.87, 168.59, 171.52, 173.87. LC-MS (retention time: 1.41, Method D), MS m/z 615 (M$^+$+1). HRMS m/z (M+H)$^+$ calcd for $C_{35}H_{43}N_4O_6$: 615.3183, found 615.3185.

To a slurry of 200 mg (0.29 mmol) of this HCl salt and 220 μL (0.93 mmol) of Et$_3$N in 4 mL of THF, was added 0.93 mL (0.63 mmol) of a 0.68M solution of 3(S)-oxo-tetrahydrofuran chloroformate, and the mixture stirred overnite. The mixture was concentrated in vacuo and the residue chromatographed over two 1000μ PTLC plates from Analtech (each 20×40 cm, eluted with 70% EtOAc-Hexanes) to afford 115 mg (56%) of the desired P4 carbamate [Tetrahydrofuran-3(S)-yl-O(C=O)]N-P3(L-t-BuGly)-P2[(4R)-(2-phenyl-7-methoxyquinoline-4-oxo)-S-proline]-P1 (1R,2S Vinyl Acca)-CO$_2$Et. $^1$H NMR (CDCl$_3$) δ 1.02 (S,9H), 1.22 (t, J=7 Hz, 3H), 1.38–1.43 (m, 1H), 1.50–2.25 (m, 4H), 2.33–2.45 (m, 1H), 2.65 (dd, J=13, 7 Hz, 1H), 3.47–4.25 (m, 8H), 4.34–4.49 (m, 1H), 4.62 (m, 1H), 4.72 (m, 1H), 5.08 (d, J=10 Hz, 1H), 5.25 (d, J=17 Hz, 1H), 5.45 (m, 1H), 5.71–5.83 (m, 1H), 6.97–7.09 (m, 1H), 7.17 (s, 1H), 7.35 (s, 1H), 7.45–7.55 (m, 3H), 7.89–8.05 (m, 3H); $^{13}$C NMR (CDCl$_3$) δ 14.64, 23.27, 26.92, 33.72, 35.01, 35.97, 36.09, 36.22, 40.87, 54.99, 55.98, 60.32, 61.03, 62.380, 67.77, 73.90, 76.68, 77.99, 100.03, 107.52, 116.48, 118.01, 119.15, 124.23, 129.07, 128.96, 129.75, 130.52, 135.18, 141.29, 152.18, 158.08, 161.10, 161.80, 163.00, 171.51, 172.84, 174.55. LC-MS (retention time: 1.35, method B), MS m/z 729.3 (M$^+$+1).

To a solution of 115 mg (0.164 mmol) in 7.1 mL of 80% THF-MeOH, was added a solution of 40 mg (1.0 mmol) of LiOH.H$_2$O in 2.8 mL of H$_2$O. The mixture was stirred 1 day, acidified to pH 7 (using 2N HCl) and was concentrated in vacuo until only the water layer remained. The solution was acidified to pH=4 (using 2N HCl) and was partitioned repeatedly (3×50 mL) with EtOAc. The combined EtOAc layers (150 mL) were dried (MgSO$_4$) and concentrated to afford 112 mg (~100%) of the desired carboxylic acid, [Tetrahydrofuran-3(S)-yl-O(C=O)]N-P3(L-t-BuGly)-P2 [(4R)-(2-phenyl-7-methoxyquinoline-4-oxo)-S-proline]-P1 (1R,2S Vinyl Acca)-CO$_2$H, as a foam. $^1$H NMR (Methanol-$d_4$) δ 1.02, 1.03 (two s (rotamers), 9H), 1.42–1.45 (m, 1H), 1.58–1.65 (m, 1H), 1.67–1.70 (m, 1H), 1.82–1.90 (m, 1H), 2.15–2.21 (m, 1H), 2.46–2.51 (m, 1H), 2.70–2.74 (m, 1H), 3.59–3.90 (m, 4H), 3.95 (s, 3H), 4.05 (dd, J=12, 3 Hz, 1H), 4.23–4.26 (m, 1H), 4.52 (d, J=12 Hz, 1H), 4.62–4.77 (m, 2H), 5.07–5.10 (m, 1H), 5.23–5.27 (m, 1H), 5.57 (m, 1H), 5.80–5.88 (m, 1H), 7.09–7.15 (m, 1H), 7.27 (m, 1H), 7.40 (m, 1H), 7.49–7.56 (m, 3H), 8.04–8.09 (m, 3H); LC-MS (retention time: 1.48, method D): MS m/e 701 (M$^+$+1).

A solution of [Tetrahydrofuran-3(S)-yl-O(C=O)]N-P3 (L-t-BuGly)-P2[(4R)-(2-phenyl-7-methoxy-quinoline-4-oxo)-S-pro-line]-P1(1R,2S Vinyl Acca)-CO$_2$H (0.156 g, 0.223 mmol) and CDI (0.0471 g, 0.291 mmol) in THF (5.8 mL) was refluxed for 40 min and allowed to cool down to rt. Cyclopropylsulfonamide (0.0533 g, 0.447 mmol), was added in one portion before the addition of a solution of DBU (0.0422 mg, 0.291 mmol). The reaction was stirred for 18 h, diluted with EtOAc (100 mL) and washed with pH 4.0 buffer (3×30 mL), water (20 mL), brine (20 mL), dried (MgSO$_4$) and purified by a Biotage 40 M column (eluted with 0% to 4% MeOH in CH$_2$Cl$_2$) to supply the desired product [Tetrahydrofuran-3(S)-yl-O(C=O)]N-P3(L-t-BuGly)-P2[(4R)-(2-phenyl-7-methoxyquinoline-4-oxo)-S-proline]-P1(1R,2S Vinyl Acca)-CONHSO$_2$-Cyclopropane or alternate designation, Compound 18, (1R,2S) P1 diastereomer of {1-[2-(1-Cyclopropanesulfonylaminocarbonyl-2-vinylcyclopropylcarbamoyl)-4-(7-methoxy-2-phenyl-quinolin-4-yloxy)-pyrrolidine-1-carbonyl]-2,2-dimethyl-propyl}carbamic acid tetrahydrofuran-3(S)-yl ester as a foam (0.117 g, 65%). $^1$H NMR (Methanol-$d_4$) δ 1.02–1.07 (m, 11H), 1.22–1.28 (m, 2H), 1.42–1.45 (m, 1H), 1.57–1.64 (m, 1H), 1.80–1.92 (m, 2H), 2.19–2.27 (m, 1H), 2.31–2.41 (m, 1H), 2.68 (dd, J=14, 7 Hz, 1H), 2.90–2.96 (m, 1H), 3.61–3.81 (m, 4H), 3.95 (s, 3H), 4.07–4.11 (m, 1H), 4.25–4.29 (m, 1H), 4.49–4.60 (m, 2H), 4.72–4.76 (m, 1H), 5.10–5.13 (m, 1H), 5.27–5.33 (m, 1H), 5.59 (m, 1H), 5.72–5.80 (m, 1H), 7.10–7.14 (m, 1H), 7.28 (m, 1H), 7.41 (m, 1H), 7.49–7.58 (m, 3H), 8.05–8.08 (m, 3H); LC-MS (retention time: 1.37, method D), MS m/z 804 (M$^+$+1).

This procedure of Example 21 can generally be used to prepare carbamate N-acylsulfonamides of the present invention.

EXAMPLE 22

Compound 19, [tert-Butyl-NH(C=O)]NH-P3(L-t-BuGly)-P2[(4R)-(2-phenyl-7-methoxyquinoline-4-oxo)-S-proline]-P1(1R,2S Vinyl Acca)-CONHSO$_2$Cyclopropane or alternate designation (1R,2S) P1 diastereomer of 1-[2-(3-tert-Butylureido)-3,3-dimethylbutyryl]-4-(7-methoxy-2-phenylquinolin-4-yloxy)pyrrolidine-2-carboxylic acid (1-cyclopropanesulfonylaminocarbonyl-2-vinylcyclopropyl)amide shown below, was prepared as described in Steps 22a–c.

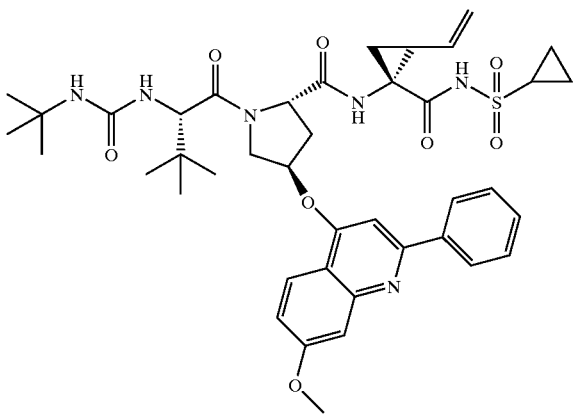

Step 22a: Preparation of [tert-Butyl-NH(C=O)]HN-P3 (L-t-BuGly)-P2[(4R)-(2-phenyl-7-methoxyquinoline-4-oxo)-S-proline]-P1(1R,2S Vinyl Acca)-CO$_2$Et. To a slurry of 175 mg (0.245 mmol) of NH$_2$-P3(L-t-BuGly)-P2[(4R)-(2-phenyl-7-methoxyquinoline-4-oxo)-S-proline]-P1(1R,2S Vinyl Acca)-CO$_2$Et dihydrochloride salt, and 139 μL (1.0 mmol) of Et$_3$N in 3 mL of THF, was added 57 μL (0.50 mmol) of commercially available tert-butyl isocyanate. The mixture stirred was overnite, diluted with 20 mL of pH 4.0 buffer and was partitioned with 4×50 mL portions of EtOAc. The combined organic layers were concentrated in vacuo, the residue chromatographed over a biotage 25 M column (eluted with 15% to 100% EtOAc/Hexanes to afford 152 mg (86%) of the titled product. $^1$H NMR (CDCl$_3$) δ 1.03 (s, 9H), 1.17 (s, 9H), 1.34–1.45 (m, 1H), 1.61–1.74 (m, 1H), 2.15–2.24 (m, 1H), 2.32–2.51 (m, 1H), 2.61–2.75 (m, 1H), 3.92 (m, 3H), 4.01–4.17 (m, 3H), 4.32 (m, 1H), 4.51–4.60 (m, 2H), 5.07 (d, J=11 Hz, 1H), 5.24 (d, J=17 Hz, 1H), 5.53 (m, 1H), 5.69–5.81 (m, 1H), 7.00–7.11 (m, 1H), 7.21 (m, 1H), 7.36 (m, 1H), 7.44–7.58 (m, 3H), 8.02–8.13 (m, 3H); LC-MS (retention time: 2.36, method A), MS m/z 714 (M$^+$+1).

Step 22b: Preparation of [tert-Butyl-NH(C=O)]HN-P3 (L-t-BuGly)-P2[(4R)-(2-phenyl-7-methoxyquinoline-4-oxo)-S-proline]-P1(1R,2S Vinyl Acca)-CO$_2$H. To a solution of 152 mg (0.21 mmol) of the product of Step 22a, in 9.4 mL of 80% THF-MeOH, was added a solution of 52 mg (1.3 mmol) of LiOH.H$_2$O in 3.9 mL of H$_2$O. The mixture was stirred 1 day, acidified to pH 7 (using 2N HCl) and was concentrated in vacuo until only the water layer remained. The solution was acidified to pH=4 (using 2N HCl) and was partitioned repeatedly (3×50 mL) with EtOAc. The combined EtOAc layers (150 mL) were dried (MgSO$_4$) and concentrated to afford 122 mg (85%) of the titled product as a foam. $^1$H NMR (Methanol-d$_4$) δ 1.01 (s, 9H), 1.30 (s, 9H), 1.38–1.42 (m, 1H), 1.81–2.28 (m, 2H), 2.22–2.64 (m, 2H), 3.94 (s, 3H), 4.12 (dd, J=12, 4 Hz, 1H), 4.34–4.41 (m, 1H), 4.51 (d, J=10 Hz, 1H), 4.69 (d, J=11 Hz, 1H), 4.79 (m, 1H), 5.08 (d, J=12 Hz, 1H), 5.21 (d, J=17 Hz, 1H), 5.33 (m, 1H), 5.57–5.72 (m, 1H), 6.95 (s, 1H), 7.05 (dd, J=9.2, 2.6 Hz, 1H), 7.40–7.53 (m, 4H), 8.01–8.03 (m, 2H), 8.09 (d, J=9.2 Hz, 1H). LC-MS (retention time: 1.37, method B) m/z 686 (M$^+$+1).

Step 22c: Preparation of Compound 19. A solution of the product of Step 22b (0.120 g, 0.0.175 mmol) and CDI (0.0368 g, 0.227 mmol) in THF (5.8 mL) was refluxed for 40 min and allowed to cool down to rt. Cyclopropylsulfonamide (0.0416 g, 0.349 mmol) was added in one portion before the addition of a solution of DBU (0.0345 mg, 0.227 mmol). The reaction was stirred for 18 h, diluted with EtOAc (100 mL) and washed with pH 4.0 buffer (3×30 mL), water (20 mL), brine (20 mL), dried (MgSO$_4$) and purified by a Biotage 40 M column (eluted with 0% to 4% MeOH in CH$_2$Cl$_2$) to supply Compound 19 as a foam (0.0872 g, 63%). $^1$H NMR (methanol-d$_4$) δ 1.04 (s, 9H), 1.17 (s, 9H), 1.15–1.31 (m, 4H), 1.40 (dd, J=9.5, 5.2 Hz, 1H), 1.86 (dd, J=8, 5 Hz, 1H), 2.16–2.22 (m, 1H), 2.30–2.37 (m, 1H), 2,65 (dd, J=14, 7, 1H), 2.90–2.95 (m, 1H), 3.94 (s, 3H), 4.11 (dd, J=11.7, 3.7 Hz, 1H), 4.35 (s, 1H), 4.50 (dd, J=10.4, 7 Hz, 1H), 4.57 (d, J=12 Hz, 1H), 5.09 (dd, J=10, 2 Hz, 1H), 5.26 (dd, J=17, 2 Hz, 1H), 5.56 (m, 1H), 5.70–5.77 (m, 1H), 7.07 (dd, J=9.2, 2 Hz, 1H), 7.25 (s, 1H), 7.38 (d, J=2 Hz, 1H), 7.48–7.55 (m, 3H), 8.04–8.06 (m, 2H), 8.10 (d, J=9.2 Hz, 1H). LC-MS (retention time: 1.51, method D) MS m/e 789 (M$^+$+1).

EXAMPLE 23

Compound 20: The (1R,2S) P1 diastereomer of 1-{2-[3-Cyclopropylmethyl-3-(3,3,3-trifluoropropyl)-ureido]-3,3-dimethylbutyryl}-4-(7-methoxy-2-phenyl-quinolin-4-yloxy)-pyrrolidine-2-carboxylic acid (1-cyclopropane-sulfonylaminocarbonyl-2-vinyl-cyclopropyl)amide, shown below, was prepared as described in Steps 23a–b.

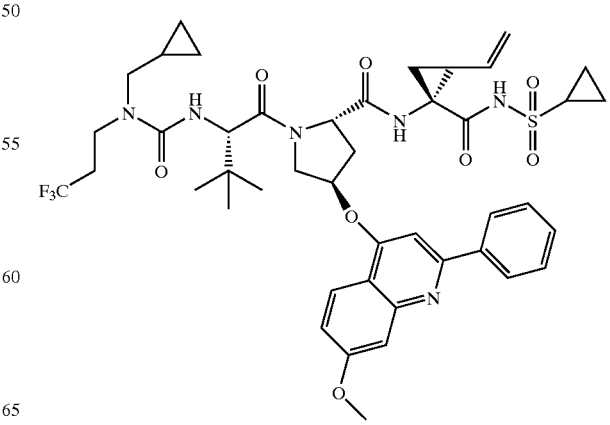

Step 23a: Preparation of cyclopropylmethyl-3,3,3-trifluoropropylamine hydrochloride

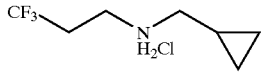

A stirred solution of 3,3,3-trifluoroacetic acid (9.7 mL, 110 mmoles) and N-hydroxysuccinimide (13.92 g, 1.1 equiv.) in $CH_2Cl_2$ (100 mL) at 0° C. was treated with EDAC (21.08 g, 1 equiv.). The mixture was allowed to warm to room temperature. After stirring overnight, the solvent was evaporated and the residue partitioned between EtOAc and water. The organic phase was washed with brine, dried over $MgSO_4$, and evaporated to give the crude active ester which was used without further purification (22.78 g, 92%). $^1$H-NMR δ ($CDCl_3$) 2.86 (s, 4H), 3.51 (m, 2H).

A stirred solution of the 3,3,3-trifluoroacetic acid N-hydroxysuccinimide active ester (12.98 g, 57.65 mmoles) in $CH_2Cl_2$ (80 mL) at 0° C. was treated with cyclopropylmethylamine (5.0 mL, 1 equiv.). The mixture was stirred at room temperature for 14 hours and then evaporated. The residue was partitioned between EtOAc and water. The organic phase was washed with water, brine, dried over $MgSO_4$, and evaporated to give the crude amide. This was dried under high vacuum for several hours and then, under a nitrogen atmosphere at 0° C., it was carefully treated with a 1M solution of borane in tetrahydrofuran (173 mL, 3 equiv., 173 mmol). The mixture was heated at reflux for 14 hours and then re-cooled to 0° C. MeOH 50 mL) was added very carefully to avoid excess foaming, and the mixture was heated at reflux for 5 hours. Upon re-cooling to 0° C., a solution of t-butylpyrocarbonate (17.62 g, 1.4 equiv.) in $CH_2Cl_2$ (25 mL) was added. The resulting mixture was stirred at room temperature overnight and then evaporated the residue was partitioned between EtOAc and water. The organic was washed with water, brine, dried over $MgSO_4$, and evaporated to give the crude Boc-protected amine. This was dissolved in $CH_2Cl_2$ (25 mL) and treated with 4M HCl in dioxane (36 mL, 2.5 equiv, 144 mmol). The mixture was stirred at room temperature overnight and then evaporated. The resulting white solid was triturated with ether and the product was collected by filtration, washed with ether, and dried in vacuo (10.10 g, 86%). $^1$H-NMR δ ($D_2O$) 0.36 (m, 2H), 0.67 (m, 2H), 1.07 (m, 1H), 2.72 (m, 2H), 2.99 (m, 2H), 3.89 (m, 2H).

The steps of this method may be used to prepare tripeptide P4 N-terminal dialkyl ureas, from dialkylamine hydrochlorides and tripeptide N-terminal isocyanates, for subsequent use in making compounds of the present invention. The tripeptide isocyanate was prepared analogously to that described in SynLett. February 1995; (2); 142–144 using an amine component, a tertiary hindered base such as DIPEA or $Et_3N$ and phosgene.

Step 23b: Preparation of Compound 20. To a slurry of 110 mg (0.0.16 mmol) of this HCl salt and 400 µL (2.30 mmol) of DIPEA in 8 mL of $CH_2Cl_2$ cooled to 0° C., was added 62 mg (0.21 mmol) of commercially triphosgene. The mixture was stirred for 3 h, 73.4 mg (0.36 mmol) of cyclopropylmethyl-3,3,3-trifluoropropylamine hydrochloride was added, and the reaction vessel was allowed warmed to rt overnite. The mixture was diluted with 20 mL of pH 4.0 buffer and was partitioned with 4×50 mL portions of EtOAc. The combined organic layers were washed once with saturated aqueous $NaHCO_3$, dried ($MgSO_4$), concentrated in vacuo, and the residue chromatographed over a biotage 40+ M column (eluted with 30% to 50% EtOAc/Hexanes to afford 68 mg (48%) of the desired P4 dialkylurea [N,N-Cyclopropylmethyl-3,3,3-trifluoropropyl]-(C=O)]HN-P3(L-t-BuGly)-P2[(4R)-(2-phenyl-7-methoxy-quinoline-4-oxo)-S-proline]-P1(1R,2S Vinyl Acca)-$CO_2$Et: $^1$H NMR ($CDCl_3$/Methanol-$d_4$) δ 0.19–0.22 (m, 2H), 0.49–0.53 (m, 2H), 0.77–0.92 (m, 1H), 1.05 (s, 9H), 1.24 (t, J=7 Hz, 3H), 1.42 (dd, J=9, 5 Hz, 1H), 1.72 (dd, J=8, 5 Hz, 1H), 2.17–2.22 (m, 1H), 2.27–2.35 (m, 2H), 2.40–2.45 (m, 1H), 2.68–2.73 (m, 1H), 3.01 (dd, J=15, 6 Hz, 1H), 3.08 (dd, J=15, 6 Hz, 1H), 3.30–3.46 (m, 2H), 3.95 (s, 3H), 4.05–4.20 (m, 3H), 4.46–4.51 (m, 2H), 4.62–4.66 (m, 1H), 5.09 (d, J=10 Hz, 1H), 5.26 (d, J=17 Hz, 1H), 5.57 (m, 1H), 5.74–5.81 (m, 1H), 7.09 (dd, J=9, 2 Hz, 1H), 7.26 (s, 1H), 7.39 (d, J=2 Hz, 1H), 7.51–7.56 (m, 3H), 8.04–8.06 (m, 3H); LC-MS (retention time: 1.79, method B) MS m/z 808 ($M^+$+1).

To a solution of 65 mg (0.081 mmol) of P4 dialkylurea [N,N—Cyclopropylmethyl-3,3,3-trifluoropropyl]-(C=O)] HN-P3(L-t-BuGly)-P2[(4R)-(2-phenyl-7-methoxy-quinoline-4-oxo)-S-proline]-P1(1R,2S Vinyl Acca)-$CO_2$Et in a solution of 4 mL of THF and 2.5 ml Of MeOH, was added a solution of 12 mg (0.48 mmol) of LiOH in 2 mL of $H_2O$. The mixture was stirred overnite, an additional 6 mg (0.24 mmol) portion of LiOH added, the mixture and the mixture stirred 12 h. The mixture was acidified to pH 5 (using 2N HCl) and was concentrated in vacuo until only the water layer remained. The solution was partitioned repeatedly (5×15 mL) with EtOAc. The combined EtOAc layers (75 mL) were dried ($MgSO_4$) and concentrated to afford 58 mg (92%) of the desired carboxylic acid, [N,N-Cyclopropylmethyl-3,3,3-trifluoropropyl]-(C=O)]HN-P3 (L-t-BuGly)-P2[(4R)-(2-phenyl-7-methoxy-quinoline-4-oxo)-S-proline]-P1(1R,2S Vinyl Acca)-$CO_2$H, as a foam: $^1$H NMR ($CDCl_3$-Methanol-$d_4$) δ 0.25–0.28 (m, 2H), 0.56–0.62 (m, 2H), 0.85–0.98 (m, 1H), 1.09 (s, 9H), 1.46–1.49 (m, 1H), 1.77 (dd, J=8, 5 Hz, 1H), 2.18–2.23 (m, 1H), 2.33–2.43 (m, 2H), 2.56–2.61 (m, 1H), 2.69 (dd, J=14, 8 Hz, 1H), 3.08 (dd, J=15, 6 Hz, 1H), 3.16 (dd, J=15, 6 Hz, 1H), 3.43–3.53 (m, 2H), 3.98 (s, 3H), 4.13 (dd, J=12, 4 Hz, H), 4.50–4.53 (m, 2H), 4.69 (t, J=8 Hz, 1H), 5.11–5.13 (m, 1H), 5.28–5.32 (m, 1H), 5.54 (m, 1H), 5.82–5.90 (m, 1H), 7.11 (dd, J=9, 2 Hz, 1H), 7.19 (s, 1H), 7.43 (d, J=2 Hz, 1H), 7.51–7.58 (m, 3H), 7.99–8.05 (m, 2H), 8.08 (d, J=9 Hz, 1H); LC-MS (retention time: 1.63, method A), MS m/z 780 ($M^+$+1).

A solution of [N,N-Cyclopropylmethyl-3,3,3-trifluoropropyl]-(C=O)]HN-P3(L-t-BuGly)-P2[(4R)-(2-phenyl-7-methoxy-quinoline-4-oxo)-S-proline]-P1(1R,2S Vinyl Acca)-$CO_2$H (58 mg, 0.74 mmol) and CDI (17 mg, 0.104 mmol) in THF (2 mL) was refluxed for 60 min and allowed to cool down to rt. Cyclopropylsulfonamide (13 mg, 0.104 mmol) was added in one portion before the addition of a solution of DBU (160 □L, 0.104 mmol). The reaction was stirred for 72 h, diluted with EtOAc (100 mL). The solution was washed with pH 4.0 buffer (2×20 mL), dried ($MgSO_4$), concentrated, and was chromatographed over one 1000µ PTLC plate (20×40 cm, eluted with 2% MeOH in $CH_2Cl_2$) from Analtech to afford 18 mg (27%) of Compound 20 as a foam: $^1$H NMR ($CDCl_3$-Methanol-$d_4$) δ 0.22–0.27 (m, 2H), 0.50–0.56 (m, 2H), 0.86–0.94 (m, 1H), 1.00–1.11 (m, 2H), 1.09 (s, 9H), 1.18–1.25 (m, 2H), 1.46–1.48 (m, 1H), 1.90 (dd, J=8, 5 Hz, 1H), 2.18–2.24 (m, 1H), 2.30–2.46 (m, 3H), 2.70 (dd, J=14, 8 Hz, 1H), 2.80 (m, 1H), 3.07 (dd, J=15, 7 Hz, 1H), 3.13 (dd, J=15, 7 Hz, 1H), 3.43–3.49 (m, 2H), 3.98 (s, 3H), 4.16 (dd, J=12, 3 Hz, 1H), 4.50–4.54 (m, 2H), 4.57–4.61 (m, 1H), 5.12 (d, J=12 Hz, 1H), 5.30 (d, J=17 Hz, 1H), 5.63 (m, 1H), 5.75 (d, J=9 Hz, 1H), 5.83–5.90 (m, 1H), 7.13 (dd, J=9, 2 Hz, 1H), 7.31 (s, 1H), 7.43 (d, J=2 Hz, 1H), 7.52–7.59 (m, 3H), 8.08–8.10 (m, 3H); LC-MS (retention time: 1.65, method A), MS m/z 883 ($M^+$+1). MS m/e 883.2 $(M+1)^+$, 881 $(M-1)^-$.

EXAMPLE 24

Compound 21, N-BOC-P3-(L-Val)-P2 [(4R)-(2-phenyl-7-methoxy-quinoline-4-oxo)-proline)]-P1-(1-aminocyclopropane-1-)CONHSO₂cyclopropane, was prepared as described in the following Steps 24a–d.

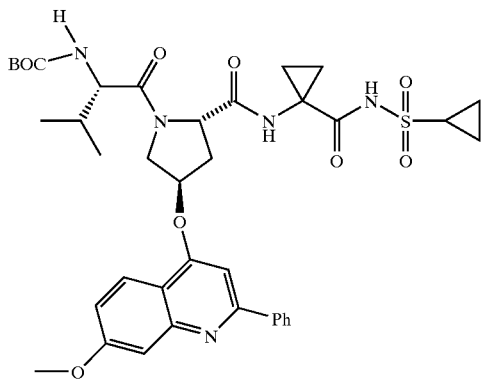

In Step 24a, the product, P2 HN-[(4R)-(2-phenyl-7-methoxyquinoline-4-oxo)-S-proline methyl ester dihydrochloride], was prepared from N-BOC-P2[(4R)-(2-phenyl-7-methoxyquinoline-4-oxo)-S-proline (N-Boc (4R)-(2-phenyl-7-methoxyquinoline-4-oxo)-S-proline, 4-(7-Methoxy-2-phenyl-quinolin-4-yloxy)-pyrrolidine-1,2-dicarboxylic acid 1-tert-butyl ester).

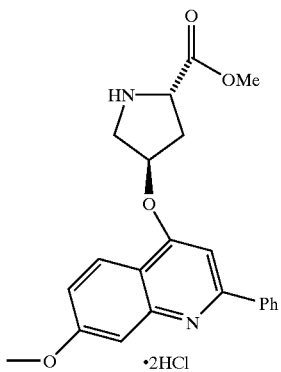

Specifically, to a solution of 10 g (21.5 mmol) of N-Boc (4R)-(2-phenyl-7-methoxyquinoline-4-oxo)-S-proline, 4-(7-Methoxy-2-phenyl-quinolin-4-yloxy)-pyrrolidine-1,2-dicarboxylic acid 1-tert-butyl ester in 500 mL of MeOH cooled to −78° C., was bubbled in gaseous HCl for 10 min. The mixture was warmed to rt, stirred overnite and concentrated in vacuo. The residue was azeotroped repeatedly with toluene and dioxane to afford 9.71 g (100%) of the titled product as an offwhite solid. $^1$H NMR (DMSO-d₆) δ 2.56–2.66 (m, 1H), 2.73–2.80 (m, 1H), 3.67–3.86 (m, 2H), 3.79 (s, 3H), 3.97 (s, 3H), 4.76–4.82 (m, 1H), 5.95 (m, 1H), 7.42 (dd, J=9, 2 Hz, 1H), 7.65–7.72 (m, 4H), 8.23–8.27 (m, 2H), 8.51 (d, J=9.2 Hz, 1H), 9.68 (bs, 1H), 11.4 (bs, 1H); LC-MS (retention time: 0.94, method D), MS m/e 379 (M⁺+1).

In Step 24b, the product 1-(2-tert-butoxycarbonylamino-3-methylbutyryl)-4-(7-methoxy-2-phenylquinolin-4yloxy)-pyrrolidine-2-carboxylic acid, shown below, which can also be named as P3 N-BOC (L-Val)-P2 [(4R)-(2-phenyl-7-methoxyquinoline-4-oxo)proline)]-CO₂H, was prepared.

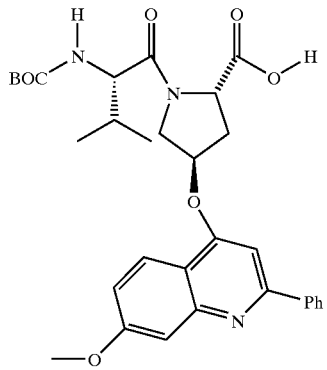

Specifically, to suspension of 1.95 g (4.32 mmol) of [HN-(4R)-(2-phenyl-7-methoxyquinoline-4-oxo)-S-proline) methyl ester, bis hydrochloride], 1.22 g (5.62 mmol), N-BOC-L-Valine, 1.89 mL (17.28 mmol) of NMM in DMF (20 mL) was added 1.81 g (4.76 mmol) of HATU at 0° C. The reaction mixture was slowly allowed to warm to rt overnite, was stirred for 2 days, diluted with EtOAc (100 mL), washed with pH 4.0 buffer (2×50 mL), saturated aqueous NaHCO₃ (50 mL), brine (50 mL), dried (MgSO₄), and purified by a Biotage 40 M column (eluted with 15% to 100% EtOAc in Hexanes) to supply 2.39 g (96%) of 1-(2-tert-butoxycarbonyl-amino-3-methylbutyryl)-4-(7-methoxy-2-phenylquinolin-4-yloxy)-pyrrolidine-2-carboxylic acid methyl ester (also named P3 N-BOC (L-Val)-P2 [(4R)-(2-phenyl-7-methoxyquinoline-4-oxo) proline)]-CO₂Me) as a foam. $^1$H NMR (CDCl₃) δ 0.98 (d, J=7 Hz, 3H), 1.05 (d, J=7 Hz, 3H), 1.34 (s, 9H), 2.00–2.11 (m, 1H), 2.31–2.40 (m, 1H), 2.79 (dd, J=14, 8 Hz, 1H), 3.77 (s, 3H), 3.96 (s, 3H), 4.04–4.14 (m, 1H), 4.21–4.26 (m, 1H), 4.49 (d, J=12 Hz, 1H), 4.75 (t, J=8 Hz, 1H), 5.13 (d, J=8 Hz, 1H), 5.35 (m, 1H), 6.96 (s, 1H), 7.09 (dd, J=9, 2 Hz, 1H), 7.41–7.55 (m, 4H), 7.99–8.04 (m, 3H); LC-MS (retention time: 1.40, method A), MS m/e 578 (M⁺+1).

A solution of 1-(2-tert-butoxycarbonylamino-3-methylbutyryl)-4-(7-methoxy-2-phenylquinolin-4-yloxy)-pyrrolidine-2-carboxylic acid methyl ester (2.865 g, 4.96 mmol) in THF (223 mL), CH₃OH (30 mL), and H₂O (119 mL) was added LiOH (952 mg, 39.7 mmol). The reaction mixture was stirred for one day, acidified to neutral pH, and concentrated in vacuo until only the aqueous layer remained. The resulting aqueous residue was acidified to pH 4.0 by addition of 1.0 N aqueous HCl and then saturated with solid NaCl. This aqueous mixture was extracted repeatedly with EtOAc (5×200 mL), the combined organic solvent dried (Mg₂SO₄), filtered, and concentrated in vacuo to supply 2.77 g (99%) of the titled product as a foam. $^1$H NMR (CDCl₃) δ 0.97 (d, J=7 Hz, 3H), 1.03 (d, J=7 Hz, 3H), 1.19 (s, 9H), 1.94–2.06 (m, 1H), 2.37–2.47 (m, 1H), 2.83 (dd, J=14, 8 Hz, 1H), 3.96 (s, 3H), 4.02–4.09 (m, 2H), 4.63–4.69 (m, 2H), 5.58 (m, 1H), 6.74 (d, J=8 Hz, 1H), 7.15 (dd, J=9 Hz, 1H), 7.29 (s, 1H), 7.40 (d, J=2 Hz, 1H), 7.51–7.61 ((m, 3H), 8.03–8.06 (2H), 8.15 (d, J=9 Hz, 1H); LC-MS (retention time: 1.36, method A), MS m/z 564 (M⁺+1).

In Step 24c, the product 1-{[1-(2-tert-butoxycarbonylamino-3-methylbutyryl)-4-(7-methoxy-2-phenylquinolin-4yl-oxy)pyrrolidine-2-carbonyl]amino}-cyclopropanecarboxylic acid, shown below, which can also be named as BOC P3-(L-Val)-P2 [(4R)-(2-phenyl-7-methoxyquinoline-4-oxo)-S-proline)]-P1-(1-aminocyclopropanecarboxylic acid), was prepared.

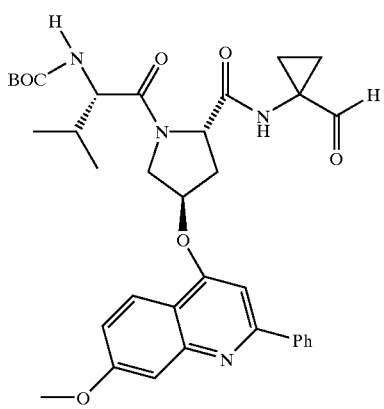

Specifically, to a solution of 3.0 g (14.9 mmol) of commercially available 1-tert-butoxycarbonylaminocyclopropane-carboxylic acid, in 60 mL of MeOH cooled to −78° C., was bubbled in gaseous HCl for 10 min. The mixture was warmed to rt, stirred overnite and concentrated in vacuo to afford the 2.26 g (100%) of 1-aminocyclopropanecarboxylic acid methyl ester, hydrochloride as a white solid. $^1$H NMR (Methanol-d$_4$) δ 1.36–1.39 (m, 2H), 1.55–1.58 (m, 2H), 3.80 (s, 3H).

Then, to suspension of 400 mg (0.71 mmol) of the product of Step 24b, 155 mg (0.92 mmol) of 1-aminocyclopropanecarboxylic acid methyl ester, dihydrochloride, and 0.40 mL (3.55 mmol) of NMM in 50% CH$_2$Cl$_2$/THF (15 mL) was added 0.43 g (0.92 mmol) of PyBrop at 0° C. The reaction mixture was slowly allowed to warm to rt overnight, diluted with EtOAc (500 mL), washed with pH 4.0 buffer (2×50 mL), saturated aqueous NaHCO$_3$ (50 mL), brine (50 mL), dried (MgSO$_4$), and purified by a Biotage 40 M column (eluted with 0% to 1% MeOH in EtOAc) to supply 308 mg (66%) of 1-{[1-(2-tert-Butoxycarbonylamino-3-methyl-butyryl)-4-(7-methoxy-2-phenyl-quinolin-4yl-oxy)pyrrolidine-2-carbonyl]amino}-cyclopropanecarboxylic acid methyl ester (also named BOC P3-(L-Val)-P2 [(4R)-(2-phenyl-7-methoxyquinoline-4-oxo)-S-proline)]-P1-(1-Aminocyclopropanecarboxylic acid methyl ester) as a foam. $^1$H NMR (Methanol-d$_4$) δ 0.95 (d, J=7 Hz, 3H), 0.98 (d, J=7 Hz, 3H), 1.24 (s, 9H), 1.39–1.56 (m, 4H), 1.89–2.05 (m, 1H), 2.41–2.48 (m, 1H), 2.70 (dd, J=14, 8 Hz, 1H), 3.66 (s, 3H), 3.91 (s, 3H), 4.02–4.05 (m, 2H), 4.52–4.63 (m, 2H), 5.47 (m, 1H), 7.04 (dd, J=9, 2 Hz, 1H), 7.18 (m, 1H), 7.34 (d, J=2 Hz, 1H), 7.45–7.55 (m, 3H), 8.03–8.06 (m, 3H); $^{13}$C NMR (Methanol-d$_4$) δ 17.36, 18.03, 18.98, 19.64, 28.54, 31.66, 34.36, 35.89, 52.92, 54.38, 55.97, 59.68, 60.42, 77.96, 80.41, 99.96, 107.55, 116.43, 119.16, 124.27, 128.96, 129.72, 130.47, 141.31, 152.22, 157.86, 161.22, 161.85, 163.03, 173.91, 174.28, 174.83; LC-MS (retention time: 1.39, method A) MS m/e 661 (M$^+$+1).

Subsequently, to a solution of 1-{[1-(2-tert-Butoxycarbonylamino-3-methylbutyryl)-4-(7-methoxy-2-phenylquinolin-4yl-oxy)pyrrolidine-2-carbonyl]amino}-cyclopropanecarboxylic acid methyl ester (308 mg, 0.47 mmol) in THF (21 mL), CH$_3$OH (3 mL), and H$_2$O (11 mL) was added LiOH (56 mg, 2.33 mmol). The reaction mixture was stirred for one day, acidified to neutral pH, and concentrated in vacuo until only the aqueous layer remained. The resulting aqueous residue was acidified to pH 4.0 by addition of 1.0 N aqueous HCl and was extracted repeatedly with EtOAc (3×50 mL), the combined organic solvent dried (Mg$_2$SO$_4$), filtered, and concentrated in vacuo to supply 292 mg (95%) of the titled product as a foam. $^1$H NMR (Methanol-d$_4$) δ 0.96 (d, J=7 Hz, 3H), 0.99 (d, J=7 Hz, 3H), 1.17 (s, 9H), 1.09–1.47 (m, 4H), 1.51–1.60 (m, 1H), 1.90–2.00 (m, 1H), 2.50–2.59 (m, 1H), 2.80 (dd, J=14, 8 Hz, 1H), 3.99 (s, 3H), 4.02–4.12 (m, 1H), 4.62(m, 2H), 5.69(m, 1H), 7.24 (dd, J=9, 2.4 Hz, 1H), 7.45 (s, 1H), 7.60–7.66(m, 3H), 8.02–8.08 (m, 2H), 8.23 (d, J=9 Hz, 1H) LC-MS (retention time: 1.50, method D) MS m/z 647 (M$^+$+1).

In Step 24d, Compound 21 was prepared by adding CDI (81.2 mg, 0.50 mmol) to a solution of the product of Step 24c (0.270 g, 0.42 mmol), in THF (3 mL), and then refluxing for 60 min. The solution was allowed to cool down to rt. Cyclopropylsulfonamide (0.0607 g, 0.50 mmol) was then added in one portion before the addition of a neat solution of DBU (0.075 mL, 0.50 mmol). The reaction was stirred for 18 h, diluted with EtOAc (200 mL) and washed pH 4.0 buffer (3×30 mL), water (2×30 mL), brine (30 mL), dried (MgSO$_4$) and purified using one 20×40 cM 1000µ Analtech PTLC plate (eluted with 2% MeOH in CH$_2$Cl$_2$) to supply Compound 21 as a foam (0.113 g, 40%): LC/MS rt-min (MH$^+$) 1.49 (750) (method A). $^1$H NMR: (methanol-d$_4$, 300 MHz) δ 0.88–1.18 (m, 10H), 1.23 (s, 9H), 1.37–1.79 (m, 4H), 2.00–2.09 (m, 1H), 2.43–2.53 (m, 1H), 2.63–2.76 (m, 1H), 2.76–2.89 (m, 1H), 3.94 (s, 3H), 4.02–4.11 (m, 2H), 4.54–4.62 (m, 2H), 5.57 (m, 1H), 7.09 (dd, J=9, 2 Hz, 1H), 7.25 (s, 1H), 7.38 (d, J=2 Hz, 1H), 7.49–7.57 (m, 3H), 8.03–8.11 (m, 3H).

EXAMPLE 25

Compound 22, 1-[2-(1-cyclopropanesulfonylaminocarbonylcyclobutylcarbamoyl)-4-(7-methoxy-2-phenylquinolin-4-yloxy)-pyrrolidine-1-carbonyl]-2,2-dimethylpropyl}carbamic acid tert-butyl ester, shown below, which is also named as BOC P3-(L-tBuGly)-P2 [(4R)-(2-phenyl-7-methoxyquinoline-4-oxo)-S-proline)]-P1-(1-aminocyclobutane-1-)CONHSO$_2$Cyclopropane, was prepared as described in the following Steps 25a–d.

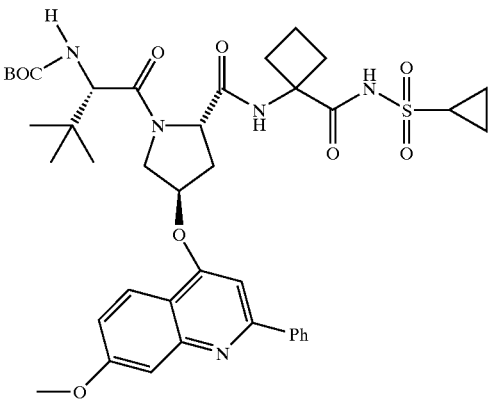

In Step 25a, the product, 1-(2-tert-butoxycarbonylamino-3,3-dimethylbutyryl)-4-(7-methoxy-2-phenylquinolin-4yloxy)pyrrolidine-2-carboxylic acid, shown below, which is also named P3 N-BOC (L-t-BuGly)-P2 [(4R)-(2-phenyl-7-methoxyquinoline-4-oxo)-S-proline)]-CO₂H, was prepared using a two step sequence.

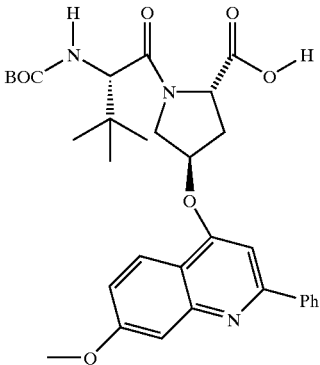

Specifically, to suspension of 3.90 g (8.60 mmol) of [HN-(4R)-(2-phenyl-7-methoxyquinoline-4-oxo)-S-proline) methyl ester, bis hydrochloride], 2.65 g (11.47 mmol) of N-BOC-L-tert-leucine (L-tBuGly), 3.48 g (34.40 mmol) of NMM in DMF (20 mL) was added 3.62 g (9.52 mmol) of HATU at 0° C. The reaction mixture was slowly allowed to warm to rt overnite, was stirred for 4 days, diluted with EtOAc (200 mL), washed with pH 4.0 buffer (3×40 mL), saturated aqueous NaHCO₃ (40 mL), dried (MgSO₄), and purified by a Biotage 40 M column (eluted with 15% to 70% EtOAc in Hexanes) to supply 4.16 g (81%) of 1-(2-tert-Butoxycarbonylamino-3,3-dimethylbutyryl)-4-(7-methoxy-2-phenylquinolin-4-yloxy)-pyrrolidine-2-carboxylic acid methyl ester, which is also named P3 N-BOC (L-tBuGly)-P2 [(4R)-(2-phenyl-7-methoxyquinoline-4-oxo)-S-proline)]—CO₂Me, as a foam. ¹H NMR (CDCl₃) δ 1.07 (s, 9H), 1.37 (s, 9H), 2.29–2.39 (m, 1H), 2.78 (dd, J=14, 8 Hz, 1H), 3.96 (s, 3H), 4.06–4.11(m, 1H), 4.31 (d, J=10 Hz, 1H), 4.54 (d, J=11 Hz, 1H), 4.72–4.77 (m, 1H), 5.23 (d, J=10 Hz, 1H), 5.34 (m, 1H), 6.96 (s, 1H), 7.07 (dd, J=9, 2 Hz, 1H), 7.44–7.52 (m, 3H), 7.99–8.03 (m, 3H). LC-MS (retention time: 1.43, method A) MS m/e 592 (M⁺+1).

Then, to a solution of 1-(2-tert-butoxycarbonylamino-3,3-dimethylbutyryl)-4-(7-methoxy-2-phenylquinolin-4-yloxy)-pyrrolidine-2-carboxylic acid methyl ester (4.179 g, 7.06 mmol) in THF (318 mL), CH₃OH (42 mL), and H₂O (170 mL) was added LiOH (1.356 g, 56.5 mmol). The reaction mixture was stirred for one day, acidified to neutral pH, and concentrated in vacuo until only the aqueous layer remained. The resulting aqueous residue was acidified to pH 4.0 by addition of 1.0 N aqueous HCl and then saturated with solid NaCl. This aqueous mixture was extracted repeatedly with 80% EtOAc/THF (4×300 mL), the combined organic solvent dried (Mg₂SO₄), filtered, and concentrated in vacuo to supply 3.69 g (91%) of the titled product as a foam. ¹H NMR (CDCl₃) δ 1.03 (s, 9H), 1.27 (s, 9H), 2.36–2.43 (m, 1H), 2.78–2.83 (m, 1H), 3.94 (s, 3H), 4.05 (d, J=10 Hz, 1H), 4.24 (d, J=9 Hz, 1H), 4.54 (d, J=12 Hz, 1H), 4.63–4.67 (m, 1H), 5.52 (m, 1H), 7.09 (dd, J=9 Hz, 1H), 7.20 (s, 1H), 7.38 (s, 1H), 7.51–7.55 (m, 3H), 7.99–8.00 (m, 3H), 8.09 (d, J=9 Hz, 1H). LC-MS (retention time: 1.44, Method A), MS m/z 578 (M⁺+1).

In Step 25b, 1-aminocyclobutanecarboxylic acid methyl ester-hydrochloride, shown below, was prepared.

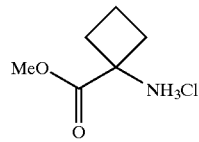

Specifically, 1-aminocyclobutanecarboxylic acid (100 mg, 0.869 mmol)(Tocris) was dissolved in 10 mL of MeOH, HCl gas was bubbled in for 2 h. The reaction mixture was stirred for 18 h, and then concentrated in vacuo to give 144 mg of a yellow oil. Trituration with 10 mL of ether provided 100 mg of the titled product as a white solid. ¹H NMR (CDCl₃) δ 2.10–2.25 (m, 1H), 2.28–2.42 (m, 1H), 2.64–2.82 (m, 4H), 3.87 (s, 3H), 9.21 (br s, 3H).

In Step 25c, the product, 1-{[1-(2-tert-butoxycarbonylamino-3,3-dimethylbutyr-yl)-4-(7-methoxy-2-phenyl-quinolin-4-yloxy)pyrrolidine-2-carbonyl]amino}-cyclobutanecarboxylic acid, shown below, which may also be named as BOC P3-(L-tBuGly)-P2 [(4R)-(2-phenyl-7-methoxyquinoline-4-oxo)-S-proline)]-P1-(1-aminocyclobutane-1-) CO₂Me, was prepared using a two step sequence.

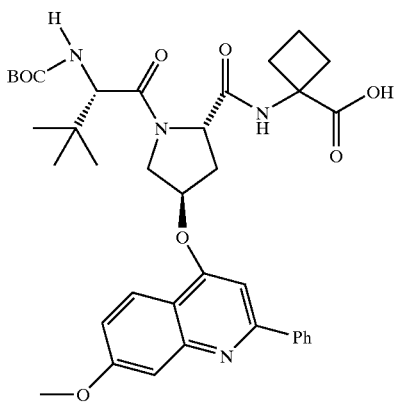

To a mixture of 1-(2-tert-butoxycarbonylamino-3,3-dimethylbutyryl)-4-(7-methoxy-2-phenyl-quinolin-4-yloxy)-pyrrolidine-2-carboxylic acid (100 mg, 0.173 mmol) in 2 mL of methylene chloride was added DIPEA (112 mg, 0.865 mmol) followed by HBTU (78.4 mg, 0.207), HOBT.H₂O (32 mg, 0.207 mmol), and finally 1-aminocyclobutane-carboxylic acid methyl ester.hydrochloride (30 mg, 0.182 mmol). The mixture was stirred at rt for 24 h, diluted with EtOAc (50 mL), washed with sat. aq. NaHCO₃ (25 mL), brine (25 mL), and dried (MgSO₄), filtered, and concentrated in vacuo to give 134 mg of the crude product as a yellow oil. Flash chromatography eluting with 1:1 ethyl acetate/hexane gave 93 mg (78%)of 1-{[1-(2-tert-Butoxycarbonylamino-3,3-dimethyl-butyl-yl)-4-(7-methoxy-2-phenyl-quinolin-4-yloxy)-pyrrolidine-2-carbonyl]amino}cyclobutanecarboxylic acid methyl ester, which is also named BOC P3-(L-tBuGly)-P2 [(4R)-(2-phenyl-7-methoxy-quinoline-4-oxo)-proline)]-P1-(1-aminocyclobutane-1-)CO₂Me, as a colorless oil. ¹H NMR (CDCl₃) δ 1.06 (s, 9H), 1.43 (s, 9H), 1.98–2.09 (m, 2H), 2.23–2.32 (m, 2H), 2.42–2.50 (m, 1H), 2.61–2.71 (m, 2H), 2.93–3.02 (m, 1H), 3.74 (s, 3H), 3.96 (s, 3H), 4.37 (d, J=12 Hz, 1H), 4.47 (d, J=9 Hz, 1H), 4.87 (t, J=7 Hz, 1H), 5.23–5.26 (d, J=9.8 Hz, 1H), 5.36 (brs, 1H), 7.04–7.08 (m, 2H), 7.45–7.54 (m, 5H), 8.05–8.08 (m, 3H); LC-MS (retention time: 1.67 minutes, Method D), MS m/z 689 (M⁺+1). HPLC retention time: 13.42 min.

To a mixture of the 1-{[1-(2-tert-butoxycarbonylamino-3,3-dimethylbutyryl)-4-(7-methoxy-2-phenylquinolin-4-yloxy)pyrrolidine-2-carbonyl]-amino}-cyclobutane-carboxylic acid methyl ester (2)(93 mg, 0.135 mmol) in THF (3 mL), methanol (1.5 mL), and water (0.4 mL) was added 30 mg of LiOH (65 mg, 2.7 mmol). The mixture was stirred at rt for 3 days, concentrated in vacuo, and then partitioned between ether (50 mL) and water (25 mL). The aqueous layer was acidified to pH 4 using 1N HCl, and was extracted with ether (3×50 mL). The combined ether layers were dried (MgSO$_4$), filtered, and concentrated in vacuo to give 81 mg (89%) of the titled product as a white foam. $^1$H NMR (CDCl$_3$) δ 1.04 (s, 9H), 1.41 (s, 9H), 1.98–2.09 (m, 2H), 2.20–2.30 (m, 2H), 2.50–2.58 (m, 1H), 2.66~2.80 (m, 2H), 2.84–2.93 (m, 1H), 3.98 (s, 3H), 4.31 (d, J=9 Hz, 1H), 4.54 (d, J=10 Hz, 1H), 4.83 (t, J=7 Hz, 1H), 5.28 (d, J=12 Hz, 1H), 5.39 (br s, 1H), 7.03 (s, 1H), 7.08 (dd, J=3,9 Hz, 1H), 7.47~7.55 (m, 4H), 7.64 (br s, 1H), 8.06~8.08 (m, 3H). LC-MS (retention time: 1.66, Method D), MS m/z 675 (M$^+$+1). HPLC retention time: 11.06 min.

In Step 25d, Compound 22 was prepared from a mixture of 64 mg (0.095 mmol) of the product of Step 25c and CDI (19.9 mg, 0.123 mmol) in THF (3 mL) which was heated at reflux for 1 h. After cooling the reaction mixture to rt, cyclopropylsulfonamide (14.9 mg, 0.123 mmol) was added followed by DBU (18.7 mg, 0.123 mmol). After stirring at rt for 24 h, the reaction was partitioned between EtOAc (50 mL) and pH 4 buffer (25 mL). The organic phase was washed with sat. aq. NaHCO$_3$ (25 mL), dried (MgSO$_4$), filtered, and concentrated in vacuo. The crude product was purified by one 1000μ 20×40 cm PTLC plate from Analtech (eluting two times with 2.5% methanol in methylene chloride) to give 30 mg (41%) of Compound 22 as a white solid. LC-MS (retention time: 1.67, Method D), MS m/z 778 (M$^+$+1). HPLC retention time: 12.03 min.

EXAMPLE 26

The following compounds of the present invention were also made by the methods described in the proceeding Examples 1–25.

Compound 23

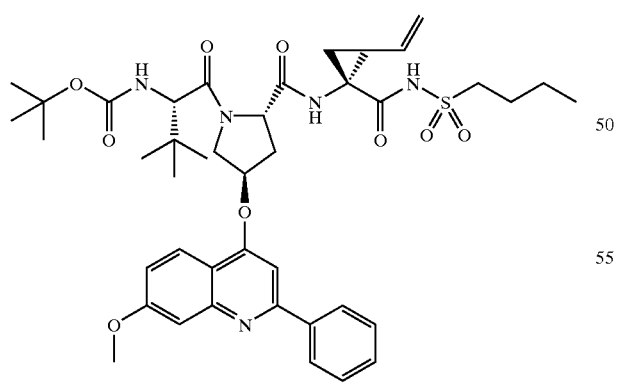

LC/MS rt-min (MH$^+$): 1.86 (806) (method D). $^1$H NMR: (methanol-d$_4$, 500 MHz) δ 0.89 (t, J=7.3 Hz, 1H), 1.04 (s, 9H), 1.26–1.44 (m, 12H), 1.67–1.73 (m, 2H), 1.78–1.80 (m, 1H), 2.01–2.09 (m, 1H), 2.53 (m, 1H), 2.68–2.72 (m, 1H), 3.06–3.17 (m, 2H), 3.92, 3.94 (2s, 3H), 4.15–4.18 (m, 1H), 4.25 (s, 1H), 4.49–4.55 (m, 2H), 5.00 (d, J=10 Hz, 1H), 5.18 (d, J=17 Hz, 1H), 5.53 (m, 1H), 5.82–5.90 (m, 1H), 7.06 (dd, J=9, 2 Hz, 1H), 7.25 (s, 1H), 7.36–7.38 (m, 1H), 7.46–7.554 (m, 3H), 8.04–8.09 (m, 3H)

Compound 24

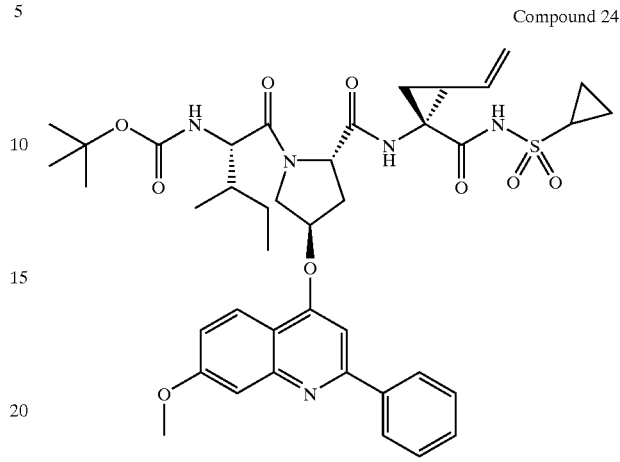

LC/MS rt-min (MH$^+$): 1.79 (790) (method D). $^1$H NMR: (methanol-d$_4$, 500 MHz) δ 0.74 (t, J=7.3 Hz, 3H), 1.08 (s, 9H), 0.79–1.29 (m, 1H), 1.34–1.42 (m, 1H), 2.00–2.15 (m, 2H), 2.28–2.35 (m, 1H), 2.39–2.44 (m, 1H), 2.65 (dd, J=14, 6 Hz, 1H), 3.99 (s, 3H), 4.13 (d, J=12 Hz, 1H), 4.22 (d, J=11 Hz, 1H), 4.28 (dd, J=12, 4 Hz, 1H), 4.57–4.61 (m, 1H), 5.00 (d, J=11 Hz, 1H), 5.13 (d, J=17 Hz, 1H), 5.51 (m, 1H), 5.92–5.99 (m, 1H), 6.73 (d, J=9 Hz, NH), 7.20 (s, 1H), 7.42 (d, J=2 Hz, 1H), 7.48–7.56 (m, 4H), 7.82 (d, J=9 Hz, 1H), 8.03–8.04 (m, 3H).

Compound 25

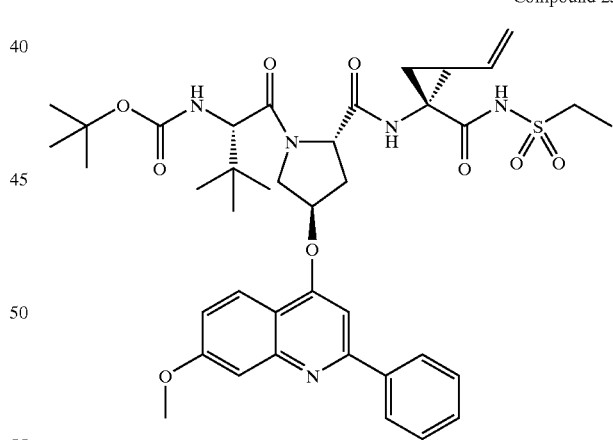

LC/MS rt-min (MH$^+$): 1.84 (778) (method D). $^1$H NMR: (methanol-d$_4$, 500 MHz) δ 1.03 (s, 9H), 1.24–1.38 (m, 3H), 1.26 (s, 9H), 1.83 (m, 1H), 2.09–2.18 (m, 1H), 2.41 (m, 1H), 2.66–2.77 (m, 1H), 3.03–3.30 (m, 2H), 3.93 (s, 3H), 4.02–4.14 (m, 1H), 4.25 (m, 1H), 4.51–4.57 (m, 2H), 5.05 (d, J=10 Hz, 1H), 5.23 (d, J=17 Hz, 1H), 5.53 (m, 1H), 5.75–5.89 (m, 1H), 7.06 (d, J=9 Hz, 1H), 7.24 (s, 1H), 7.37 (s, 1H), 7.47–7.54 (m, 3H), 8.03–8.10 (m, 3H).

Compound 26

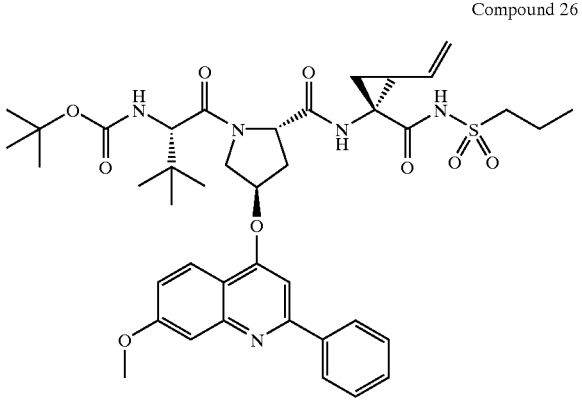

LC/MS rt-min (MH⁺): 1.85 (792) (method D). ¹H NMR: (methanol-d₄, 500 MHz) δ 1.04 (s, 9H), 1.26–1.30 (m, 12H), 1.34 (m, 1H), 1.56–1.66 (m, 1H), 1.69–1.83 (m, 2H), 2.00–2.11 (m, 1H), 2.46–2.55 (m, 1H), 2.64–2.73 (m, 1H), 3.13–3.19 (m, 2H), 3.93 (s, 3H), 4.12–4.18 (m, 1H), 4.25 (m, 1H), 4.50–4.58 (m, 2H), 5.01 (d, J=10 Hz, 1H), 5.19 (d, J=17 Hz, 1H), 5.54 (m, 1H), 5.80–5.92 (m, 1H), 7.06 (d, J=9 Hz, 1H), 7.25 (s, 1H), 7.37 (m, 1H), 7.47–7.55 (m, 3H), 8.04–8.12 (m, 3H).

Compound 27

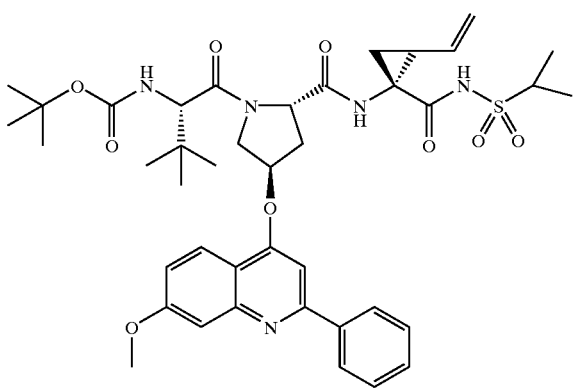

LC/MS rt-min (MH⁺): 1.80 (792) (method D).

Compound 28

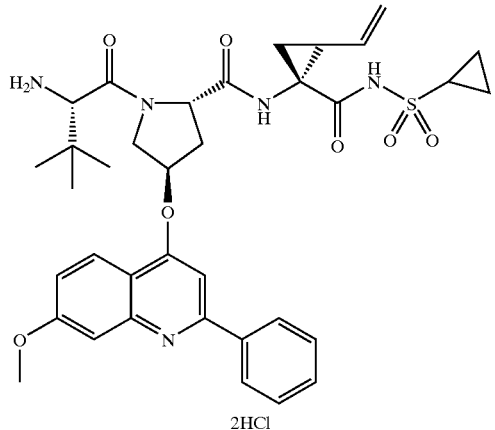

2HCl

LC/MS rt-min (MH⁺): 1.57 (690) (method D). ¹H NMR: (methanol-d₄, 500 MHz) δ 1.04–1.33 (m, 4H), 1.17 (s, 9H), 1.42 (m, 1H), 1.89 (m, 1H), 2.33 (m, 1H), 2.43 (m, 1H), 2.84 (m, 1H), 2.95 (s, 1H), 4.06 (s, 3H), 4.19 (m, 2H), 4.56 (m, 1H), 4.76 (m, 1H), 5.13 (d, J=10 Hz, 1H), 5.32 (d, J=17 Hz, 1H), 5.65–5.76 (m, 1H), 5.90 (m, 1H), 7.47 (m, 1H), 7.63 (s, 2H), 7.74 (m, 3H), 8.15 (m, 2H), 8.48 (m, 1H).

Compound 29

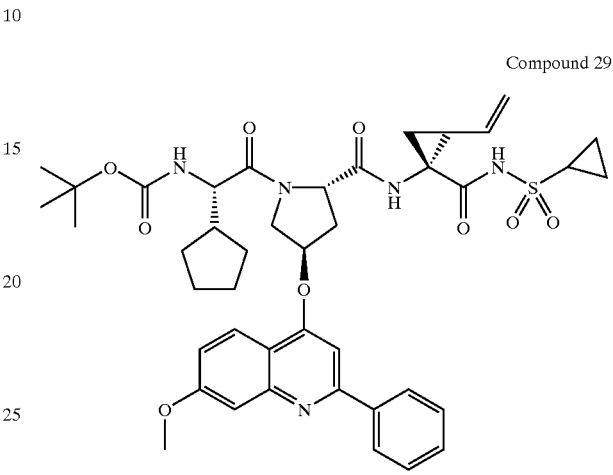

LC/MS rt-min (MH⁺): 1.57 (802) (method D). ¹H NMR: (CDCl₃, 500 MHz) δ 0.94–1.78 (m, 13H), 1.07 (s, 9H), 1.87–2.03 (m, 2H), 2.16–2.19 (m, 1H), 2.32–2.45 (m, 2H), 2.64–2.68 (m, 1H), 3.91–3.96 (m, 1H), 3.96 (s, 3H), 4.06 (d, J=12 Hz, 1H), 4.20 (dd, J=12, 4 Hz, 1H), 4.56–4.60 (m, 1H), 4.98–5.01 (m, 1H), 5.13–5.16 (m, 1H), 5.29 (m, 1H), 6.01–6.08 (m, 1H), 6.88 (s, 1H), 6.92 (dd, J=9, 2 Hz, 1H), 7.42–7.51 (m, 4H), 7.86 (d, J=9 Hz, 1H), 7.99–8.03 (m, 2H).

Compound 30

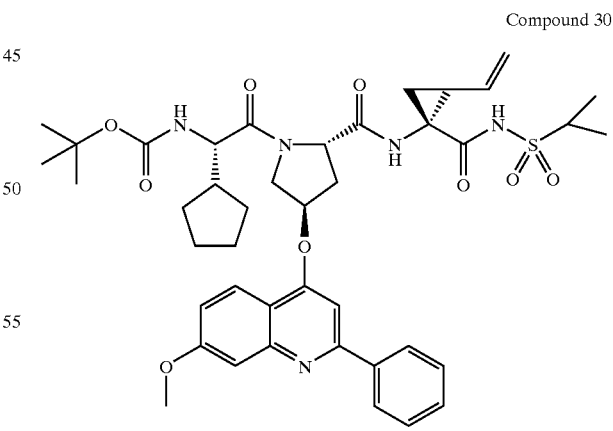

LC/MS rt-min (MH⁺): 1.90 (804) (method D). ¹H NMR: (CDCl₃, 500 MHz) δ 1.20–1.34 (m, 10H), 1.30 (s, 9H), 1.39–1.42 (m, 1H), 1.44–1.55 (m, 2H), 1.55–1.64 (m, 2H), 1.64–1.75 (m, 2H), 1.92 (dd, J=8, 6 Hz, 1H), 2.25–2.30 (m, 1H), 2.39–2.44 (m, 1H), 2.58–2.62 (m, 1H), 3.76–3.82 (m, 1H), 3.93 (s, 3H), 4.03 (dd, J=12, 4 Hz, 1H), 4.19 (t, J=9 Hz, 1H), 4.49 (dd, J=9, 7 Hz, 1H), 4.64 (d, J=12 Hz, 1H), 5.09 (d, J=11 Hz, 1H), 5.20 (d, J=17 Hz, 1H), 5.32 (m, 1H), 5.54 (d, J=8 Hz, 1H), 5.73–5.80 (m, 1H), 6.94 (s, 1H), 7.01 (dd, J=9, 2 Hz, 1H), 7.41–7.50 (m, 4H), 7.98–8.00 (m, 3H).

Compound 31

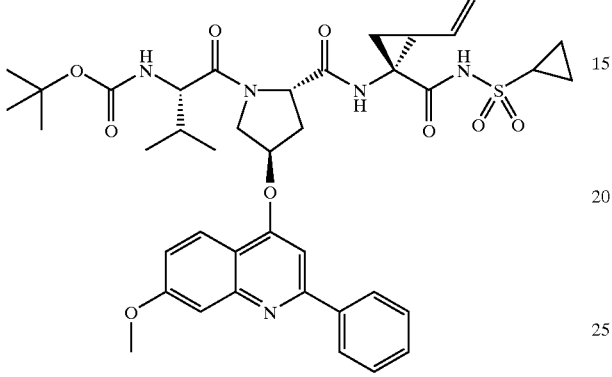

LC/MS rt-min (MH+): 1.80 (776) (method D).

Compound 32

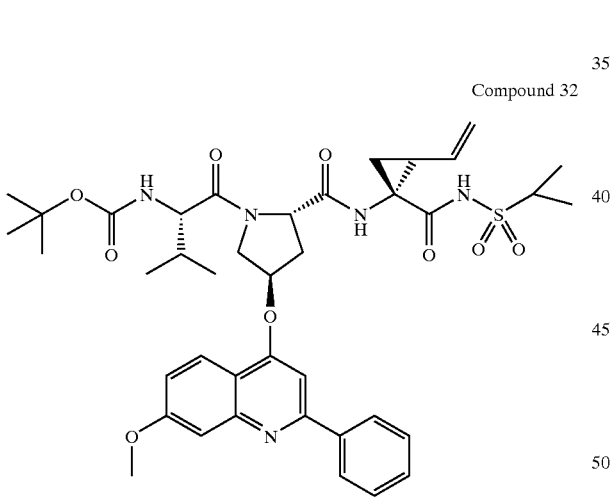

LC/MS rt-min (MH+) 1.85 (778) (method D). $^1$H NMR: (methanol-d$_4$, 500 MHz) δ 0.87 (d, J=7 Hz, 1H), 1.06–1.08 (m, 9H), 1.29–1.37 (m, 10H), 1.96–2.06 (m, 1H), 2.04–2.12 (m, 1H), 2.27–2.40 (m, 1H), 2.64–2.68 (m, 1H), 2.94–2.99 (m, 1H), 3.76 (d, J=11.0 Hz, 1H), 3.94, 3.96 (2s, 3H), 4.07 (d, J=11.6 Hz, 1H), 4.18 (dd, J=11.6, 4.6 Hz, 1H), 4.63 (dd, J=10.7, 6.4 Hz, 1H), 4.99 (dd, J=10.4, 1.6 Hz, 1H), 5.31 (m, 1H), 6.01–6.09 (m, 1H), 6.94 (dd, J=9, 2.4 Hz, 1H), 7.43 (d, J=2.4 Hz, 1H), 7.46–7.54 (m, 4H), 7.89 (d, J=9.1 Hz, 1H), 7.98–8.03 (m, 2H).

Compound 33

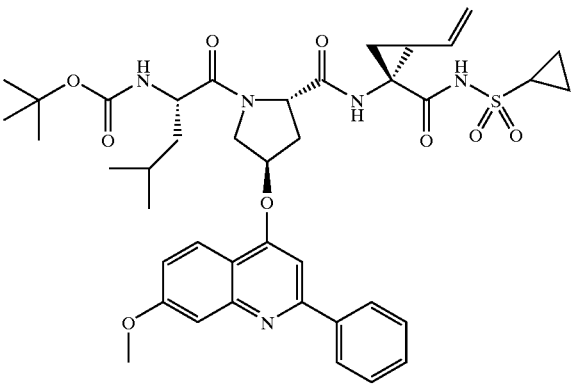

LC/MS rt-min (MH+): 1.87 (790) (method D). $^1$H NMR: (methanol-d$_4$, 500 MHz) δ 0.84 (d, J=6.4 Hz, 3H), 1.14–1.19 (m, 2H), 0.89–0.94 (m, 6H), 1.28 (s, 9H), 1.51 (m, 1H), 1.61–1.75 (m, 2H), 2.01–2.07 (m, 2H), 2.32–2.36 (m, 1H), 2.49 (m, 1H), 2.68 (dd, J=13.9, 6.3 Hz, 1H), 3.90, 4.01 (2s, 3H), 4.11 (d, J=11.9 Hz, 1H), 4.20 (dd, J=11.9, 3.4 Hz, 1H), 4.54–4.60 (m, 2H), 4.99 (d, J=11.0 Hz, 1H), 5.13 (d, J=17.4 Hz, 1H), 5.53, 5.57 (m, 1H), 5.87–5.97 (m, 1H), 6.87 (d, J=7.6 Hz, 1H), 7.23 (s, 1H), 7.43 (d, J=2.1 Hz, 1H), 7.47–7.55 (m, 4H), 7.86 (d, J=8.6 Hz, 1H), 8.02–8.07 (m, 3H).

Compound 34

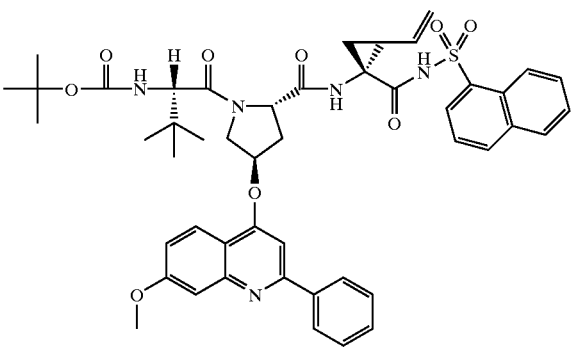

LC/MS rt-min (MH+): 1.93 (792) (method D).

Compound 35

LC/MS rt-min (MH+): 1.65 (877) (method B). ¹H NMR: (methanol-d₄, 500 MHz) δ 1.06 (s, 9H), 1.27 (s, 9H), 1.29–1.33 (m, 1H), 1.70–1.73 (m, 1H), 2.06–2.12 (m, 1H), 2.36 (m, 1H), 2.60–2.71 (m, 1H), 3.94 (s, 3H), 4.08–4.12 (m, 1H), 4.25–4.28 (m, 1H), 4.52–4.57 (m, 2H), 4.91 (d, J=11 Hz, 1H), 5.14 (d, J=17 Hz, 1H), 5.53 (m, 2H), 6.97–7.08 (m, 4H), 7.24 (s, 1H), 7.39 (s, 1H), 7.47–7.55 (m, 3H), 7.81–7.88 (m, 4H), 8.04–8.09 (m, 3H).

4.05–4.11 (m, 1H), 4.25 (s, 1H), 4.48–4.55 (m, 2H), 4.90 (d, J=11 Hz, 1H), 5.13 (d, J=17 Hz, 1H), 5.40–5.87 (m, 2H), 7.06 (dd, J=9, 2 Hz, 1H), 7.18–7.25 (m, 3H), 7.37 (d, J=2 Hz, 1H), 7.46–7.53 (m, 3H), 7.80 (d, J=8.2, 2H), 8.03–8.10 (m, 3H).

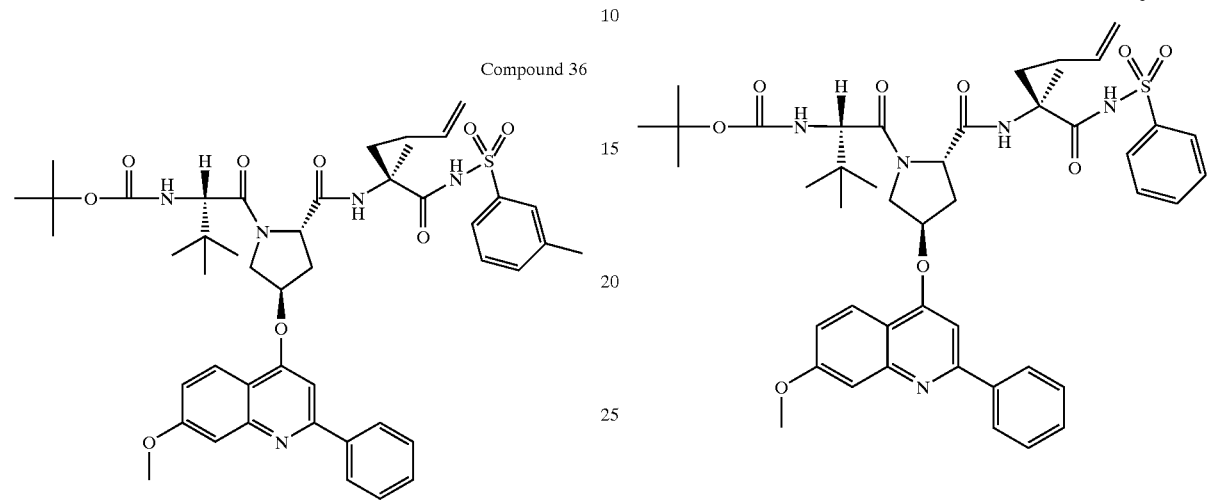

Compound 36

Compound 38

LC/MS rt-min (MH+) 1.73 (841) (method A). ¹H NMR: (methanol-d₄, 500 MHz) δ 1.06 (s, 9H), 1.28 (s, 9H), 1.32–1.35 (m, 1H), 1.69 (dd, J=8, 5.5 Hz, 1H), 2.11–2.18 (m, 1H), 2.31–2.37 (m, 1H), 2.40 (s, 3H), 2.62 (dd, J=14, 7 Hz, 1H), 3.95 (s, 3H), 4.08–4.13 (m, 1H), 4.25–4.29 (m, 1H), 4.52–4.57 (m, 2H), 4.92 (d, J=12 Hz, 1H), 5.16 (d, J=17 Hz, 1H), 5.37–5.46 (m, 1H), 5.58 (m, 1H),), 7.10 (dd, J=9, 2 Hz, 1H), 7.27 (2s, 1H), 7.38–7.42 (m, 2H), 7.44–7.47 (m, 1H), 7.49–7.58 (m, 3H), 7.77 (m, 2H), 8.04, 8.06 (2s, 2H), 8.10 (d, J=9 Hz, 1H).

LC/MS rt-min (MH+) 1.66 (826) (method A). ¹H NMR: (methanol-d₄, 500 MHz) δ 1.06 (s, 9H), 1.28 (s, 9H), 1.31–1.34 (m, 1H), 1.71 (dd, J=8, 5.5 Hz, 1H), 2.11–2.16 (m, 1H), 2.30–2.39 (m, 1H), 2.64–2.72 (m, 1H), 3.95 (s, 3H), 4.11 (dd, J=12, 2.6 Hz, 1H), 4.25–4.29 (m, 1H), 4.52–4.57 (m, 2H), 4.91 (d, J=10 Hz, 1H), 5.15 (d, J=17 Hz, 1H), 5.37–5.46 (m, 1H), 5.57 (m, 1H), 7.10 (dd, J=9, 2 Hz, 1H), 7.27 (s, 1H), 7.40 (d, J=2 Hz, 1H), 7.49–7.58 (m, 5H), 7.61–7.65 (m, 1H), 7.96–7.97 (m, 2H), 8.04, 8.05 (2s, 2H), 8.10 (d, J=9 Hz, 1H).

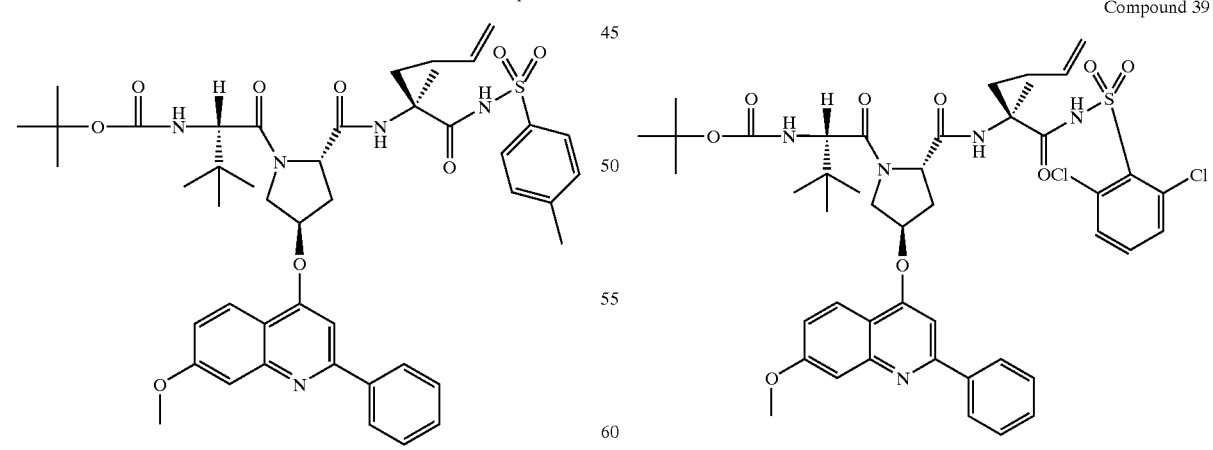

Compound 37

Compound 39

LC/MS rt-min (MH+): 1.59 (841) (method B). ¹H NMR: (methanol-d₄, 500 MHz) δ 1.04 (s, 9H), 1.26 (s, 9H), 1.21–1.43 (m, 1H), 1.72 (dd, J=7, 5 Hz, 1H), 2.06–2.21 (m, 1H), 2.34 (m, 4H), 2.56–2.72 (m, 1H), 3.93 (s, 3H), LC/MS rt-min (MH+): 1.73 (895) (method A). ¹H NMR: (methanol-d₄, 500 MHz) δ 1.03 (s, 9H), 1.26 (s, 9H), 1.32 (m, 1H), 1.69–1.73 (m, 1H), 2.00–2.06 (m, 1H), 2.43–2.50

(m, 1H), 2.56–2.60 (m, 1H), 3.93 (s, 3H), 4.04–4.17 (m, 1H), 4.22 (s, 1H), 4.45 (d, J=12 Hz, 1H), 4.52 (t, J=8.5 Hz, 1H), 4.84 (d, J=10 Hz, 1H), 5.09 (d, J=17 Hz, 1H), 5.46 (m, 1H), 5.70 (m, 1H), 7.04–7.25 (m, 4H), 7.33–7.40 (m, 2H), 7.47–7.57 (m, 3H), 8.02–8.11 (m, 3H).

1H), 2.41–2.50 (m, 1H), 2.62–2.69 (m, 1H), 3.92, 3.94 (2s, 3H), 4.07–4.11 (m, 1H), 4.22 (s, 1H), 4.48 (d, J=12 Hz, 2H), 4.52–4.59 (m, 1H), 5.13 (d, J=17 Hz, 1H), 5.48 (m, 1H), 5.72–5.80 (m, 1H), 7.04 (dd, J=9, 2 Hz, 1H), 7.21 (s, 1H), 7.35–7.39 (m, 1H), 7.46–7.54 (m, 3H), 7.73 (m, 2H), 7.89–8.10(m, 5H).

Compound 40

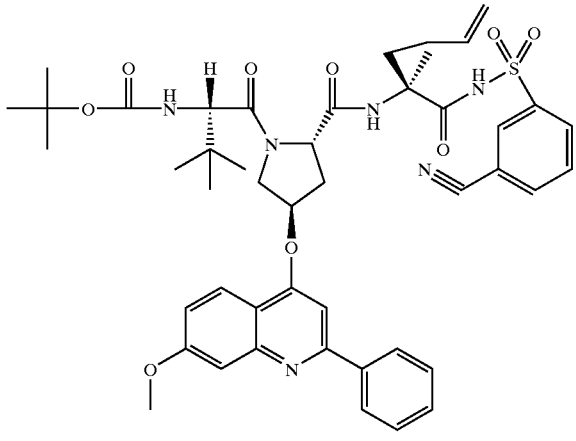

LC/MS rt-min (MH$^+$): 1.66 (851) (method A). $^1$H NMR: (methanol-d$_4$, 500 MHz) δ 1.02 (s, 9H), 1.26 (s, 9H), 1.31 (m, 1H), 1.74 (dd, J=7, 5 Hz, 1H), 2.05–2.11 (m, 1H), 2.46 (m, 1H), 2.61–2.73 (m, 1H), 3.91, 3.94 (2s, 3H), 4.06–4.11 (m, 1H), 4.22 (s, 1H), 4.48 (d, J=12 Hz, 1H), 4.56 (t, J=9 Hz, 1H), 4.90–4.95 (m, 1H), 5.14 (d, J=17 Hz, 1H), 5.48 (m, 1H), 5.69–5.76 (m, 1H), 7.02–7.08 (m, 1H), 7.21 (s, 1H), 7.35–7.39 (m, 1H), 7.47–7.59 (m, 3H), 7.76–7.79 (m, H), 8.01–0.22 (m, 5H).

Compound 42

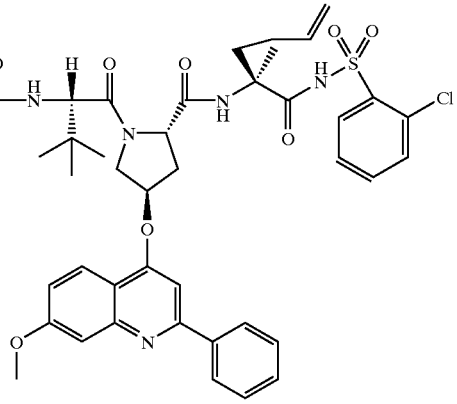

LC/MS rt-min (MH$^+$) 1.70 (860) (method B). $^1$H NMR: (methanol-d$_4$, 500 MHz) δ 1.04 (s, 9H), 1.27 (s, 9H), 1.31–1.35 (m, 1H), 1.71 (dd, J=8, 5 Hz, 1H), 2.11–2.17 (m, 1H), 2.37–2.44 (m, 1H), 2.67 (dd, J=14, 7 Hz, 1H) 3.95 (s, 3H), 4.12 (dd, J=11.9, 3.1 Hz, 1H), 4.24–4.27 (m, 1H), 4.53–4.60 (m, 2H), 4.81–4.84 (m, 1H), 5.12 (d, J=16.2 Hz, 1H), 5.19–5.28 (m, 1H), 5.58 (s, 1H), 7.10 (dd, J=9, 2 Hz, 1H), 7.28 (s, 1H), 7.30 (d, J=2 Hz, 1H), 7.42–7.47 (m, 1H), 7.50–7.59 (m, 5H), 8.04–8.13 (m, 4H).

Compound 41

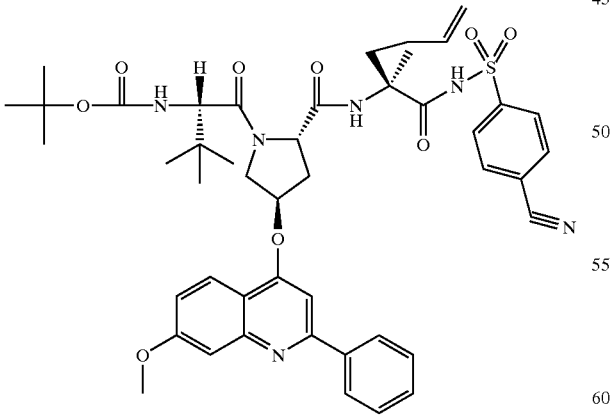

LC/MS rt-min (MH$^+$): 1.65 (851) (method A). $^1$H NMR: (methanol-d$_4$, 500 MHz) δ 1.02 (s, 9H), 1.26 (s, 9H), 1.21–1.30 (m, 1H), 1.73 (dd, J=7, 5 Hz, 1H), 2.03–2.09 (m, Compound 43

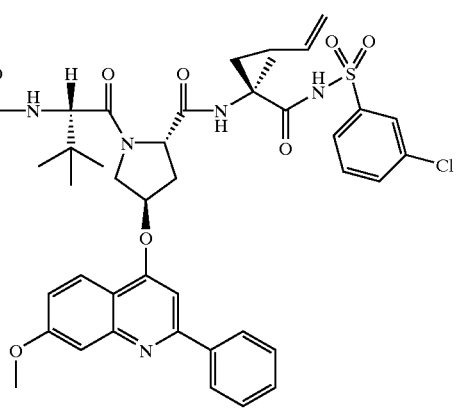

LC/MS rt-min (MH⁺): 1.63 (860) (method B).

Compound 44

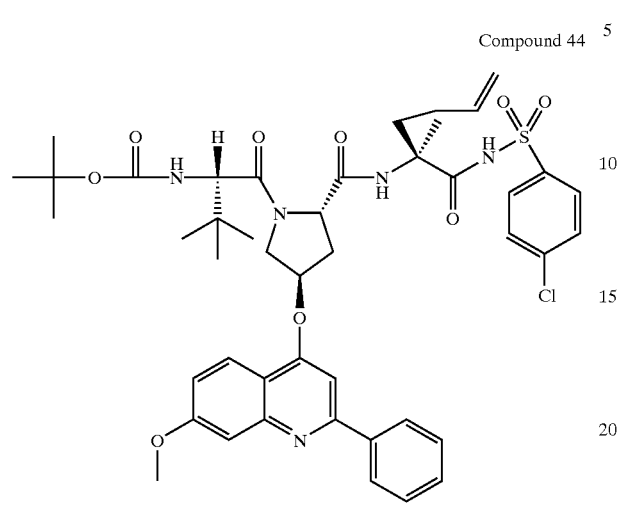

LC/MS rt-min (MH⁺): 1.78 (860) (method B). ¹H NMR: (methanol-d$_4$, 500 MHz) δ 1.06 (s, 9H), 1.27 (s, 9H), 1.30–1.34 (m, 1H), 1.72 (dd, J=8, 5.5 Hz, 1H), 2.11–2.16 (m, 1H), 2.32–2.43 (m, 1H), 2.68 (dd, J=14, 7 Hz, 1H), 3.95 (s, 3H), 4.07–4.12 (m, 1H), 4.24–4.27 (m, 1H), 4.53–4.57 (m, 2H), 4.92 (d, J=10 Hz, 1H), 5.15 (d, J=17 Hz, 1H), 5.37–5.45 (m, 1H), 5.58 (m, 1H), 7.11 (d, J=9 Hz, 1H), 7.29 (s, 1H), 7.39 (s, 1H), 7.52–7.57 (m, 5H), 7.91–7.94 (m, 2H), 8.04, 8.05 (2s, 2H), 8.10–8.13 (m, 1H).

Compound 46

LC/MS rt-min (MH⁺): 1.76 (858) (method B). ¹H NMR: (methanol-d$_4$, 500 MHz) δ 1.03 (s, 9H), 1.27 (s, 9H), 1.33 (dd, J=9.5, 5 Hz, 1H), 1.72 (dd, J=8, 6 Hz, 1H), 2.12–2.18 (m, 1H), 2.36–2.43 (m, 1H), 2.58 (s, 3H), 2.70 (dd, J=14, 7 Hz, 1H), 3.95 (s, 3H), 4.12 (dd, J=12, 3 Hz, 1H), 4.22–4.26 (m, 1H), 4.54–4.59 (m, 2H), 5.15 (d, J=17 Hz, 1H), 5.28–5.35 (m, 1H), 5.59 (m, 1H), 7.11 (dd, J=9, 2 Hz, 1H), 7.20–7.27 (m, 3H), 7.40 (d, J=2 Hz, 1H), 7.51–7.57 (m, 3H), 7.72 (dd, J=9, 3 Hz, 1H), 8.04, 8.05 (2s, 2H), 8.12 (d, J=9 Hz, 1H).

Compound 45

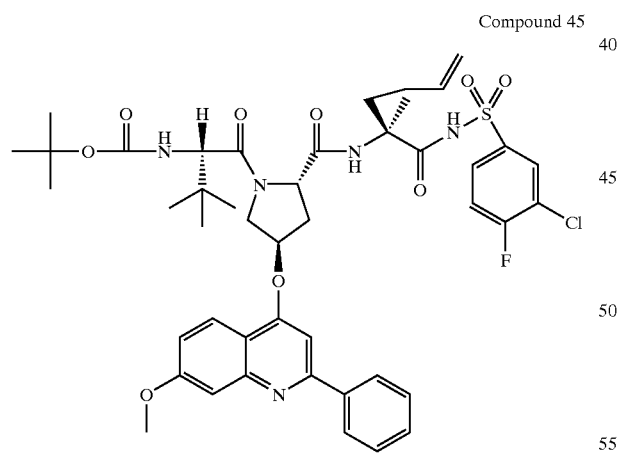

LC/MS rt-min (MH⁺): 1.82 (879) (method B). ¹H NMR: (methanol-d$_4$, 500 MHz) δ 1.06 (s, 9H), 1.26 (s, 9H), 1.33 (dd, J=9, 5 Hz, 1H), 1.73 (dd, J=8, 5 Hz, 1H), 2.11–2.17 (m, 1H), 2.36–2.43 (m, 1H), 2.71 (dd, J=14, 7 Hz, 1H), 3.96 (s, 3H), 4.13 (dd, J=12, 3 Hz 1H), 4.25 (s, 1H), 4.53–4.58 (m, 2H), 4.94 (d, J=10 Hz, 1H), 5.17 (d, J=17 Hz, 1H), 5.46–5.53 (m, 1H), 5.60 (m, 1H), 7.13 (dd, J=9, 2 Hz, 1H), 7.31 (s, 1H), 7.37–7.42 (m, 2H), 7.53–7.58 (m, 3H), 7.92–7.95 (m, 1H), 8.04–8.06 (m, 3H), 8.13 (d, J=9.5 Hz, 1H).

Compound 47

LC/MS rt-min (MH⁺): 1.79 (894) (method A). ¹H NMR: (methanol-d$_4$, 500 MHz) δ 1.05 (s, 9H), 1.26, 1.28 (2s, 9H), 1.31–1.34 (m, 1H), 1.72 (m, 1H), 2.08–2.16 (m, 1H), 2.37–2.42 (m, 1H), 2.68 (dd, J=14, 7 Hz, 1H), 3.96 (s, 3H), 4.13 (dd, J=12 Hz, 1H), 4.25 (s, 1H), 4.53–4.57 (m, 2H), 5.13 (d, J=17 Hz, 1H), 5.42–5.49 (m, 1H), 5.59 (m, 1H), 7.12 (d, J=9 Hz, 1H), 7.31 (s, 1H), 7.40 (s, 1H), 7.54–7.57 (m, 3H), 7.70–7.74 (m, 1H), 7.93 (d, J=7 Hz, 1H), 8.04, 8.05 (2s, 2H), 8.12–8.22 (m, 3H).

Compound 48

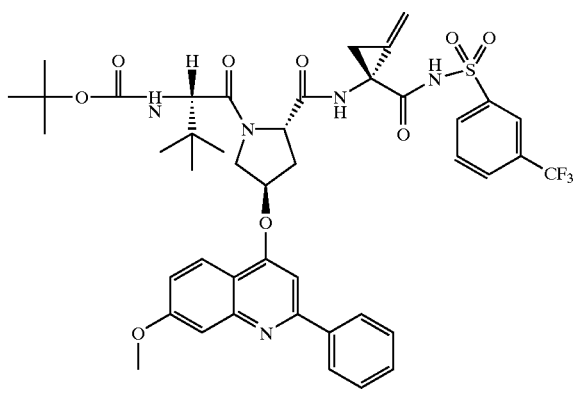

LC/MS rt-min (MH$^+$) 1.74 (894) (method A). $^1$H NMR: (methanol-d$_4$, 500 MHz) δ 1.01 (s, 9H), 1.26, 1.28 (2s, 9H), 1.30–1.33 (m, 1H), 1.72 (dd, J=8, 5 Hz, 1H), 2.21–2.26 (m, 1H), 2.38–2.44 (m, 1H), 2.69 (dd, J=14, 7 Hz, 1H), 3.96 (s, 3H), 4.12–4.15 (m, 1H), 4.25 (s, 1H), 4.54–4.59 (m, 2H), 4.82 (dd, J=10, 2 Hz, 1H), 5.10 (d, J=17 Hz, 1H), 5.23–5.30 (m, 1H), 5.60 (m, 1H), 7.12 (dd, J=9, 2 Hz, 1H), 7.30 (s, 1H), 7.40 (d, J=2 Hz, 1H), 7.51–7.58 (m, 3H), 7.74–7.81 (m, 2H), 7.87–7.91 (m, 1H), 8.04, 8.05 (2s, 2H), 8.12 (d, J=9 Hz, 1H), 8.32 (d, J=7 Hz, 1H).

Compound 49

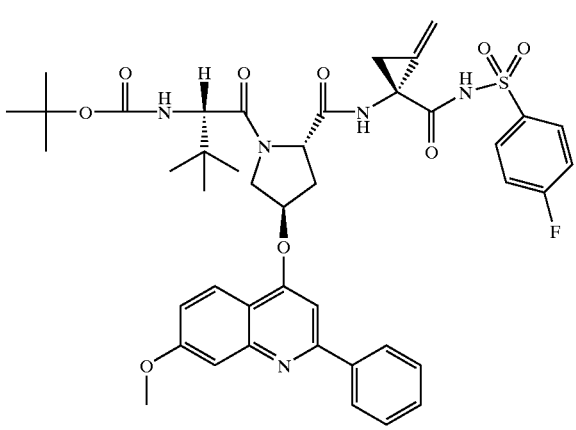

LC/MS rt-min (MH$^+$): 1.67 (844) (method A). $^1$H NMR: (methanol-d$_4$, 500 MHz) δ 1.04 (s, 9H), 1.26 (s, 9H), 1.43 (m, 1H), 1.68–1.70 (m, 1H), 1.92–2.00 (m, 1H), 2.57–2.65 (m, 1H), 2.74 (dd, J=14, 8 Hz, 1H), 3.95 (s, 3H), 4.18–4.27 (m, 2H), 4.49–4.59 (m, 2H), 4.89–4.93 (m, 1H), 5.11 (dd, J=17, 2 Hz, 1H), 5.56 (m, 1H), 5.62–5.72 (m, 1H), 7.04–7.14 (m, 3H), 7.28 (s, 1H), 7.39–7.41 (m, 1H), 7.48–7.55 (m, 3H), 7.87–7.93 (m, 2H), 8.06–8.13 (m, 3H).

Compound 50

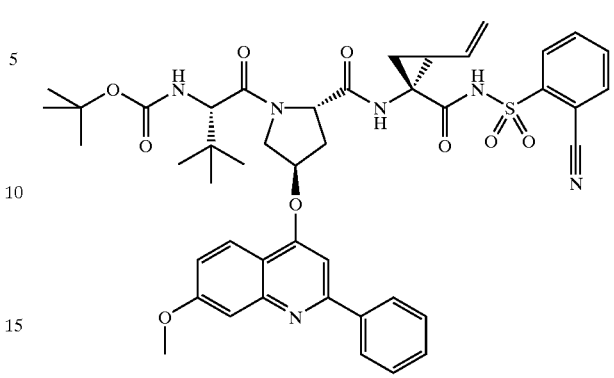

LC/MS rt-min (MH$^+$): 1.55 (851) (method A). $^1$H NMR: (methanol-d$_4$, 500 MHz) δ 0.76 (s, 9H), 1.35 (s, 9H), 1.49 (dd, J=9.5, 5.5 Hz, 1H), 2.03–2.05 (m, 1H), 2.31–2.43 (m, 2H), 2.71 (dd, J=13, 6 Hz, 1H), 3.95 (s, 3H), 4.04–4.13 (m, 1H), 4.48–4.64 (m, 2H), 5.07–5.16 (m, 1H), 5.23–5.34 (m, 1H), 5.55–5.76 (m, 2H), 7.05–7.10 (m, 1H), 7.25 (s, 1H), 7.40 (d, J=2 Hz, 1H), 7.47–7.58 (m, 4H), 7.78–7.89 (m, 1H), 7.92–7.99 (m, 1H), 8.03, 8.05 (2s, 2H), 8.09–8.17 (m, 1H), 8.39 (d, J=7.3 Hz, 1H).

Compound 51

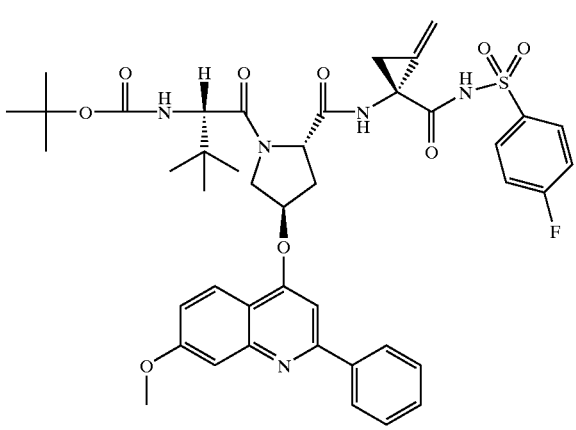

LC/MS rt-min (MH$^+$): 1.66 (871) (method A). $^1$H NMR: (methanol-d$_4$, 500 MHz) δ 1.06 (s, 9H), 1.26 (s, 9H), 1.43 (m, 1H), 1.69–1.72 (m, 1H), 2.09–2.15 (m, 1H), 2.42–2.48 (m, 1H), 2.71 (dd, J=14, 7 Hz, 1H), 3.96 (s, 3H), 4.13–4.16 (m, 1H), 4.22–4.26 (m, 1H), 4.55–4.58 (m, 2H), 4.89 (d, J=10 Hz, 1H), 5.14 (d, J=17 Hz, 1H), 5.47–5.54 (m, 1H), 5.62 (m, 1H), 6.63 (d, J=8.8 Hz, 1H), 7.13–7.15 (m, 1H), 7.35 (s, 1H), 7.40 (s, 1H), 7.54–7.61 (m, 3H), 8.04, 8.06 (2s, 2H), 8.15 (d, J=9 Hz, 1H), 8.31 (d, J=8 Hz, 1H), 8.44 (d, J=8 Hz, 1H), 8.72 (d, J=9 Hz, 1H).

Compound 52

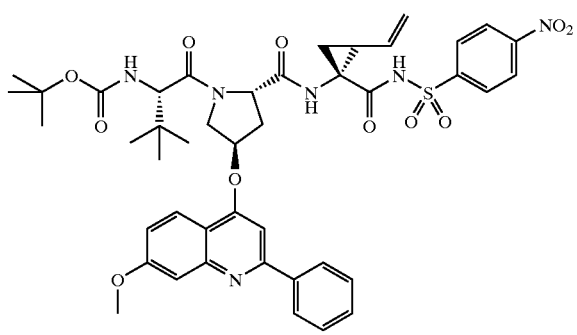

LC/MS rt-min (MH⁺): 1.70 (871) (method A). ¹H NMR: (methanol-d₄, 500 MHz) 1.05 (s, 9H), 1.26 (s, 9H), 1.27–1.31 (m, 1H), 1.70 (dd, J=8, 5 Hz, 1H), 2.10–2.16 (m, 1H), 2.42–2.50 (m, 1H), 2.71 (dd, J=14, 7 Hz, 1H), 3.95 (s, 3H), 4.12–4.14 (m, 1H), 4.24 (s, 1H), 4.54–4.60 (m, 2H), 4.91 (d, J=12 Hz, 1H), 5.15 (d, J=17 Hz, 1H), 5.51–5.59 (m, 2H), 7.13 (dd, J=9, 2 Hz, 1H), 7.31 (s, 1H), 7.38 (d, J=2 Hz, 1H), 7.53–7.56 (m, 3H), 7.99–8.04 (m, 2H), 8.09–8.31 (m, 3H), 8.27 (d, J=9 Hz, 1H).

Compound 53

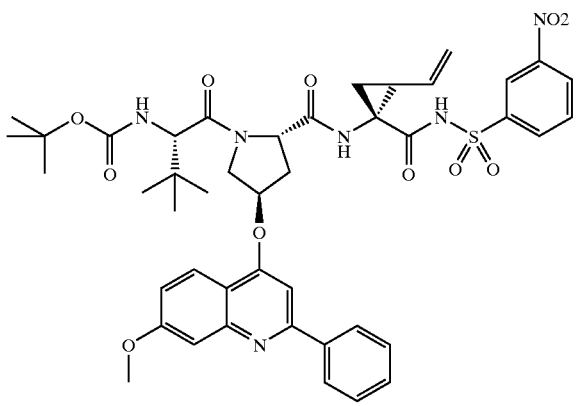

LC/MS rt-min (MH⁺) 1.70 (871) (method A). ¹H NMR: (methanol-d₄, 300 MHz) δ 1.02 (s, 9H), 1.26 (s, 9H), 1.42 (m, 1H), 1.66–1.72 (m, 1H), 1.90–1.98 (m, 1H), 2.56–2.66 (m, 1H), 2.70–2.80 (m, 1H), 3.93 (s, 3H), 4.16–4.26 (m, 2H), 4.47–4.59 (m, 2H), 5.09 (dd, J=17, 1.5 Hz, 1H), 5.54 (m, 1H), 5.60–5.78 (m, 1H), 6.60 (d, J=8.8 Hz, 1H), 7.06 (dd, J=9, 2 Hz, 1H), 7.26 (s, 1H), 7.37–7.40 (m, 1H), 7.48–7.65 (m, 4H), 8.04–8.10 (m, 3H), 8.18–8.29 (m, 2H), 8.67 (s, 1H).

Compound 54

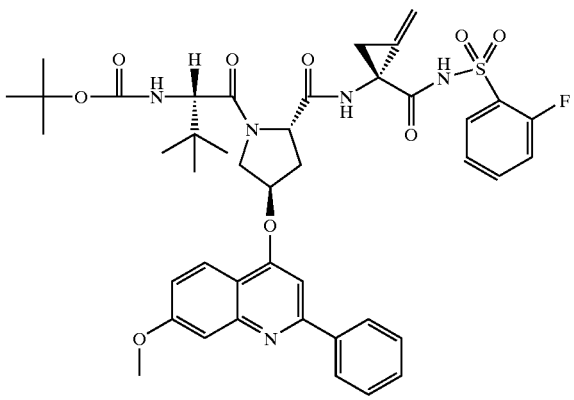

LC/MS rt-min (MH⁺): 1.79 (844) (method B). ¹H NMR: (methanol-d₄, 300 MHz) δ 1.02 (s, 9H), 1.25 (s, 9H), 1.43 (m, 1H), 1.77 (dd, J=8, 5 Hz, 1H), 2.00–2.19 (m, 1H), 2.38–2.69 (m, 2H), 3.91 (s, 3H), 4.03–4.14 (m, 1H), 4.20–4.33 (m, 1H), 4.45 (d, J=12 Hz, 1H), 4.55 (t, J=9 Hz, 1H), 5.12 (d, J=17 Hz, 1H), 5.44 (m, 1H), 5.67–5.88 (m, 1H), 7.01–7.18 (m, 4H), 7.34 (s, 1H), 7.40–7.57 (m, 3H), 7.82–7.92 (m, 1H), 8.01–8.10 (m, 3H).

Compound 55

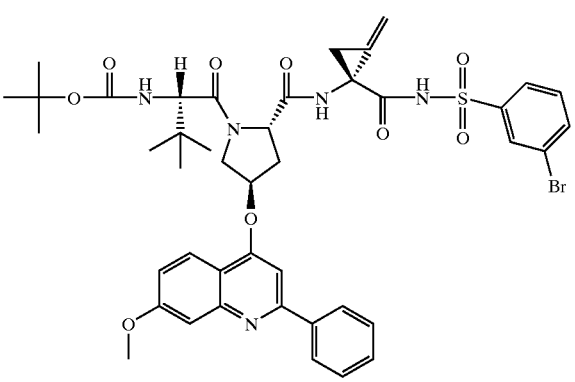

LC/MS rt-min (MH⁺) 1.75 (905 in MS) (method A). ¹H NMR: (methanol-d₄, 300 MHz) δ 1.02 (s, 9H), 1.25 (s, 9H), 1.42 (m, 1H), 1.75 (dd, J=8, 5 Hz, 1H), 2.00–2.12 (m, 1H), 2.38–2.46 (m, 1H), 2.57–2.69 (m, 1H), 3.90 (s, 3H), 4.03–4.10 (m, 1H), 4.23 (s, 1H), 4.47 (d, J=12 Hz, 1H), 4.54 (t, J=9 Hz, 2H), 4.93 (d, J=11 Hz, 1H), 5.14 (d, J=17 Hz, 1H), 5.44 (m, 1H), 5.62–5.84 (m, 1H), 7.04 (dd, J=9, 2.6 Hz, 1H), 7.19 (s, 1H), 7.29–7.37 (m, 2H), 7.45–7.61 (m, 4H), 7.77–7.88 (m, 1H), 7.98–8.11 (m, 4H).

Compound 56

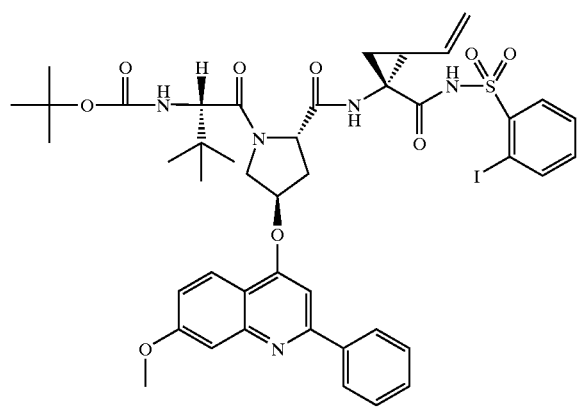

LC/MS rt-min (MH+): 1.72 (952 in MS) (method A). ¹H NMR: (methanol-d₄, 300 MHz), δ 1.02 (s, 9H), 1.26 (s, 9H), 1.32 (m, 1H), 1.84 (dd, J=7.5, 5 Hz, 1H), 2.06–2.13 (m, 1H), 2.43–2.52 (m, 1H), 2.63 (dd, J=14, 7 Hz 1H), 3.92 (s, 3H), 4.03–4.10 (m, 1H), 4.23 (s, 1H), 4.45 (d, J=11 Hz, 2H), 4.53–4.58 (m, 2H), 4.89 (m, 1H), 5.08–5.20 (m, 1H), 5.36, 5.42 (m, 1H), 5.71–5.99 (m, 1H), 7.02–7.08 (m, 2H), 7.16 (s, 1H), 7.31–7.38 (m, 2H), 7.44–7.53 (m, 3H), 7.90–8.13 (m, 5H). HRMS cald for $C_{44}H_{51}N_5O_9S$ 952.2452 found 952.2476.

Compound 58

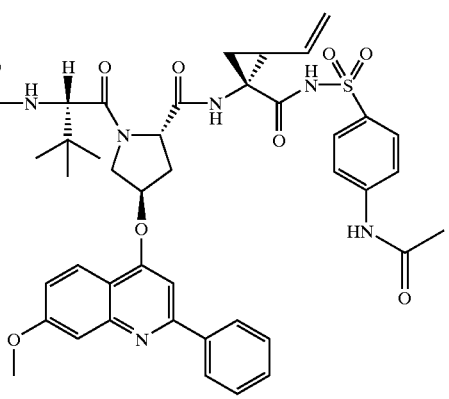

LC/MS rt-min (MH+) 1.57 (884) (method B). ¹H NMR: (methanol-d₄, 300 MHz) δ 1.03 (s, 9H), 1.24, 1.29 (2s, 10H), 1.43 (s, 1H), 1.55–1.86 (m, 2H), 2.00 (m, 1H), 2.09 (s, 3H), 2.36–2.45 (m, 1H), 2.59–2.66 (m, 1H), 3.92, 3.94 (2s, 3H), 4.10 (m, 1H), 4.23–4.26 (m, 1H), 4.45–4.58 (m, 2H), 4.91 (d, J=11.7 Hz, 1H), 5.12 (d, J=16.8 Hz, 1H), 5.44 (s, 1H), 5.64–5.76 (m, 1H), 7.05 (dd, J=9.2, 2.4 Hz, 1H), 7.20 (s, 1H), 7.36 (d, J=2.4 Hz, 2H), 7.47–7.55 (m, 3H), 7.59–7.64 (m, 2H), 7.79–7.84 (m, 2H), 8.02–8.08 (m, 3H).

Compound 57

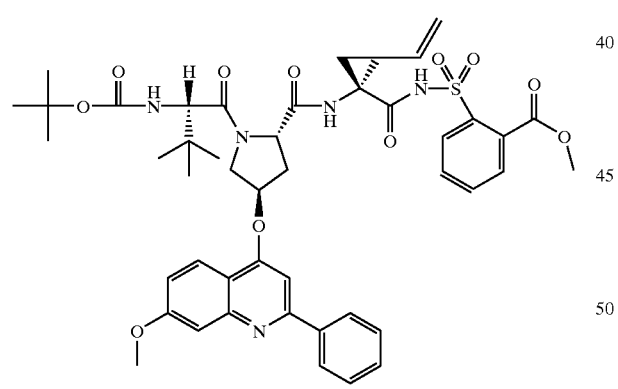

LC/MS rt-min (MH+): 1.64 (884) (method A). ¹H NMR: (methanol-d₄, 300 MHz) δ 1.04 (s, 9H), 1.23 (s, 9H), 1.28–1.37 (m, 1H), 1.72 (dd, J=7.9, 5.7 Hz, 1H), 2.11–2.20 (m, 1H), 2.45–2.54 (m, 1H), 2.78 (dd, J=13.4, 6.8 Hz, 1H), 3.95 (s, 3H), 4.03 (s, 3H), 4.10–4.19 (m, 1H), 4.25–4.35 (m, 1H), 4.64–4.73 (m, 2H), 5.04 (d, J=17.9 Hz, 1H), 5.16–5.28 (m, 1H), 5.80 (m, 1H), 7.30 (dd, J=9.2, 1.8 Hz, 1H), 7.50 (d, J=2.2 Hz, 1H), 0.7.56 (s, 1H), 7.60 (m, 6H), 8.06–8.08 (m, 2H), 8.15 (d, J=7.3 Hz, 1H), 8.30 (d, J=9.2 Hz, 1H).

Compound 59

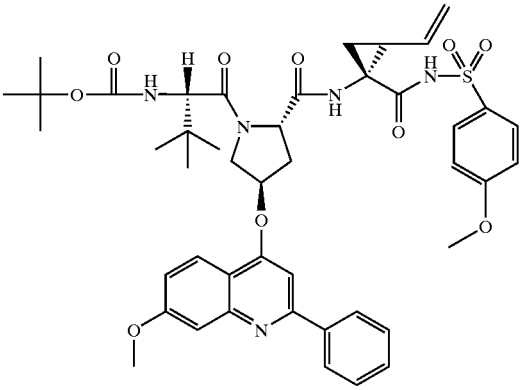

LC/MS rt-min (MH+): 1.74 (857) (method B). ¹H NMR: (methanol-d₄, 300 MHz) d 1.05 (s, 9H), 1.26 (s, 9H), 1.43 (m, 1H), 1.70–1.79, (m, 1H), 2.10 (q, J=8.8 Hz, 1H), 2.32–2.41 (m, 1H), 2.62 (dd, J=13, 7 Hz, 1H), 3.79 (s, 3H), 3.93 (s, 3H), 4.06–4.11 (m, 1H), 4.24–4.33 (m, 1H), 4.48–4.57 (m, 2H), 5.00 (d, J=12.1 Hz, 1H), 5.14 (d, J=17.2 Hz, 1H), 5.48 (m, 1H), 5.64–5.66 (m, 1H), 6.91–6.96 (m, 1H), 7.01–7.07 (m, 1H), 7.18–7.41 (m, 3H), 7.47–7.55 (m, 3H), 7.80–7.78 (m, 2H), 8.02–8.08 (m, 3H).

Compound 60

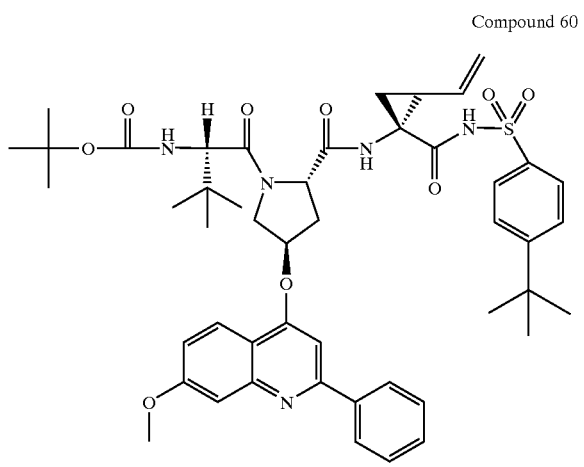

¹H NMR: (methanol-d₄, 300 MHz) δ 1.04 (s, 9H), 1.24–1.44 (m, 19H), 1.76 (dd, J=8, 5 Hz, 1H), 2.03–2.21 (m, 1H), 2.40–2.50 (m, 1H), 2.58–2.65 (m, 1H), 3.93 (s, 3H), 4.08–4.14 (m, 1H), 4.24 (s, 1H), 4.45–4.58 (m, 2H), 4.92 (dd, J=10.4, 2 Hz, 1H), 5.15 (d, J=17.2 Hz, 1H), 5.47 (m, 1H), 5.71 (m, 1H), 7.05 (dd, J=9, 2 Hz, 1H), 7.20 (s, 1H), 7.34–7.68 (m, 6H), 7.77–7.83 (m, 2H), 7.95–8.07 (m, 3H).

Compound 61

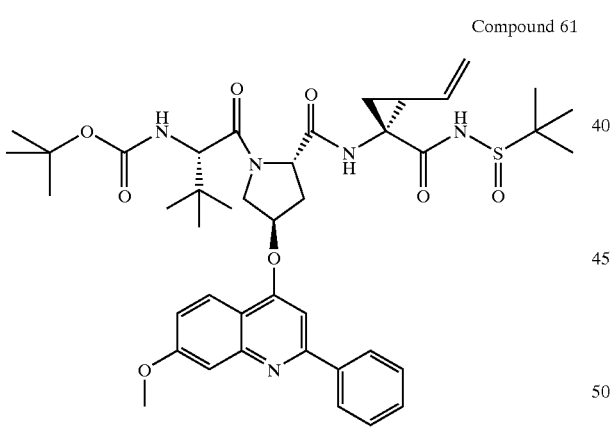

LC/MS rt-min (MH⁺) 1.58 (790)(method A) ¹H NMR: (methanol-d₄, 300 MHz) δ 1.05 (s, 9H), 1.26, 1.27 (2s, 18H), 1.33–1.44 (m, 1H), 1.81–1.85 (m, 1H), 2.18–2.35 (m, 2H), 2.67–2.74 (m, 1H), 3.95 (s, 3H), 4.01–4.10 (m, 1H), 4.19–4.25 (m, 1H), 4.57–4.62 (m, 2H), 5.10 (d, J=12 Hz, 1H), 5.24 (d, J=17 Hz, 1H), 5.53–5.65 (m, 2H), 6.51 (d, J=9 Hz, 1H), 7.07 (dd, J=9, 2 Hz, 1H), 7.25 (s, 1H), 7.40 (d, J=2 Hz, 1H), 7.47–7.57 (m, 3H), 8.03–8.06 (m, 2H), 8.10 (d, J=9 Hz, 1H); HRMS m/z (M+H)⁺ calcd for C₄₂H₅₆N₅SO₈: 790.3850 found: 790.3834.

Compound 62

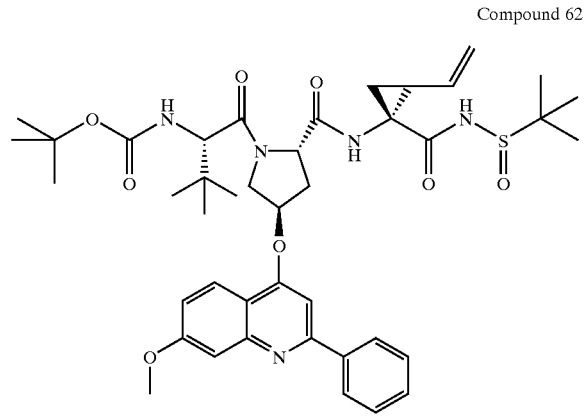

LC/MS rt-min (MH⁺): 1.61(790) (method A). ¹H NMR: (methanol-d₄, 300 MHz) δ 1.03 (s, 9H), 1.21–1.37 (m, 1H), 1.23 (s, 9H), 1.29 (s, 9H), 1.79–1.86 (m, 1H), 2.00–2.39 (m, 1H), 2.68–2.72 (m, 1H), 3.95 (s, 3H), 4.04–4.13 (m, 1H), 4.24–4.33 (m, 1H), 4.54–4.69 (m, 2H), 5.09 (d, J=10 Hz, 1H), 5.28 (d, J=17 Hz, 1H), 5.48–5.67 (m, 2H), 7.05–7.09 (m, 1H), 7.26 (s, 1H), 7.40 (m, 1H), 7.49–7.62 (m, 3H), 8.04–8.11 (m, 3H); HRMS m/z (M+H)⁺ calcd for C₄₂H₅₆N₅SO₈: 790.3850 found: 790.3827.

Compound 63

LC/MS rt-min (MH⁺): 1.78(841) (method D).

Compound 64

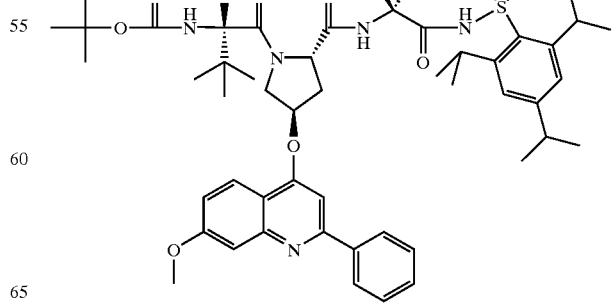

LC/MS rt-min (MH+): 2.04 (953 in MS) (method B). ¹H NMR: (methanol-d₄, 300 MHz) δ 1.06, 1.08 (2s, 9H), 1.20–1.29 (m, 28H), 1.43 (m, 1H), 1.73 (dd, J=7.9, 5.7 Hz 1H), 2.03–2.14 (m, 1H), 2.38 (m, 1H), 2.68 (dd, J=13.9, 6.2 Hz, 1H), 2.85–2.94 (m, 1H), 3.95 (s, 3H), 4.14 (dd, J=11.9, 2.7 Hz, 1H), 4.24–4.36 (m, 3H), 4.48–4.61 (m, 2H), 4.78 (d, J=11.3 Hz, 1H), 5.06 (d, J=17.2 Hz, 1H), 5.58 (m, 1H), 7.07–7.11 (m, 1H), 7.18 (s, 2H), 7.27 (s, 1H), 7.40 (d, J=1.8, 1H), 7.47–7.57 (m, 3H), 8.04–8.11 (m, 3H). HRMS cald for C₅₃H₇₀N₅O₉S 952.4894 found 952.4898.

LC/MS rt-min (MH+): 1.86 (909) (method B). ¹H NMR: (methanol-d₄, 300 MHz) δ 1.03 (s, 9H), 1.25, 1.30 (2s, 9H), 1.43 (m, 1H), 1.72–1.76 (m, 1H), 2.02–2.11 (m, 1H), 2.42–2.51 (m, 1H), 2.61–2.71 (m, 1H), 3.93, 3.94 (2s, 3H), 4.08–4.13 (m, 1H), 4.23 (s, 1H), 4.47–4.58 (m, 2H), 5.12 (d, J=17.2 Hz, 1H), 5.50 (m, 1H), 5.64–5.78 (m, 1H), 7.06 (dd, J=9.2, 2.6 Hz, 1H), 7.23 (s, 1H), 7.28–7.32 (m, 2H), 7.37–7.39 (m, 1H), 7.47–7.55 (m, 3H), 7.89–8.12 (m, 5H). HRMS cald for C₄₅H₅₁F₃N₅O₁₀S 910.3309 found 910.3298.

Compound 65

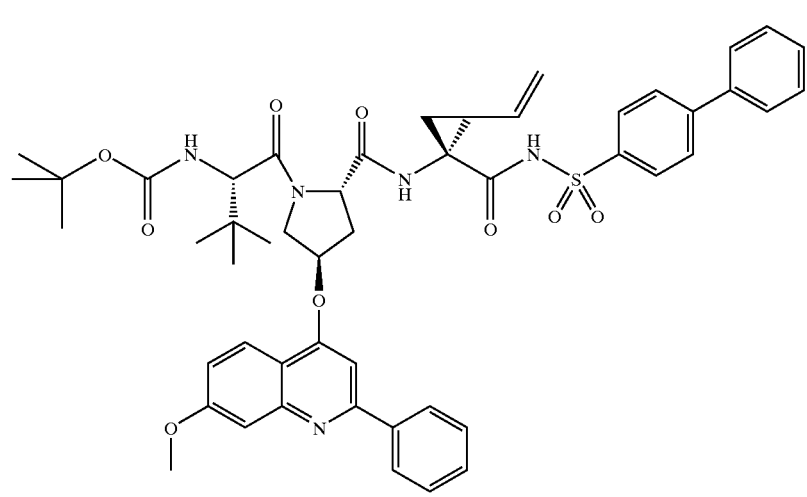

LC/MS rt-min (MH+): 1.77 (902) (method B). ¹H NMR: (methanol-d₄, 300 MHz) δ 1.04 (s, 9H), 1.27 (s, 9H), 1.43 (m, 1H), 1.74 (m, 1H), 2.06 (m, 1H), 2.33–2.71 (m, 2H), 3.94 (s, 3H), 4.09 (m, 1H), 4.24 (m, 1H), 4.42–4.58 (m, 2H), 4.91–4.94 (m, 1H), 5.15 (d, J=16.5 Hz, 1H), 5.47 (m, 1H), 5.74 (m, 1H), 7.04–7.07 (m, 1H), 7.34–7.68 (m, 12H), 7.94–8.07 (m, 5H). HRMS cald for C₅₀H₅₆N₅O₉S 902.3799 found 902.3790.

Compound 67

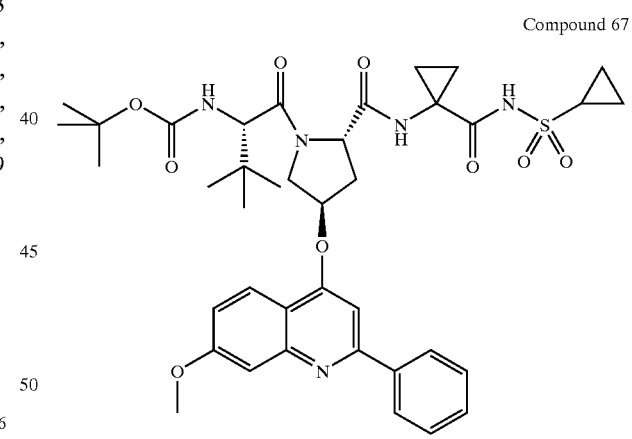

Compound 66

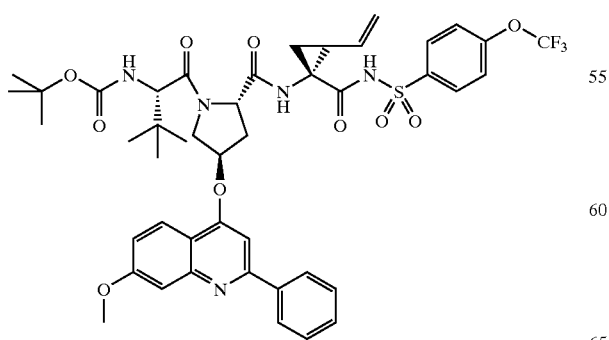

LC/MS rt-min (MH+): 1.43 (764) (method A). ¹H NMR: (methanol-d₄, 300 MHz) δ 1.03 (S, 9H), 1.26 (s, 9H), 1.44–1.52 (m, 1H), 1.52–1.65 (m, 11H), 2.27–2.37 (m, 1H), 2.65 (dd, J=13.7, 6.8 Hz, 1H), 2.92–3.01 (m, 1H), 3.94 (s, 3H), 4.07–4.13 (m, 1H), 4.26 (d, J=9.2 Hz, 1H), 4.48–4.53 (m, 1H), 5.56 (s, 1H), 6.67 (d, J=9.5 Hz, NH), 7.24 (s, 1H), 7.36–7.38 (m, 1H), 7.38 (d, J=2.2 Hz, 1H), 7.47–7.57 (m, 3H), 8.03–8.07 (m, 3H).

Compound 68

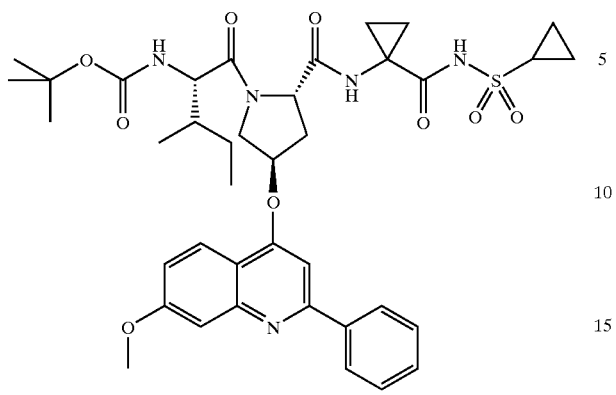

LC/MS rt-min (MH⁺): 1.49 (764) (method A). ¹H NMR: (methanol-$d_4$, 300 MHz) δ 0.86–1.16 (m, 6H), 1.19 (s, 9H), 1.43–1.91 (m, 3H), 2.33–2.42 (m, 1H), 2.51–2.68 (m, 2H), 2.92–3.03 (m, 1H), 3.95 (s, 3H), 4.05–4.12 (m, 2H), 4.54 (dd, J=10.6, 6.2 Hz, 1H), 4.67 (d, J=12.1 Hz, 1H), 5.58 (s, 1H), 6.78 (d, J=9.5 Hz, NH), 7.09 (dd, J=9.2, 2.4 Hz, 1H), 7.25 (s, 1H), 7.38 (d, J=2.4 Hz, 1H), 7.47–7.57 (m, 3H), 8.03–8.10 (m, 3H).

Compound 69

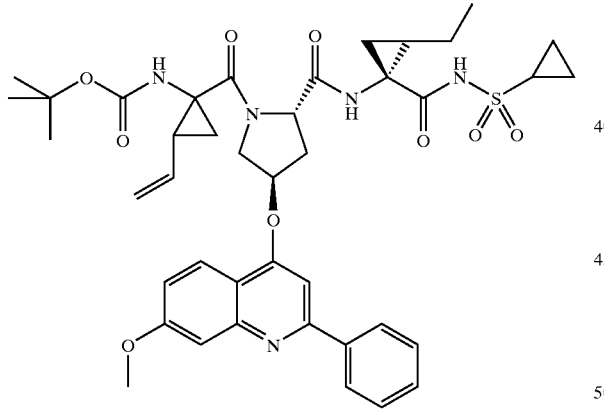

High Rf Isomer (MeOH/CH₂Cl₂)

LC/MS rt-min (MH⁺): 1.49 (788) (method B). ¹H NMR: (methanol-$d_4$, 300MHz) δ 0.85–1.75 (m, 13H), 1.47 (s, 9H), 1.75–1.80 (m, 1H), 1.95–2.04 (m, 1H), 2.47–3.03 (m, 3H), 3.93 (s, 3H), 4.0 (m, 2H), 4.51–4.69 (m, 2H), 4.93–5.02 (m, 1H), 5.31–5.40 (m, 1H), 5.46, 5.55 (2s, 1H), 5.80–5.94 (m, 1H), 7.12 (dd, J=9.2, 2.2 Hz, 1H), 7.18 (s, 1H), 7.37 (d, J=2.2 Hz, 1H), 7.46–7.57 (m, 3H), 7.95 (d, J=9.2 Hz, 1H), 8.04–8.11 (m, 2H); HRMS m/z (M+H)⁺ calcd for C₄₁H₅₀N₅SO₉: 788.3329, found 788.3322.

Compound 70

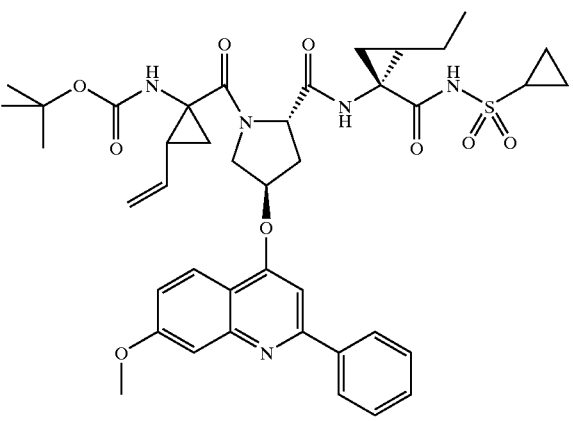

Low Rf Isomer (MeOH/CH₂Cl₂)

LC/MS rt-min (MH⁺): 1.55 (788) (method B). ¹H NMR: (methanol-$d_4$, 300 MHz) δ 0.98 (t, J=7.3 Hz, 3H), 1.09 (s, 9H), 1.26–1.93 (m, 10H), 2.12–2.21 (m, 1H), 2.32–2.40 (m, 1H), 2.53–2.65 (m, 1H), 2.80 (brs, 1H), 3.95 (s, 3H), 4.09–4.18 (m, 1H), 4.37 (d, J=12 Hz, 1H), 4.54–4.59 (m, 2H), 5.19 (d, J=9.2 Hz, 1H), 5.33 (d, J=16.5 Hz, 1H), 5.46–5.60 (m, 2H), 7.11–7.15 (m, 1H), 7.22 (s, 1H), 7.43 (d, J=2 Hz, 1H), 7.48–7.58 (m, 3H), 8.01–8.07 (m, 3H). HRMS m/z (M+H)⁺ calcd for C₄₁H₅₀N₅SO₉: 788.3329, found 788.3330.

Compound 71

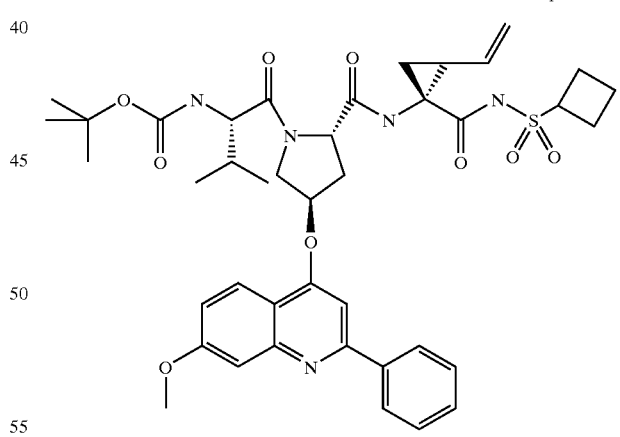

LC/MS rt-min (MH⁺): 1.53 (790) (method A). ¹H NMR: (methanol-$d_4$, 300 MHz) δ 0.94 (d, J=6.2 Hz, 6H), 1.08 (s, 9H), 1.28–1.33 (m, 1H), 1.70–2.74 (m, 10H), 3.68 (m, 1H), 3.93, 3.98 (2s, 3H), 4.04–4.33 (m, 2H), 4.45–4.60 (m, 2H), 5.14 (d, J=17.6 Hz, 1H), 5.53 (s, 1H), 5.78–5.90 (m, 1H), 7.20, 7.25 (2s, 1H), 7.37–7.42 (m, 1H), 7.49–7.56 (m, 4H), 8.03–8.06 (m, 3H).

Compound 72

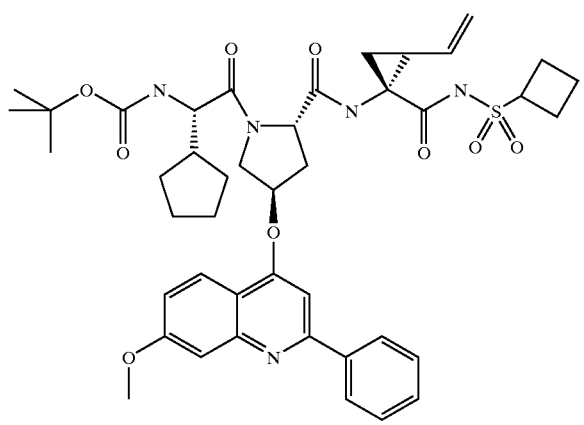

Compound 74 and 75

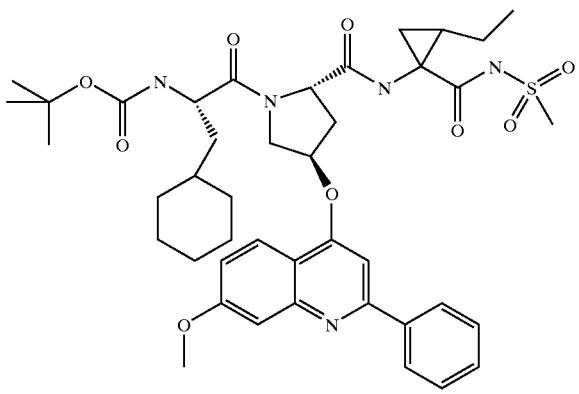

Compound 74—(1S,2S) isomer: LC/MS rt-min (MH+): 1.71 (806).

Compound 75—(1R,2R) isomer: LC/MS rt-min (MH+): 1.69 (806).

LC/MS rt-min (MH+): 1.62 (816). $^1$H NMR: (methanol-$d_4$, 300MHz) δ 1.24 (s, 9H), 1.39–1.58 (m, 2H), 1.50–2.53 (m, 17H), 2.72–2.80 (m, 1H), 3.75–3.89 (m, 1H), 3.94 (s, 3H), 4.02–4.13 (m, 2H), 4.54–4.67 (m, 2H), 5.03 (d, J=10.2 Hz, 1H), 5.24 (d, J=17.2 Hz, 1H), 5.54 (s, 1H), 5.78–5.93 (m, 1H), 7.08 (dd, J=9.2, 2 Hz, 1H), 7.25, 7.27 (2s, 1H), 7.39 (d, J=2.2 Hz, 1H), 7.46–7.57 (m, 3H), 8.04–8.06 (m, 2H), 8.13 (d, J=9.2 Hz, 1H).

Compound 76

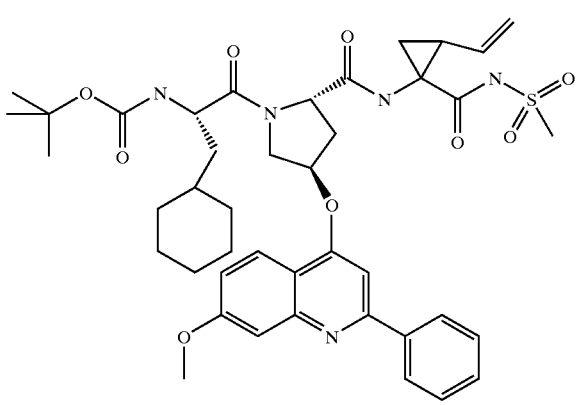

(1R,2S/1S,2R 1:1 mixture): LC/MS rt-min (MH+) 1.69 (804).

Compound 73

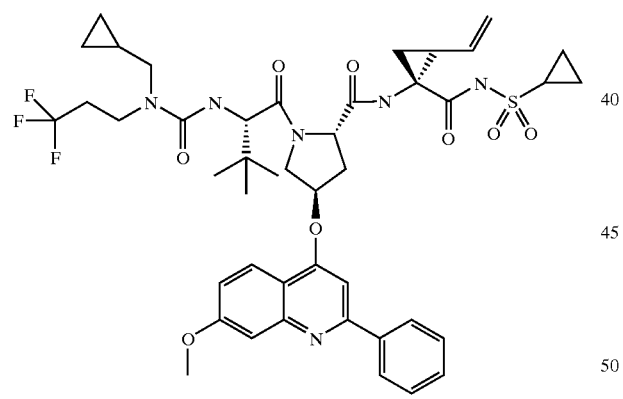

Compounds 77 and 78

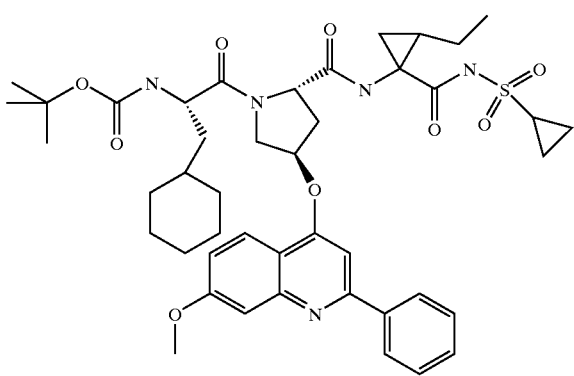

LC/MS rt-min (MH+): 1.65 (883) (method A). $^1$H NMR: (methanol-$d_4$, 500 MHz) δ 0.22–0.27 (m, 2H), 0.50–0.56 (m, 2H), 0.86–1.36 (m, 1H), 1.09 (s, 9H), 1.46–1.48 (m, 1H), 1.90 (dd, J=8, 5 Hz, 1H), 2.18–2.24 (m, 1H), 2.30–2.46 (m, 1H), 2.70 (dd, J=14, 7 Hz, 1H), 3.07 (dd, J=15, 7 Hz, 1H), 3.13 (dd, J=15, 7 Hz, 1H), 3.43–3.49 (m, 2H), 3.98 (s, 3H), 4.16 (dd, J=12, 3 Hz, 1H), 4.50–4.54 (m, 2H), 4.57–4.61 (m, 1H), 5.12 (d, J=12 Hz, 1H), 5.30 (d, J=17 Hz, 1H), 5.63 (m, 1H), 5.75 (d, J=9 Hz, NH), 5.83–5.90 (m, 1H), 7.13 (dd, J=9, 2 Hz, 1H), 7.31 (s, 1H), 7.43 (d, J=2 Hz, 1H), 7.52–7.59 (m, 3H), 8.08–8.10 (m, 3H).

Compound 77—(1S,2S) isomer: LC/MS rt-min (MH+): 2.10 (832).

Compound 78—(1R,2R) isomer: LC/MS rt-min (MH+): 1.73 (832).

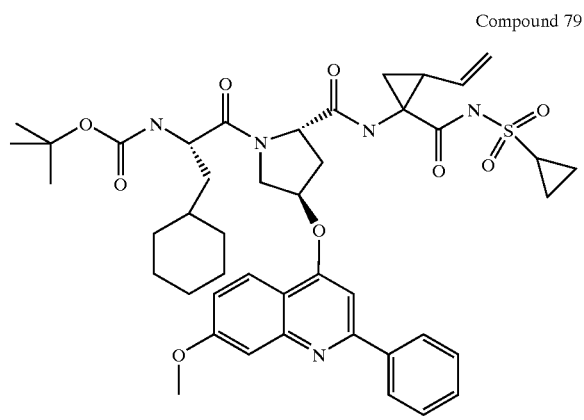

Compound 79

(1R,2S/1S,2R 1:1 mixture): LC/MS rt-min (MH+): 1.72 (830).

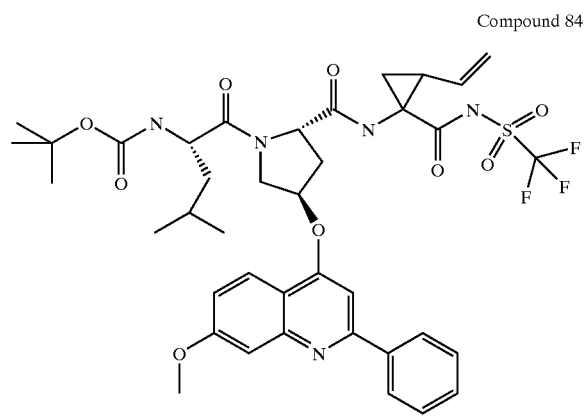

Compound 84

(1R,2S) isomer: LC/MS rt-min (MH+): 1.66 (818).

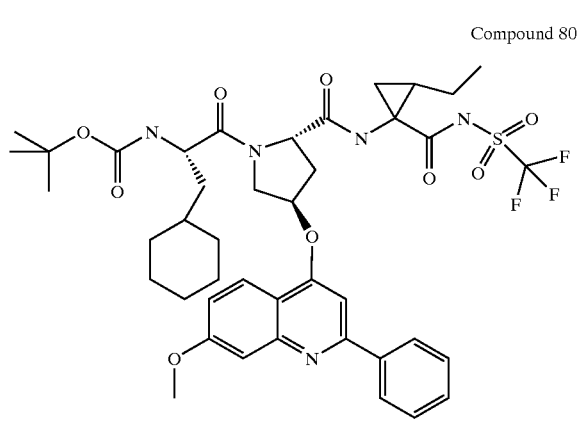

Compound 80

(1R,2R) isomer: LC/MS rt-min (MH+): 1.87 (861).

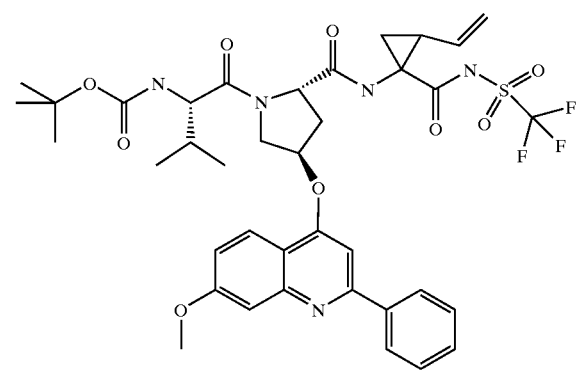

Compound 85

(1R,2S) isomer: LC/MS rt-min (MH+): 1.57 (804).

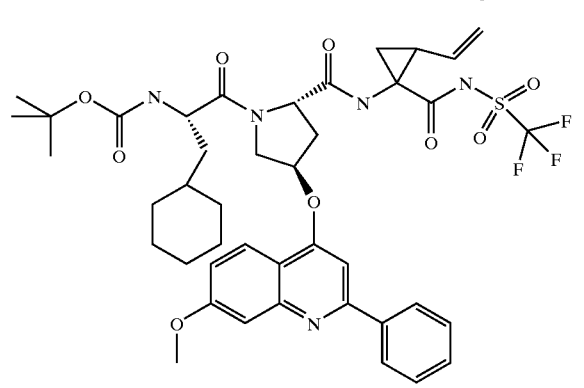

Compound 81–83

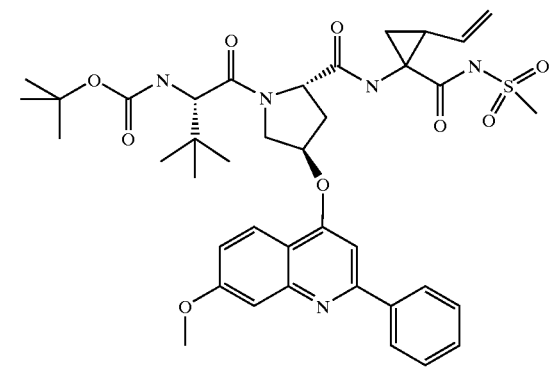

Compound 86–88

Compound 81—(1R,2S/1S,2R 1:1 mixture): LC/MS rt-min (MH+): 1.86 (858).

Compound 82—(1S,2R) isomer: LC/MS rt-min (MH+) 1.87 (858).

Compound 83—(1R,2S) isomer: LC/MS rt-min (MH+): 1.87 (858).

Compound 86—(1R,2S/1S,2R 1:1 mixture): LC/MS rt-min (MH+): 1.51 (764).

Compound 87—(1R, 2S) isomer: LC/MS rt-min (MH+): 1.50 (764).

Compound 88—(1S, 2R) isomer: LC/MS rt-min (MH+): 1.52 (764).

Compound 89

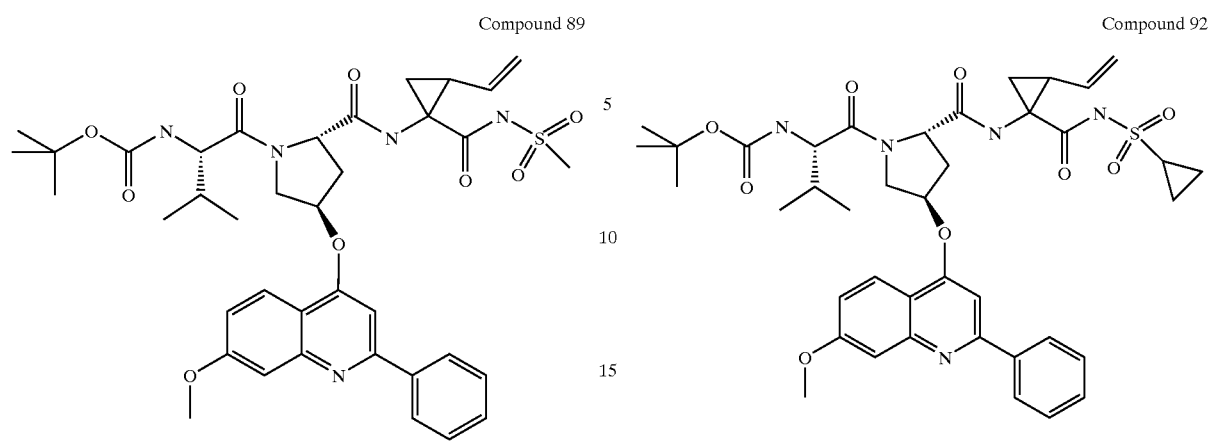

(1R,2S/1S,2R 1:1 mixture): LC/MS rt-min (MH⁺): 1.44 (750).

Compound 90

(1R, 2S/1S, 2R 1:1 mixture): LC/MS rt-min (MH⁺): 1.54 (764).

Compound 91

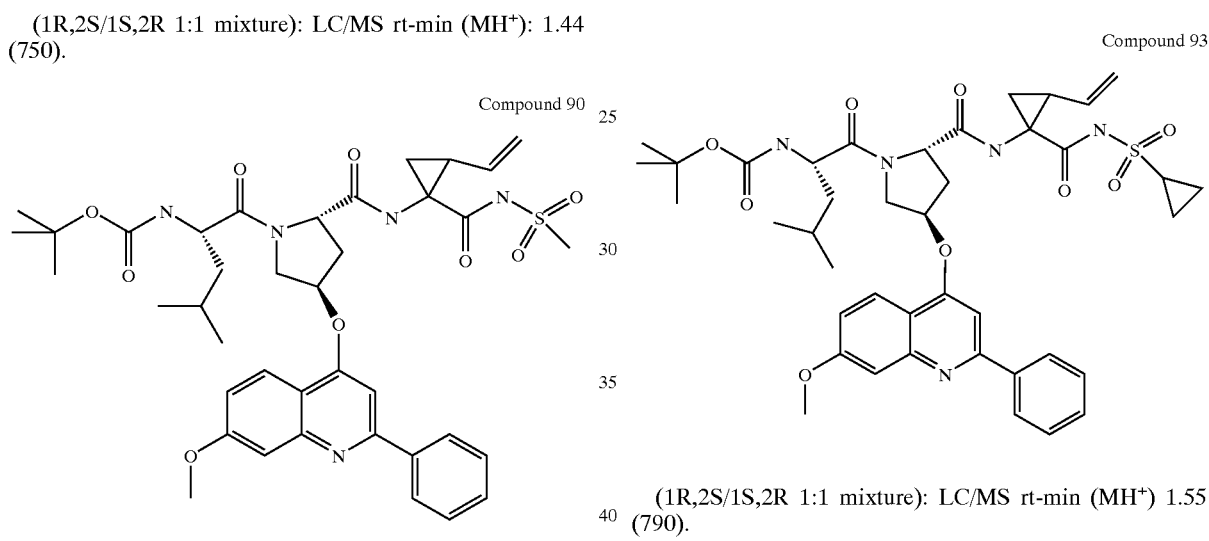

(1R,2S/1S,2R 1:1 mixture) LC/MS rt-min (MH⁺) 1.52 (790).

Compound 92

(1R,2S/1S,2R 1:1 mixture): LC/MS rt-min (MH⁺): 1.45 (776).

Compound 93

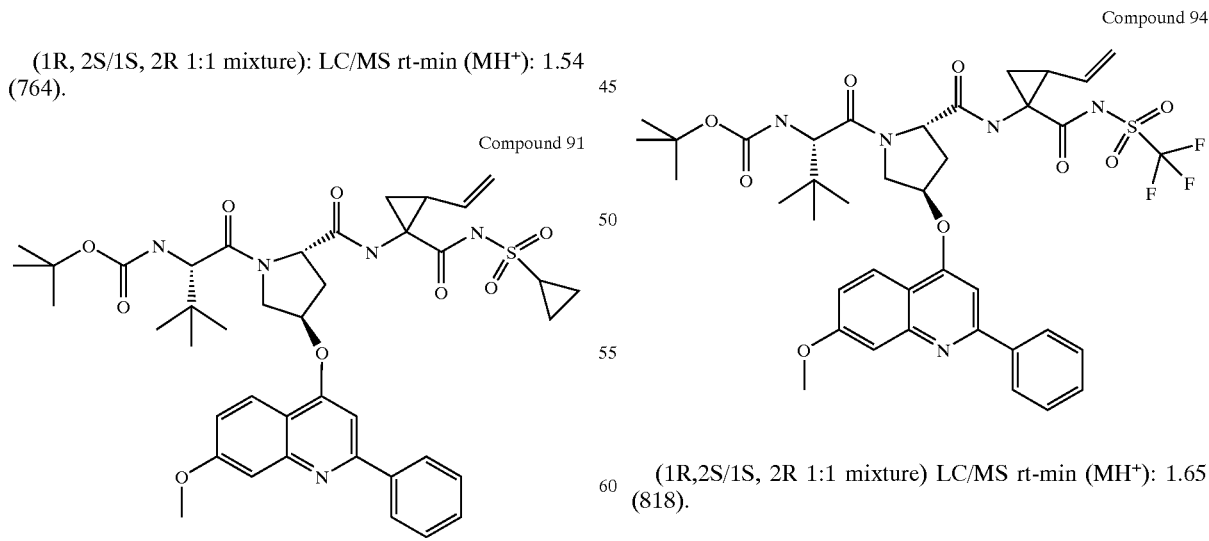

(1R,2S/1S,2R 1:1 mixture): LC/MS rt-min (MH⁺) 1.55 (790).

Compound 94

(1R,2S/1S, 2R 1:1 mixture) LC/MS rt-min (MH⁺): 1.65 (818).

EXAMPLE 27

Compound 95, 1-{2-[Bis-(2-hydroxy-ethyl)-amino]-acetyl}-4(R)-(7-methoxy-2-phenyl-quinolin-4-yloxy)-pyrrolidine-2(S)-carboxylic acid (1(R)-cyclopropanesulfonylamino-carbonyl-2(S)- vinylcyclopropyl)amide, shown below, was prepared as described in the following Steps 27a–e.

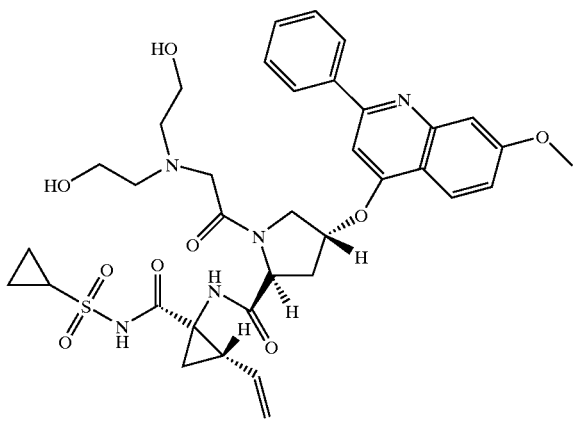

Step 27a: Preparation of 2(S)-(1(R)-ethoxycarbonyl-2(S)-vinyl-cyclopropylcarbamoyl)-4(R)-(7-methoxy-2-phenyl-quinolin-4-yloxy)-pyrrolidine-1-carboxylic acid tert-butyl ester, shown below.

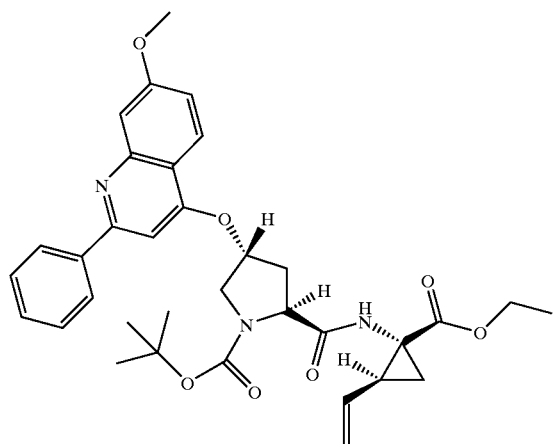

The product of Step 12a (7.5 g, 39.1 mmol) was combined with diisopropylethylamine (32.5 mL, 186 mmol) in dichloromethane (150 mL). To the resulting mixture was added HOBT hydrate (6.85 g, 44.7 mmol) and the product of Step 1c (17.3 g, 37.3 mmol) followed by addition of HBTU (16.96 g, 44.7 mmol). A slight exotherm occurred immediately, and the mixture was stirred at room temperature overnight. The mixture was then concentrated in vacuo and redissolved in ethyl acetate (600 mL). The solution was washed with water (2×200 mL), then with 10% aqueous sodium bicarbonate (2×200 mL), then with water (150 mL) and finally with brine (150 mL). The organic was dried over anhydrous magnesium sulfate and filtered, and the filtrate was concentrated in vacuo to a beige glassy solid. Purification was performed in multiple batches (7 g each) by flash chromatography on a Biotage Flash 75M cartridge (66% hexanes/ethyl acetate) to provide the (1R,2S) vinyl acca P1 isomer of BOC-NH-P2-P1-COOEt as the initial eluted isomer (9.86 g total, 44.0% yield), followed by elution of the (1S,2R) vinyl acca P1 isomer of BOC-NH-P2-P1-COOEt as the second eluted isomer (10.43 g total, 46.5% yield). A total of 1.97 g of mixed fractions were recovered to give an overall conversion of 99.3% to the two diastereomers.

(1R,2S) isomer—$^1$H NMR: (methanol-$d_4$) δ 1.23 (t, J=7.2 Hz, 3H), 1.4 (s, 4H), 1.45 (s, 6H), 1.73 (dd, J=7.9, 1.5 Hz, 0.4H), 1.79 (dd, J=7.8, 2.4 Hz, 0.6H), 2.21 (q, J=8.2 Hz, 1H), 2.44–2.49 (m, 1H), 2.66–2.72 (m, 0.4H), 2.73–2.78 (m, 0.6H), 3.93–3.95 (m, 2H), 3.96 (s, 3H), 4.10–4.17 (m, 2H), 4.44 (q, J=7.8 Hz, 1H), 5.13 (d, J=10.7 Hz, 1H), 5.31 (d, J=17.7 Hz, 0.4H), 5.32 (d, J=17.4 Hz, 0.6H), 5.49 (bs, 1H), 5.66–5.82 (m, 1H), 7.16 (dd, J=9.2, 2.5 Hz, 1H), 7.26 (s, 1H), 7.42 (d, J=2.4 Hz, 1H), 7.48–7.55 (m, 3H), 8.02–8.05 (m, 3H); LC-MS (HPLC conditions "B", retention time: 1.55), MS m/z 602 ($M^+$+1).

Step 27b: Preparation of 2(S)-(1(R)-carboxy-2(S)-vinyl-cyclopropylcarbamoyl)-4(R)-(7-methoxy-2-phenylquinolin-4-yloxy)-pyrrolidine-1-carboxylic acid tert-butyl ester, shown below.

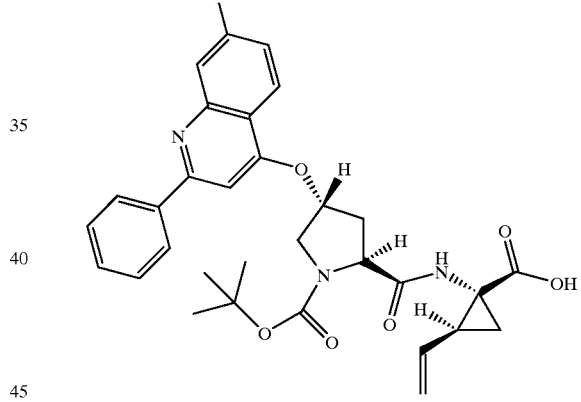

The (1R,2S) isomer of Step 27a (9.86 g, 16.4 mmol) was treated with 1N NaOH (50 mL, 50 mmol) in a mixture of THF (150 mL) and methanol (80 mL) for 12 h. The mixture was concentrated in vacuo until only the aqueous remained. Water (100 mL) was added and 1N HCl was added slowly until pH=3 was achieved. The mixture was then extracted with ethyl acetate (3×200 mL), and the combined organic extracts were washed with brine, dried over anhydrous sodium sulfate, and filtered. The filtrate was concentrated in vacuo to give the titled compound as a white powder (9.2 g, 98% yield). $^1$H NMR (methanol-$d_4$) δ 1.41 (s, 2H), 1.45 (s, 9H), 1.77 (dd, J=7.9, 5.5 Hz, 1H), 2.16–2.21 (m, 1H), 2.44–2.51 (m, 1H), 2.74–2.79 (m, 1H), 3.93–3.96 (m, 2H), 3.98 (s, 3H), 4.44 (t, J=7.9 Hz, 1H), 5.11 (d, J=9.5 Hz, 1H), 5.30 (d, J=17.1 Hz, 1H), 5.52 (s, 1H), 5.79–5.86 (m, 1H), 7.22 (dd, J=9.16, 2.14 Hz, 1H), 7.32 (s, 1H), 7.43 (d, J=2.14

Hz, 1H), 7.54–7.60 (m, 3H), 8.04 (dd, J=7.8, 1.4 Hz, 2H), 8.08 (d, J=9.1 Hz, 1H); LC-MS (HPLC conditions "B", retention time: 1.46), MS m/z 574 (M++1).

Step 27c: Preparation of 2(S)-(1(R)-cyclopropanesulfonylamino-carbonyl-2(S)-vinylcyclopropylcarbamoyl)-4(R)-(7-methoxy-2-phenylquinolin-4-yloxy)-pyrrolidine-1-carboxylic acid tert-butyl ester, shown below.

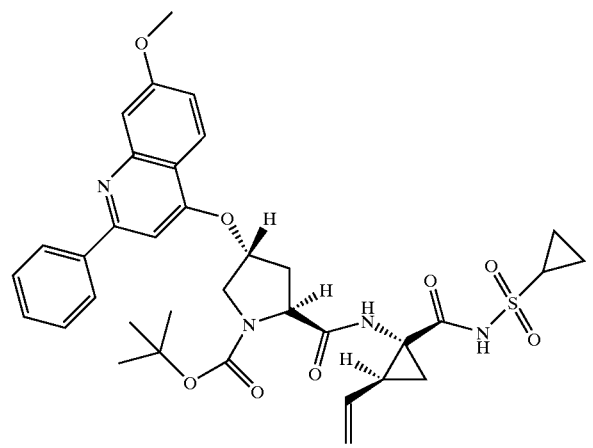

The product of Step 27b (7.54 g, 13.14 mmol) was combined with CDI (3.19 g, 19.7 mmol) and DMAP (2.41 g, 19.7 mmol) in anhydrous THF, and the resulting mixture was heated to reflux for 45 min. The slightly opaque mix was allowed to cool to room temperature, and to it was added cyclopropylsulfonamide (1.91 g, 15.8 g). Upon addition of DBU (5.9 mL, 39.4 mmol), the mixture became completely clear. The brown solution was stirred overnight. The mixture was then concentrated in vacuo to an oil, and was redissolved in ethyl acetate (500 mL). The solution was washed with pH=4 buffer (3×200 mL), and the combined buffer washes were back-extracted with ethyl acetate (200 mL). The combined organics were washed with brine (150 mL) and dried over anhydrous sodium sulfate and filtered. Concentration of the filtrate in vacuo gave a beige solid. The crude product was purified by flash chromatography on a Biotage Flash 75M cartridge (25% hexanes/ethyl acetate) to give the titled product (5.85 g, 6% yield). $^1$H NMR (methanol-$d_4$) δ 1.03–1.09 (m, 2H), 1.15–1.28 (m, 2H), 1.40–1.44 (m, 2H), 1.74 (s, 9H), 1.87 (dd, J=8.1, 5.6 Hz, 1H), 2.21–2.27 (m, 1H), 2.36–2.42 (m, 1H), 2.65 (dd, J=13.7, 6.7 Hz, 1H), 2.93–2.97 (m, 1H), 3.90–3.96 (m, 2H), 4.00 (s, 3H), 4.40 (dd, J=9.5, 7.0 Hz, 1H), 5.12 (d, J=10.4 Hz, 1H), 5.31 (d, J=17.4 Hz, 1H), 5.64 (s, 1H), 5.73–5.80 (m, 1H), 7.30 (dd, J=9.2, 2.1 Hz, 1H), 7.40 (s, 1H), 7.47 (s, 1H), 7.61–7.63 (m, 3H), 8.04–8.05 (m, 2H), 8.15 (d, J=9.5 Hz, 1H); LC-MS (HPLC conditions "B", retention time: 1.48), MS m/z 677 (M++1).

Step 27d: Preparation of 4(R)-(7-methoxy-2-phenyl-quinolin-4-yloxy)-pyrrolidine-2(S)-carboxylic acid (1(R)-cyclopropanesulfonylaminocarbonyl-2(S)-vinyl-cyclopropyl)-amide, shown below.

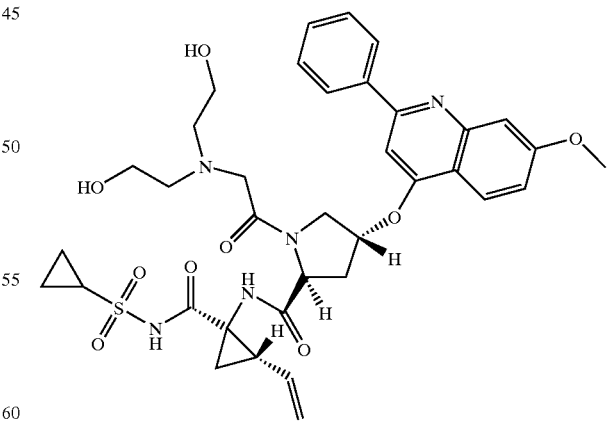

The product of Step 27c (5.78 g, 8.54 mmol) was treated with 4.0M HCl in 1,4-dioxane (50 mL, 200 mmol) overnight. The reaction mixture was concentrated in vacuo and placed in a vacuum oven at 50° C. for several days. Thus was obtained the bis-hydrochloride salt of the titled compound (5.85 g, quantitative) as a beige powder. $^1$H NMR (methanol-$d_4$) δ 1.03–1.18 (m, 3H), 1.26–1.30 (m, 1H), 1.36–1.40 (m, 2H), 1.95 (dd, J=8.2, 5.8 Hz, 1H), 2.37 (q, J=8.9 Hz, 1H), 2.51–2.57 (m, 1H), 2.94–2.98 (m, 1H), 3.09 (dd, J=14.6, 7.3 Hz, 1H), 3.98 (d, J=3.7 Hz, 1H), 3.99 (s, 1H), 4.08 (s, 3H), 4.80 (dd, J=10.7, 7.6 Hz, 1H), 5.15 (dd, J=10.2, 1.4 Hz, 1H), 5.32 (dd, J=17.1, 1.2 Hz, 1H), 5.61–5.69 (m, 1H), 5.99 (t, J=3.7 Hz, 1H), 7.51 (dd, J=9.3, 2.3 Hz, 1H), 7.59 (d, J=2.4 Hz, 1H), 7.65 (s, 1H), 7.72–7.79 (m, 3H), 8.09 (dd, J=7.0, 1.5 Hz, 2H), 8.53 (d, J=9.2 Hz, 1H); LC-MS (HPLC conditions "B", retention time: 1.01), MS m/z 577 (M++1).

Step 27e: Preparation of Compound 95

To a reaction vessel containing PS-DIEA resin (Argonaut Technologies, 0.047 g, 0.175 mmol) was added a solution of bicine (0.044 mmol) in DMF (0.25 mL), followed by the addition of a solution of compound 6 (0.020 g, 0.029 mmol) in DMF (0.50 mL), followed by addition of a solution of HATU (0.017 g, 0.044 mmol) in DMF (0.25 mL). The mixture was shaken for 3 d at room temperature. To the reaction was added PS-trisamine resin (Argonaut Technologies, 0.025 g, 0.086 mmol) and the mixture was shaken for 18 h at room temperature. The reaction mixture was concentrated in vacuo and redissolved in 10:1 mixture of 1,2-dichloroethane and methanol (1 mL). MP-carbonate resin (Argonaut Technologies, 0.056 g, 0.175 mmol) was added, and the mixture was shaken for 5 d at room temperature. The reaction miture was filtered, passed through 0.25 g of silica gel and eluted with 1.5 mL of 10:1 1,2-dichloroethane:methanol. Solvent was removed in vacuo to give crude product, which was purified by preparative HPLC (Prep HPLC method "A") and isolated as the bis-trifluoroacetic acid salt: LC-MS (HPLC conditions "G", retention time: 1.16), MS m/z 722 (M$^+$+1).

EXAMPLE 28

Compound 96, 1-(2-Acetylamino-pent-4-ynoyl)-4(R)-(7-methoxy-2-phenyl-quinolin-4-yloxy)-pyrrolidine-2(S)-carboxylic acid (1(R)-cyclopropanesulfonylaminocarbonyl-2(S)-vinyl-cyclopropyl)amide is shown below.

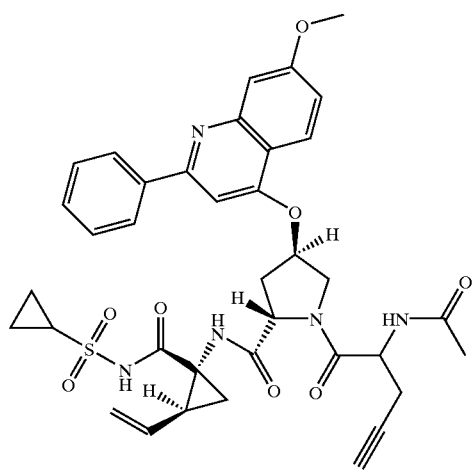

This compound was prepared according to the method of Example 27 and then purified by preparative HPLC (Prep HPLC method "A") and isolated as the monotrifluoroacetic acid salt. LC-MS (HPLC conditions "G", retention time: 1.28), MS m/z 714 (M$^+$+1).

EXAMPLE 29

Compound 97, {1S-[2S-(1R-cyclopropanesulfonyl-amino-carbonyl-2S-vinylcyclopropylcarbamoyl)-4R-(7-methoxy-2-phenyl-quinolin-4-yloxy)-pyrrolidine-1-carbonyl]-2-vinyl-cyclopropyl}-carbamic acid tert-butyl ester, shown below, was prepared as described in Steps 29a–b.

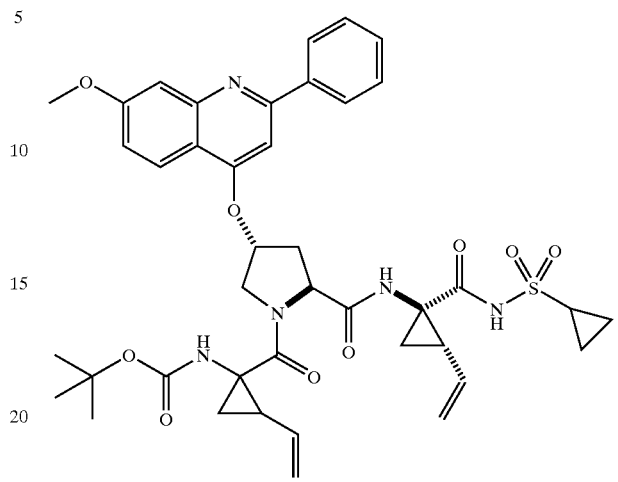

Step 29a: Preparation of 4R-(7-methoxy-2-phenylquinolin-4-yloxy)-pyrrolidine-2S-carboxylic acid (1R-cyclopropanesulfonylamino-carbonyl-2S-vinylcyclopropyl)amide, shown below.

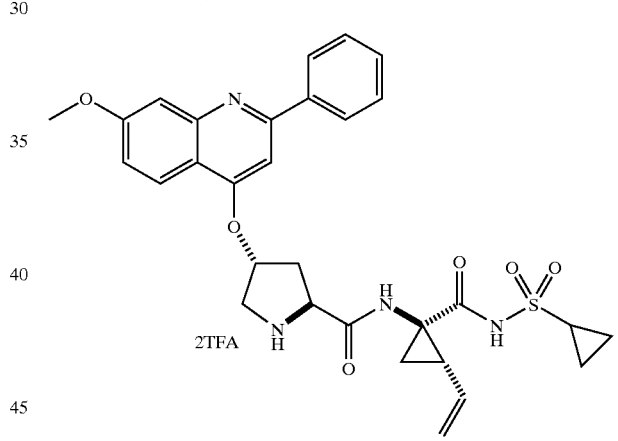

The product of Step 27c (505.0 mg, 0.746 mmol) was treated with 50% TFA (10 mL) slowly to control CO$_2$ gas from vigorously bubbling. After stirring at rt for 0.5 hr, the solvent was concentrated and the resulting viscous brown oil was dried under vacuo overnight to give brown solid in quantitative yield. The product was used without further purification. $^1$H NMR (methanol-d$_4$) δ 1.03–1.06 (m, 1H), 1.07–1.13 (m, 1H), 1.14–1.19 (m, 1H), 1.25–1.30 (m, 1H), 1.37 (dd, J=9.6, 5.6 Hz, 1H), 1.96 (dd, J=7.9, 5.5 Hz, 1H), 2.31 (q, J=8.5 Hz, 1H), 2.52–2.58 (m, 1H), 2.93–3.01 (m, 2H), 3.94 (dd, J=13.3, 4.0 Hz, 1H), 4.02 (dd, J=13.3, 1.4 Hz, 1H), 4.07 (s, 3H), 4.76 (dd, J=10.4, 7.6 Hz, 1H), 5.15 (dd, J=10.4, 1.5 Hz, 1H), 5.31 (dd, J=17.3, 1.4 Hz, 1H), 5.61–5.69 (m, 1H), 5.96–5.98 (m, 1H), 7.46 (dd, J=9.2, 1.4 Hz, 1H), 7.56 (d, J=2.1 Hz, 1H), 7.63 (s, 1H), 7.71–7.79 (m, 3H) 8.05–8.07 (dd, J=8.5, 1.5 Hz, 2H), 8.40 (d, J=9.4 Hz, 1H); LC-MS (retention time: 1.10), MS m/z 577 (M$^+$+1).

Step 29b: Preparation of Compound 97

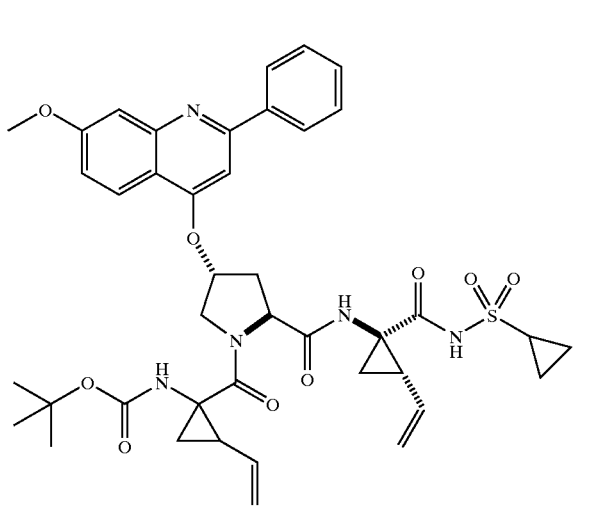

To a solution of the product of step 29a (70.0 mg, 0.087 mmol) in DCM (3 mL) was added DIEA (76 μL, 0.43 mmol), HBTU (40 mg, 0.104 mmol), HOBt (16 mg, 0.104 mmol) and amino-2-vinylcyclopropanecarboxylic acid (0.104 mmol). After stirring at rt for 14 hr, the solvent was concentrated and the resulting material was separated and purified by flashed column chromatography (SiO$_2$, eluted with 5% MeOH in DCM) to give 41% of a higher RF isomer (IC$_{50}$=250 nM, NMR was messy thus was not included here) and 50% of a lower RF isomer (IC$_{50}$=24 nM)). $^1$H NMR (lower RF isomer) (MeOH) δ 0.85–0.92 (m, 1H), 0.97–1.03 (m, 3H), 1.06–1.10 (m, 1H), 1.15–1.21 (m, 2H), 1.26–1.33 (m, 2H), 1.38 (dd, J=9.2, 4.6 Hz, 1H), 1.46 (s, 9H), 1.58–1.66 (m, 1H), 1.80 (t, J=5.8 Hz, 1H), 1.86 (t, J=6.3 Hz, 1H), 2.01 (q, J=8.9 Hz, 1H), 2.40 (q, J=7.9 Hz, 1H), 2.46–2.49 (m, 1H), 2.72 (dd, J=13.7, 7.0 Hz, 1H), 2.84–2.94 (m, 1H), 3.95 (s, 3H), 4.10 (s, 2H), 4.63–4.70 (m, 2H), 4.94–4.99 (m, 1H), 5.07 (d, J=10.4 Hz, 1H), 5.30 (d, J=16.8 Hz, 1H), 5.54 (bs, 1H), 5.82–5.87 (m, 1H), 7.14 (dd, J=9.2, 2.1 Hz, 1H), 7.21 (s, 1H), 7.39 (s, 1H), 7.50–7.56 (m, 3H), 7.98 (d, J=8.9 Hz, 1H), 8.06 (d, J=6.7 Hz, 1H); LC-MS (retention time: 1.51), MS m/z 786 (M$^+$+1).

EXAMPLE 30

Compound 98, 1-(2S-Acetylamino-3,3-dimethyl-butyryl)-4R-(7-methoxy-2-phenyl-quinolin-4-yloxy)-pyrrolidine-2S-carboxylic acid (1R-cyclopropanesulfonyl-aminocarbonyl-2S-vinyl-cyclopropyl)amide, shown below, was prepared as described in the following Steps 30a–c.

Step 30a: Preparation of {1S-[2S-(1R-cyclopropanesulfonylamino-carbonyl-2S-vinylcyclopropyl-carbamoyl)-4R-(7-methoxy-2-phenyl-quinolin-4-yloxy)-pyrrolidine-1-carbonyl]-2,2-dimethyl-propyl}-carbamic acid tert-butyl ester, shown below.

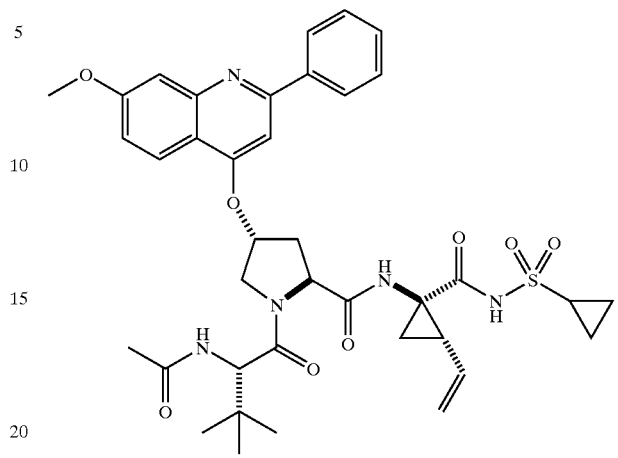

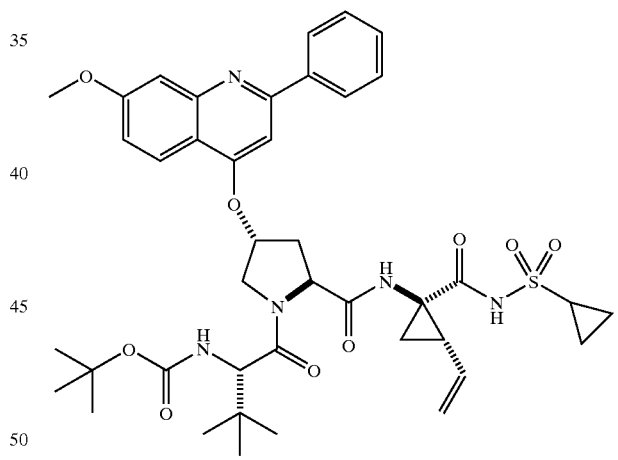

To a solution of the product of Step 29a (0.671 mmol) in DCM (10 mL) was added DIEA (542 μL, 3.36 mmol), HATU (354 mg, 1.01 mmol), HOAt (127 mg, 1.01 mmol), and Boc-Tle-OH (173 mg, 0.805 mmol). After stirring at rt for 16 hr, the solvent was concentrated and the resulting brown viscous oil was purified by flash column chromatography (SiO$_2$, eluted with 95% MeOH in DCM) to give a slightly yellow foarmy solid (527 mg, 99% yield). LC-MS (retention time: 1.57), MS m/z 790 (M$^+$+1).

Step 30b: Preparation of 1S-(2-amino-3,3-dimethyl-butyryl)-4R-(7-methoxy-2-phenyl-quinolin-4-yloxy)- pyrrolidine-2S-carboxylic acid (1R-cyclopropane-sulfonylaminocarbonyl-2S-vinylcyclopropyl)-amide, shown below.

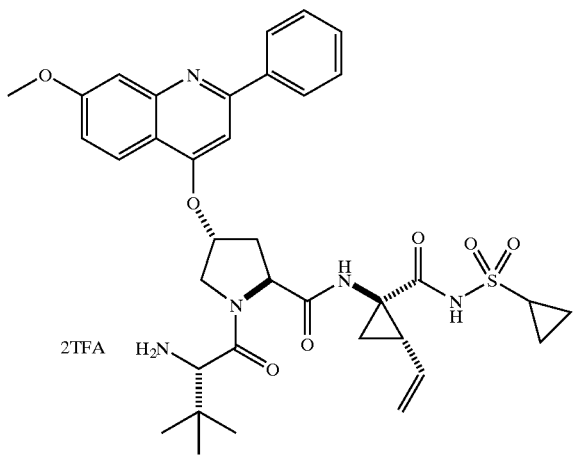

The product of Step 30a (950 mg, 1.20 mmol) was treated with 25% TFA (25 mL) slowly to control $CO_2$ gas from vigorously bubbling. After stirring at rt for 1.5 hr, the solvent was concentrated to give a slurry of light brown solution and $Et_2O$ was added to effect a precipitation. The light brown product (1.10 g 99% yield) was obtained by a vacuum filtration and used without further purification. LC-MS (retention time: 1.13), MS m/z 690 ($M^+$+1).

Step 30c: Preparation of Compound 98. To a solution of the product of Step 30b (11.1 mg, 0.0121 mmol) in DCM (1 mL) was added polyvinylpyridine (6.4 mg, 0.0605 mmol) and acetic anhydride (30 µL). The reaction vial was rotated for 14 h and the contents were filtered and washed with DCM. The solvent was concentrated and the residue was purified by reverse phase preparative HPLC to give a white glassy solid as a TFA salt (4.0 mg, 45% yield).

$^1$H NMR (MeOH) δ 1.06 (s, 9H), 1.08–1.10 (m, 2H), 1.23–1.26 (m, 2H), 1.45 (dd, J=9.5, 5.5 Hz, 1H), 1.81 (s, 3H), 1.90 (dd, J=7.9, 5.5 Hz, 1H), 2.25 (q, J=8.9 Hz, 1H), 2.24–2.46 (m, 1H), 2.75 (dd, J=14.2, 6.9 Hz, 1H), 2.93–2.98 (m, 1H), 4.06 (s, 3H), 4.17 (dd, J=12.4, 3.2 Hz, 1H), 4.50 (t, J=4.3 Hz, 1H), 4.57–4.61 (m, 2H), 5.14 (dd, J=10.4, 1.5 Hz, 1H), 5.31 (dd, J=17.2, 1.4 Hz, 1H), 5.71–5.78 (m, 1H), 5.86 (d, J=3.1, 1H), 4.45 (dd, J=9.2, 2.4 Hz, 1H), 7.54 (d, J=2.1 Hz, 1H), 7.64 (s, 1H), 7.71–7.79 (m, 3H), 8.08 (dd, J=8.2, 1.5 Hz, 3H), 8.30 (d, J=9.5 Hz, 1H); LC-MS (retention time: 1.35), MS m/z 732 ($M^+$+1).

EXAMPLE 32

The following compounds were prepared according to the method of Example 30.

Compound 99

Compound 99, 1-[3,3-dimethyl-2S-(2,2,2-trifluoro-acetylamino)-butyryl]-4R-(7-methoxy-2-phenylquinolin-4-yloxy)pyrrolidine-2S-carboxylic acid(1R-cyclopropanesulfonylaminocarbonyl-2S-vinylcyclopropyl) amide, is shown below.

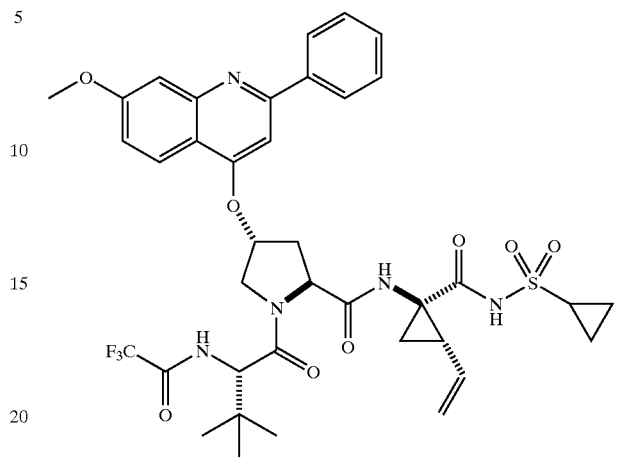

Compound 99 was prepared using fluoroacetic anhydride.
$^1$H NMR (MeOH) δ 0.99–1.03 (m, 4H), 1.09 (s, 9H), 1.23–1.26 (m, 3H), 1.46 (dd, J=9.5, 5.2 Hz, 1H), 1.91 (dd, J=8.2, 5.5 Hz, 1H), 2.24 (q, J=9.0 Hz, 1H), 2.41–2.47 (m, 1H), 4.06 (s, 3H), 4.16 (dd, J=12.5, 3.1 Hz, 1H), 4.59–4.63 (m, 3H), 5.14 (dd, J=10.2, 1.7 Hz, 1H), 5.30 (dd, J=17.3, 1.1 Hz, 1H), 5.72–5.79 (m, 1H), 5.87 (d, J=4.0, 1H), 7.40 (dd, J=9.2, 2.4 Hz, 1H), 7.54 (d, J=2.4 Hz, 1H), 7.65 (s, 1H), 7.73–7.79 (m, 4H), 8.08 (d, J=6.7 Hz, 3H), 8.29 (d, J=9.5 Hz, 1H); LC-MS (retention time: 1.50), MS m/z 786 ($M^+$+1).

Compound 100

Compound 100, N-{1S-[2S-(1R-cyclopropanesulfonyl-aminocarbonyl-2S-vinyl-cyclopropylcarbamoyl)-4R-(7-methoxy-2-phenyl-quinolin-4-yloxy)-pyrrolidine-1-carbonyl]-2,2-dimethyl-propyl}-succinamic acid, is shown below.

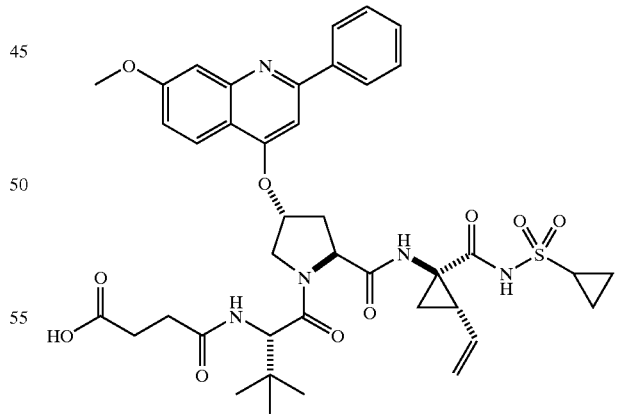

Compound 100 was prepared using succinic anhydride.
$^1$H NMR (MeOH) δ 1.04–1.09 (m, 2H), 1.10 (s, 9H), 1.23–1.25 (m, 2H), 1.44 (dd, J=9.5, 5.5 Hz, 1H), 1.90 (dd, J=8.2, 5.5 Hz, 1H), 2.20–2.29 (m, 4H), 2.39–2.50 (m, 2H), 2.76 (d, J=6.71 Hz, 1H), 2.93–2.98 (m, 1H), 4.06 (s, 3H), 4.12 (dd, J=12.7, 3.2 Hz, 1H), 4.49 (d, J=5.2 Hz, 1H), 4.59 (dd, J=10.2, 6.9 Hz, 1H), 4.65 (d, J=11.9 Hz, 1H), 5.14 (dd, J=10.6, 1.5 Hz, 1H), 5.31 (dd, J=17.1, 1.2 Hz, 1H), 5.71–5.78 (m, 1H), 5.85 (d, J=3.1 Hz, 1H), 7.47 (dd, J=9.3, 2.3 Hz, 1H), 7.54 (d, J=2.4 Hz, 1H), 7.63 (d, J=2.4 Hz, 1H), 7.71–7.79 (m, 3H), 8.08 (d, J=7.0 Hz, 2H), 8.31 (dd, J=11.6, 2.5 Hz, 1H); LC-MS (retention time: 1.31), MS m/z 790 (M⁺+1).

Compound 101

Compound 101, 1-[2S-(2,2-Dimethylpropionylamino)-3,3-dimethyl-butyryl]-4R-(7-methoxy-2-phenyl-quinolin-4-yloxy)-pyrrolidine-2S-carboxylic acid (1R-cyclopropanesulfonylaminocarbonyl-2S-vinylcyclopropyl)-amide, is shown below.

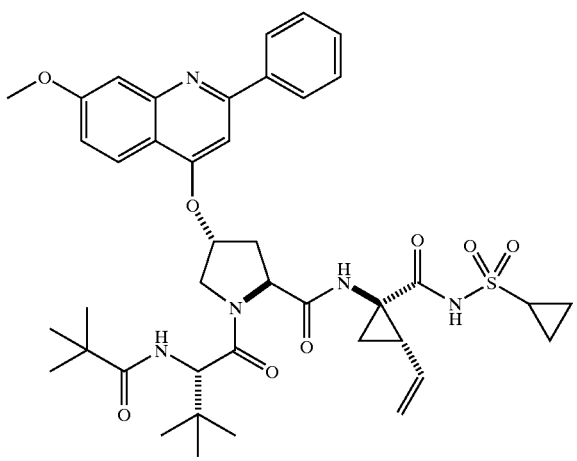

Compound 101 was prepared using trimethylacetyl chloride. ¹H NMR (MeOH) δ 1.01 (bs, 9H), 1.02–1.04 (m, 4H), 1.05 (bs, 9H), 1.23–1.29 (m, 5H), 1.49 (dd, J=9.6, 6.5 Hz, 1H), 1.90 (dd, J=8.1, 5.7 Hz, 1H), 2.40–2.47 (m, 1H), 2,72–2.79 (m, 1H), 2.92–2.96 (m, 1H), 4.06 (s, 3H), 4.20 (d, J=12.5 Hz, 1H), 4.54–4.60 (m, 3H), 5.14 (dd, J=10.5, 1.7 Hz, 1H), 5.32 (dd, J=17.4, 1.0 Hz, 1H), 5.75–5.82 (m, 1H), 6.92 (d, J=8.9 Hz, 1H), 7.40–7.43 (m, 1H), 7.54 (t, J=2.3 Hz, 1H), 7.66 (d, J=3.1 Hz, 1H), 7.72–7.78 (m, 4H), 8.07–8.10 (m, 2H), 8.31 (dd, J=9.2, 2.7 Hz, 1H); LC-MS (retention time: 1.54), MS m/z 774 (M⁺+1).

EXAMPLE 33

Compound 102

Compound 102, 1-[2S-(2-hydroxy-acetylamino)-3,3-dimethyl-butyryl]-4R-(7-methoxy-2-phenyl-quinolin-4-yloxy)-pyrrolidine-2S-carboxylic acid (1R-cyclopropanesulfonylamino-carbonyl-2S-vinylcyclopropyl)-amide, is shown below.

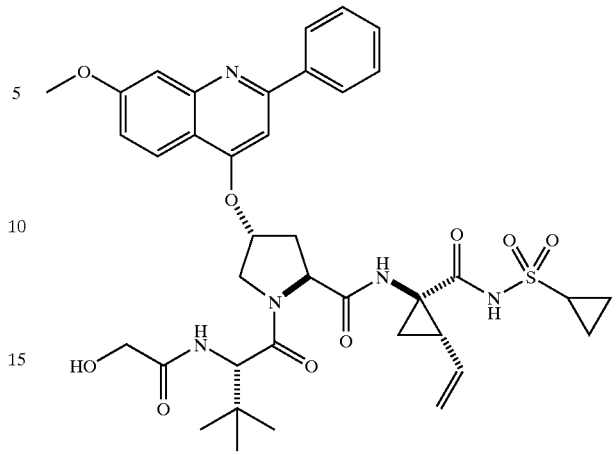

To a solution of the product of Step 30b (11.1 mg, 0.0121 mmol) in DCM (1 mL) was added DIEA (11 μL, 0.0605 mmol), HATU (6.9 mg, 0.0182 mmol), HOAt (2.5 mg, 0.01812 mmol) and glycolic acid (1.4 mg, 0.0182 mmol). After stirring at rt for 16 hr, the solvent and excess DIEA was concentrated and the resulting residue was purified by reverse phase preparative HPLC to give white solid as a TFA salt (3.5 mg, 39% yield). ¹H NMR (MeOH) δ 1.06–1.07 (m, 2H), 1.07 (s, 9H), 1.22–1.25 (m, 2H), 1.45 (dd, J=9.6, 5.3 Hz, 1H), 1.90 (dd, J=8.2, 5.5 Hz, 1H), 2.24 (q, J=8.9 Hz, 1H), 2.42–2.47 (m, 1H), 2.76 (dd, J=7.3 Hz, 1H), 2.92–2.98 (m, 1H), 3.74 (d, J=16.5 Hz, 1H), 3.90 (d, J=16.2 Hz, 1H), 4.60 (s, 3H), 4.19 (dd, J=12.5, 3.4 Hz, 1H), 4.56–4.61 (m, 3H), 5.14 (d, J=10.4 Hz, 1H), 5.30 (d, J=17.1 Hz, 1H), 5.72–5.79 (m, 1H), 5.86 (bs, 1H), 7.45 (dd, J=9.3, 2.3 Hz, 1H), 7.54 (d, J=2.4 Hz, 1H), 7.64 (s, 1H), 7.72–7.79 (m, 4H), 8.08 (d, J=7.0 Hz, 2H), 8.28 (d, J=9.2 Hz, 1H); LC-MS (retention time: 1.30), MS m/z 748 (M⁺+1).

EXAMPLE 34

The following compounds were prepared according to the method of Example 33.

Compound 103

Compound 103, 1-[2S-(3,3-Dimethyl-butyrylamino)-3,3-dimethyl-butyryl]-4R-(7-methoxy-2-phenyl-quinolin-4-yloxy)-pyrrolidine-2S-carboxylic acid (1R-cyclopropanesulfonylaminocarbonyl-2S-vinyl-cyclopropyl) amide, is shown below.

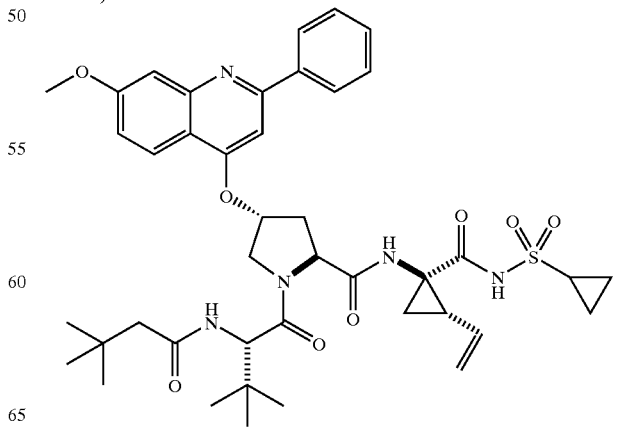

Compound 103 was prepared using t-butylacetic acid. ¹H NMR (MeOH) δ 0.78 (s, 9H), 0.90–0.98 (m, 2H), 1.04 (s, 9H), 1.23–1.29 (m, 5H), 1.45 (dd, J=9.5, 5.5 Hz, 1H), 1.86–1.91 (m, 2H), 1.97 (d, J=12.8 Hz, 1H), 2.24 (d, 8.9 Hz, 1H), 2.39–2.45 (m, 1H), 2.76 (dd, J=13.6, 6.0 Hz, 1H), 2.93–2.97 (m, 1H), 4.06 (s, 3H), 4.16 (dd, J=12.4, 2.9 Hz, 1H), 4.52 (t, J=4.4 Hz, 1H), 4.60 (dd, J=10.5, 6.9 Hz, 1H), 4.65 (dd, J=13.3, 1.1 Hz, 1H), 5.14 (dd, J=10.5, 1.4 Hz, 1H), 5.31 (dd, J=17.2, 1.1 Hz, 1H), 5.72–5.79 (m, 1H), 5.85 (bs, 1H), 7.42 (dd, J=9.3, 2.3 Hz, 1H), 7.53 (d, J=2.1 Hz, 1H), 7.66 (s, 1H), 7.72–7.79 (m, 4H), 8.08 (d, J=7.0 Hz, 3H), 8.30 (d, J=9.2 Hz, 2H); LC-MS (retention time: 1.58), MS m/z 788 (M⁺+1).

Compound 104

Compound 104, 1-[2S-(2-cyclopropyl-acetylamino)-3,3-dimethyl-butyryl]-4R-(7-methoxy-2-phenyl-quinolin-4-yloxy)-pyrrolidine-2S-carboxylic acid (1R-cyclopropanesulfonylaminocarbonyl-2S-vinyl-cyclopropyl)-amide, is shown below.

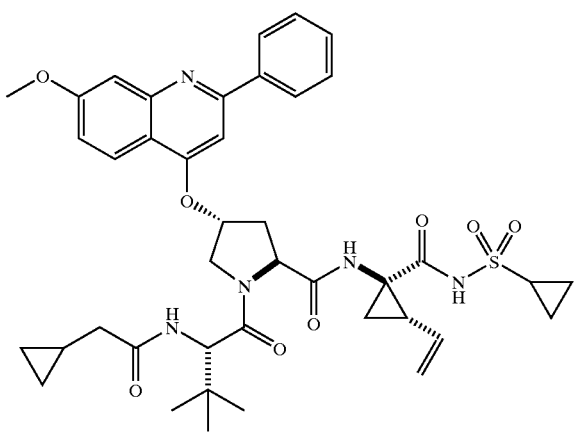

Compound 104 was prepared with cyclopropypacetic acid. ¹H NMR (MeOH) δ 0.07–0.10 (m, 2H), 0.39–0.34 (m, 2H), 0.77–0.82 (m, 1H), 1.00–1.07 (m, 4H),1.08 (s, 9H), 1.21–1.26 (m, 3H), 1.46 (dd, J=9.6, 5.3 Hz, 1H), 1.90 (dd, J=8.2, 5.5 Hz, 1H), 1.96–2.02 (m, 2H), 2.25 (dd, J=17.7, 8.6 Hz, 1H), 2.43–2.46 (m, 1H), 2.78 (dd, J=13.9, 6.6 Hz, 1H), 2.92–2.98 (m, 1H), 4.07 (s, 3H), 4.19 (dd, J=12.5, 3.4 Hz, 1H), 4.55 (s, 1H), 4.60 (dd, J=10.7, 7.7 Hz, 2H), 5.15 (dd, J=10.4, 1.5 Hz, 1H), 5.31 (dd, J=17.2, 1.4 Hz, 1H), 5.72–5.87 (m, 1H), 5.87 (d, J=3.4 Hz, 1H), 7.42 (dd, J=9.3, 2.3 Hz, 1H), 7.54 (d, J=2.4 Hz, 1H), 7.65 (s, 1H), 7.72–7.79 (m, 4H), 8.09 (d, J=7.6 Hz, 2H), 8.30 (d, J=9.2 Hz, 1H); LC-MS (retention time: 1.49), MS m/z 772 (M⁺+1).

Compound 105

Compound 105, 1-{2S-[(bicyclo[1.1.1]pentane-2-carbonyl)-amino]-3,3-dimethyl-butyryl}-4R-(7-methoxy-2-phenyl-quinolin-4-yloxy)-pyrrolidine-2S-carboxylic acid (1R-cyclopropanesulfonylaminocarbonyl-2S-vinylcyclopropyl)amide, is shown below.

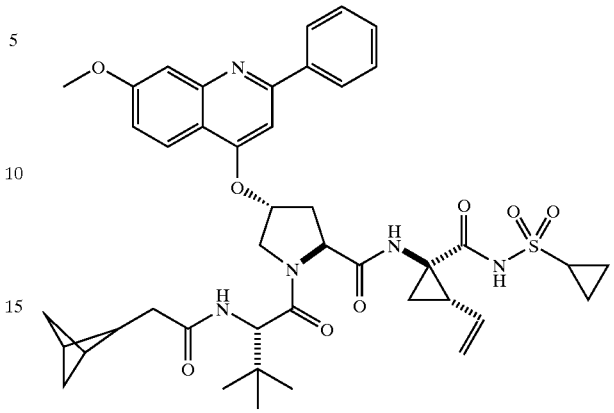

Compound 105 was prepared with bicyclo[1.1.1]pentane-2-carboxylic acid. ¹H NMR (MeOH) δ 1.05 (s, 9H), 1.06–1.10 (m, 4H), 1.23–1.26 (m, 2H), 1.44–1.48 (m, 1H), 1.60–1.62 (m, 1H), 1.68 (d, J=2.4 Hz,1H), 1.91 (dd, J=7.7, 4.7 Hz, 1H), 2.01 (dd, J=9.8, 3.1 Hz, 1H), 2.22–2,27 (m, 1H), 2.40–2.46 (m, 1H), 2.55–2.60 (m, 2H), 2.75–2.81 (m, 1H), 2.92–2.98 (m, 1H), 4.06 (s, 3H), 4.16 (dd, J=12.7, 3.2 Hz, 1H), 4.57–4.64 (m, 3H), 5.15 (dd, J=10.4, 1.5 Hz, 1H) 5.32 (dd, J=17.4, 1.5 Hz, 1H), 5.74–5.80 (m, 1H), 5.87 (d, J=2.1 Hz, 1H), 7.39–7.42 (m, 1H), 7.53 (t, J=2.3 Hz, 1H), 7.72–7.78 (m, 4H), 8.06–8.10 (m, 2H), 8.30 (dd, J=9.2, 3.8 Hz, 1H). LC-MS (retention time: 1.52), MS m/z 784 (M⁺+1).

EXAMPLE 35

Compound 106

Compound 106, acetic acid {1S-[2S-(1R-cyclopropanesulfonylaminocarbonyl-2S-vinyl-cyclopropylcarbamoyl)-4R-(7-methoxy-2-phenyl-quinolin-4-yloxy)-pyrrolidine-1-carbonyl]-2,2-dimethyl-propylcarbamoyl}-methyl ester, is shown below.

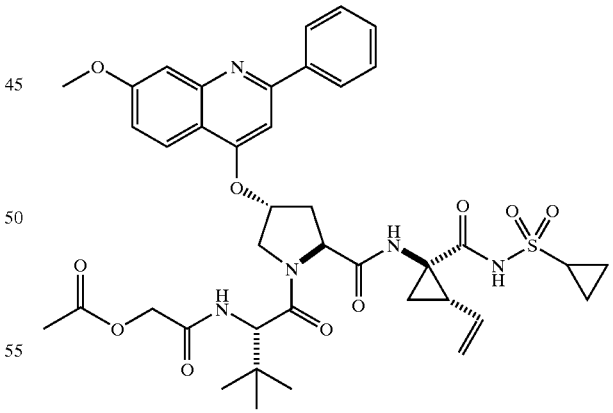

To a solution of the product of Step 30b (35.0 mg, 0.0381 mmol) in DCM (2 mL) was added DIEA (40 µL, 0.0191 mmol), HATU (29 mg, 0.0762 mmol), and acetoacetic acid (6.7 mg, 0.0572 mmol). After rotation at rt for 16 hr, the solvent was concentrated and the resulting residue was purified by a flash column (SiO₂, eluted with 5% MeOH in DCM) to give a yellow solid (30 mg, 99% yield). ¹H NMR (MeOH) δ 0.87–0.93 (m, 1H), 0.96–1.02 (m, 1H), 1.06 (s, 11H), 1.20–1.26 (m, 2H), 1.27–1.29 (M, 1H), 1.45 (dd, J=9.5, 5.2 Hz, 1H), 1.87 (dd, J=7.9, 5.5 Hz, 1H), 2.08 (s, 3H), 2.22 (q, J=8.9 Hz, 1H), 2.33–2.36 (m, 1H), 2.66 (dd, J=13.1, 6.9 Hz, 1H), 2.92–2.96 (m, 1H), 3.22 (q, J=7.3 Hz, 2H), 3.69–3.76 (m, 2H), 3.95 (s, 3H), 4.16 (dd, J=12.1, 3.5 Hz, 1H), 4.40 (d, J=12.2 Hz, 1H), 4.48 (s, 2H), 4.52 (dd, J=10.1, 6.7 Hz, 1H), 4.67 (s, 1H), 5.11 (d, J=10.4 Hz, 1H), 5.29 (d, J=17.1 Hz, 1H), 5.59 (bs, 1H), 5.73–5.80 (m, 1H), 7.17 (dd, J=9.0, 2.3 Hz, 1H), 7.27 (s, 1H), 7.40 (d, J=2.1 Hz, 1H), 7.49–7.56 (m, 3H), 8.04 (d, J=8.9 Hz, 1H), 8.06 (d, J=6.7 Hz, 2H); LC-MS (retention time: 1.33), MS m/z 790 (M$^+$+1).

EXAMPLE 36

The following compounds were prepared according to the method of Example 35.

Compound 107

Compound 107, 1-[2S-(2-methoxy-acetylamino)-3,3-dimethyl-butyryl]-4R-(7-methoxy-2-phenyl-quinolin-4-yloxy)-pyrrolidine-2S-carboxylic acid (1R-cyclopropanesulfonylamino-carbonyl-2S-vinylcyclopropyl)-amide, is shown below.

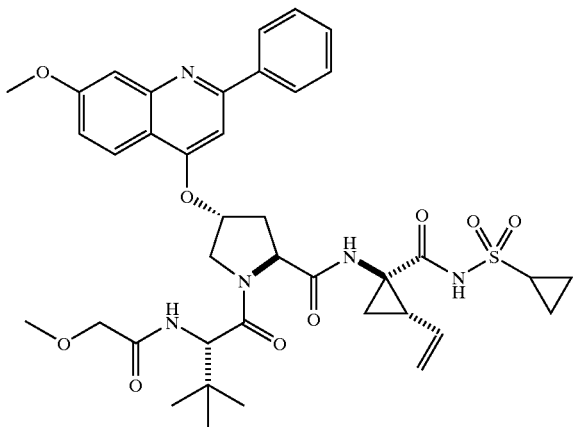

Compound 107 was prepared with methoxyacetic acid and was purified by reverse phase preparative HPLC to give white solid as a TFA salt (18.8 mg, 56% yield). $^1$H NMR (MeOH) δ 1.04–1.12 (m, 2H), 1.06 (s, 9H), 1.24–1.26 (m, 2H), 1.37 (dd, J=6.4, 4.0 Hz, 1H), 1.46 (dd, J=9.5, 5.5 Hz, 1H), 1.90 (dd, J=8.2, 5.5 Hz, 1H), 2.24 (q, J=8.9 Hz, 1H), 2.39–2.45 (m, 1H), 2.74 (dd, J=13.3, 7.2 Hz, 1H), 2.93–2.96 (m, 1H), 3.34 (s, 3H), 3.73 (dd, J=74.2, 15.2 Hz, 2H), 4.05 (s, 3H), 4.18 (dd, J=12.5, 3.1 Hz, 1H), 4.56–4.60 (m; 3H), 5.14 (dd, J=10.2, 1.5 Hz, 1H), 5.31 (dd, J=16.8, 1.2 Hz, 1H), 5.73–5.80 (m, 1H), 5.82 (bs, 1H), 7.39 (dd, J=9.2, 2.1 Hz, 1H), 7.51 (d, J=2.1 Hz, 1H), 7.58 (s, 1H), 7.61 (d, J=9.2 Hz, 1H), 7.69–7.72 (m, 3H), 8.08 (dd, J=7.9, 1.5 Hz, 1H), 8.24 (dd, J=9.2 Hz, 1H); LC-MS (retention time: 1.35), MS m/z 762 (M$^+$+1).

Compound 108

Compound 108, 1-{2S-[2-(4-methoxy-phenoxy)-acetylamino]-3,3-dimethyl-butyryl}-4R-(7-methoxy-2-phenyl-quinolin-4-yloxy)-pyrrolidine-2S-carboxylic acid (1R-cyclopropanesulfonylamino-carbonyl-2S-vinylcyclopropyl)amide, is shown below.

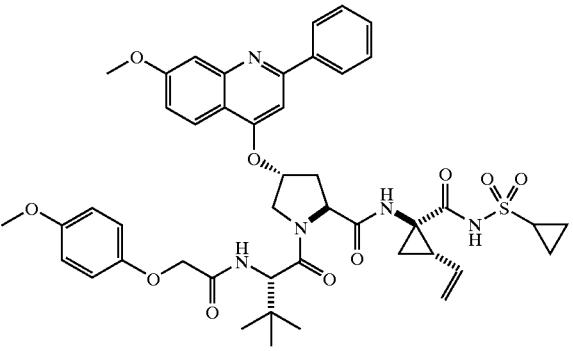

Compound 108 was prepared with 4-methoxyphenoxyacetic acid. $^1$NMR (MeOH) δ 1.04 (s, 9H), 1.08–1.10 (m, 2H), 1.23–1.27 (m, 2H), 1.47 (dd, J=9.5, 5.5 Hz, 1H), 1.91 (dd, J=8.2, 5.5 Hz, 1H), 2.24 (q, J=8.9 Hz, 1H), 2.41–2.47 (m, 1H), 2.76 (dd, J=13.7, 7.0 Hz, 1H), 2.93–2.98 (m, 1H), 3.73 (s, 3H), 4.02 (s, 3H), 4.18 (dd, J=12.4, 3.2 Hz, 1H), 4.23 (d, J=15.0 Hz, 1H), 4.37 (d, J=15.0 Hz, 1H), 4.58–4.62 (m, 3H), 5.14 (d, J=10.4 Hz, 1H), 5.31 (d, J=16.2 Hz, 1H), 5.73–5.81 (m, 1H), 5.86 (bs, 1H), 6.85 (d, J=5.5 Hz, 4H), 7.33 (dd, J=9.2, 2.4 Hz, 1H), 7.49 (d, J=2.1 Hz, 1H), 7.63 (s, 1H), 7.71–7.78 (m, 3H), 7.82 (d, J=8.6 Hz, 1H), 8.08 (d, J=8.2 Hz, 1H), 8.25 (d, J=9.5 Hz, 1H); LC-MS (retention time: 1.54), MS m/z 854 (M$^+$+1).

Compound 109

Compound 109, 1-{2S-[2-(4-Fluoro-phenoxy)-acetylamino]-3, 3-dimethyl-butyryl}-4R-(7-methoxy-2-phenyl-quinolin-4-yloxy)-pyrrolidine-2S-carboxylic acid (1R-cyclopropanesulfonylaminocarbonyl-2S-vinylcyclopropyl)-amide, is shown below.

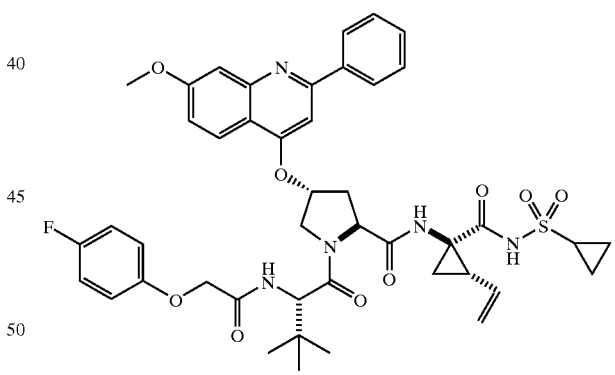

Compound 109 was prepared with 4-fluoropheoxyacetic acid. $^1$H NMR (MeOH) δ 1.04 (s, 3.6H), 1.05 (s, 5.4H), 1.07–0.10 (m, 2H), 1.22–1.27 (m, 2H), 1.44–1.48 (m, 1H), 1.88–1.92 (m, 1H), 2.21–2.26 (m, 1H), 2.41–2.47 (m, 1H), 2.76 (dd, J=13.4, 6.7 Hz, 1H), 2.93–2.97 (m, 1H), 4.01 (s, 1.2H), 4.02 (s, 1.8H), 4.16–4.20 (m, 1H), 4.28 (d, J=5.2 Hz, 0.4H), 4.31 (d, J=0.2 Hz, 1H), 4.40 (d, J=5.2 Hz, 0.6H), 4.41 (d, J=5.2 Hz, 0.4H), 4.58–4.62 (m, 3H), 5.12–5.15 (m, 1H), 5.30 (dd, J=17.1, 0.91 Hz, 0.4H), 5.31 (dd, J=17.1, 1.2 Hz, 0.6H), 5.73–5.81 (m, 1H), 5.86 (bs, 1H), 6.88–6.92 (m, 2H), 6.97–7.02 (m, 2H), 7.31–7.35 (m, 1H), 7.49 (d, J=2.4 Hz, 0.4H), 7.50 (d, J=2.4 Hz, 0.6H), 7.63 (s, 0.4H), 7.64 (s, 0.6H), 7.70–7.77 (m, 3H), 7.86–7.89 (m, 1H), 8.05–8.08 (m, 2H), 8.4 (d, J=9.5 Hz, 0.4H), 8.5 (d, J=9.2 Hz, 0.6H); LC-MS (retention time: 1.56), MS m/z 842 (M$^+$+1).

Compound 110

Compound 110, 1-{2S-[(furan-2-carbonyl)-amino]-3,3-dimethyl-butyryl}-4R-(7-methoxy-2-phenyl-quinolin-4-yloxy)-pyrrolidine-2S-carboxylic acid (1R-cyclopropanesulfonylaminocarbonyl-2S-vinyl-cyclopropyl)-amide, is shown below.

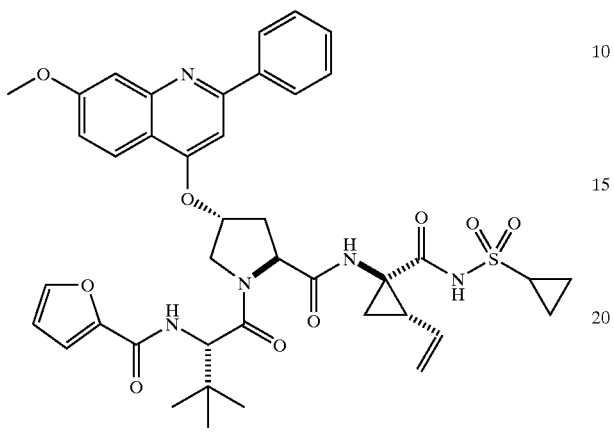

Compound 110 was prepared with furoic acid. $^1$H NMR (MeOH) δ 1.09 (s, 3.6H), 1.10 (s, 5.4H), 1.11–1.15 (m, 2H), 1.25–1.28 (m, 2H), 1.47 (q, J=5.5 Hz, 1H), 1.91 (q, J=5.5 Hz, 1H), 2.25 (q, J=8.9 Hz, 1H), 2.42–2.47 (m, 1H), 2.79 (dd, J=14.7, 7.5 Hz, 1H), 2.95–2.99 (m, 1H), 4.04 (s, 1.2H), 4.05 (s, 1.8H), 4.14–4.19 (m, 1H), 4.61–4.66 (m, 1H), 4.73 (d, J=9.2 Hz, 1H), 5.15 (dd, J=10.1, 0.9 Hz, 1H), 5.32 (d, J=17.4 Hz, 0.6H), 5.33 (d, J=16.5 Hz, 0.4H), 5.74–5.81 (m, 1H), 5.87 (bs, 1H), 6.52–6.53 (m, 1H), 6.85 (d, J=3.4 Hz, 1H), 7.28 (dd, J=9.2, 2.5 Hz, 1H), 7.48 (dd, J=8.6, 2.4 Hz, 1H), 7.60–7.66 (m, 2H), 7.73–7.78 (m, 3H), 7.85 (d, J=8.9 Hz, 1H), 8.10 (d, J=8.2 Hz, 1H), 8.18 (d, J=9.2 Hz, 1H); LC-MS (retention time: 1.42), MS m/z 784 (M$^+$+1).

Compound 111

Compound 111, 1-{2S-[(1-hydroxy-cyclopropane-carbonyl)-amino]-3,3-dimethyl-butyryl}-4R-(7-methoxy-2-phenyl-quinolin-4-yloxy)pyrrolidine-2S-carboxylic acid (1R-cyclopropanesulfonylaminocarbonyl-2S-vinylcyclopropyl)amide, is shown below.

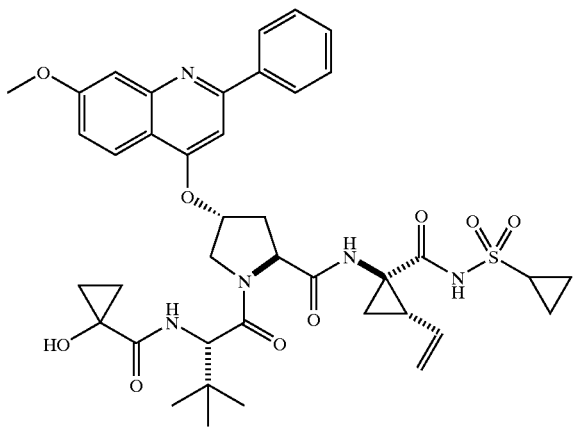

Compound 111 was prepared with 1-hydroxy-1-cyclopropanecarboxylic acid. $^1$H NMR (MeOH) δ 0.64–0.68 (m, 1H), 0.79–0.84 (m, 1H), 0.89–0.93 (m, 1H), 0.99–1.04 (m, 1H), 1.04–1.08 (m, 2H), 1.09 (s, 9H), 1.23–1.26 (m, 2H), 1.45 (dd, J=9.5, 5.2 Hz, 1H), 1.91 (dd, J=8.2, 5.5 Hz, 1H), 2.25 (q, J=8.9 Hz, 1H), 2.41–2.47 (m, 1H), 2.76 (dd, J=14.2, 6.9 Hz, 1H), 2.93–2.97 (m, 1H), 4.06 (s, 3H), 4.17 (dd, J=12.4, 3.2 Hz, 1H), 4.52 (d, J=9.2 Hz, 1H), 4.59–4.62 (m 2H), 5.14 (dd, J=10.4, 1.5 Hz, 1H), 5.31 (dd, J=17.1, 1.2 Hz, 1H), 5.72–5.79 (m, 1H), 5.85 (bs, 1H), 7.41 (dd, J=9.3, 2.3 Hz, 1H), 7.53 (d, J=2.1 Hz, 1H), 7.63 (s, 1H), 7.71–7.78 (m, 4H), 8.07 (dd, J=6.7, 1.5 Hz, 1H), 8.27 (d, J=9.2 Hz, 1H); LC-MS (retention time: 1.33), MS m/z 774 (M$^+$+1).

Compound 112

Compound 112, 1-[2S-(2-Fluoro-acetylamino)-3,3-dimethyl-butyryl]-4R-(7-methoxy-2-phenyl-quinolin-4-yloxy)-pyrrolidine-2S-carboxylic acid (1R-cyclopropanesulfonylaminocarbonyl-2S-vinyl-cyclopropyl)-amide, is shown below.

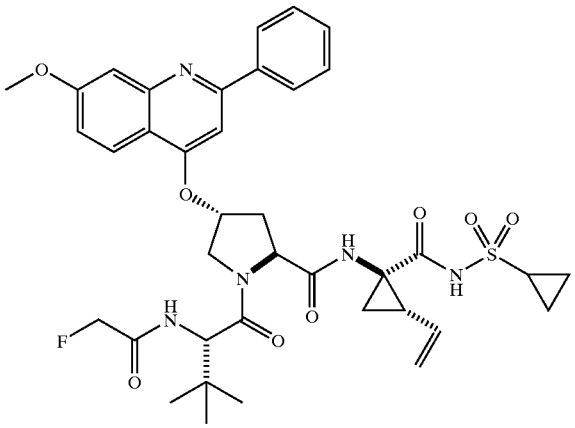

Compound 112 was prepared with fluoroacetic acid sodium salt. $^1$H NMR (MeOH) δ 1.08 (s, 9H), 1.03–1.12 (m, 3H), 1.22–1.26 (m, 2H), 1.45 (q, J=5.5 Hz, 1H), 1.90 (q, J=5.5 Hz, 1H), 2.25 (q, J=8.9 Hz, 1H), 2.41–2.27 (m, 1H), 2.27 (dd, J=14.0, 6.7 Hz, 1H), 2.92–2.97 (m, 1H), 3.97 (s, 1H), 4.06 (s, 3H), 4.19 (dd, J=12.5, 3.1 Hz, 1H), 4.58–4.62 (m, 3H), 4.64 (q, J=14.0 Hz, 1H), 4.73 (q, J=14.0 Hz, 1H), 5.14 (dd, J=10.4, 1.5 Hz, 1H), 5.31 (dd, J=17.1, 1.2 Hz, 1H), 5.71–5.77 (m, 1H), 5.87 (bs, 1H), 7.44, J=9.2, 2.4 Hz, 1H), 7.55 (d, J=2.1 Hz, 1H), 7.64 (s, 1H), 7.71–7.79 (m, 3H), 8.08 (dd, J=8.5, 1.5 Hz, 2H), 8.31 (d, J=9.5 Hz, 1H); LC-MS (retention time: 1.42), MS m/z 750 (M$^+$+1).

EXAMPLE 37

Compound 113

Compound 113, {1S-[2S-(1R-cyclopropanesulfonyl-aminocarbonyl-2S-vinyl-cyclopropylcarbamoyl)-4R-(7-methoxy-2-phenyl-quinolin-4-yloxy)-pyrrolidine-1-carbonyl]-2,2-dimethyl-propyl}carbamic acid methyl ester, is shown below.

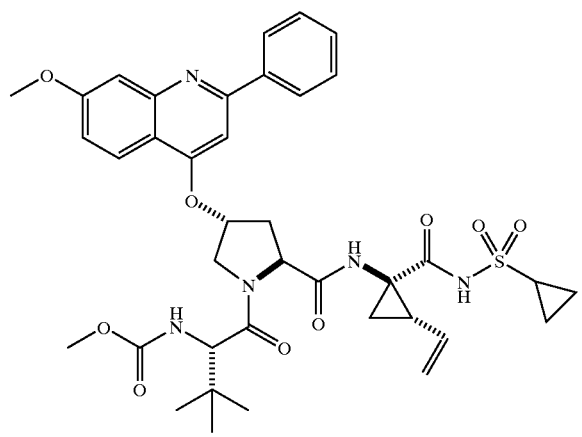

To a solution of the product of Step 30b (35 mg, 0.0381 mmol) in DCM (2 mL) was added 1,3-dimethylperhydro-1,2,3-diazaphosphine on polystyrene (100 mg, 2.3 mmol/g, 0.229 mmol), and methylchloroformate (9 μL, 0.114 mmol). The reaction vial was rotated for 16 h and was filtered and washed with DCM. The solvent was concentrated and the residue was purified by reverse phase preparative HPLC to give white solid product as a TFA salt (14.7 mg, 35% yield). $^1$H NMR (MeOH) δ 1.05 (s, 9H), 1.07–1.11 (m, 2H), 1.22–1.26 (m, 2H), 1.44 (q, J=5.2 Hz, 1H), 1.90 (q, J=5.7 Hz, 1H), 2.24 (q, J=8.7 Hz, 1H), 2.40–2.46 (m, 1H), 2.77 (dd, J=13.9, 6.9 Hz, 1H), 2.92–2.97 (m, 1H) 3.38 (s, 3H), 4.06 (s, 3H), 4.14 (dd, J=12.2, 3.1 Hz, 1H), 4.23 (s, 1H), 4.58–4.64 (m, 2H), 5.13 (dd, J=10.4, 1.5 Hz, 1H), 5.30 (dd, J=17.1, 1.2 Hz, 1H), 5.70–5.77 (m, 1H), 5.86 (bs, 1H), 7.43 (dd, J=9.3, 2.3 Hz, 1H), 7.54 (d, J=2.1 Hz, 1H), 7.65 (s, 1H), 7.72–7.79 (m, 3H), 8.09 (dd, J=6.9, 1.7 Hz, 1H), 8.36 (d, J=9.5 Hz, 1H),; LC-MS (retention time: 1.47), MS m/z 748 (M$^+$+1).

EXAMPLE 38

The following compounds were prepared according to the method of Example 37.

Compound 114

Compound 114, {1S-[2S-(1R-cyclopropanesulfonyl-aminocarbonyl-2S-vinyl-cyclopropylcarbamoyl)-4R-(7-methoxy-2-phenyl-quinolin-4-yloxy)-pyrrolidine-1-carbonyl]-2,2-dimethyl-propyl}-carbamic acid benzyl ester, is shown below.

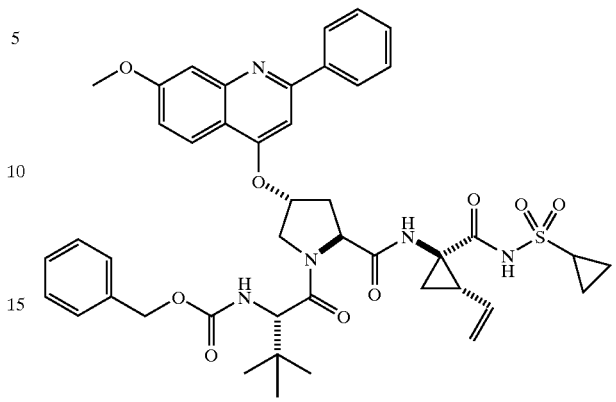

Compound 114 was prepared with benzylchloroformate. $^1$H NMR (MeOH) δ 1.05 (s, 9H), 1.06–1.09 (m, 2H), 1.23–1.24 (m, 2H), 1.45 (q, J=5.5 Hz, 1H), 1.90 (q, J=5.5 Hz, 1H), 2.25 (q, J=8.7 Hz, 1H), 2.40–2.46 (m, 1H), 2.77 (dd, J=13.4, 7.0 Hz, 1H), 2.92–2.97 (m, 1H), 3.98 (s, 3H), 4.12 (dd, J=12.2, 2.4 Hz, 1H), 4.23 (s, 1H), 4.59–4.73 (m, 4H), 5.14 (dd, J=10.2, 1.4 Hz, 1H), 5.31 (d, J=17.1 Hz, 1H), 5.71–5.67 (m, 1H), 5.86 (bs, 1H), 7.15 (dd, J=7.3, 1.8 Hz, 1H), 7.27 (d, J=6.7 Hz, 1H), 7.32 (dd, J=9.3, 2.0 Hz, 1H), 7.48 (d, J=2.1 Hz, 1H), 7.65 (s, 1H), 7.72–7.79 (m, 3H), 8.07 (d, J=7.0 Hz, 1H), 8.31 (d, J=9.2 Hz, 1H); LC-MS (retention time: 1.67), MS m/z 824 (M$^+$+1).

Compound 115

Compound 115, {1S-[2S-(1R-cyclopropanesulfonyl-aminocarbonyl-2S-vinyl-cyclopropylcarbamoyl)-4R-(7-methoxy-2-phenyl-quinolin-4-yloxy)-pyrrolidine-1-carbonyl]-2,2-dimethyl-propyl}-carbamic acid ethyl ester, is shown below.

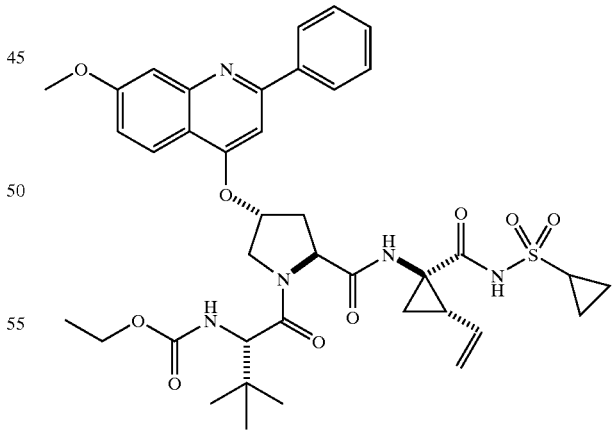

Compound 115 was prepared with ethylchloroformate. $^1$H NMR (MeOH) δ 1.04 (s, 9H), 1.06–1.11 (m, 4H), 1.23–1.28 (m, 2H), 1.44 (q, J=5.5 Hz, 1H), 1.90 (q, J=5.5 Hz, 1H), 2.24 (q, J=8.7 Hz, 1H), 2.39–2.45 (m, 1H), 2.76 (dd, J=14.5, 6.9 Hz, 1H), 2.92–2.97 (m, 1H), 4.05 (s, 3H), 4.13 (dd, J=12.2, 2.8 Hz, 1H), 4.58–4.63 (m, 2H), 5.14 (dd, J=10.4, 1.5 Hz, 1H), 5.31 (d, J=17.1 Hz, 1H), 5.71–5.78 (m, 1H), 5.84 (bs, 1H), 7.39 (dd, J=9.3, 2.0 Hz, 1H), 7.52 (d, J=2.1 Hz, 1H), 7.62 (s, 1H), 7.70–7.75 (m, 3H), 8.08 (dd, J=7.9, 1.5 Hz, 1H), 8.32 (d, J=9.2 Hz, 1H) LC-MS (retention time: 1.53), MS m/z 762 (M$^+$+1).

Compound 116

Compound 116, {1S-[2S-(1R-cyclopropanesulfonyl-aminocarbonyl-2S-vinyl-cyclopropylcarbamoyl)-4R-(7-methoxy-2-phenyl-quinolin-4-yloxy)-pyrrolidine-1-carbonyl]-2,2-dimethyl-propyl}-carbamic acid phenyl ester, is shown below.

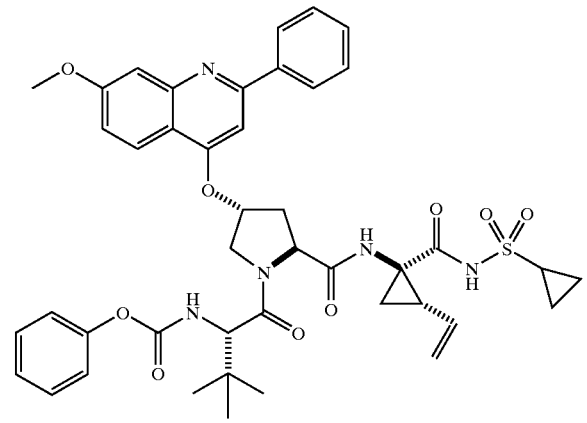

Compound 116 was prepared with phenylchlororformate. $^1$H NMR (MeOH) δ 1.01–1.10 (m, 5H), 1.13 (s, 7H), 1.23–1.26 (m, 2H), 1.42–1.47 (m, 1H), 1.90 (dd, J=7.8, 6.0 Hz, 1H), 2.25 (q, J=8.7 Hz, 1H), 2.39–2.45 (m, 1H), 2.76 (dd, J=13.9, 6.9 Hz, 1H), 2.93–2.97 (m, 1H), 4.03 (s, 2H), 4.06 (s, 1H), 4.11 (dd, J=12.4, 2.9 Hz, 0.7H), 4.16 (dd, J=12.7, 2.9 Hz, 0.3H), 4.62 (q, J=7.8 Hz, 1H), 4.69 (d, J=12.5 Hz, 1H), 5.14 (d, J=10.4 Hz, 1H), 5.31 (d, J=17.1 Hz, 1H), 5.69–5.77 (m, 1H), 5.81 (bs, 0.7H), 5.87 (bs, 0.3H), 6.92 (d, J=7.93 Hz, 1H), 7.04 (dd, J=9.3, 2.3 Hz, 1H), 7.21 (t, J=7.3 Hz, 0.70H), 7.30 (t, J=7.8 Hz, 1.4H), 7.41 (d, J=2.4 Hz, 0.7H), 7.55 (d, J=2.1 Hz, 0.3H), 7.57 (s, 0.7H), 7.65 (s, 0.3H), 7.69–7.77 (m, 3H), 8.01 (d, J=7.3 Hz, 1.4H), 8.08 (d, J=7.0 Hz, 0.6H), 8.28 (t, J=9.2 Hz, 1H). LC-MS (retention time: 1.62), MS m/z 810 (M$^+$+1).

Compound 117

Compound 117, 1-(2S-methanesulfonylamino-3,3-dimethyl-butyryl)-4R-(7-methoxy-2-phenyl-quinolin-4-yloxy)-pyrrolidine-2S-carboxylic acid (1R-cyclopropanesulfonylamino-carbonyl-2S-vinyl-cyclopropyl)-amide, is shown below.

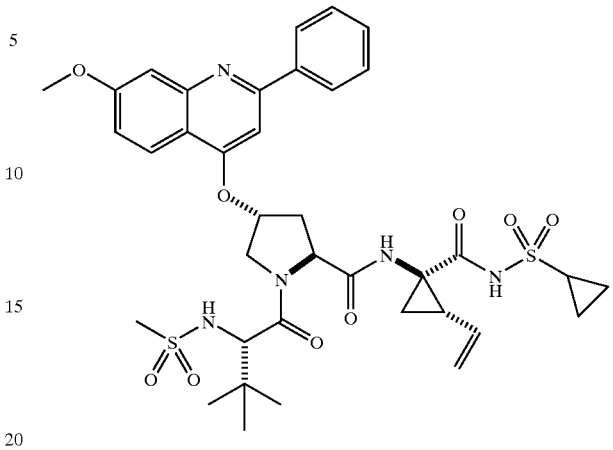

Compound 117 was prepared with methanesulfonyl chloride. $^1$H NMR (MeOH) δ 1.09–1.12 (m, 2H), 1.08 (s, 9H), 1.23–1.26 (m, 2H), 1.45 (dd, J=9.5, 5.5 Hz, 1H), 1.90 (dd, J=7.9, 5.5 Hz, 1H), 2.23 (q, J=8.7 Hz, 1H), 2.40–2.47 m, 1H), 2.74 (s, 3H), 2.78 (dd, J=14.0, 7.0 Hz, 1H), 2.93–2.96 (m, 1H), 4.01 (s, 1H), 4.06 (s, 3H), 4.10 (dd, J=12.5, 3.1 Hz, 1H), 4.58 (d, J=14.4 Hz, 1H), 4.61 (dd, J=10.4, 6.7 Hz, 1H), 5.15 (dd, J=10.5, 1.4 Hz, 1H), 5.31 (dd, J=17.0, 1.2 Hz, 1H), 5.71–5.78 (m, 1H), 7.45 (dd, J=9.2, 2.4 Hz, 1H), 7.54 (d, J=2.4 Hz, 1H), 7.63 (s, 1H), 7.71–7.79 (m, 3H), 8.06 (dd, J=6.9, 1.7 Hz, 1H), 8.37 (d, J=9.5 Hz, 1H); LC-MS (retention time: 1.38), MS m/z 768 (M$^+$+1).

Compound 118

Compound 118, 1-(2S-cyclopropanesulfonylamino-3,3-dimethyl-butyryl)-4R-(7-methoxy-2-phenyl-quinolin-4-yloxy)-pyrrolidine-2S-carboxylic acid (1R-cyclopropanesulfonylamino-carbonyl-2S-vinyl-cyclopropyl)-amide, is shown below.

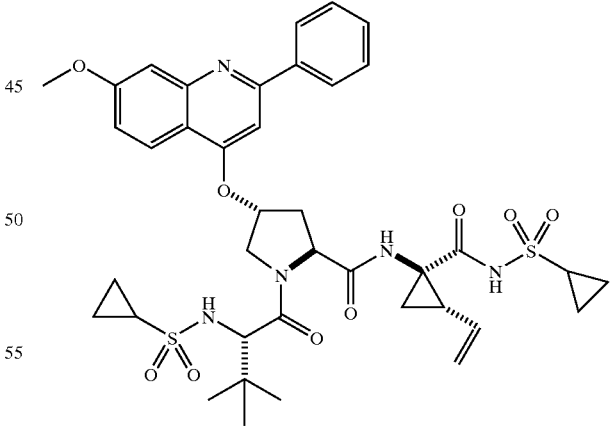

Compound 118 was prepared with cyclopropanesulfornyl chloride. $^1$H NMR (MeOH) δ 0.73–0.78 (m, 2H), 0.83–0.91 (m, 2H), 1.06–1.10 (m, 2H), 1.08 (s, 9H), 1.22–1.26 (m, 2H), 1.45 (dd, J=9.5, 5.5 Hz, 1H), 1.90 (dd, J=7.9, 5.5 Hz, 1H), 2.25 (q, J=8.9 Hz, 1H), 2.32–2.36 (m, 1H), 2.41–2.47 (m, 1H), 2.79 (dd, J=13.9, 6.7 Hz, 1H), 2.92–2.96 (m, 1H), 3.95 (s, 1H), 4.06 (s, 3H), 4.13 (dd, J=12.4, 2.9 Hz, 1H), 4.52 (d, J=12.5 Hz, 1H), 4.61 (q, J=7.0 Hz, 1H), 5.14 (dd, J=10.4, 1.5 Hz, 1H), 5.31 (dd, J=17.2, 1.4 Hz, 1H), 5.71–5.76 (m, 1H), 5.81 (bs, 1H), 7.43 (dd, J=9.5, 2.5 Hz, 1H), 7.54 (dd, J=2.4 Hz, 1H), 7.63 (s, 1H), 7.71–7.79 (m, 3H), 8.07 (dd, J=7.0, 1.5 Hz, 1H), 8.36 (d, J=9.5 Hz, 1H); LC-MS (retention time: 1.44), MS m/z 794 (M$^+$+1).

Compound 119

Compound 119, 1-[2S-(4-fluoro-benzenesulfonylamino)-3,3-dimethyl-butyryl]-4R-(7-methoxy-2-phenylquinolin-4-yloxy)-pyrrolidine-2S-carboxylic acid (1R-cyclopropanesulfonylaminocarbonyl -2S-vinyl-cyclopropyl)amide, is shown below.

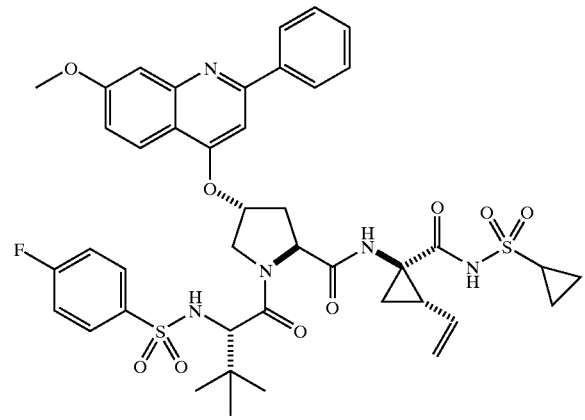

Compound 119 was prepared with 4-fluorobenzenesulfornyl chloride. $^1$H NMR (MeOH) δ 0.93 (s, 3.6H), 1.01 (s, 2H), 1.08 (s, 5.4H), 1.22–1.26 (m, 2H), 1.41–1.47 (m, 1H), 1.85–1.91 (m, 1H), 2.22–2.27 (m, 1H), 2.40–2.46 (m, 1H), 2.75 (dd, J=014.0, 7.3 Hz, 0.4H), 2.79 (dd, J=14.7, 7.6 Hz, 0.6H), 2.91 (m, 1H), 4.0 (s, 1H), 4.05 (s, 3H), 4.15 (t, J=3.5 Hz, 0.4H), 4.17 (t, J=3.7 Hz, 0.6H), 4.44 (d, J=12.5 Hz, 10.4H), 4.47–4.51 (m, 1H), 4.58 (d, J=12.5 Hz, 0.6H), 4.60–4.64 (m, 1H), 5.13 (dd, J=10.4, 1.5 Hz, 1H), 5.31 (d, J=17.1, 12.1 Hz, 1H), 5.68–5.78 (m, 1H), 5.83 (bs, 0.6H), 5.87 (bs, 0.4H), 7.07–7.12 (m, 1H), 7.40 (dd, J=9.2, 2.4 Hz, 0.4H), 7.44 (dd, J=9.2, 2.4 Hz, 0.6H), 7.55 (d, J=1.5 Hz, 1H), 7.64 (d, J=6.7 Hz, 1H), 7.71–7.81 (m, 4H), 7.93 (d, J=8.5 Hz, 0.6H), 8.07–8.11 (m, 2H), 8.18 (d, J=9.2 Hz, 0.4H), 8.28 (d, J=9.5 Hz, 0.6H), 8.41 (d, J=9.5 Hz, 0.4H); LC-MS (retention time: 1.35), MS m/z 732 (M$^+$+1).

Compound 120

Compound 120, 1-[2S-(2-chloro-acetylamino)-3,3-dimethyl-butyryl]-4R-(7-methoxy-2-phenyl-quinolin-4-yloxy)-pyrrolidine-2S-carboxylic acid (1R-cyclopropanesulfonylaminocarbonyl-2S-vinylcyclopropyl)-amide, is shown below.

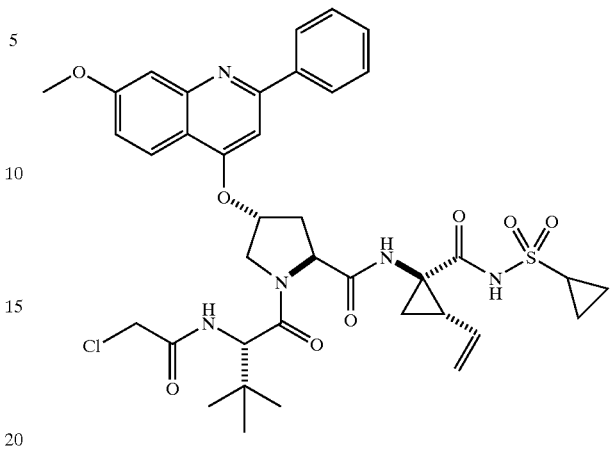

Compound 120 was prepared with chloroacetic anhydride. $^1$H NMR (MeOH) δ 1.04–1.11 (m, 3H), 1.08 (s, 9H), 1.22–1.25 (m, 2H), 1.44 (q, J=5.2 Hz, 1H), 1.90 (q, J=5.5 Hz, 1H), 2.24 (q, J=8.8 Hz, 1H), 2.40–2.46 (m, 1H), 2.77 (dd, J=14.2, 6.6 Hz, 1H), 2.92–2.97 (m, 1H), 3.91 (d, J=13.1 Hz, 1H), 3.99 (d, J=13.4 Hz, 1H), 4.06 (s, 3H), 4.16 (dd, J=12.4, 3.2 Hz, 1H), 4.52 (t, J=4.3 Hz, 1H), 4.59 (q, J=7.0 Hz, 1H), 4.64 (d, J=12.5 Hz, 1H), 5.13 (dd, J=10.2, 1.7 Hz, 1H), 5.31 (dd, J=17.1, 1.5 Hz, 1H), 5.70–5.78 (m, 1H), 5.86 (bs, 1H), 7.43 (dd, J=9.3, 2.3 Hz, 1H), 7.54 (d, J=2.1 Hz, 1H), 7.64 (s, 1H), 7.71–7.79 (m, 3H), 8.08 (dd, J=8.2, 1.5 Hz, 1H), 8.34 (d, J=9.5 Hz, 1H). LC-MS (retention time: 1.47), MS m/z 767 (M$^+$+1).

Compound 121

Compound 121, N-{1S-[2S-(1R-cyclopropanesulfonyl-aminocarbonyl-2S-vinyl-cyclopropylcarbamoyl)-4R-(7-methoxy-2-phenyl-quinolin-4-yloxy)-pyrrolidine-1-carbonyl]-2,2-dimethyl-propyl}-oxalamic acid methyl ester, is shown below.

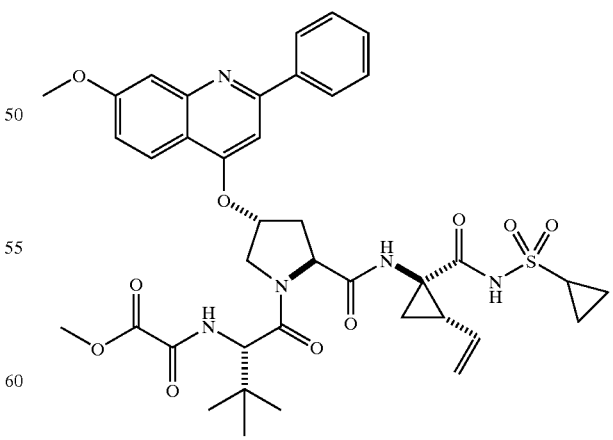

Compound 121 was prepared with methyl oxalyl chloride. $^1$H NMR (MeOH) δ 1.02–1.12 (m, 3H), 1.07 (s, 9H), 1.23–1.26 (m, 2H), 1.45 (q, J=5.5 Hz, 1H), 1.90 (q, J=5.5

Hz, 1H), 2.25 (d, J=8.9 Hz, 1H), 2.41–2.47 (m, 1H), 2.77 (dd, J=13.9, 6.6 Hz, 1H), 2.92–2.97 (m, 1H), 3.79 (s, 3H), 4.07 (s, 3H), 4.16 (dd, J=12.7, 2.9 Hz, 1H), 4.57–4.62 (m, 2H), 5.14 (dd, J=10.4, 1.5 Hz, 1H), 5.31 (dd, J=17.1, 1.2 Hz, 1H), 5.72–5.77 (m, 1H), 5.86 (bs, 1H), 7.41 (dd, J=9.3, 2.3 Hz, 1H), 7.54 (d, J=2.4 Hz, 1H), 7.64 (s, H), 7.71–7.79 (m, 3H), 8.08 (dd, J=8.2, 1.5 Hz, 1H), 8.27 (d, J=9.2 Hz, 1H); LC-MS (retention time: 1.43), MS m/z 776 (M$^+$+1).

Compound 122

Compound 122, {1S-[2S-(1R-cyclopropanesulfonyl-aminocarbonyl-2S-vinyl-cyclopropylcarbamoyl)-4R-(7-methoxy-2-phenyl-quinolin-4-yloxy)-pyrrolidine-1-carbonyl]-2,2-dimethyl-propyl}-carbamic acid 2-fluoroethyl ester, is shown below.

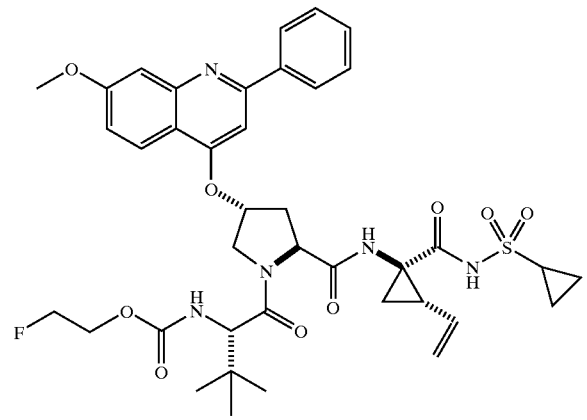

Compound 122 was prepared with 2-fluoroethylchloroformate. $^1$H NMR (MeOH) δ 1.01–1.09 (m, 3H), 1.05 (s, 9H), 1.23–1.25 (m, 2H), 1.44 (q, J=5.3 Hz, 1H), 1.89 (q, J=5.5 Hz, 1H), 2.24 (q, J=8.9 Hz, 1H), 2.40–2.46 (m, 1H), 2.77 (dd, J=13.9, 6.9 Hz, 1H), 2.92–2.97 (m, 1H), 3.92 (dd, J=5.7, 2.9 Hz, 0.5H), 3.95 (dd, J=5.5, 2.8 Hz, 0.5H), 3.97 (dd, J=5.5, 2.8 HZ, 0.5H), 4.01 (dd, J=5.0, 2.6 Hz, 0.5H), 4.05 (s, 3H), 4.14 (dd, J=12.2, 2.8 Hz, 1H) 4.24 (s, 1H), 4.36–4.38 (m, 1H), 4.45–4.48 (m, 1H), 4.59–4.64 (m, 2H), 5.14 (dd, J=10.4, 1.2 Hz, 1H), 5.30 (d, J=17.1 Hz, 1H), 5.70–5.77 (m, 1H), 5.86 (bs, 1H), 7.42 (dd, J=9.3, 2.3 Hz, 1H), 7.55 (d, J=2.4 Hz, 1H), 7.64 (s, 1H), 7.71–7.78 (m, 3H), 8.09 (d, J=8.2 Hz, 2H), 8.33 (d, J=9.5 Hz, 1H); LC-MS (retention time: 1.46), MS m/z 780 (M$^+$+1).

Compound 123

Compound 123, {1S-[2S-(1R-cyclopropanesulfonyl-aminocarbonyl-2S-vinyl-cyclopropylcarbamoyl)-4R-(7-methoxy-2-phenyl-quinolin-4-yloxy)-pyrrolidine-1-carbonyl]-2,2-dimethyl-propyl}-carbamic acid vinyl ester, is shown below.

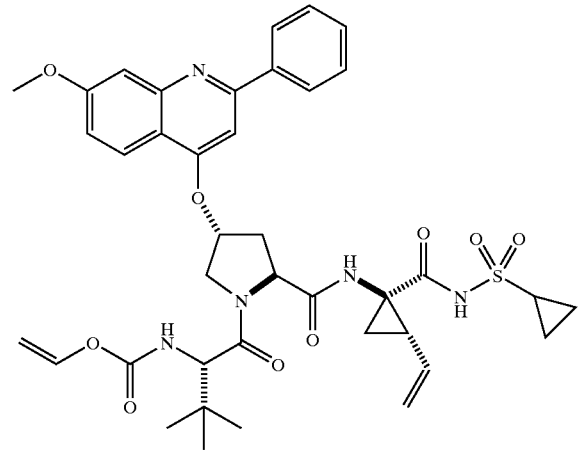

Compound 123 was prepared with vinylchloroformate. $^1$H NMR (MeOH) δ 1.05 (m, 9H), 1.01–1.13 (m, 3H), 1.24 (d, J=2.4 Hz, 2H), 1.29 (bs, 1H), 1.44 (dd, J=9.5, 5.5 Hz, 1H), 1.90 (dd, J=8.1, 5.7 Hz, 1H), 2.24 (q, J=8.6 Hz, 1H), 2.40–2.45 (m, 1H), 2.78 (dd, J=13.6, 7.2 Hz, 1H), 2.92–2.97 (m, 1H), 4.06 (s, 3H), 4.11 (dd, J=12.2, 2.8 Hz, 1H), 4.24 (d, J=8.9 Hz, 1H), 4.32 (d, J=5.5 Hz, 1H), 4.60–4.66 (m, 3H), 5.14 (d, J=10.7 Hz, 1H), 5.31 (d, J=17.1 Hz, 1H), 5.70–5.77 (m, 1H), 5.86 (bs, 1H), 6.68 (dd, J=14.2, 6.3 Hz, 1H), 7.40 (dd, J=9.5, 2.1 Hz, 1H), 7.54 (d, J=1.8 Hz, 1H), 7.55 (s, 1H), 7.65 (s, 1H), 7.72–7.79 (m, 3H), 8.08 (d, J=7.02 Hz, 1H), 8.30 (d, J=9.5 Hz, 1H); LC-MS (retention time: 1.56), MS m/z 760 (M$^+$+1).

Compound 124

Compound 124, {1S-[2S-(1R-cyclopropanesulfonyl-aminocarbonyl-2S-vinyl-cyclopropylcarbamoyl)-4R-(7-methoxy-2-phenyl-quinolin-4-yloxy)-pyrrolidine-1-carbonyl]-2,2-dimethyl-propyl}-carbamic acid prop-2-ynyl ester, is shown below.

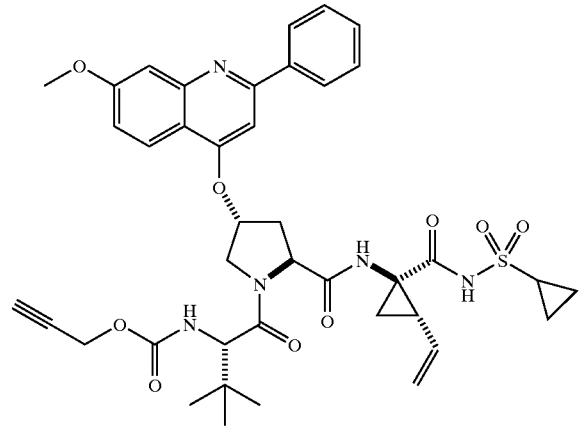

Compound 124 was prepared with propargylchloroformate. $^1$H NMR (MeOH) δ 1.01–1.09 (m, 3H), 1.05 (s, 9H), 1.21–1.26 (m, 2H), 1.44 (dd, J=9.5, 5.5 Hz, 1H), 1.90 (dd, J=7.9, 5.5 Hz, 1H), 2.24 (q, J=8.9 Hz, 1H), 2.40–2.46 (m, 1H), 2.77 (dd, J=14.2, 6.9 Hz, 1H), 2.83 (t, J=2.1 Hz, 1H), 2.93–2.97 (m, 1H), 4.06 (s, 3H), 4.12 (dd, J=12.2, 2.9 Hz, 1H), 4.22 (s, 1H), 4.33 (d, J=2.4 Hz, 2H), 4.59–4.66 (m, 2H), 5.14 (dd, J=10.4, 1.5 Hz, 1H), 5.30 (d, J=17.4 Hz, 1H), 5.70–5.77 (m, 1H), 5.86 (bs, 1H), 7.46 (dd, J=9.2, 2.1 Hz, 1H), 7.54 (d, J=2.1 Hz, 1H), 7.65 (s, 1H), 7.71–7.79 (m, 3H), 8.08 (dd, J=7.0, 1.5 Hz, 2H), 8.37 (d, J=9.5 Hz, 1H); LC-MS (retention time: 1.49), MS m/z 772 (M$^+$+1).

Compound 125

Compound 125, {1S-[2S-(1R-cyclopropanesulfonyl-aminocarbonyl-2S-vinyl-cyclopropylcarbamoyl)-4R-(7-methoxy-2-phenyl-quinolin-4-yloxy)-pyrrolidine-1-carbonyl]-2,2-dimethyl-propyl}-carbamic acid 2,2-dimethyl-propyl ester, is shown below.

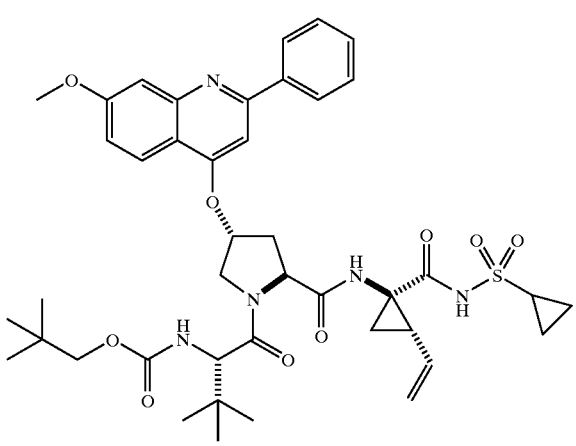

Compound 125 was prepared with neopentylchloroformate. $^1$H NMR (MeOH) δ 0.81 (s, 9H), 1.04 (s, 9H), 1.06–1.12 (m, 3H), 1.23–1.25 (m, 2H), 1.29 (s, 1H), 1.45 (dd, J=9.5, 5.5 Hz, 1H), 1.91 (dd, J=8.1, 5.5 Hz, 1H), 2.25 (q, J=8.8, 1H), 2.40–2.46 (m, 1H), 2.77 (dd, J=14.4, 7.5 Hz, 1H), 2.93–2.98 (m, 1H), 3.17 (d, J=10.1 Hz, 1H), 3.41 (d, J=10.4 Hz, 1H), 4.05 (s, 3H), 4.11 (dd, J=12.4, 2.3 Hz, 1H), 4.21 (s, 1H), 4.61–4.66 (m, 2H), 5.14 (dd, J=10.4, 1.5 Hz, 1H), 5.31 (dd, J=17.2, 1.1 Hz, 1H, 5.71–5.79 (m, 1H), 5.85 (bs, 1H), 7.40 (dd, J=9.3, 2.0 Hz, 1H), 7.53 (d, J=2.1 Hz, 1H), 7.65 (s, 1H), 7.71–7.79 (m, 3H), 8.08 (dd, J=8.2, 1.5 Hz, 2H), 8.32 (d, J=9.5 Hz, 1H); LC-MS (retention time: 1.74), MS m/z 804 (M$^+$+1).

Compound 126

Compound 126, {1S-[2S-(1R-cyclopropanesulfonyl-aminocarbonyl-2S-vinyl-cyclopropylcarbamoyl)-4R-(7-methoxy-2-phenyl-quinolin-4-yloxy)-pyrrolidine-1-carbonyl]-2,2-dimethyl-propyl}-carbamic acid allyl ester, is shown below.

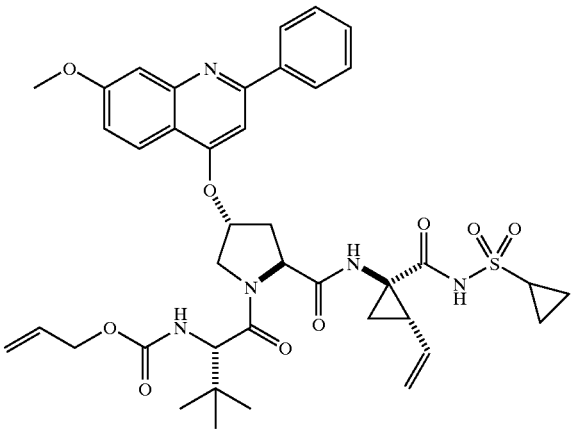

Compound 126 was prepared with allylchloroformate. $^1$H NMR (MeOH) δ 1.05 (s, 9H), 1.06–1.09 (m, 4H), 1.22–1.25 (m, 2H), 1.44 (q, J=5.5 Hz, 1H), 1.90 (q, J=5.5 Hz, 1H), 2.25 (q, J=8.9 Hz, 1H), 2.40–2.46 (m, 1H), 2.78 (q, J=14.0, 7 Hz, 1H), 2.92–2.97 (m, 1H), 4.05 (s, 3H), 4.10–4.15 (m, 1H), 4.21 (d, J=5.5 Hz, 1H), 4.22 (s, 1H), 4.60–4.66 (m, 2H), 5.08 (dd, J=10.5, 1.1 Hz, 1H), 5.14 (dd, J=10.4, 1.2 Hz, 1H), 5.17 (dd, J=17.1, 1.5 Hz, 1H), 5.31 (dd, J=17.1, 1.2 Hz, 1H), 7.42 (dd, J=9.5, 2.1 Hz, 1H), 7.55 (d, J=2.1 Hz, 1H), 7.66 (s, 1H), 7.71–7.79 (m, 3H), 8.08 (dd, J=6.9, 1.7 Hz, 2H), 8.33 (d, J=9.5 Hz, 1H); LC-MS (retention time: 1.56), MS m/z 774 (M$^+$+1).

Compound 127

Compound 127, {1S-[2S-(1R-cyclopropanesulfonyl-aminocarbonyl-2S-vinyl-cyclopropylcarbamoyl)-4R-(7-methoxy-2-phenyl-quinolin-4-yloxy)-pyrrolidine-1-carbonyl]-2,2-dimethyl-propyl}-carbamic acid butyl ester, is shown below.

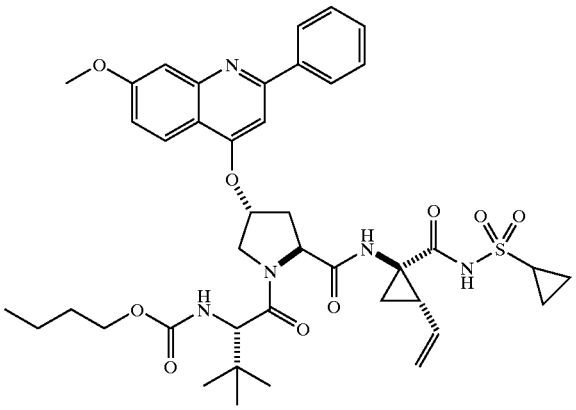

Compound 127 was prepared with n-butylchloroformate. $^1$H NMR (MeOH) 0.87 (t, J=7.3 Hz, 3H), 1.04 (s, 9H), 1.07–1.11 (m, 2H), 1.23–1.31 (m, 4H), 1.40–1.46 (m, 3H), 1.90 (q, J=5.5 Hz, 1H), 2.25 (q, J=8.7 Hz, 1H), 2.40–2.46 (m, 1H), 2.77 (dd, J=14.2, 6.9 Hz, 1H), 2.92–2.97 (m, 1H), 3.55–3.60 (m, 1H), 3.71–3.76 (m, 1H), 3.97 (s, 1H), 4.06 (s, 3H), 4.13 (dd, J=12.2, 2.4 Hz, 1H), 4.21 (s, 1H), 4.60–4.66 (m, 2H), 5.13 (dd, J=10.4, 2 Hz, 1H), 5.31 (d, J=17.1 Hz), 1H), 5.70–5.78 (m, 1H), 5.86 (bs, 1H), 7.41 (dd, J=9.3, 2.0

Hz, 1H), 7.55 (d, J=1.8 Hz, 1H), 7.66 (s, 1H), 7.72–7.79 (m, 3H), 8.07 (d, J=7.0 Hz, 1H), 8.34 (d, J=9.5 Hz, 1H); LC-MS (retention time: 1.68), MS m/z 790 (M⁺+1).

EXAMPLE 39

Compound 128

Compound 128, 1-[3,3-dimethyl-2S-(2-nitrophenylamino)-butyryl]-4R-(7-methoxy-2-phenyl-quinolin-4-yloxy)-pyrrolidine-2S-carboxylic acid (1R-cyclopropanesulfonyl-aminocarbonyl-2S-vinylcyclopropyl) amide, shown below, was prepared by the methods of the following Steps 39a–b.

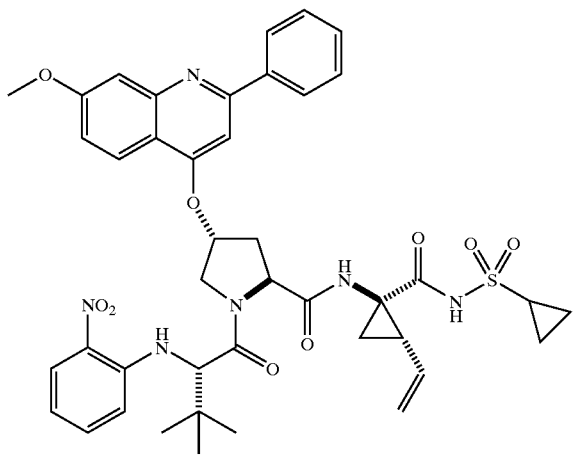

Step 39a: Preparation of 3,3-Dimethyl-2S-(2-nitrophenylamino)-butyric acid, shown below.

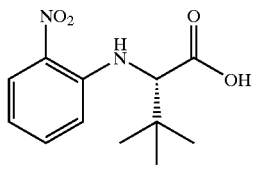

To a slurry of L-tert-leucine (1.0 g, 7.7 mmol) in EtOH (absolute, 25 mL) in a medium pressure flak was added 1-fluoro-2-nitrobenzene (812 μL, 7.7 mmol) and K₂CO₃ (2.3 g, 15.4 mmol). After heating to 105 C. for 2 hr, the resulting red reaction mixture was filtered to remove excess K₂CO₃ and washed with DCM. Solvent was concentrated and the red paste was re-dissolved with DCM and neutralized with 1N HCl. The aqueous layer was extracted with DCM. The combined DCM layer was dried over MgSO₄ and concentrated. The red solid was re-dissolved with MeOH, concentrated to a slurry and Et₂O was added to effect the precipitation. Red solid product was obtained by vacumm filtration (1.6 g, 82% yield). ¹H NMR (MeOH) δ 1.09 (s, 1H), 1.14 (s, 9H), 3.80 (s, 3H), 6.60 (ddd, J=8.6, 7.0, 1.2 Hz, 1H), 6.97 (d, J=8.5 Hz, 1H), 7.41 (ddd, J=8.9, 7.0, 1.8 Hz, 1H), 8.11 (dd, J=8.6, 1.5 Hz, 1H); LC-MS (retention time: 1.60), MS m/z 253 (M⁺+1).

Step 39b: Preparation of Compound 128

To a solution of the product of Step 27d (48.4 mg, 0.0745 mmol) in DMF (2 mL) was added DIEA (65 μL, 0.372 mmol), HATU (57 mg, 0.149 mmol), and the product of Step 39a (38.0 mg, 0.149 mmol). After stirring at rt for 16 hr, the solvent was concentrated and the residue was purified by reverse phase preparative HPLC to give orange solid as a TFA salt (22.1 mg, 32% yield). ¹H NMR (MeOH) δ 1.07–1.10 (m, 2H), 1.13 (s, 9H), 1.21–1.30 (m, 2H), 1.42 (dd, J=9.5, 5.5 Hz, 1H), 1.91 (dd, J=8.2, 5.5 Hz, 1H), 2.24 (q, J=8.7 Hz, 1H), 2.40–2.46 (m, 1H), 2.75 (dd, J=13.9, 7.2 Hz, 1H), 2.94–2.99 (m, 1H), 4.08 (s, 3H), 4.12 (dd, J=12.5, 2.4 Hz, 1H), 4.48 (d, J=11.0 Hz, 1H), 4.67 (d, J=7.6 Hz, 1H), 5.14 (dd, J=10.7, 1.5 Hz, 1H), 5.30 (d, J=17.1 Hz, 1H), 5.68 (m, 1H), 5.89 (br, s, 1H), 6.49 (t, J=7.8 Hz, 1H), 6.87 (d, J=8.9 Hz, 1H), 6.91 (dd, J=7.0, 1.5 Hz, 1H), 7.28 (dd, J=9.3, 2.3 Hz, 1H), 7.48 (d, J=2.1 Hz, 1H), 7.60 (s, 1H), 7.73–7.79 (m, 3H), 7.96 (t, J=9.5 Hz, 2H), 8.08 (d, J=8.2 Hz, 1H); LC-MS (retention time: 1.67), MS m/z 811 (M⁺+1).

EXAMPLE 40

Compound 129

Compound 129, 1-[3,3-dimethyl-2S-(3-nitropyridin-4-ylamino)-butyryl]-4R-(7-methoxy-2-phenylquinolin-4-yloxy)-pyrrolidine-2S-carboxylic acid (1R-cyclopropanesulfonylaminocarbonyl-2S-vinylcyclopropyl) amide shown below was prepared according to the method of the following Steps 40a–b.

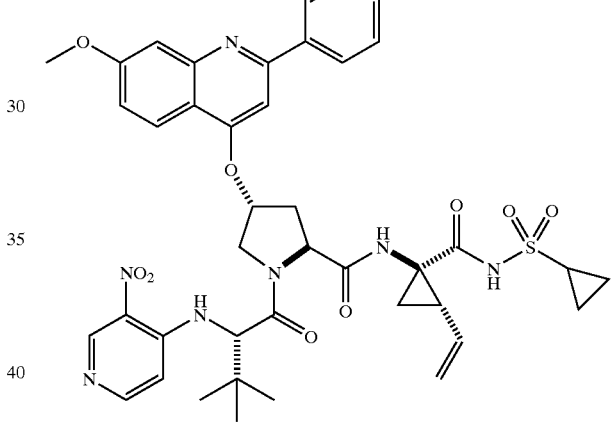

Step 40a: Preparation of 3,3-Dimethyl-2S-(3-nitro-pyridin-4-ylamino)-butyric acid potassium salt, shown below.

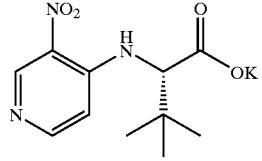

To a slurry of L-tert-leucine (3.0 g, 21.93 mmol) in EtOH (absolute, 75 mL) in a medium pressure flak was added 4-methoxy-3-nitropyridine (3.38 g, 21.93 mmol) and K₂CO₃ (6.7 g, 48.25 mmol). After heating to 105 C. 14 hr, the resulting yellow reaction mixture was filtered to remove excess K₂CO₃ and washed with DCM. The solvent was concentrated and the resulting yellow paste was triturated with MeOH and more K₂CO₃ was removed by filtration. The product was then dissolved with hot MeOH, concentrated to a slurry and Et₂O was added to effect the precipitation of yellow-green solid (4.95 g, 77% yield). ¹H NMR (MeOH) δ 0.97 (s, 1H), 1.13 (s, 9H), 3.88 (s, 1H), 6.92 (d, J=6.4 Hz, 1H), 8.15 (d, J=6.4 Hz, 1H), 9.07 (s, 1H); LC-MS (retention time: 0.81), MS m/z 254 (M⁺+1).

Step 40a: Preparation of Compound 129. Compound 129 was prepared according to the method of Step 39b. ¹H NMR (MeOH) δ 1.07–1.11 (m, 2H), 1.16 (s, 9H), 1.21–1.31 (m, 2H), 1.46 (dd, J=9.5, 5.5 Hz, 1H), 1.91 (dd, J=8.1, 5.6 Hz, 1H), 2.27 (q, J=8.7 Hz, 1H), 2.45–2.50 (m 1H), 2.79 (dd, J=14.4, 7.0 Hz, 1H), 2.94–2.99 (m, 1H), 4.04 (s, 3H), 4.25 (dd, J=12.7, 3.2 Hz, 1H), 4.58 (d, J=11.3 Hz, 1H), 4.71 (dd, J=10.4, 7.3 Hz, 1H), 4.80 (s, 1H), 5.14 (d, J=10.4 Hz, 1H), 5.31 (d, J=17.1 Hz, 1H), 5.71–5.78 m, 1H), 5.95 (bs, 1H), 7.31 (d, J=7.6 Hz, 1H),7.32 (dd, J=9.5, 2.1 Hz, 1H), 7.53 (d, J=2.1 Hz, 1H), 7.65 (s, 1H), 7.71–7.79 (m, 3H), 7.99 (d, J=7.0 Hz, 1H), 8.10 (d, J=7.0 Hz, 1H), 8.15 (d, J=9.2 Hz, 1H), 9.22 (s, 1H); LC-MS (retention time: 1.36), MS m/z 812 (M⁺+1).

EXAMPLE 41

Compounds 130 and 131

Compounds 130 and 131, specifically the P3 isomers of 1-{3,3-dimethyl-2S-[methyl-(2-nitro-benzenesulfonyl)-amino]-butyryl}-4R-(7-methoxy-2-phenyl-quinolin-4-yloxy)-pyrro-lidine-2S-carboxylic acid (1R-cyclopropanesulfonyl-aminocarbonyl-2S-vinylcyclopopyl) amide, were prepared as described in the following Steps 41a–d.

Step 41a: Preparation of 3,3-dimethyl-2S-(2-nitro-benzenesulfonylamino)butyric acid methyl ester, shown below.

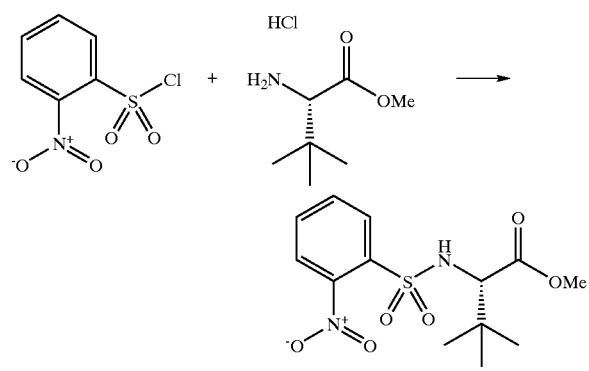

To a solution of L-(+)-methyl tert-leucinate hydrochloride (2.5 g, 13.8 mmol) in DCM (50 mL)was added DIEA (7.2 mL, 41.4 mmol), and 2-nitrobenzenesulfornyl chloride (3.5 g, 15.2 mmol). After stirring at rt for 24 hr, the reaction mixture was washed with 1N HCl (20 mmL) and extracted with DCM (25 mL). The combined DCM layer was washed H₂O (10 mL), neutralized with 1N NaOH. It was then dried over MgSO₄ and concentrated to a slurry, Et₂O was added to effect the precipitation of yellow solid product (3.05 g, 67% yield). ¹H NMR (MeOH) δ 0.98 (s, 9H), 3.38 (s, 3H), 3.79 (s, 1H), 7.77–7.83 (m, 2H), 7.84–7.86 (m, 1H), 8.04–8.05 (m, 1H); LC-MS (retention time: 1.39), MS m/z 353 (M⁺+1+Na).

Step 41b: Preparation of 3,3-dimethyl-2S-[methyl-(2-nitro-benzenesulfonyl)-amino]-butyric acid methyl ester

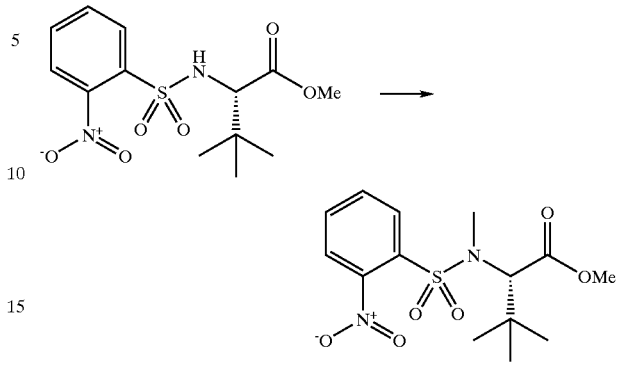

To a solution of 3,3-dimethyl-2S-[(2-nitrobenzenesulfonyl)-amino]-butyric acid methyl ester (505 mg, 1.53 mmol) in DMF (10 mL) was added K₂CO₃ (423 mg, 3.06 mmol). After stirring at rt for 20 mins, was added iodomethane (476 μL, 7.65 mmol) dropwise and continued to stir at rt. After 2 hr, the excess K₂CO₃ was removed by vacuum filtration and washed with MeOH. Solvent was concentrated and the resulting paste was re-dissolved with DCM (30 mL) and washed with H₂O (3 mL). The aqueous layer was extracted with 2×25 mL DCM. The combined DCM was washed with brine, dried over MgSO₄ and concentrated to give a yellow solid (484 mg, 92% yield). ¹H NMR (MeOH) δ 1.11 (s, 9H), 3.10 (s, 3H), 3.49 (s, 3H), 4.44 (s, 1H), 7.73 (dd, J=7.6, 1.8 Hz, 1H), 7.77–7.83 (m, 2H), 8.02 (dd, J=7.3, 1.8 Hz, 1H); LC-MS (retention time: 1.49), MS m/z 345 (M⁺+1).

Step 41c: Preparation of 3,3-dimethyl-2S-[methyl-(2-nitro-benzenesulfonyl)-amino]butyric acid, shown below.

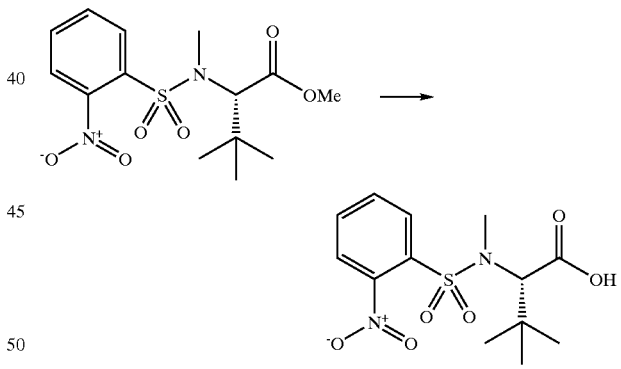

To a solution of the product of Step 41b (250 mmg, 0.73 mmol) in 1:1 THF/MeOH (4 mL) was added a solution on LIOH (122 mg, 2.90 mmol) in H₂O (2 mL). After stirring at rt for 24 hr, solvent was concentrated, diluted with H₂O (5 mL) and extracted with 2×20 mL DCM. The DCM layer was dried over MgSO₄ and concentrated to give brown viscous starting material (72 mg). The aqueous layer was acidified with concentrated HCl (~pH 3) and extracted with 3×20 ml DCM. The combined DCM layer was dried over MgSO₄ and concentrated to give a light yellow solid product (140 mg, 82% yield based on recovered starting material (72 mg, 29%)). ¹H NMR (MeOH) δ 1.14 (s, 9H), 3.12 (s, 3H), 4.43 (s, 1H), 7.71 (dd, J=7.63, 1.52 Hz, 1H), 7.74–7.78 (m, 2H), 8.03 (dd, J=7.32, 1.83 Hz, 1H); LC-MS (retention time: 1.33), MS m/z 331 (M⁺+1).

Step 41d: Preparation of Compounds 130 and 131, shown below.

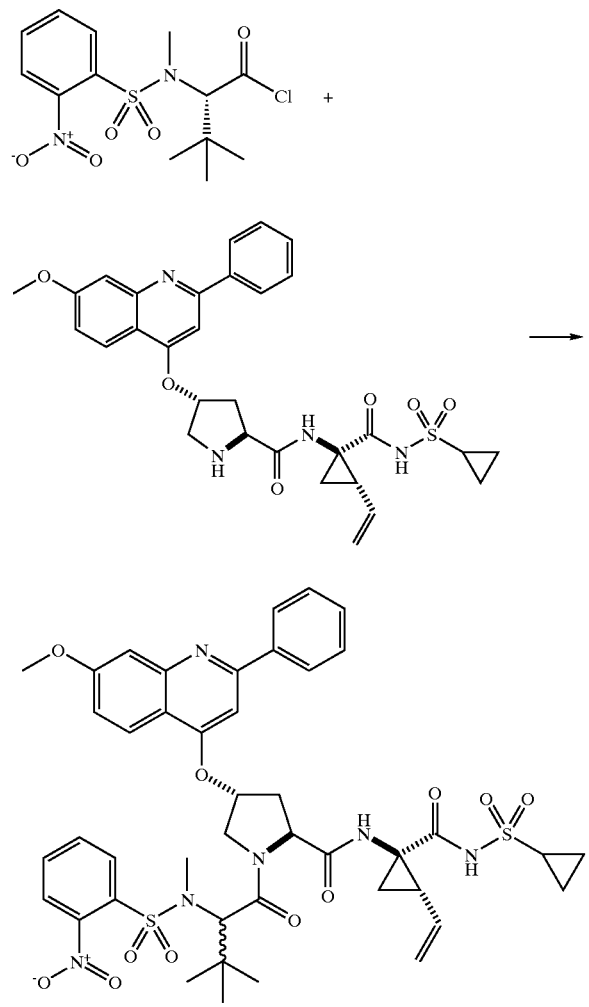

To a solution of the product of Step 41c (44.1 mg, 0.133 mmol) in DCM (2 mL) was added oxalylchloride (59 μL, 0.67 mmol) and DMF (1 μL). After stirring st rt for 0.5 hr. the solvent was concentrated and the resulting acid chloride residue was dried under vacuuo for 0.5 hr and used as crude for the next reaction. The crude acid chloride was then treated with a solution of the product of step 29a, (107 mg, 0.133 mmol) and phosphazene base P1-t-butyl-tris-(tetramethylene) (249 μL, 1.33 mmol, Fluka) in DMF (1 mL). After stirring at rt for 14 hr, the reaction mixture was diluted with DCM (20 mL), and washed with 1N HCl (3 mL). The aqueous layer was extracted with DCM (20 mL). The combined organic layer was washed with brine, dried over MgSO$_4$ and concentrated. The resulting residue was purified by reverse phase HPLC to give a first isomer (16.2 mg, 12% yield) and a second isomer (11.4 mg, 9% yield).

For the first isomer, shown below, which is Compound 130, the analytical data was as follows:

$^1$H NMR: (MeOH) δ 0.97–1.01 (m, 3H), 1.03 (s, 9H), 1.04 (s, 2H), 1.13–1.16 (m, 2H), 1.44 (dd, J=9.5, 5.2 Hz, 1H), 1.93 (dd, J=7.9, 5.5 Hz, 1H), 2.27 (q, J=8.7 Hz, 1H), 2.45–2.51 m, 1H), 2.80 (dd, J=14.3, 7.3 Hz, 1H), 2.83–2.88 (m, 1H), 3.16 (s, 3H), 3.97 (s, 1H), 4.06 (s, 3H), 4.21 (dd, J=12.5, 3.7 Hz, 1H), 4.38 (d, J=12.5 Hz, 1H), 4.60 (dd, J=9.3, 7.5 Hz, 1H), 4.75 (s, 1H), 5.13 (dd, J=10.7, 1.8 Hz, 1H), 5.31 (dd, J=17.1, 1.2 Hz, 1H), 5.70–5.78 (m, 1), 5.89 (bs, 1H), 7.46 (dd, J=9.5, 2.4 Hz, 1H), 7.56 (d, J=2.4 Hz, 1H), 7.65 (s, 1H), 7.70–7.81 (m, 6H), 7.89 (dd, J=8.6, 0.9 Hz, 1H), 7.92–7.95 (m, 1H), 8.07 (dd, J=8.2–1.2 Hz, 2H), 8.19 (d, J=9.2 Hz, 1H), LC-MS (retention time: 1.39), MS m/z 890 (M$^+$+1).

For the second isomer, shown below, which is Compound 131, the analytical data was as follows:

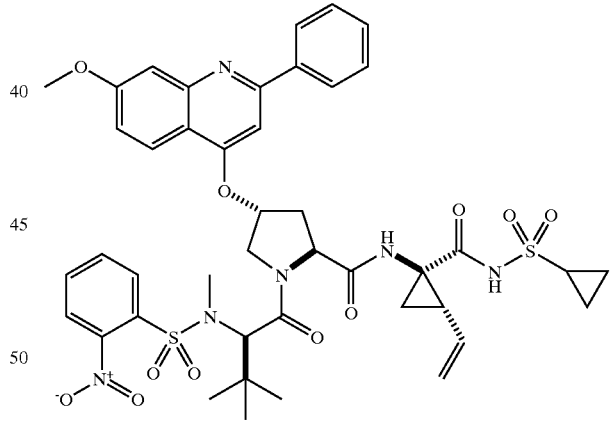

$^1$H NMR: (MeOH) δ 1.01 (s, 9H), 1.03–1.08 (m, 2H), 1.19–1.24 (m, 2H), 1.54 (dd, J=9.5, 5.5 Hz, 1H), 1.81–1.86 (m, 2H), 1.92 (dd, J=7.8, 5.6 Hz, 1H), 2.24–2.31 (m, 1H), 2.41–2.50 (m, 1H), 2.80 (dd, J=13.9, 6.9 Hz, 1H), 2.90–2.95 (m, 1H), 3.08–3.17 (m, 2H), 3.11 (s, 3H), 3.97 (s, 1H), 4.04 (s, 3H), 4.06 (s, 1H), 4.12 ((dd, J=12.2, 2.8 Hz, 1H), 4.40 (s, 1H), 4.48 (d, J=12.2 Hz, 1H), 4.72 (dd, J=10.5, 6.9 Hz, 1H), 5.14 (d, J=10.4 Hz, 1H), 5.34 (d, J=17.1 Hz, 1H), 5.79–5.84 (m, 1H), 5.87 (bs, 1H), 7.39 (dd, J=9.2, 2.4 Hz, 1H), 7.45–7.48 (m, 1H), 7.51 (d, J=2.1 Hz, 1H), 7.65–7.69 (m, 3H), 7.70–7.80 (m, 6H), 8.06 (dd, J=8.2, 1.2 Hz, 1H), 8.11 (dd, J=8.2, 1.5 Hz, 2H), 8.24 (d, J=9.5 Hz, 1H); LC-MS (retention time: 1.65), MS m/z 890 (M$^+$+1).

EXAMPLE 42

Compounds 132 and 133

Compounds 132 and 133, which are the 2S and 2R P3 isomers of (3,3-dimethyl-2-methylamino-butyryl)-4R-(7-methoxy-2-phenyl-quinolin-4-yloxy)-pyrrolidine-2S-carboxylic acid (1R-cyclopropanesulfonylaminocarbonyl-2S-vinyl-cyclo-propyl)amide, were prepared as described below.

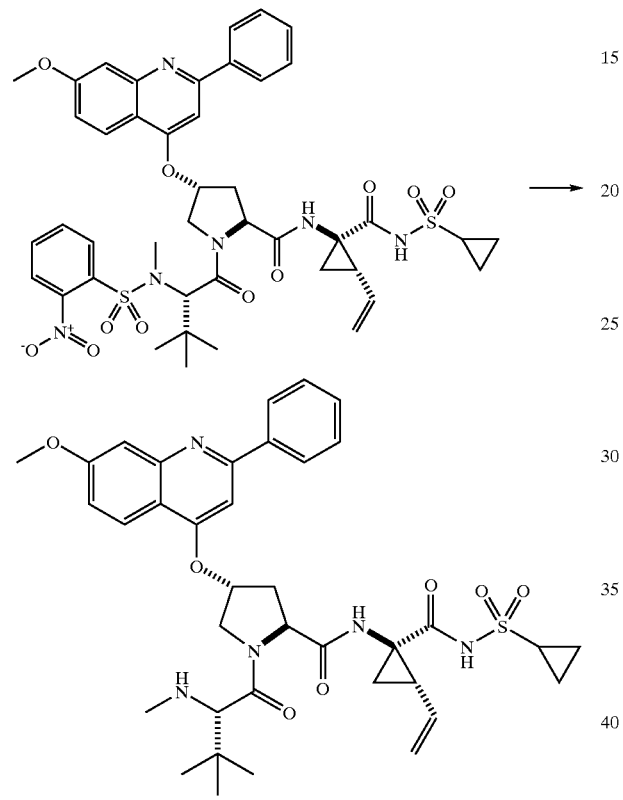

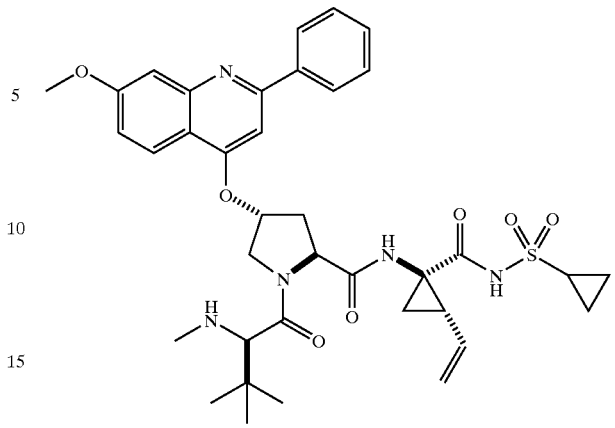

The preparation of Compound 132 is shown above. Specifically, to a solution of Compound 130 (13.9 mg, 0.016 mmol) in DMF (1 mL) was added 2-mercaptoethanol (3 drops), and DBU (5 drops) and stirred at rt ON. After 24 hr, the solvent was concentrated and the residue was purified by reverse phase HPLC to give a white solid product as a bis-TFA salt (7.2 mg, 48% yield). $^1$H NMR (MeOH) δ 0.86–0.91 (m, 1H), 1.07–1.14 (m, 3H), 1.16 (s, 9H), 1.19–1.22 (m, 1H), 1.25–1.33 (m, 4), 1.42 (dd, J=9.5, 5.5 Hz, 1H), 1.92 (dd, J=8.1, 5.7 Hz, 1H), 2.27 (q, J=8.7 Hz, 1H), 2.41–2.47 (m, 1H), 2.54 (s, 3H), 2.79–2.84 (m, 1H), 2.93–2.97 (m, 1H), 4.03 (s, 3H), 4.13 (dd, J=12.2, 3.1 Hz, 1H), 4.47 (d, J=12.2 Hz, 1H), 4.76 (dd, J=9.3, 7.5 Hz, 1H), 5.15 (dd, J=10.4, 1.5 Hz, 1H), 5.30 (dd, J=17.4 Hz, 1H), 5.68–5.75 (m, 1H), 5.86 (bs, 1H), 7.37 (dd, J=9.2, 2.1 Hz, 1H), 7.52 (bs, 1H), 7.56 (s, 1H), 7.65–7.70 (m, 3H), 8.05–8.09 (m, 2H), 8.13 (d, J=9.2 Hz, 1H); LC-MS (retention time: 1.18), MS m/z 704 (M$^+$+1).

Compound 133, shown below, was prepared using Compound 131 by the method of making Compound 132.

$^1$H NMR (MeOH) δ 0.86–0.93 (m, 1H), 1.09 (s, 9H), 1.15–1.23 (m, 4H), 1.27–1.33 (m, 3H), 1.37–1.45 (m, 3H), 1.92 (dd, J=7.9, 5.5 Hz, 1H), 2.32 (q, J=8.7 Hz, 1H), 2.49–2.57 (m, 1H), 2.75 (s, 3H), 2.86 (dd, J=14.0, 7.6 Hz, 1H), 2.95–3.00 (m, 1H), 3.38–3.49 (m, 1H), 4.04 (s, 3H), 4.15 (s, 1H), 4.29 (dd, J=12.5, 3.1 Hz, 1H), 4.39 (d, J=12.2 Hz, 1H), 4.75 (t, J=8.2 Hz, 1H), 5.16 (dd, J=10.4, 1.2 Hz, 1H), 5.34 (d, J=17.1 Hz, 1H), 5.70–5.77 m, 1H), 5.97 (bs, 1H), 7.44 (dd, J=9.5, 2.4 Hz, 1H), 7.56 (d, J=2.4 Hz, 1H), 7.63 (s, 1H), 7.69–7.76 (m, 3H), 8.09 (dd, J=7.0, 0.9 Hz, 1H), 8.14 (d, J=9.2 Hz, 1H); LC-MS (retention time: 1.21), MS m/z 704 (M$^+$+1);

EXAMPLE 43

Compound 134

Compound 134, 1-(2R-Dimethylamino-3-phenylpropionyl)-4R-(7-methoxy-2-phenyl-quinolin-4-yloxy)-pyrrolidine-2S-carboxylic acid (1R-cyclopropanesulfonylaminocarbonyl-2S-vinyl-cyclopropyl) amide, shown below, was prepared as follows.

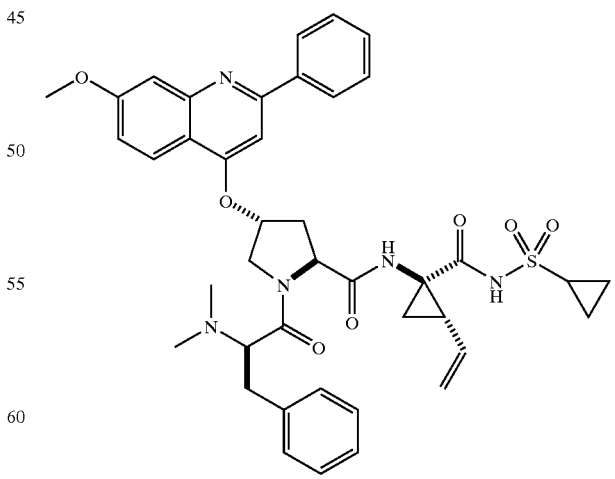

To a solution of 4R-(7-methoxy-2-phenylquinolin-4-yloxy)pyrrolidine-2S-carboxylic acid (1R-cyclopropanesulfonylaminocarbonyl-2S-vinylcyclopropyl)

amide dihydrochloride (49.5 mg, 0.061 mmol) in DCM (2 mL) was added DIEA (64 µL, 0.37 mmol), HATU (28.0 mg, 0.074 mmol)and N,N-dimethyl-L-phenyl-alanine (14.0 mg, 0.061 mmol). After stirring at rt for 0.5 hr, the solvent and excess DIEA was concentrated and the resulting residue was purified by reverse phase preparative HPLC to give the compound as a bis-TFA salt white solid (14.0 mg, 23% yield) of Compound 134 as a bis-TFA salt yellow solid (6.1 mg, 10% yield)of Compound 135. $^1$H NMR (MeOH of Compound 134) δ 1.12–1.16 (m, 2H), 1.20–1.25 (m, 1H), 1.28–1.33 (m, 1H), 1.42 (dd, J=9.5, 5.2 Hz, 1H), 1.98 (dd, J=7.9, 5.2 Hz, 1H), 2.26–2.31 (m, 2H), 2.64 (dd, J=12.8, 8.1 Hz, 1H), 3.01 (bs, 6H), 3.05–3.09 (m, 2H), 3.42 (dd, J=13.4, 3.7 Hz, 1H), 4.03 (s, 3H), 4.08 (s, 1H), 4.48 (dd, J=10.1, 4.0 Hz, 1H), 4.58 (dd, J=9.8, 7.0 Hz, 1H), 5.17 (dd, J=10.4, 1.5 Hz, 1H), 5.33 (d, J=17.4 Hz, 1H), 5.60 (bs, 1H), 5.76–5.81 (m, 1H), 7.32–7.35 (m, 2H), 7.36–7.40 (m, 4H), 7.42 (d, J=8.2 Hz, 1H), 7.51 (d, J=2.1 Hz, 1H), 7.67–7.71 (m, 4H), 8.02–8.04 (m, 2H), 8.13 (d, J=9.2 Hz, 1H); LC-MS (retention time: 1.37), MS m/z 752 (M$^+$+1).

EXAMPLE 44

Compound 135

Compound 135, 1-(2S-dimethylamino-3-phenylpropionyl)-4R-(7-methoxy-2-phenyl-quinolin-4-yloxy)-pyrrolidine-2S-carboxylic acid (1R-cyclopropanesulfonylamino-carbonyl-2S-vinylcyclopropyl)amide, shown below, was prepared by the method of Example 43.

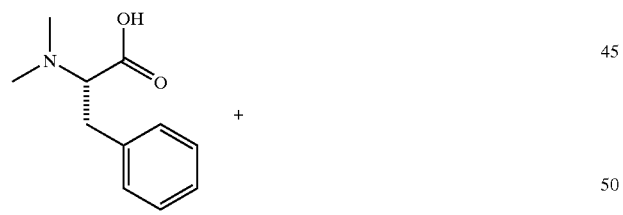

+

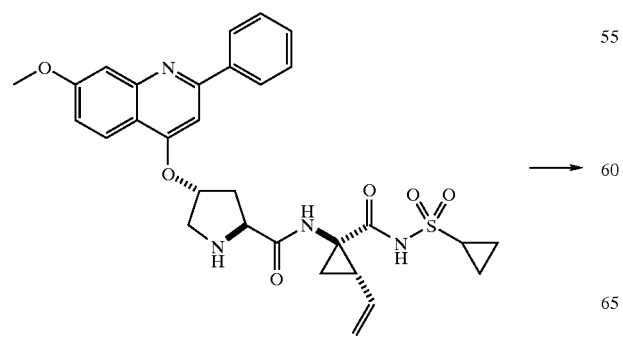

→

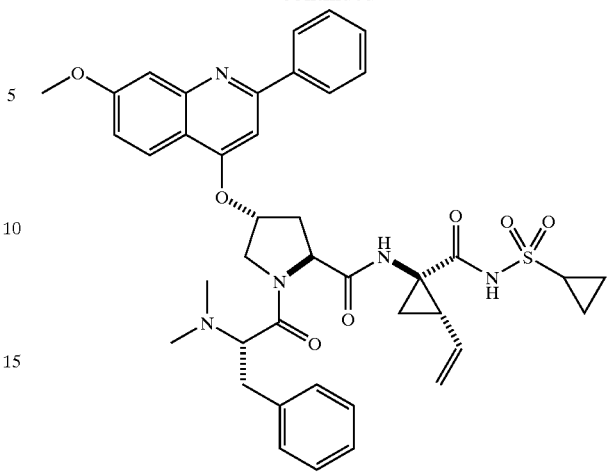

$^1$H NMR (MeOH) δ 1.10–1.22 (m, 2H), 1.21–1.28 (m, 1H), 1.29–1.35 (m, 1H), 1.42 (dd, J=9.5, 5.2 Hz, 1H), 1.97 (dd, J=8.2, 5.2 Hz, 1H), 2.28–2.36 (m 2H), 2.58–2.36 (m, 2H), 3.03 (s, 6H), 3.06–3.08 (m, 3H), 3.39 (dd, J=12.5, 4.0 Hz, 1H), 4.04 (s, 3H), 4.08 (s, 1H), 4.11 (d, J=12.8 Hz, 1H), 4.51 (dd, J=10.7, 4.0 Hz, 1H), 4.62 (dd, J=9.8, 7.0 Hz, 1H), 5.16 (dd, J=10.2, 1.7 Hz, 1H), 5.34 (dd, J=16.8, 1.5 Hz, 1H), 5.63 (bs, 1H), 5.75–5.83 (m, 1H), 7.33 (dd, J=6.1, 2.4 Hz, 1H), 7.38–7.42 (m, 5H), 7.47 (s, 1H), 7.54 (d, J=2.4 Hz, 1H), 7.69–7.76 (m, 4H), 8.02–8.02 (m, 2H), 8.18 (d, J=9.2 Hz, 1H); LC-MS (retention time: 1.30), MS m/z 752 (M$^+$+1);

EXAMPLE 45

1-Amino-spiro[2.3]hexane-1-carboxylic acid methyl ester hydrochloride salt, shown below, was prepared as described below in Steps 45a–45c.

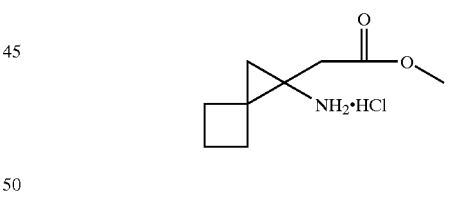

Step 45a: Preparation of [2,3]hexane-1,1-dicarboxylic acid dimethyl ester, shown below.

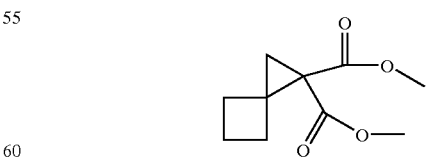

To a mixture of methylene-cyclobutane (1.5 g, 22 mmol) and Rh$_2$(OAC)$_4$ (125 mg, 0.27 mmol) in anhydrous CH$_2$Cl$_2$ (15 mL) was added 3.2 g (20 mmol) of dimethyl diazomalonate (prepared according to J. Lee et al. *Synth. Comm.,*

1995, 25, 1511–1515) at 0° C. over a period of 6 h. The reaction mixture was then warmed to rt and stirred for another 2 h. The mixture was concentrated and purified by flash chromatography (eluting with 10:1 hexane/Et$_2$O to 5:1 hexane/Et$_2$O) to give 3.2 g (72%) of [2,3]hexane-1,1-dicarboxylic acid dimethyl ester as a yellow oil. $^1$H NMR (300 MHz, CDCl$_3$) δ 3.78 (s, 6H), 2.36 (m, 2H), 2.09 (m, 3H), 1.90 (m, 1H), 1.67 (s, 2H). LC-MS: MS m/z 199 (M$^+$+1) (Method D).

Step 45b: Preparation of spiro[2,3]hexane-1,1-dicarboxylic acid methyl ester, shown below.

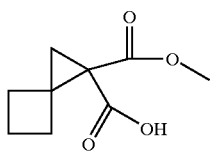

To the mixture of spiro [2,3]hexane-1,1-dicarboxylic acid dimethyl ester 1 (200 mg, 1.0 mmol) in 2 mL of MeOH and 0.5 mL of water was added KOH (78 mg, 1.4 mmol). This solution was stirred at rt for 2 days. It was then acidified with dilute HCl and extracted two times with ether. The combined organic phases were dried (MgSO$_4$) and concentrated to yield 135 mg (73%) of 2 as a white solid. $^1$H NMR (300 MHz, CDCl$_3$) δ 3.78 (s, 3H), 2.36–1.90 (m, 8H). LC-MS: MS m/z 185 (M$^+$+1) (Method D).

Step 45c: Preparation of the titled product, 1-amino-spiro [2.3]hexane-1-carboxylic acid methyl ester hydrochloride salt. To a mixture of spiro[2,3]hexane -1,1-dicarboxylic acid methyl ester 2 (660 mg, 3.58 mmol) in 3 mL of anhydrous t-BuOH was added 1.08 g (3.92 mmol) of DPPA and 440 mg (4.35 mmol) of Et$_3$N. The mixture was heated at reflux for 21 h and then partitioned between H$_2$O and ether. The ether phase was dried over magnesium sulfate, filtered and concentrated in vacuo to yield an oil. To this oil was added 3 mL of a 4 M HCl/dioxane solution. This acidic solution was stirred at rt for 2 h and then concentrated in vacuo. The residue was triturated with ether to give 400 mg (58%) of 3 as a white solid. $^1$H NMR (300 MHz, d6-DMSO) δ 8.96 (br s, 3H), 3.71 (s, 3H), 2.41 (m, 1H), 2.12 (m, 4H), 1.93 (m, 1H), 1.56 (q, 2H, J=8 Hz). LC-MS of free amine: MS m/z 156 (M$^+$+1) (Method D).

EXAMPLE 46

Compound 136

Compound 136, {1-[2-(1-Cyclopropanesulfonyl-aminocarbonyl-spiro[2.3]hex-1-ylcarbamoyl)-4-(7-methoxy-2-phenyl-quinolin-4-yloxy)-pyrrolidine-1-carbonyl]-2,2-dimethyl-propyl}-carbamic acid tert-butyl ester, shown below, was prepared as described in Steps 46a–c.

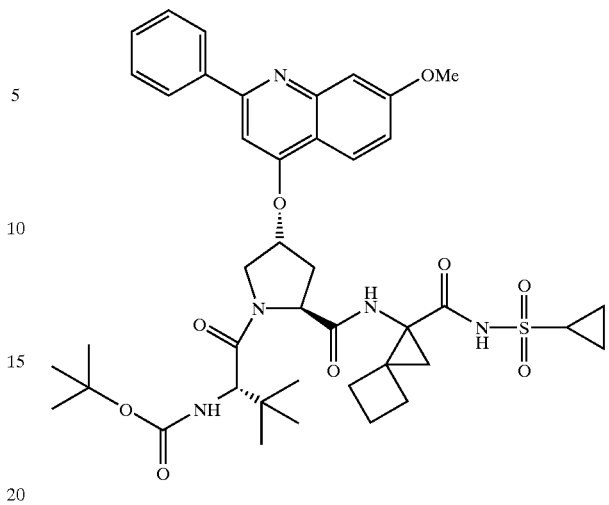

Step 46a: Preparation of 1-{[1-(2-tert-butoxycarbonylamino-3,3-dimethyl-butyryl)-4-(7-methoxy-2-phenyl-quinolin-4-yloxy)-pyrrolidine-2-carbonyl]-amino}-spiro[2.3]hexane-1-carboxylic acid methyl ester, shown below.

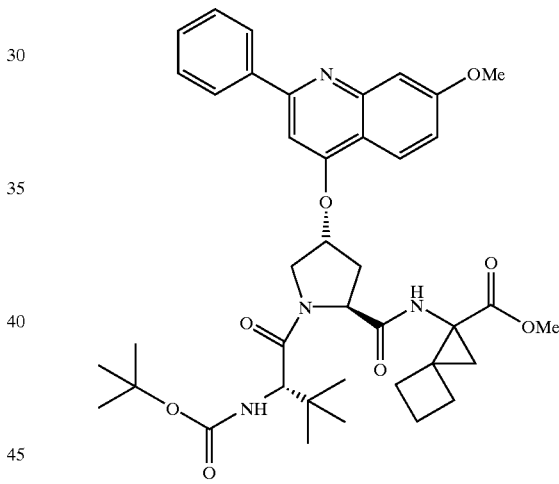

To a mixture of 1-(2-tert-butoxycarbonylamino-3,3-dimethyl-butyryl)-4-(7-methoxy-2-phenyl-quinolin-4-yloxy)-pyrrolidine-2-carboxylic acid (50 mg, 0.087 mmol) in CH$_2$Cl$_2$ was added iPr$_2$EtN (56 mg, 0.43 mmol) and then HBTU (40 mg, 0.10 mmol), HOBT.H$_2$O (16 mg, 0.10 mmol) and 1-amino-spiro[2,3]-carboxylic methyl ester hydrochloride salt (18 mg, 0.094 mmol). It was stirred at rt overnight. The reaction mixture was then diluted with EtOAc, washed with sat. aq. NaHCO$_3$, brine, dried over MgSO$_4$, filtered and concentrated in vacuo. The residue was purified by a flash chromatography eluting with 1:1 hexane/EtOAc to give the titled product as a white solid (60 mg, 96%). LC-MS: (retention time 1.74 min), MS m/z 715 (M$^+$+1) (Method D).

Step 46b: Preparation of 1-{[1-(2-tert-butoxycarbonylamino-3,3-dimethyl-butyryl)-4-(7-methoxy-2-phenyl-quinolin-4-yloxy)-pyrrolidine-2-carbonyl]-amino}-spiro[2.3]hexane-1-carboxylic acid, shown below.

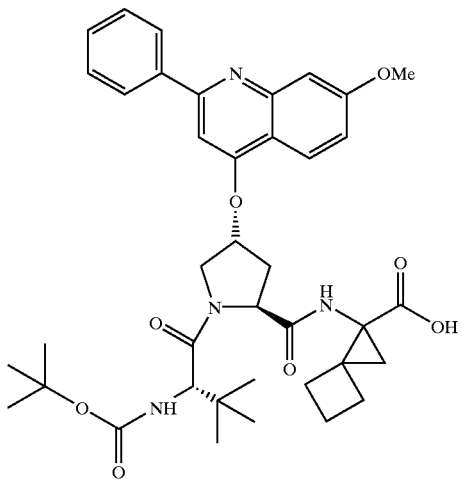

To a mixture of 1-{[1-(2-tert-butoxycarbonylamino-3,3-dimethyl-butyryl)-4-(7-methoxy-2-phenyl-quinolin-4-yloxy)-pyrrolidine-2-carbonyl]-amino}-spiro[2.3]-hexane-1-carboxylic acid methyl ester (60 mg, 0.084 mmol) in 3 mL of THF, 1.5 mL of MeOH and 0.4 mL of H$_2$O was added LiOH (30 mg, 1.5 mmol). The mixture was stirred at rt for 3 days. It was then concentrated and partitioned between sat. aq. NaHCO$_3$ and ether. The aqueous layer was acidified to pH=4 with dilute HCl, and extracted three times with EtOAc. The combined EtOAc extracts were dried over magnesium sulfate, filtered and concentrated to provide 55 mg of 1-{[1-(2-tert-butoxycarbonylamino-3,3-dimethyl-butyryl)-4-(7-methoxy-2-phenyl-quinolin-4-yloxy)-pyrrolidine-2-carbonyl]-amino}-spiro[2.3]hexane-1-carboxylic acid as a white solid (93%). LC-MS: (retention time 1.71 min), MS m/z 701 (M$^+$+1) (Method D).

Step 46c: Preparation of Compound 136. To a mixture of CDI (17 mg, 0.10 mmol) in THF (3 mL) was added 1-{[1-(2-tert-Butoxycarbonylamino-3,3-dimethylbutyryl)-4-(7-methoxy-2-phenyl-quinolin-4-yloxy)-pyrrolidine-2-carbonyl]-amino}-spiro[2.3]-hexane-1-carboxylic acid (55 mg, 0.078 mmol). The mixture was heated at reflux for 1 h and allowed to cool to rt. Cyclopropylsulfonamide (13 mg, 0.10 mmol) was added followed by DBU (16 mg, 0.10 mmol). The mixture was stirred at rt for 24 h and then diluted with EtOAc. The solution was washed with pH=4 buffer, sat. aq. NaHCO$_3$ and brine, dried over MgSO$_4$, filtered and concentrated. The residue was purified using preparative TLC eluting three times with 2.5% MeOH in CH$_2$Cl$_2$ to yield 13 mg of Compound 148, {1-[2-(1-cyclopropanesulfonylaminocarbonyl-spiro[2.3]hex-1-ylcarbamoyl)-4-(7-methoxy-2-phenyl-quinolin-4-yloxy)-pyrrolidine-1-carbonyl]-2,2-dimethyl-propyl}-carbamic acid tert-butyl ester, as a white solid (20%). LC-MS: (retention time 1.63 min), MS m/z 804 (Method D).

EXAMPLE 47

The following compounds were also prepared, using the product of Step 45c, according to the method of Example 46.

Compound 137

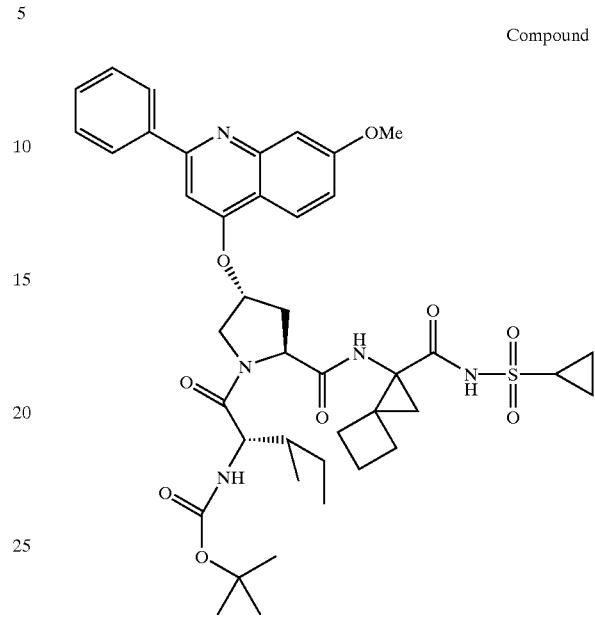

LC-MS: (retention time 1.62 min), MS m/z 804 (Method D).

Compound 138

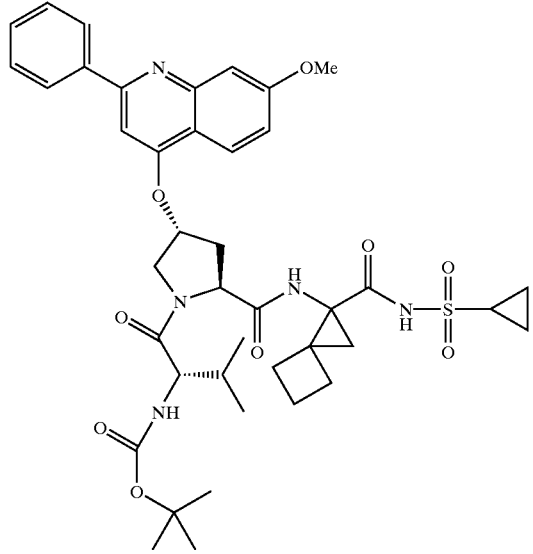

LC-MS: (retention time 1.56 min), MS m/z 790 (Method D).

EXAMPLE 48

Compound 139

Compound 139, {1-[2-(1-Cyclopropanesulfonyl-aminocarbonyl-spiro[2.4]hept-1-ylcarbamoyl)-4-(7-methoxy-2-phenyl-quinolin-4-yloxy)-pyrrolidine-1- carbonyl]-2,2-dimethyl-propyl}carbamic acid tert-butyl ester, shown below, was prepared as described in Steps 48a–d.

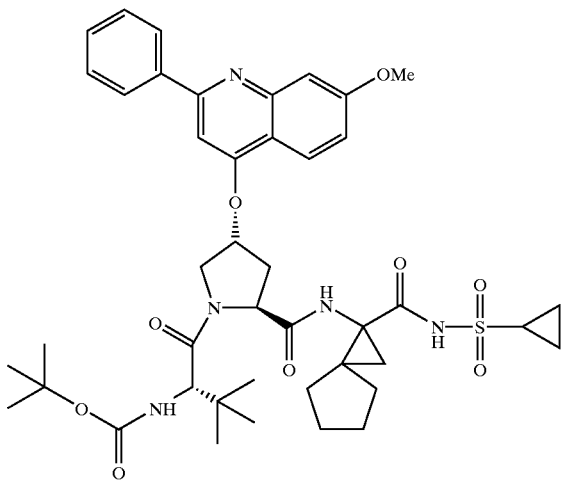

Step 48a: Spiro[2.4]heptane-1,1-dicarboxylic acid dimethyl ester, shown below, was prepared as follows.

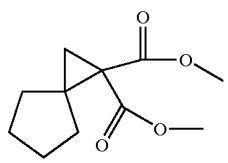

Using the method of Step 45a, 1.14 g (13.9 mmol) of methylenecyclopentane and 2.0 g (12.6 mmol) of dimethyl diazomalonate were reacted to yield 1.8 g (67%) of the dimethyl ester. $^1$H NMR (300 MHz, CDCl$_3$) δ 3.73 (s, 6H), 1.80 (m, 2H), 1.70 (m, 4H), 1.60 (m, 4H). LC-MS: MS m/z 213 (M$^+$+1) (Method D).

Step 48b: Spiro[2.4]heptane-1,1-dicarboxylic acid methyl ester, shown below, was prepared as follows.

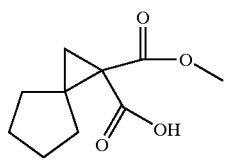

Using the method of Step 45b, 1.7 g (8.0 mmol) of the produc of Step 48a and 493 mg (8.8 mmol) of KOH gave 1.5 g (94%) of spiro[2.4]heptane-1,1-dicarboxylic acid methyl ester. $^1$H NMR (300 MHz, CDCl$_3$) δ 3.80 (s, 3H), 2.06 (d, 1H, J=5 Hz), 1.99 (d, 1H, J=5 Hz), 1.80–1.66 (m, 8H). LC-MS: MS m/z 199 (M$^+$+1) (Method D).

Step 48c: 1-Amino-spiro[2.4]heptane-1-carboxylic acid methyl ester hydrochloride salt, shown below, was prepared as follows.

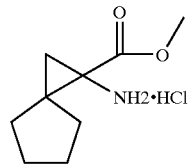

Using the method of Step 45c, 500 mg (2.5 mmol) of the product of Step 48b, 705 mg (2.5 mmol) of DPPA and 255 mg (2.5 mmol) of Et$_3$N gave 180 mg (35%) of this hydrochloride salt. $^1$H NMR (300 MHz, d6-DMSO) δ 8.90 (br s, 3H), 3.74 (s, 3H), 1.84 (m, 1H), 1.69 (m, 4H), 1.58 (m, 4H), 1.46 (d, 1H, J=6 Hz). LC-MS of free amine: MS m/z 170 (M$^+$+1) (Method D).

Step 48d: Compound 139 was prepared, using the product of Step 48c, according to the method of Example 46. Retention Time (min.) 1.69 MS data (M+1) m/z 818 (Method D).

EXAMPLE 49

Compound 140

Compound 140, {1-[2-(1-Cyclopropanesulfonyl-aminocarbonyl-spiro[2.2]pentane-1-ylcarbamoyl)-4-(7-methoxy-2-phenyl-quinolin-4-yloxy)-pyrrolidine-1-carbonyl]-2,2-dimethyl-propyl}-carbamic acid tert-butyl ester, shown below, was prepared as described in Steps 49a–d.

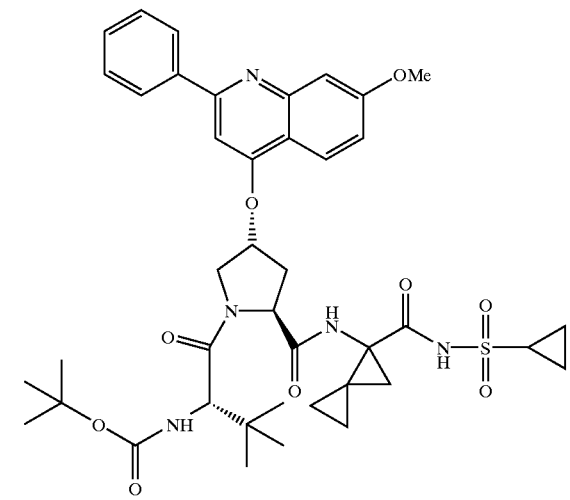

Step 49a: Spiro[2.2]pentane-1,1-dicarboxylic acid dimethyl ester, shown below, was prepared as follows.

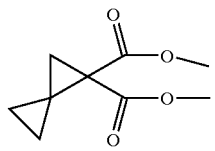

To a mixture of methylenecyclopropane (1.0 g, 18.5 mmol) (prepared according to P. Binger U.S. Pat. No.

5,723,714) and Rh$_2$(OAc)$_4$ (82 mg, 0.185 mmol) in anhydrous CH$_2$Cl$_2$ (10 mL), was added dimethyl diazomalonate (2.9 g, 18.3 mmol) at 0° C. At the top of the flask was installed a cold finger, the temperature of which was kept at −10° C. The reaction mixture was warmed to rt and stirred for another 2 h. The mixture was concentrated in vacuo and purified by flash chromatography (eluting with 10:1 hexane/Et$_2$O to 5:1 hexane/Et$_2$O) to give 0.85 g (25%) of the dimethyl ester as a yellow oil. $^1$H NMR (300 MHz, CDCl$_3$) δ 3.73 (s, 6H), 1.92 (s, 2H), 1.04 (d, 4H, J=3 Hz).

Step 49b: Spiro[2.2]pentane-1,1-dicarboxylic acid methyl ester, shown below, was prepared as follows.

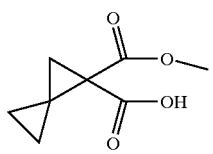

Using the method of Step 45b, 800 mg (4.3 mmol) of the product of Step 49a and 240 mg (4.3 mmol) of KOH gave 600 mg (82%) of Spiro[2.2]pentane-1,1-dicarboxylic acid methyl ester. $^1$H NMR (300 MHz, CDCl$_3$) δ 3.82 (s, 6H), 2.35 (d, 1H, J=3 Hz), 2.26 (d, 1H, J=3 Hz), 1.20 (m, 1H), 1.15 (m, 1H), 1.11 (m, 1H), 1.05 (m, 1H). LRMS: MS m/z 169 (M$^+$−1) (Method D).

Step 49c: 1-Amino-spiro[2.2]pentane-1-carboxylic acid methyl ester hydrochloride salt, shown below, was prepared as follows.

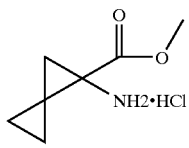

Using the method of Step 45c, 400 mg (2.3 mmol) of the product of Step 49b, 700 mg (2.5 mmol) of DPPA and 278 mg (2.7 mmol) of Et$_3$N gave 82 mg (20%) of the hydrochloride salt. $^1$H NMR (300 MHz, CDCl$_3$) δ 9.19 (br s, 3H), 3.81 (s, 3H), 2.16, (d, J=5.5 Hz, 1H), 2.01 (d, J=5.5 Hz, 1H), 1.49 (m, 1H), 1.24, (m, 1H), 1.12 (m, 2H). LRMS of free amine: MS m/z 142 (M$^+$+1) (Method D).

Step 49d: Compound 140 was prepared, using the product of Step 49c, according to the method of Example 46. Retention Time (min.) 1.59 MS data (M+1) m/z 790 (Method D).

EXAMPLE 50

Compound 141

Compound 141, {1-[2-(1-Cyclopropanesulfonyl-aminocarbonyl-spiro[2.2]pentane-1-ylcarbamoyl)-4-(7-methoxy-2-phenyl-quinolin-4-yloxy)-pyrrolidine-1-carbonyl]-2,2-dimethyl-propyl}-carbamic acid tert-butyl ester, shown below, was prepared as described in Steps 50a–d.

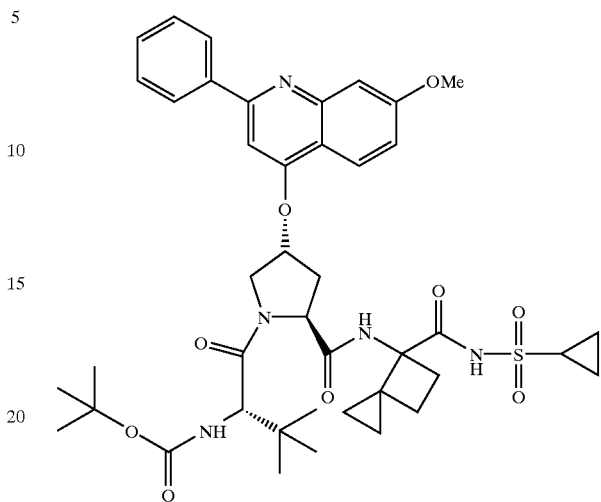

Step 50a: 5-Amino-spiro[2.3]hexane-5-carboxylic acid ethyl ester, shown below, was prepared as follows.

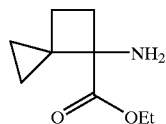

Spiro[2.3]hexan-4-one 13 (500 mg, 5 mmol), which was prepared from bicyclopropylidene (A. Meijere et al. Org. Syn. 2000, 78, 142–151) according to A. Meijere et al. J. Org. Chem. 1988, 53, 152–161, was combined with ammonium carbamate (1.17 g, 15 mmol) and potassium cyanide (812 mg, 12.5 mmol) in 50 mL of EtOH and 50 mL of water. The mixture was heated at 55° C. for 2 days. Then NaOH (7 g, 175 mmol) was added and the solution was heated under reflux overnight. The mixture was then chilled to 0° C., acidified to pH 1 with concentrated HCl, and concentrated in vacuo. EtOH was added to the crude amino acid mixture and then concentrated to dryness (5×) so as to remove residual water. The residue dissolved in 100 mL of EtOH was cooled to 0° C. It was then treated with 1 mL of SOCl$_2$ and refluxed for 3 days. The solids were removed by filtration, and the filtrate was concentrated in vacuo to give the crude product. The crude product was partitioned between 3 N NaOH, NaCl and EtOAc. The organic phase was dried over potassium carbonate and concentrated. The residue was purified using column chromatography on C18 silica gel (eluting with MeOH/H$_2$O) to yield 180 mg (21%) of 15 as an oil. $^1$H NMR (300 MHz, CDCl$_3$) δ 8.20 (br s, 2H), 4.27 (s, 2H), 2.80 (s, 1H), 2.54 (s, 1H), 2.34 (m, 2H), 1.31 (s, 3H), 1.02 (s, 1H), 0.66 (m, 3H). $^{13}$C NMR (300 MHz, CDCl$_3$) δ 170.2(s), 63.0(s), 62.8 (s), 26.1 (s), 26.0 (s), 24.9 (s), 13.9 (s), 11.4 (s), 10.9 (s). LC-MS: MS m/z 170 (M$^+$+1) (Method D).

Step 50d: Compound 141 was prepared, using the product of Step 50c, according to the method of Example 46. Retention Time (min.) 1.87 MS data (M+1) m/z 804 (Method D).

EXAMPLE 51

Preparation of Salts

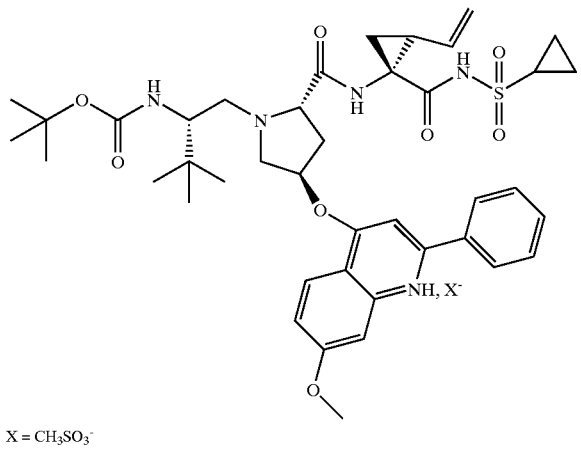

X = CH₃SO₃⁻

The salt, BOCNH-P3(L-t-BuGly)-P2[(4R)-(2-phenyl-7-methoxyquinoline-4-oxo)-S-proline]-P1(1R, 2S Vinyl Acca)-CONHSO₂-cyclopropane methanesulfonate salt, shown above, was prepared as follows.

To a solution of 100 mg (0.124 mmol) of BOCNH-P3(L-t-BuGly)-P2[(4R)-(2-phenyl-7-methoxyquinoline-4-oxo)-S-proline]-P1(1R, 2S Vinyl Acca)-CONHSO₂-cyclopropane dissolved in 5 mL of CH₂Cl₂ cooled to −78° C., was added 8.4 μL (0.13 mmol) of methanesulfonic acid and the mixture warmed to rt over 10 min. The mixture was concentrated in vacuo, precipitated from the minimum amount of CH₂Cl₂ in Et₂O, filtered and concentrated to afford 98 mg of BOCNH-P3 (L-t-BuGly)-P2[(4R)-(2-phenyl-7-methoxyquinoline-4-oxo)-S-proline]-P1(1R,2S Vinyl Acca)-CONHSO₂-cyclopropane methanesulfonate salt as a white solid: LC-MS (retention time: 1.63, method A), MS m/z 790 (M⁺+1). HRMS m/z (M+H)⁺ calcd for $C_{41}H_{52}N_5SO_9$:790.3486, found 790.3505.

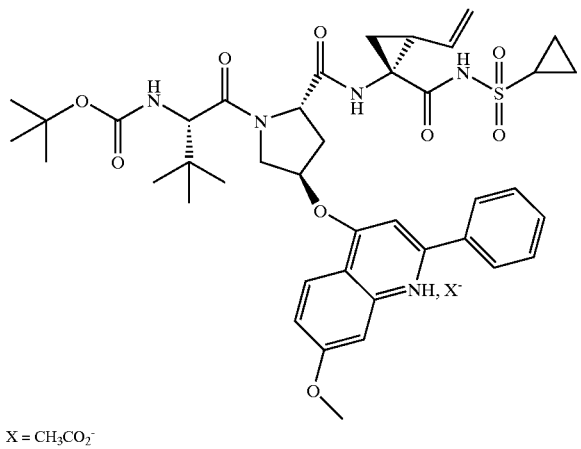

X = CH₃CO₂⁻

The salt, BOCNH-P3(L-t-BuGly)-P2[(4R)-(2-phenyl-7-methoxyquinoline-4-oxo)-S-proline]-P1(1R,2S Vinyl Acca)-CONHSO₂-cyclopropane trifluoroacetate salt, shown above, was prepared as follows.

To a solution of 100 mg (0.124 mmol) of BOCNH-P3(L-t-BuGly)-P2[(4R)-(2-phenyl-7-methoxyquinoline-4-oxo)-S-proline]-P1(1R,2S Vinyl Acca)-CONHSO₂-cyclopropane dissolved in 5 mL of CH₂Cl₂ cooled to −78° C., was added 10.7 μL (0.14 mmol) of TFA and the mixture warmed to rt over 10 min. The mixture was concentrated in vacuo, precipitated from the minimum amount of CH₂Cl₂ in Et₂O, filtered and concentrated to afford 98.4 mg of BOCNH-P3 (L-t-BuGly)-P2[(4R)-(2-phenyl-7-methoxyquinoline-4-oxo)-S-proline]-P1(1R,2S Vinyl Acca)-CONHSO₂-cyclopropane trifluoroacetate salt as a white solid: LC-MS (retention time: 1.61, method A), MS m/z 790 (M⁺+1). HRMS m/z (M+H)⁺ calcd for $C_{41}H_{52}N_5SO_9$: 790.3486, found 790.3505.

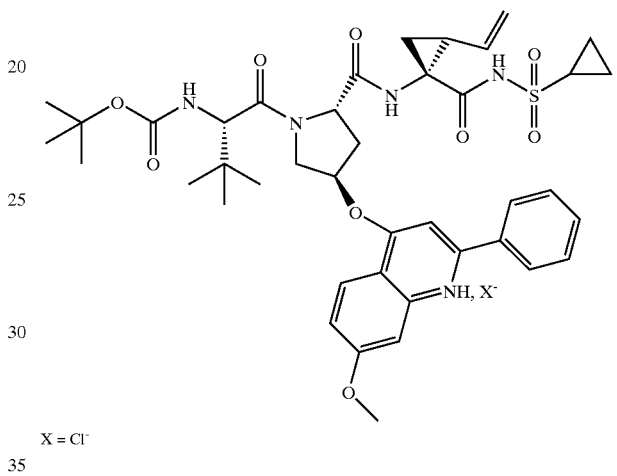

X = Cl⁻

The salt, BOCNH-P3(L-t-BuGly)-P2[(4R)-(2-phenyl-7-methoxyquinoline-4-oxo)-S-proline]-P1(1R,2S Vinyl Acca)-CONHSO₂-cyclopropane hydrochloric acid salt, shown above, was prepared as follows.

To a solution of 100 mg (0.124 mmol) of BOCNH-P3(L-t-BuGly)-P2[(4R)-(2-phenyl-7-methoxyquinoline-4-oxo)-S-proline]-P1(1R,2S Vinyl Acca)-CONHSO₂ cyclopropane dissolved in 5 mL of CH₂Cl₂ cooled to −78° C., was added 47 μL (0.19 mmol) of 4N HCl in dioxanes and the mixture warmed to rt over 10 min and then concentrated in vacuo. The procedure was repeated with an additional 20 μL (0.08 mmol). The mixture was precipitated from the minimum amount of CH₂Cl₂ in Et₂O, filtered and concentrated to afford 94 mg of BOCNH-P3(L-t-BuGly)-P2[(4R)-(2-phenyl-7-methoxyquinoline-4-oxo)-S-proline]-P1(1R,2S Vinyl Acca)-CONHSO₂ cyclopropane hydrochloric acid salt as a white solid: LC-MS (retention time: 1.66, method A), MS m/z 790 (M⁺+1). HRMS m/z (M+H)⁺ calcd for $C_{41}H_{52}N_5SO_9$: 790.3486, found 790.3495.

EXAMPLE 52

Biological Studies

Recombinant HCV NS3/4A Protease Complex FRET Peptide Assay

The purpose of this in vitro assay was to measure the inhibition of HCV NS3 protease complexes, derived from the BMS, H77C or J416S strains, as described below, by compounds of the present invention. This assay provides an indication of how effective compounds of the present invention would be in inhibiting HCV visual proteolytic activity.

Serum from an HCV-infected patient was obtained from Dr. T. Wright, San Francisco Hospital. An engineered full-length cDNA template of the HCV genome (BMS strain) was constructed from DNA fragments obtained by reverse transcription-PCR (RT-PCR) of serum RNA and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A Follett, P L Yap and H Marsden, J. Clin. Microbiol., 31(6), 1493–1503 (1993)). The amino acid sequence of the nonstructural region, NS2-5B, was shown to be >97% identical to HCV genotype 1a (H77C) and 87% identical to genotype 1b (J4L6S). The infectious clones, H77C (1a genotype) and J4L6S (1b genotype) were obtained from R. Purcell (NIH) and the sequences are published in genebank (AAB67036, see Yanagi, M., Purcell, R. H., Emerson, S. U. and Bukh, J. Proc. Natl. Acad. Sci. U.S.A. 94(16),8738–8743 (1997); AF054247, see Yanagi, M., St Claire, M., Shapiro, M., Emerson, S. U., Purcell, R. H. and Bukh, J, Virology 244 (1), 161–172. (1998)).

The BMS, H77C and J4L6S strains were used for production of recombinant NS3/4A protease complexes. DNA encoding the recombinant HCV NS3/4A protease complex (amino acid 1027 to 1711) for these strains were manipulated as described by P. Gallinari et al. (see Gallinari P, Paolini C, Brennan D, Nardi C, Steinkuhler C, De Francesco R. Biochemistry. 38(17):5620–32, (1999)). Briefly, a three-lysine solubilizing tail was added at the 3'-end of the NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector and the NS3/4A complex was expressed in $E.$ $coli$ BL21 (DE3) following the protocol described by P. Gallinari et al. (see Gallinari P, Brennan D, Nardi C, Brunetti M, Tomei L, Steinkuhler C, De Francesco R., J Virol. 72(8):6758–69 (1998)) with modifications. Briefly, NS3/4A expression was induced with 0.5 mM IPTG for 22 hr at 20° C. A typical fermentation (10 L) yielded approximately 80 g of wet cell paste. The cells were resuspended in lysis buffer (10 mL/g) consisting of 25 mM HEPES, pH 7.5, 20% glycerol, 500 mM NaCl, 0.5% Triton-X100, 1 ug/ml lysozyme, 5 mM MgCl2, 1 ug/ml DNaseI 5 mM β-Mercaptoethanol (βME), Protease inhibitor—EDTA free, homogenized and incubated for 20 mins at 4° C. The homogenate was sonicated and clarified by ultra-centrifugation at 235000 g for 1 hr at 4° C. Imidazole was added to the supernatant to a final concentration of 15 mM and the pH adjusted to 8.0. The crude protein extract was loaded on a Ni-NTA column pre-equilibrated with buffer B (25 mM HEPES, pH 8.0, 20% glycerol, 500 mM NaCl, 0.5% Triton-X100, 15 mM imidazole, 5 mM βME). The sample was loaded at a flow rate of 1 mL/min. The column was washed with 15 column volumes of buffer C (same as buffer B except with 0.2% Triton-X100). The protein was eluted with 5 column volumes of 200 mM Imidazole in buffer.

NS3/4A protease complex-containing fractions were pooled and loaded on a desalting column Superdex-S200 pre-equilibrated with buffer D (25 mM HEPES, pH 7.5, 20% glycerol, 300 mM NaCl, 0.2% Triton-X100, 10 mM βME). Sample was loaded at a flow rate of 1 mL/min. NS3/4A protease complex-containing fractions were pooled and concentrated to approximately 0.5 mg/ml. The purity of the NS3/4A protease complexes, derived from the BMS, H77C and J4L6S strains, were judged to be greater than 90% by SDS-PAGE and mass spectrometry analyses.

The enzyme was stored at −80° C., thawed on ice and diluted prior to use in assay buffer. The substrate used for the NS3/4A protease assay, described by Taliani et al. in Anal. Biochem. 240(2):60–67 (1996), was cleaved at the ester linkage by the enzyme. The sequence is loosely based on the NS4A/NS4B natural cleavage site. The peptide substrate was incubated with one of the three recombinant NS3/4A complexes, in the absence or presence of a compound of the present invention, and the reaction followed in real time using a Cytofluor Series 4000.

The reagents were as follow: HEPES and Glycerol (Ultrapure) were obtained from GIBCO-BRL. DMSO was obtained from Sigma. β-Mercaptoethanol was obtained from Bio Rad.

Assay buffer: 50 mM HEPES, pH 7.5; 0.15M NaCl; 0.1% Triton; 15% Glycerol; 10 mM βME. Substrate: 2 $\mu$M final concentration (from a 2 mM stock solution in DMSO stored at −20° C.). HCV NS3/4A type 1a (1b), 2–3 nM final concentration (from a 5 $\mu$M stock solution in 25 mM HEPES, pH 7.5, 20% glycerol, 300 mM NaCl, 0.2% Triton-X100, 10 mM βME).

The assay was performed in a 96-well polystyrene plate from Falcon. Each well contained 25 $\mu$l NS3/4A protease complex in assay buffer, 50 $\mu$l of a compound of the present invention in 10% DMSO/assay buffer and 25 $\mu$l substrate in assay buffer. A control (no compound) was also prepared on the same assay plate. The enzyme complex was mixed with compound or control solution for 1 min before initiating the enzymatic reaction by the addition of substrate. The assay plate was read immediately using the Cytofluor Series 4000 (Perspective Biosystems). The instrument was set to read an emission of 340 nm and excitation of 490 nm at 25° C. Reactions were generally followed for approximately 15 minutes.

The percent inhibition was calculated with the following equation:

$$100-[(\delta F_{inh}/\delta F_{con})\times 100]$$

where δF is the change in fluorescence over the linear range of the curve. A non-linear curve fit was applied to the inhibition-concentration data, and the 50% effective concentration ($IC_{50}$) was calculated by the use of Excel Xl-fit software.

All of the compounds tested were found to have IC50s of 9 $\mu$M or less. Preferred compounds had IC50s of 0.021 $\mu$M, as was found for Compound 58, or less. Further, compounds of the present invention, which were tested against more than one type of NS3/4A complex, were found to have similar inhibitory properties though the compounds uniformly demonstrated greater potency against the 1b strains as compared to the 1a strains.

Specificity Assays

The specificity assays were performed to demonstrate the selectivity of the compounds of the present invention in inhibiting HCV NS3/4A protease as compared to other serine or cysteine proteases.

The specificities of compounds of the present invention were determined against a variety of serine proteases: human leukocyte elastase, porcine pancreatic elastase and bovine pancreatic α-chymotrypsin and one cysteine protease: human liver cathepsin B. In all cases a 96-well plate format protocol using calorimetric β-nitroaniline (pNA) substrate specific for each enzyme was used as described previously (Patent WO 00/09543) with some modifications.

Each assay included a 1 h enzyme-inhibitor pre-incubation at RT followed by addition of substrate and hydrolysis to ~30% conversion as measured on a Spectramax Pro microplate reader. Compound concentrations varied from 100 to 0.4 µM depending on their potency.

The final conditions and protocol for each assay was as reported previously (Patent WO 00/09543) with the inclusion of an additional assay:

50 mM Tris-HCl pH 8, 0.5M $Na_2SO_4$, 50 mM NaCl, 0.1 mM EDTA, 3% DMSO, 0.01% Tween-20 with 133 µM succ-AAA-PNA and 20 nM Elastase The percentage of inhibition was calculated using the formula:

$$[1-((UV_{inh}-UV_{blank})/(UV_{ctl}-UV_{blank}))]\times 100$$

A non-linear curve fit was applied to the inhibition-concentration data, and the 50% effective concentration ($IC_{50}$) was calculated by the use of Excel Xl-fit software.

HCV Replicon Cell-Based Assay

An HCV replicon whole cell system was established as described by Lohmann V, Korner F, Koch J, Herian U, Theilmann L, Bartenschlager R., Science 285(5424):110–3 (1999). This system enabled us to evaluate the effects of our HCV Protease compounds on HCV RNA replication. Briefly, using the HCV strain 1B sequence described in the Lohmann paper (Assession number:AJ238799), an HCV cDNA was generated encoding the 5' internal ribosome entry site (IRES), the neo gene, the EMCV-IRES and the HCV nonstructural proteins, NS3-NS5B, and 3' NTR. In vitro transcripts of the cDNA were transfected into Huh7 cells and selection for cells constitutively expressing the HCV replicon was achieved in the presence of the selectable marker, neomycin (G418). Resulting cell lines were characterized for positive and negative RNA production and protein production over time.

Huh7 cells, constitutively expressing the HCV replicon, were grown in DMEM containing 10% FCS (Fetal calf serum) and 1 mg/ml G418 (Gibco-BRL). Cells were seeded the night before ($1.5\times10^4$ cells/well) in 96-well tissue-culture sterile plates. Compound was prepared in DMEM containing 4% FCS, 1:100 Penicillin/Streptomysin, 1:100 L-glutamine and 0.5% DMSO. Compound/DMSO mixes were added to the cells and incubated for 4 days at 37° C. After 4 days, cells were either lyzed using the Rneasy kit (Qiagen) to isolate and purify RNA for an $EC_{50}$ determination or assessed for cytotoxicity using alamar Blue (Trek Diagnotstic Systems) for a $CC_{50}$ reading. For an $EC_{50}$ determination, purified total RNA was normalized using RiboGreen (Jones L J, Yue S T, Cheung C Y, Singer V L, Anal. Chem., 265(2):368–74 (1998)) and relative quantitation of HCV RNA expression assessed using the Taqmann procedure (Kolykhalov A A, Mihalik K, Feinstone S M, Rice C M, Journal of Virology 74, 2046–2051 (2000)). Briefly, RNA made to a volume of 5 µl ($\leq$1 ng) was added to a 20 µl Ready-Mix containing the following: 5×EZ rTth buffer, 3 mM $MnOAc_2$, 3 mM dNTPs, 200 nM forward primer, 600 nM reverse primer, 100 nM probe and rTth polymerase. Samples containing known concentrations of HCV RNA transcript were run as standards. Using the following cycling protocol (95° C., 1 min; 60° C., 0.5 min; 95° C., 2 min; 40 cycles of 94° C., 0.5 min, 60° C.; 1 min; and completing with 60° C., 10 min), HCV RNA expression was quantitated as described in the Perkin Elmer manual. The toxicity of compound ($CC_{50}$) was determined by adding $\frac{1}{10}^{th}$ volume of alamar Blue to the media incubating the cells. After 4 hr, the fluorescence signal from each well was read, with an excitation wavelength at 530 nM and an emission wavelength of 580 nM, using the Cytofluor Series 4000 (Perspective Biosystems).

In vivo Rat PK Studies

All animal experimentation was conducted in accordance with USDA guidelines under the Animal Welfare Act. To assess the systemic and liver exposure, representative compounds were orally (gastric intubation) or intravenously (bolus or infusion) administered to male Sprague Dawley rats bearing indwelling jugular vein cannulae. At predetermined times after dosing, serial blood samples were taken from the implanted cannulae. Plasma was separated from EDTA-treated blood by centrifugation and stored at −20° C. until analysis. The liver was removed from rats after carbon dioxide asphyxiation, rinsed with saline and blotted dry. For analysis, a 2 g portion of the outer part of one lobe was minced and homogenized with 4 ml of 80% acetonitrile/HBSS buffer. After centrifugation, the supernatant was kept at −20° C. until analysis. Quantitation of represenatative compounds in plasma and liver homogenate samples was performed by a specific LC/MS/MS method optimized for each compound.

Biological Examples

The following Table 1 lists representative compounds I of the invention which were assayed in vitro according to the method previously described.

Activity in cells and specificity: Representative compounds of the invention were assessed in the HCV replicon cell assay and in or several of the outlined specificity assays. For example, Compound 58 was found to have an $IC_{50}$ of 17 nM against the NS3/4A BMS strain in the enzyme assay. Similar potency values were obtained with the published H77C ($IC_{50}$ of 10 nM) and J4L6S ($IC_{50}$ of 8 nM) strains. The $EC_{50}$ value in the replicon assay was 250 nM. This compound also demonstrated a potential for in vivo efficacy since viral target exposure was achieved when compound was dosed orally or intravenously.

In the specificity assays, the same compound was found to have the following activity:HLE=35 µM; PPE>100 µM; Chymotrypsin>100 µM; Cathepsin B>100 µM. These results indicate this family of compounds are highly specific for the NS3 protease and many of these members inhibit HCV replicon replication.

The compounds tested were found to have activities in the ranges as follow:

IC50 Activity Ranges: A is <50 µM; B is <5 µM; C is <0.5 µM; D is <0.05 µM
EC50 Activity Range: A is <50 µM; B is <5 µM; C is <0.5 µM; D is <0.05 µM.

| Compound | IC50 | EC50 | Compound | IC50 | EC50 |
| --- | --- | --- | --- | --- | --- |
| 1 | C | | 2 | D | D |
| 3 | D | D | 5 | D | D |
| 6 | D | D | 7 | D | C |
| 8 | D | D | 9 | D | C |
| 10 | D | D | 11 | D | D |
| 12 | C | C | 13 | C | C |
| 14 | C | C | 15 | C | B |
| 16 | C | C | 17 | C | C |
| 18 | D | D | 19 | D | D |
| 20 | D | C | 21 | D | B |
| 22 | D | C | 23 | D | C |
| 24 | C | C | 25 | D | C |

-continued

| Compound | IC50 | EC50 | Compound | IC50 | EC50 |
|---|---|---|---|---|---|
| 26 | D | C | 27 | D | C |
| 28 | D | B | 29 | D | D |
| 30 | D | D | 31 | D | D |
| 32 | D | D | 33 | D | D |
| 34 | D | C | 35 | D | C |
| 36 | D | C | 37 | D | D |
| 38 | D | D | 39 | D | C |
| 40 | D | C | 41 | D | C |
| 42 | D | C | 43 | D | C |
| 44 | D | C | 45 | D | C |
| 46 | D | C | 47 | D | C |
| 48 | D | C | 49 | D | C |
| 50 | C | B | 51 | D | C |
| 52 | C | C | 53 | D | A |
| 54 | D | C | 55 | D | D |
| 56 | D | C | 57 | C | C |
| 58 | D | C | 59 | D | D |
| 60 | C | C | 61 | C | B |
| 62 | B |   | 63 | D | C |
| 64 | B |   | 65 | C |   |
| 66 | C |   | 67 | D | B |
| 68 | D | B | 69 | C | C |
| 70 | C |   | 71 | D | D |
| 72 | C | C | 73 | D | C |
| 74 | B |   | 75 | C |   |
| 76 | C |   | 77 | A |   |
| 78 | D |   | 79 | C |   |
| 80 | B |   | 81 | B |   |
| 82 | A |   | 83 | B |   |
| 84 | B |   | 85 | C |   |
| 86 | D | C | 87 | D |   |
| 88 | C |   | 89 | C | B |
| 90 | C |   | 91 | D | D |
| 92 | D |   | 93 | D |   |
| 97 | C |   | 98 | D | C |
| 99 | D | C | 100 | D | C |
| 101 | D | C | 102 | D | C |
| 103 | D | D | 104 | D | D |
| 105 | D | D | 106 | D | C |
| 107 | D | C | 108 | D | C |
| 109 | D | C | 110 | D | C |
| 111 | D | B | 112 | D | D |
| 113 | D | D | 114 | D | D |
| 115 | D | D | 116 | D | D |
| 117 | D | C | 118 | D | C |
| 119 | D | C | 120 | D | D |
| 121 | D | C | 122 | D | D |
| 123 | D | D | 124 | D | D |
| 125 | D | D | 126 | D | D |
| 127 | D | D | 128 | B | B |
| 129 | B | A | 132 | D | B |
| 136 | C | B | 137 | B | B |
| 138 | B |   | 139 | B |   |
| 140 | D | C | 141 | C | B |

What is claimed is:

1. A compound having the formula

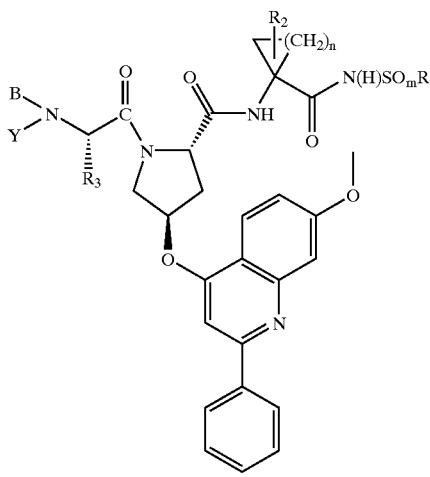

(I)

wherein:
(a) $R_1$ is $C_{1-8}$ alkyl, $C_{3-7}$ cycloalkyl, or $C_{4-10}$ (alkylcycloalkyl), which are all optionally substituted from one to three times with halo, cyano, nitro, $C_{1-6}$ alkoxy, amido, amino or phenyl, or $R_1$ is $C_6$ or $C_{10}$ aryl which is optionally substituted from one to three times with halo, cyano, nitro, $C_{1-6}$ alkyl, $C_{1-6}$ alkoxy, amido, amino or phenyl;

(b) m is 1 or 2;

(c) n is 1 or 2;

(d) $R_2$ is $C_{1-6}$ alkyl, $C_{2-6}$ alkenyl or $C_{3-7}$ cycloalkyl, each optionally substituted from one to three times with halogen, or $R_2$ is H;

(e) $R_3$ is $C_{1-8}$ alkyl optionally substituted with phenyl, $C_{3-12}$ alkenyl, $C_{3-7}$ cycloalkyl, or $C_{4-10}$ (alkylcycloalkyl), wherein the cycloalkyl or alkylcycloalkyl are optionally substituted with hydroxy, $C_{1-6}$ alkyl, $C_{2-6}$ alkenyl; or $C_{1-6}$ alkoxy or $R_3$ together with the carbon atom to which it is attached forms a $C_{3-7}$ cycloalkyl group optionally substituted with $C_{2-6}$ alkenyl;

(f) Y is H, phenyl substituted with nitro, pyridyl substituted with nitro, or $C_{1-6}$ alkyl wherein said alkyl is optionally substituted with cyano, OH or $C_{3-7}$ cycloalkyl;

(g) B is H, $C_{1-6}$ alkyl, $R_4$—(C=O)—, $R_4O(C=O)$—, $R_4$—N($R_6$)—C(=O)—, $R_4$—N($R_5$)—C(=S)—, $R_4SO_2$—, or $R_4$—N($R_5$)—$SO_2$—;

(h) $R_4$ is (i) $C_{1-10}$ alkyl optionally substituted with phenyl, carboxyl, $C_{1-6}$ alkanoyl, 1–3 halogen, hydroxy, —OC(O)$C_{1-6}$ alkyl, $C_{1-6}$ alkoxy, amino optionally mono-or-di substituted with $C_{1-6}$ alkyl, amido, or (lower alkyl) amido; or —O-phenyl optionally substituted with halogen or $C_{1-6}$ alkoxy; (ii) $C_{3-7}$ cycloalkyl, $C_{3-7}$ cycloalkoxy, or $C_{4-10}$ alkylcyclo-alklyl, all optionally substituted with hydroxy, carboxyl, ($C_{1-6}$ alkoxy) carbonyl, amino optionally mono- or disubstituted with $C_{1-6}$ alkyl, amido, or (lower alkyl) amido; (iii) amino optionally mono-or-di-substituted with $C_{1-6}$ alkyl; amido; or (lower alkyl)amido; (iv) $C_6$ or $C_{10}$ aryl or $C_{7-16}$ aralkyl, all optionally substituted with $C_{1-6}$ alkyl, halogen, nitro, hydroxy, amido, (lower alkyl) amido, or amino optionally mono-or-di-substituted with $C_{1-6}$ alkyl; or (v) Het or (lower alkyl)-Het, both optionally substituted with $C_{1-6}$ alkyl, hydroxy, amido, (lower alkyl) amido, or amino optionally mono-or-di-substituted with $C_{1-6}$ alkyl; (vi) bicyclo(1.1.1)pentane; (vii) —C(O)OC$_{1-6}$ alkyl, $C_{2-6}$alkenyl, $C_{2-6}$alkynyl; and (i) $R_5$ is H or $C_{1-6}$ alkyl, said $C_{1-6}$alkyl optionally substituted with 1–3 halogens;

or a pharmaceutically acceptable salt, solvate or prodrug thereof.

2. A compound of claim 1 wherein m is 2.
3. A compound of claim 1 wherein n is 1.
4. A compound of claim 1 wherein $R_1$ is cyclopropyl.
5. A compound of claim 1 wherein $R_1$ is cyclobutyl.
6. A compound of claim 1 wherein $R_1$ is optionally substituted phenyl.
7. A compound of claim 1 wherein $R_2$ is ethyl or vinyl.
8. A compound of claim 1 wherein $R_3$ is $C_{1-6}$ alkyl.
9. A compound of claim 1 wherein m is 2, n is 1 and $R_2$ is ethyl.
10. A compound of claim 9 wherein $R_1$ is cyclopropyl.
11. A compound of claim 9 wherein $R_1$ is cyclobutyl.
12. A compound of claim 9 wherein $R_1$ is optionally substituted phenyl.
13. A compound of claim 1 wherein m is 2, n is 1 and $R_2$ is vinyl.
14. A compound of claim 13 wherein $R_1$ is cyclopropyl.
15. A compound of claim 13 wherein $R_1$ is cyclobutyl.
16. A compound of claim 13 wherein $R_1$ is optionally substituted phenyl.
17. A compound having the formula

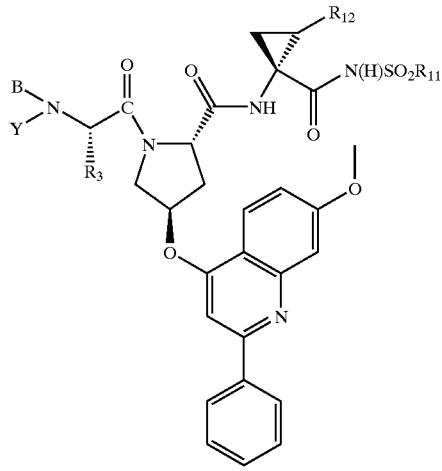

wherein:
(a) $R_{11}$ is $C_{1-8}$ alkyl, $C_{3-7}$ cycloalkyl, or $C_{4-10}$ (alkylcycloalkyl), naphthyl, or phenyl wherein said phenyl is optionally substituted from one to three times with halo, cyano, nitro, $C_{1-6}$ alkyl, $C_{1-6}$ alkoxy, amido, or phenyl;
(b) $R_{12}$ is $C_{1-6}$ alkyl, $C_{2-6}$ alkenyl or H;
(c) $R_3$ is $C_{1-8}$ alkyl, $C_{3-12}$ alkenyl, $C_{3-7}$ cycloalkyl, or $C_{4-10}$ (alkylcycloalkyl), wherein the cycloalkyl or alkylcycloalkyl are optionally substituted with hydroxy, $C_{1-6}$ alkyl, $C_{1-6}$ alkenyl, or $C_{1-6}$ alkoxy;
(d) Y is H or $C_{1-6}$ alkyl wherein said alkyl is optionally substituted with cyano or $C_{3-7}$ cycloalkyl;
(e) B is H, $R_4$—(C=O)—, $R_4$O(C=O)—, $R_4$—N($R_5$)—C(=O)—, $R_4$—N($R_5$)—C(=S)—, $R_4$SO$_2$—, or $R_4$—N($R_5$)—SO$_2$—;

(f) $R_4$ is (i) $C_{1-10}$ alkyl optionally substituted with carboxyl, $C_{1-6}$ alkanoyl, hydroxy, $C_{1-6}$ alkoxy, amino optionally mono-or-di substituted with $C_{1-6}$ alkyl, amido, or (lower alkyl) amido; (ii) $C_{3-7}$ cycloalkyl, $C_{3-7}$ cycloalkoxy, or $C_{4-10}$ alkylcyclo-alklyl, all optionally substituted with hydroxy, carboxyl, ($C_{1-6}$ alkoxy) carbonyl, amino optionally mono- or disubstituted with $C_{1-6}$ alkyl, amido, or (lower alkyl) amido; (iii) amino optionally mono-or-di-substituted with $C_{1-6}$ alkyl; amido; or (lower alkyl)amido; (iv) $C_6$ or $C_{10}$ aryl or $C_{7-16}$ aralkyl, all optionally substituted with $C_{1-6}$ alkyl, hydroxy, amido, (lower alkyl) amido, or amino optionally mono-or-di-substituted with $C_{1-6}$ alkyl; or (v) Het or (lower alkyl)-Het, both optionally substituted with $C_{1-6}$ alkyl, hydroxy, amido, (lower alkyl) amido, or amino optionally mono-or-di-substituted with $C_{1-6}$ alkyl; and (g) $R_5$ is H or $C_{1-6}$ alkyl, or a pharmaceutically acceptable salt, solvate or prodrug thereof.

18. A compound of claim 17 wherein $R_{11}$ is selected from cyclopropyl, cyclobutyl or optionally substituted phenyl.

19. A compound having the formula

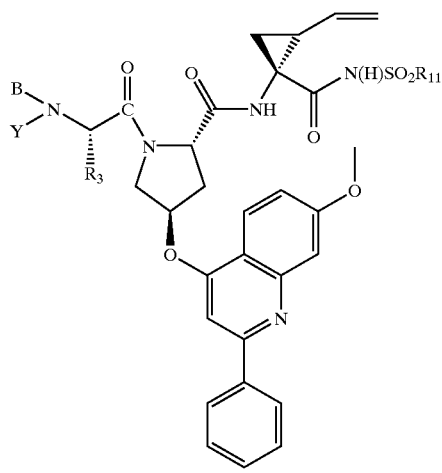

wherein:
(a) $R_{11}$ is $C_{1-8}$ alkyl, $C_{3-7}$ cycloalkyl, or $C_{4-10}$ (alkylcycloalkyl), naphthyl, or phenyl wherein said phenyl is optionally substituted from one to three times with halo, cyano, nitro, $C_{1-6}$ alkyl, $C_{1-6}$ alkoxy, amido, or phenyl;
(b) $R_3$ is $C_{1-8}$ alkyl, $C_{3-12}$ alkenyl, $C_{3-7}$ cycloalkyl, or $C_{4-10}$ (alkylcycloalkyl), wherein the cycloalkyl or alkylcycloalkyl are optionally substituted with hydroxy, $C_{1-6}$ alkyl, $C_{1-6}$ alkenyl, or $C_{1-6}$ alkoxy;
(c) Y is H or $C_{1-6}$ alkyl wherein said alkyl is optionally substituted with cyano or $C_{3-7}$ cycloalkyl;
(d) B is H, $R_4$—(C=O)—, $R_4$O(C=O)—, $R_4$—N($R_5$)—C(=O)—, $R_4$—N($R_5$)—C(=S)—, $R_4$SO$_2$—, or $R_4$—N($R_5$)—SO$_2$—;
(e) $R_4$ is (i) $C_{1-10}$ alkyl optionally substituted with carboxyl, $C_{1-6}$ alkanoyl, hydroxy, $C_{1-6}$ alkoxy, amino optionally mono-or-di substituted with $C_{1-6}$ alkyl, amido, or (lower alkyl) amido; (ii) $C_{3-7}$ cycloalkyl, $C_{3-7}$ cycloalkoxy, or $C_{4-10}$ alkylcyclo-alklyl, all optionally substituted with hydroxy, carboxyl, ($C_{1-6}$ alkoxy) carbonyl, amino optionally mono- or disubstituted with $C_{1-6}$ alkyl, amido, or (lower alkyl) amido; (iii) amino optionally mono-or-di-substituted with $C_{1-6}$ alkyl; amido; or (lower alkyl)amido; (iv) $C_6$ or $C_{10}$ aryl or $C_{7-16}$ aralkyl, all optionally substituted with $C_{1-6}$ alkyl, hydroxy, amido, (lower alkyl) amido, or amino optionally mono-or-di-substituted with $C_{1-6}$ alkyl; or (v) Het or (lower alkyl)-Het, both optionally substituted with $C_{1-6}$ alkyl, hydroxy, amido, (lower alkyl) amido, or amino optionally mono-or-di-substituted with $C_{1-6}$ alkyl; and (f) $R_5$ is H or $C_{1-6}$ alkyl;

or a pharmaceutically acceptable salt, solvate or prodrug thereof.

20. A compound of claim 19 wherein $R_{11}$ is selected from cyclopropyl, cyclobutyl or optionally substituted phenyl.

21. A compound having the formula

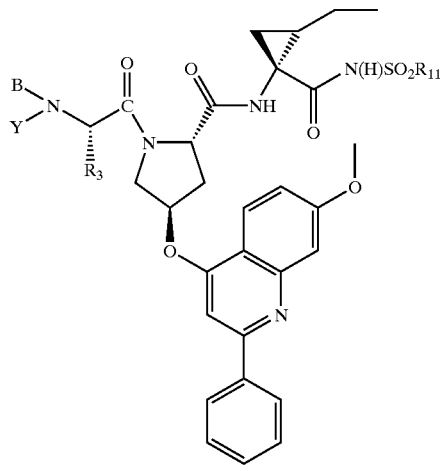

wherein:

(a) $R_{11}$ is $C_{1-8}$ alkyl, $C_{3-7}$ cycloalkyl, or $C_{4-10}$(alkylcycloalkyl), naphthyl, or phenyl wherein said phenyl is optionally substituted from one to three times with halo, cyano, nitro, $C_{1-6}$ alkyl, $C_{1-6}$ alkoxy, amido, or phenyl;

(b) $R_3$ is $C_{1-8}$ alkyl, $C_{3-12}$ alkenyl, $C_{3-7}$ cycloalkyl, or $C_{4-10}$ (alkylcycloalkyl), wherein the cycloalkyl or alkylcycloalkyl are optionally substituted with hydroxy, $C_{1-6}$ alkyl, $C_{1-6}$ alkenyl, or $C_{1-6}$ alkoxy;

(c) Y is H or $C_{1-6}$ alkyl wherein said alkyl is optionally substituted with cyano or $C_{3-7}$ cycloalkyl;

(d) B is H, $R_4$—(C=O)—, $R_4O(C=O)$—, $R_4$—$N(R_5)$—C(=O)—, $R_4$—$N(R_5)$—C(=S)—, $R_4SO_2$—, or $R_4$—$N(R_5)$—$SO_2$—;

(e) $R_4$ is (i) $C_{1-10}$ alkyl optionally substituted with carboxyl, $C_{1-6}$ alkanoyl, hydroxy, $C_{1-6}$ alkoxy, amino optionally mono-or-di substituted with $C_{1-6}$ alkyl, amido, or (lower alkyl) amido; (ii) $C_{3-7}$ cycloalkyl, $C_{3-7}$ cycloalkoxy, or $C_{4-10}$ alkylcyclo-alklyl, all optionally substituted with hydroxy, carboxyl, ($C_{1-6}$ alkoxy) carbonyl, amino optionally mono- or disubstituted with $C_{1-6}$ alkyl, amido, or (lower alkyl) amido; (iii) amino optionally mono-or-di-substituted with $C_{1-6}$ alkyl; amido; or (lower alkyl)amido; (iv) $C_6$ or $C_{10}$ aryl or $C_{7-16}$ aralkyl, all optionally substituted with $C_{1-6}$ alkyl, hydroxy, amido, (lower alkyl) amido, or amino optionally mono-or-di-substituted with $C_{1-6}$ alkyl; or (v) Het or (lower alkyl)-Het, both optionally substituted with $C_{1-6}$ alkyl, hydroxy, amido, (lower alkyl) amido, or amino optionally mono-or-di-substituted with $C_{1-6}$ alkyl; and (f) $R_5$ is H or $C_{1-6}$ alkyl;

or a pharmaceutically acceptable salt, solvate or prodrug thereof.

22. A compound of claim 21 wherein $R_{11}$ is selected from cyclopropyl, cyclobutyl or optionally substituted phenyl.

23. A compound having the formula

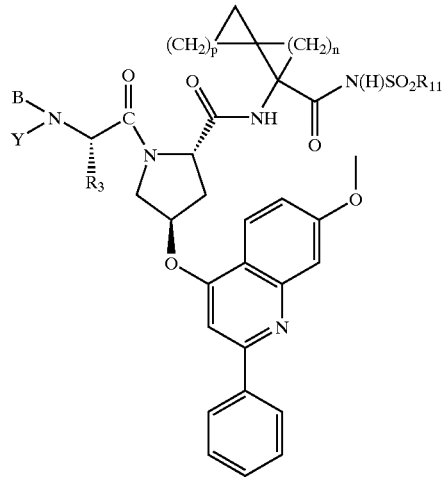

wherein:

(a) $R_{11}$ is $C_{1-8}$ alkyl, $C_{3-7}$ cycloalkyl, or $C_{4-10}$ (alkylcycloalkyl), naphthyl, or phenyl wherein said phenyl is optionally substituted from one to three times with halo, cyano, nitro, $C_{1-6}$ alkyl, $C_{1-6}$ alkoxy, amido, or phenyl;

(b) $R_3$ is $C_{1-8}$ alkyl, $C_{3-12}$ alkenyl, $C_{3-7}$ cycloalkyl, or $C_{4-10}$ (alkylcycloalkyl), wherein the cycloalkyl or alkylcycloalkyl are optionally substituted with hydroxy, $C_{1-6}$ alkyl, $C_{1-6}$ alkenyl, or $C_{1-6}$ alkoxy;

(c) Y is H or $C_{1-6}$ alkyl wherein said alkyl is optionally substituted with cyano or $C_{3-7}$ cycloalkyl;

(d) B is H, $R_4$—(C=O)—, $R_4O(C=O)$—, $R_4$—$N(R_5)$—C(=O)—, $R_4$—$N(R_5)$—C(=S)—, $R_4SO_2$—, or $R_4$—$N(R_5)$—$SO_2$—;

(e) $R_4$ is (i) $C_{1-10}$ alkyl optionally substituted with carboxyl, $C_{1-6}$ alkanoyl, hydroxy, $C_{1-6}$ alkoxy, amino optionally mono-or-di substituted with $C_{1-6}$ alkyl, amido, or (lower alkyl) amido; (ii) $C_{3-7}$ cycloalkyl, $C_{3-7}$ cycloalkoxy, or $C_{4-10}$ alkylcyclo-alklyl, all optionally substituted with hydroxy, carboxyl, ($C_{1-6}$ alkoxy) carbonyl, amino optionally mono- or disubstituted with $C_{1-6}$ alkyl, amido, or (lower alkyl) amido; (iii) amino optionally mono-or-di-substituted with $C_{1-6}$ alkyl; amido; or (lower alkyl)amido; (iv) $C_6$ or $C_{10}$ aryl or $C_{7-16}$ aralkyl, all optionally substituted with $C_{1-6}$ alkyl, hydroxy, amido, (lower alkyl) amido, or amino optionally mono-or-di-substituted with $C_{1-6}$ alkyl; or (v) Het or (lower alkyl)-Het, both optionally substituted with $C_{1-6}$ alkyl, hydroxy, amido, (lower alkyl) amido, or amino optionally mono-or-di-substituted with $C_{1-6}$ alkyl;

(f) $R_5$ is H or $C_{1-6}$ alkyl;

(g) n is 1 or 2; and (h) p is 1, 2, 3, 4 or 5, or a pharmaceutically acceptable salt, solvate or prodrug thereof.

24. A compound of claim 23 wherein $R_{11}$ is selected from cyclopropyl, cyclobutyl or optionally substituted phenyl.

25. A compound having the formula

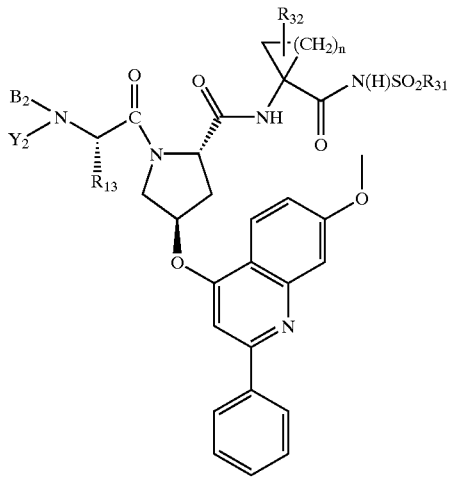

wherein:
- (a) $R_{31}$ is $C_{1-8}$ alkyl, $C_{3-7}$ cycloalkyl, or $C_{4-10}$ (alkylcycloalkyl), all optionally substituted with hydroxy, halo, $C_{1-6}$ alkoxy, $C_{1-6}$ thioalkyl, amido, amino, ($C_{1-6}$ alkyl)amido, $C_6$ or $C_{10}$ aryl, $C_{7-16}$ aralkyl, Het, or ($C_{1-6}$ alkyl)-Het, said aryl, arylalkyl or Het being optionally substituted with halo, alkyl or lower alkyl Het;
- (b) n is 1 or 2;
- (c) $R_{32}$ is H, $C_{1-6}$ alkyl, $C_{1-3}$ alkoxy, $C_{3-7}$ cycloalkyl, $C_{2-6}$ alkenyl, or $C_{2-6}$ alkynyl, all optionally substituted with halogen;
- (d) $R_{13}$ is $C_{1-8}$ alkyl, $C_{3-12}$ alkenyl, $C_3$–$C_7$ cycloalkyl, $C_{4-13}$ cycloalkenyl, or $C_4$–$C_{10}$ (alkylcycloalkyl), all optionally substituted with hydroxy, $C_1$–$C_6$ alkoxy, $C_1$–$C_6$ thioalkyl, amino, amido, (loweralkyl) amido, $C_6$ or $C_{10}$ aryl, or $C_7$–$C_{16}$ aralkyl;
- (e) $Y_2$ is H or $C_1$–$C_6$ alkyl;
- (f) $B_2$ is H, $R_{14}$—(C=O)—; $R_{14}$O(C=O)—, $R_{14}$—N($R_{15}$)—C(=O)—; $R_{14}$—N($R_{15}$)—C(=S)—; $R_{14}SO_2$—, or $R_{14}$—N($R_{15}$)—$SO_2$—;
- (g) $R_{14}$ is (i) $C_{1-10}$ alkyl optionally substituted with carboxyl, $C_{1-6}$ alkanoyl, hydroxy, $C_{1-6}$ alkoxy, amino optionally mono-or-di substituted with $C_{1-6}$ alkyl, amido, or (lower alkyl) amido; (ii) $C_{3-7}$ cycloalkyl, $C_{3-7}$ cycloalkoxy, or $C_{4-10}$ alkylcycloalkyl, all optionally substituted with hydroxy, carboxyl, ($C_{1-6}$ alkoxy) carbonyl, amino optionally mono- or disubstituted with $C_{1-6}$ alkyl, amido, or (lower alkyl) amido; (iii) amino optionally mono-or-di-substituted with $C_{1-6}$ alkyl; amido; or (lower alkyl)amido; (iv) $C_6$ or $C_{10}$ aryl or $C_{7-16}$ aralkyl, all optionally substituted with $C_{1-6}$ alkyl, hydroxy, amido, (lower alkyl) amido, or amino optionally mono-or-di-substituted with $C_{1-6}$ alkyl; or (v) Het or (lower alkyl)-Het, both optionally substituted with $C_1$ alkyl, hydroxy, amido, (lower alkyl) amido, or amino optionally mono-or-di-substituted with $C_{1-6}$ alkyl; and
- (h) $R_{15}$ is H or $C_{1-6}$ alkyl.

26. A salt, solvate or prodrug of a compound of claim 25.

27. A compound of claim 25 wherein $R_{31}$ is $C_{3-6}$ cycloalkyl, $C_{4-10}$ alkylcycloalkyl, $C_{1-8}$ alkyl $CF_3$ or $CCl_3$.

28. A compound of claim 25 wherein $B_2$ is an acyl derivative of formula $R_{14}$—O—(C=O)— or a carboxyl of formula $R_{14}$—O—(C=O)—.

29. A compound of claim 25 wherein $R_2$ is H, $C_{1-3}$ alkyl, $C_{3-5}$ cycloalkyl, or $C_{2-4}$ alkenyl, all optionally substituted with halo.

30. A compound of claim 25 wherein $R_{31}$ is $C_{1-8}$ alkyl, $C_{3-7}$ cycloalkyl, or $C_{4-10}$ alkylcycloalkyl, all optionally substituted with hydroxy, $C_{1-6}$ alkoxy, $C_{1-6}$ thioalkyl, acetamido or $C_6$ or $C_{10}$ aryl.

31. A compound of claim 25 wherein
- $B_2$ is $(CH_3)_3$—O—CO—;
- $Y_2$ is H; n is 1;
- $R_{31}$ is methyl, cyclopropyl or —$CF_3$;
- $R_{32}$ is ethyl or vinyl; and
- $R_{13}$ is t-butyl, i-propyl, s-butyl, i-butyl or cyclohexylmethyl.

32. A composition, comprising
- (a) a compound of claim 1–31, or a pharmaceutically acceptable salt, solvate or prodrug thereof; and
- (b) a pharmaceutically acceptable carrier.

33. A method of inhibiting HCV NS3 protease which comprises administering to a mammal in need of such treatment a therapeutically effective amount a compound of claim 1–31 or a pharmaceutically acceptable salt, solvate or prodrug thereof.

* * * * *